(12) United States Patent
Xu et al.

(10) Patent No.: US 10,494,378 B2
(45) Date of Patent: Dec. 3, 2019

(54) FUSED RING PYRIMIDINE COMPOUND, INTERMEDIATE, AND PREPARATION METHOD, COMPOSITION AND USE THEREOF

(71) Applicant: GUANGZHOU MAXINOVEL PHARMACEUTICALS CO., LTD., Guangzhou (CN)

(72) Inventors: Zusheng Xu, Shanghai (CN); Nong Zhang, Shanghai (CN); Tinghan Wang, Shanghai (CN); Qingrui Sun, Shanghai (CN); Yuguang Wang, Shanghai (CN)

(73) Assignee: GUANGZHOU MAXINOVEL PHARMACEUTICALS CO., LTD. (CN)

( * ) Notice: Subject to any disclaimer, the term of this patent is extended or adjusted under 35 U.S.C. 154(b) by 0 days.

(21) Appl. No.: 15/746,254

(22) PCT Filed: Jul. 21, 2016

(86) PCT No.: PCT/CN2016/090798
§ 371 (c)(1),
(2) Date: Jan. 19, 2018

(87) PCT Pub. No.: WO2017/012559
PCT Pub. Date: Jan. 26, 2017

(65) Prior Publication Data
US 2018/0208604 A1    Jul. 26, 2018

(30) Foreign Application Priority Data
Jul. 21, 2015 (CN) .......................... 2015 1 0430641

(51) Int. Cl.
| | |
|---|---|
| *C07D 495/04* | (2006.01) |
| *C07D 401/14* | (2006.01) |
| *C07D 405/14* | (2006.01) |
| *A61K 31/519* | (2006.01) |
| *C07D 471/04* | (2006.01) |
| *A61K 9/127* | (2006.01) |
| *A61K 31/517* | (2006.01) |

(Continued)

(52) U.S. Cl.
CPC ............ *C07D 495/04* (2013.01); *A61K 9/127* (2013.01); *A61K 31/517* (2013.01); *A61K 31/519* (2013.01); *A61K 31/5377* (2013.01); *A61K 45/06* (2013.01); *C07D 401/14* (2013.01); *C07D 405/14* (2013.01); *C07D 471/04* (2013.01); *C07D 495/14* (2013.01)

(58) Field of Classification Search
CPC .. C07D 495/04; C07D 401/14; C07D 405/14; C07D 471/04; C07D 495/14; A61K 9/127; A61K 31/517; A61K 31/519; A61K 31/5377; A61K 45/06
See application file for complete search history.

(56) References Cited

U.S. PATENT DOCUMENTS 7,528,143 B2 * 5/2009 Noronha .............. C07D 239/42
514/275
7,932,262 B2 * 4/2011 Ramurthy ............ C07D 239/94
514/266.4

(Continued)

FOREIGN PATENT DOCUMENTS

| WO | 2009062258 A1 | 5/2009 |
|---|---|---|
| WO | 2011049332 A2 | 4/2011 |

(Continued)

OTHER PUBLICATIONS

B Testa et al., Prodrug Design in, 5 Encyclopedia of Pharmaceutical Technology, 3008-3014 (J. Swarbrick ed., 3rd ed., 2007) (Year: 2007).*

(Continued)

*Primary Examiner* — Alexander R Pagano
(74) *Attorney, Agent, or Firm* — Dilworth IP, LLC

(57) ABSTRACT

Disclosed area fused ring pyrimidine compound, and an intermediate, a preparation method, a composition and a use thereof. The fused ring pyrimidine compound is a compound as shown in formula I, a tautomer, an enantiomer, a diastereoisomer, a pharmaceutically acceptable salt, a metabolite, a metabolic precursor or a prodrug thereof, wherein the above-mentioned compound is used for the preparation of a medicine for preventing, remitting or treating one or more of immune system diseases, autoimmune diseases, cell proliferative diseases, allergic disorders and cardiovascular diseases, and the compound has a strong inhibitory effect on the Janues kinase, FGFR kinase, FLT3 kinase and Src family kinase.

18 Claims, No Drawings

(51) Int. Cl.
*A61K 31/5377* (2006.01)
*A61K 45/06* (2006.01)
*C07D 495/14* (2006.01)

(56) References Cited

U.S. PATENT DOCUMENTS

| | | | | |
|---|---|---|---|---|
| 8,486,952 | B2* | 7/2013 | Boy | A61K 31/517 |
| | | | | 514/258.1 |
| 8,586,580 | B2* | 11/2013 | Sim | C07D 519/00 |
| | | | | 514/232.5 |
| 9,550,770 | B2* | 1/2017 | Qian | A61K 45/06 |
| 9,840,516 | B2* | 12/2017 | Li | C07D 495/04 |
| 9,849,139 | B2* | 12/2017 | Qian | A61K 45/06 |
| 10,111,874 | B2* | 10/2018 | Janes | A61K 31/00 |
| 2015/0152089 | A1* | 6/2015 | Boy | A61K 31/517 |
| | | | | 514/210.21 |
| 2015/0175601 | A1 | 6/2015 | Qian et al. | |
| 2018/0072678 | A1* | 3/2018 | Xu | A61K 31/472 |
| 2018/0118757 | A1* | 5/2018 | Li | C07D 495/04 |
| 2018/0127420 | A1* | 5/2018 | Zhang | C07D 401/14 |

FOREIGN PATENT DOCUMENTS

| | | |
|---|---|---|
| WO | 2011079231 A1 | 6/2011 |
| WO | 2012030894 A1 | 3/2012 |
| WO | 2014023385 A1 | 2/2014 |
| WO | 2014037750 A1 | 3/2014 |
| WO | 2015027222 A2 | 2/2015 |
| WO | 2016133935 A1 | 8/2016 |

OTHER PUBLICATIONS

S.K. Bhatia et al., Autoimmunity and autoimmune disease in 6 Principles of Medical Biology 239-263, 244 (1996) (Year: 1996).*
S.M. Hayter et al., Autoimmunity Reviews, 754-765, 756 (2012) (Year: 2012).*
A. Ghigo et al., 32 BioEssays, 185-196 (2010) (Year: 2010).*
I.V. Turko et al., Pharmacological Reviews, 619-634 (2002) (Year: 2002).*
F.A. Scappaticci et al., 99 Journal of the National Cancer Institute, 1232-1239 (2007) (Year: 2007).*
C. Ha et al., 104 the American Journal of Gastroenterology, 1445-1451 (2009) (Year: 2009).*
R.J. Kok, 25 Pharmaceutical Research, 2413-2415 (2008) (Year: 2008).*
Z. Ghiassi-Nejad et al. 2 Expert Review of Gastroenterology & Hepatology, 803-816 (2008) (Year: 2008).*
Kinase Inhibitors, Methods in Molecular Biology 795 (B. Kuster ed., 2012) (Year: 2012).*
R.J. Riese et al., 24 Best Practice & Research Clinical Rheumatology, 513-526 (2010) (Year: 2010).*
N.K. Williams et al., 387 Journal of Molecular Biology, 219-232 (2009) (Year: 2009).*
B.H. Kim et al., 7 Molecular Cancer Therapeutics, 2672-2680 (2008) (Year: 2008).*
J.M. Kremer et al., 60 Arthritis & Rheumatism, 1895-1905 (2009) (Year: 2009).*
G.W. Booz et al., 34 Journal of molecular and cellular cardiology, 1443-1453 (2002) (Year: 2002).*
A. Kirabo et al., 3, Pharmaceuticals, 3478-3493 (2010) (Year: 2010).*
M. Kurdi et al., 297 American Journal of Physiology—Heart and Circulatory Physiology, 1545-1556 (2009) (Year: 2009).*
M.P. Kim et al., 335 Cell and Tissue Research, 249-259 (2009) (Year: 2009).*
G. Liu et al., 31 Arteriosclerosis, Thrombosis and Vascular Biology, 1342-1350 (2011) (Year: 2011).*
M. Touat et al., 21 Clinical Cancer Research, 2684-2694 (2015) (Year: 2015).*
M. Levis et al., International Journal of Hematology (2005) (Year: 2005).*
P. Brown et al., 40 European Journal of Cancer, 707-721 (2004) (Year: 2004).*
W-H. Lin et al., PLOS One, (2014) (Year: 2014).*
Extended European Search Report issued in European Patent Application No. 16827250.8 dated Jul. 30, 2018.
Aaronson, DS et al. Science 2002, 296, 1653-1655.
O 'Shea, JJ et al. Nat. Rev. Drug Discovery 2004, 3, 555-564.
Kiesseleva T. et al. J. Gene, 2002, 285, 1-24.
Buettner R. et al. Clin. Cancer Res. 2002, 8(4), 945-954.
Niu G. et al. Oncogene 2002, 21(13), 2000-2008.
Mora L.B. et al. J. Cancer Res. 2002, 62(22), 6659-6666.
J.K. Wang et al., Oncogene1997, 14, 1767-1778.
R. Shang et al., Cell1994, 78, 335-342.
J. Folkman. Nat. Med. 1995, 1, 27-31.
PCT International Search Report and Written Opinion dated Sep. 27, 2016 from corresponding Application No. PCT/CN2016/090798, 12 pages.
English translation of Chinese Priority Application No. 201510430641.5 filed on Jul. 21, 2015.

* cited by examiner

FUSED RING PYRIMIDINE COMPOUND, INTERMEDIATE, AND PREPARATION METHOD, COMPOSITION AND USE THEREOF

The present application claims the priority of Chinese Patent Application CN201510430641.5 filed on Jul. 21, 2015, the contents of which are incorporated herein by reference in their entireties.

FIELD OF INVENTION

The present invention relates to a fused ring pyrimidine compound, an intermediate, a preparation method, a composition and a use thereof.

BACKGROUND OF THE INVENTION

JAK-STAT (Janus kinase-signal transducer and activator of transcription) signal pathway is a cytokine-stimulated signal transduction pathway found in recent years and is involved in many important biological processes such as cell proliferation, differentiation, apoptosis and immune regulation (Aaronson, D S et al. *Science* 2002, 296, 1653-1655; O'Shea, J J et al. *Nat. Rev. Drug Discovery* 2004, 3, 555-564). Compared with other signal pathways, this signal pathway is relatively simple. It mainly consists of three components which area tyrosine kinase related receptor, a tyrosine kinase JAK and a transcription factor STAT. JAK (Janus Kinase), a class of molecules in the cells, is rapidly raised on the receptor and activated, after receiving signals from the upstream receptor molecules. The activated JAK catalyzes tyrosine phosphorylation of the receptor, and phosphorylated tyrosine on the receptor molecules is the recognition and binding site of STAT SH2, a class of signal molecules. Tyrosine phosphorylation also occurs after STAT binds to the receptor. Tyrosine phosphorylated STAT forms dimer and enters the nucleus. As an active transcription factor, dimeric STAT molecules directly affect the expression of related genes, thereby changing the proliferation or differentiation of target cells.

The JAK-STAT pathway widely presents in various tissue cells in vivo, and plays an important role in differentiation, proliferation and anti-infection of lymphocyte lines and is involved in the interaction and signal transduction of various inflammatory factors (Kiesseleva T. et al. *J. Gene*, 2002, 285, 1-24). Abnormal activation of this pathway is closely related to many diseases. To find and screen JAK inhibitors can help further study the regulation mechanism of JAK-STAT and provide new drugs and methods for the prevention and treatment of related diseases.

The formation, growth, invasion and metastasis of tumors are related to JAK-STAT signal transduction pathway. The activation of STATs in normal signal transduction is rapid and transient, and the persistent activation of STATs is closely related to the malignant transformation process of cells (Buettner R. et al. *Clin. Cancer Res.* 2002, 8(4), 945-954). STAT3 is the focal point of many oncogenic tyrosine kinase signal pathways such as EGFR, IL-6/JAK and Src etc. and is activated in many tumor cells and tissues such as breast cancer, ovarian cancer, head and neck squamous cell carcinoma cancer, prostate cancer, malignant melanoma, multiple myeloma, lymphoma, brain tumor, non-small cell lung cancer and various leukemias (Niu G. et al. *Oncogene* 2002, 21(13), 2000-2008). JAK-STAT pathway inhibitor belongs to PTK inhibitors, and the enzyme is a member of the oncogene protein and proto-oncoprotein family and plays an important role in the normal and abnormal proliferation of cells. The development and growth of tumors cannot be separated from PTK, therefore, JAK-STAT pathway inhibitor inhibits tumor growth by antagonizing PTK and has obvious anti-tumor effect (Mora L. B. et al. *J. Cancer Res.* 2002, 62(22), 6659-6666).

In addition, recent studies have shown that organ transplant rejection, psoriasis, tissue and organ fibrosis, bronchial asthma, ischemic cardiomyopathy, heart failure, myocardial infarction, hematological and immune system diseases are all closely related to JAK-STAT signal transduction pathway. This signal pathway is not only important for maintaining the normal physiological function of cells, but also plays an important regulatory role in the occurrence and development of the disease.

The family of fibroblast growth factor receptors belongs to a new family of receptor kinases, and includes four receptor subtypes encoded by four closely related genes (FGFR-1, 2, 3 and 4) and some isomeric molecules which participate in regulating physiological processes in living organisms through forming ternary complexes with fibroblast growth factor (FGF) and heparan sulfate and then triggering a series of signal transduction pathways. FGFR has a wide range of physiological and pathological functions in the body: (1) Embryonic development. Studies have shown that during the process of embryonic development, FGFR signal transduction is crucial for most organ development and embryonic pattern formation. (2) Cell division, migration and differentiation. FGFR, which stimulates cell proliferation and is involved in the regulation of cell transformation during pathological process, has many parallel pathways that enable FGFR-mediated signal transduction of cell division as evidenced by many studies (J. K. Wang et al., *Oncogene* 1997, 14, 1767-1778.). (3) Bone disease. Bone growth and differentiation are also regulated by the FGF family, and mutations in FGFR can lead to skeletal deformities (R. Shang et al., *Cell* 1994, 78, 335-342.). (4) Tumor development. FGFR promotes the migration, proliferation and differentiation of endothelial cells and plays an important role in the regulation of vascularization and angiogenesis. Uncontrolled angiogenesis may lead to the development of tumors and the growth of metastases (J. Folkman. *Nat. Med.* 1995, 1, 27-31.).

FMS-like tyrosine kinase 3 (FLT3) is a family member of receptor tyrosine kinase III (RTK III), and is composed of three parts, extracellular region, intracellular region and transmembrane region. It is first expressed in human hematopoietic stem cells, where FLT3 interacts with its ligand FL to stimulate or act on stem cells, which is of great importance for the growth and differentiation of stem cell. FLT3 kinase has wild type FLT3-WT and its major activating mutations FLT3-ITD and FLT3-D835Y. FLT3 is mainly expressed in the precursors of normal myeloid cells, but its abnormal expression is also found in a large part of acute myeloid leukemia (AML). In recent years, many large sample studies have confirmed that activating mutations of FLT3 play a very important pathological role in the pathogenesis and progression of acute myeloid leukemia. FLT3 has become an important target for the treatment of acute myeloid leukemia.

Src family kinase (SFK) is a family of non-receptor tyrosine kinases, including c-Src, LYN, FYN, LCK, HCK, FGR, BLK, YES and YRK, among which LYN kinase has two subtypes of LYNα and LYNβ, and LYN kinase and its two subtypes can cause similar intracellular tyrosine phosphorylation. According to the amino acid sequence, SFK can be divided into two subfamilies: a subfamily of c-Src, FYN, YES and FGR, widely expressed in different tissues; the other subfamily of LCK, BLK, LYN and HCK, closely related to hematopoietic cells. SFK is linked to multiple in vivo signal transduction pathways and is activated by growth factors, cytokines and immune cell receptors, G-protein coupled receptors, and integrins and other cell adhesion molecules, and then activating the corresponding signal transduction pathway, causing a variety of physiological effects of the cell. The activity of SFK mainly includes the regulation of cell morphology, cell motility, cell proliferation and survival. Abnormal activation and expression of these kinases lead to the development and progression of a wide range of diseases, such as a large number of solid tumors, a variety of hematological malignancies and some neuronal pathologies. Therefore, finding SFK inhibitors is a promising research topic in the field of medicinal chemistry.

SUMMARY OF THE INVENTION

The technical problem to be solved in the present invention is to provide a fused ring pyrimidine compound, an intermediate, a preparation method, a composition and a use thereof. The compound has a strong inhibitory effect on Janus kinase (JAK), FGFR kinase, FLT3 kinase and Src family kinase.

The present invention provides a fused ring pyrimidine compound of formula I, a tautomer, an enantiomer, a diastereoisomer, a pharmaceutically acceptable salt, a metabolite, a metabolic precursor or a prodrug thereof:

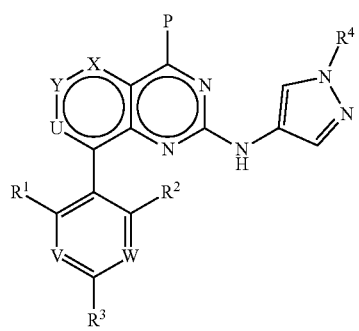

I wherein, P is selected from a hydrogen atom or a deuterium atom;
X is selected from CH or S;
Y is selected from N or $CR^5$;
U is selected from a chemical bond or CH;
V is selected from N or CH;
W is selected from N or $CR^6$;
each of $R^1$, $R^2$, $R^3$ and $R^6$ is independently selected from the group consisting of a hydrogen, a deuterium, a halogen, a substituted or unsubstituted alkyl,

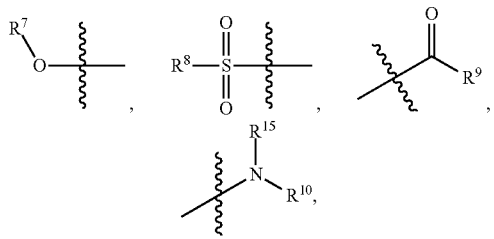

a cycloalkyl or a heterocycloalkyl; each of $R^7$, $R^8$, $R^9$, $R^{10}$ and $R^{15}$ is independently selected from the group consisting of a hydrogen, a deuterium, a halogen, a hydroxyl, an amino, a substituted or unsubstituted alkyl, an alkoxy,

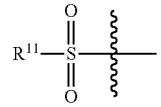

or a heterocycloalkyl; $R^{11}$ is a hydrogen, a deuterium or an alkyl (preferably a $C_{1-4}$ alkyl, such as a methyl); or, $R^6$, $R^2$ and the two atoms on the ring to which they are attached form a "substituted or unsubstituted 5- to 7-membered carbon heterocycle"; or, $R^6$, $R^3$ and the two atoms on the ring to which they are attached form a "substituted or unsubstituted 5- to 7-membered carbon heterocycle"; the heteroatom contained in the "substituted or unsubstituted 5- to 7-membered carbon heterocycle" is selected from the group consisting of nitrogen, oxygen and sulfur;

$R^4$ is a hydrogen, a deuterium, a substituted or unsubstituted alkyl, an alkoxy, a cycloalkyl, or a substituted or unsubstituted heterocycloalkyl;

$R^5$ is a hydrogen, a deuterium, a halogen, or an alkyl;

in the definitions of $R^1$, $R^2$, $R^3$ and $R^6$, the "substituted" in "a substituted or unsubstituted alkyl" means to be substituted with the substituents selected from the group consisting of a halogen (preferably fluorine), a hydroxyl, an amino, an alkyl (preferably a $C_{1-10}$ alkyl, more preferably a $C_{1-4}$ alkyl, such as a methyl), an alkoxy (preferably a $C_{1-10}$ alkoxy, more preferably a $C_{1-4}$ alkoxy, such as a methoxy),

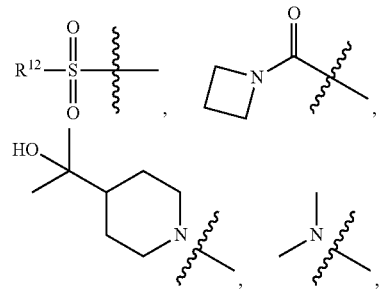

and a heterocycloalkyl (the heterocycloalkyl may be linked to other groups via a carbon atom or a heteroatom thereof; preferably, "a heterocycloalkyl with 1-4 heteroatoms and 3-8 carbon atoms in which the heteroatom is oxygen and/or nitrogen"; more preferably, "a heterocycloalkyl with 1-4 (for example 1 or 2) heteroatoms and 3-6 carbon atoms in which the heteroatom is oxygen and/or nitrogen"; most preferably,

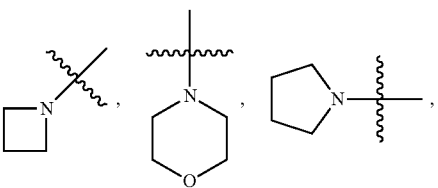

-continued

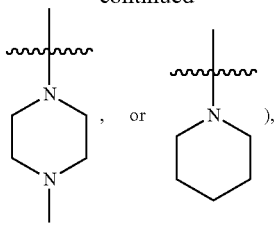

in the case when multiple substituents are present, the substituents are the same or different; $R^{12}$ is a hydrogen, a deuterium, or an alkyl (preferably a $C_{1-4}$ alkyl, such as a methyl);

in the definitions of $R^7$, $R^8$, $R^9$, $R^{10}$ and $R^{15}$, the "substituted" in "a substituted or unsubstituted alkyl" means to be substituted with the substituents selected from the group consisting of a deuterium, a halogen (preferably fluorine), a hydroxyl, an amino, an alkyl (preferably a $C_{1-10}$ alkyl, more preferably a $C_{1-4}$ alkyl, such as a methyl), an alkoxy (preferably a $C_{1-10}$ alkoxy, more preferably a $C_{1-4}$ alkoxy, such as a methoxy),

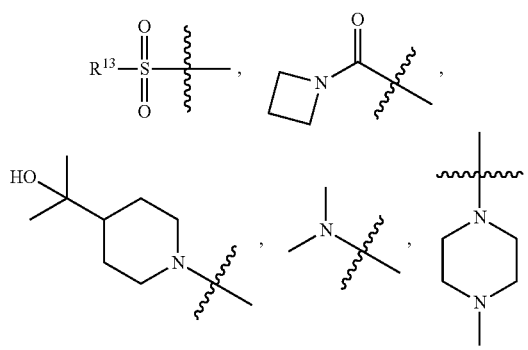

and a heterocycloalkyl (the heterocycloalkyl may be linked to other groups via a carbon atom or a heteroatom thereof; preferably, "a heterocycloalkyl with 1-4 heteroatoms and 3-8 carbon atoms in which the heteroatom is oxygen and/or nitrogen"; more preferably, "a heterocycloalkyl with 1-4 (for example 1 or 2) heteroatoms and 3-6 carbon atoms in which the heteroatom is oxygen and/or nitrogen"; most preferably,

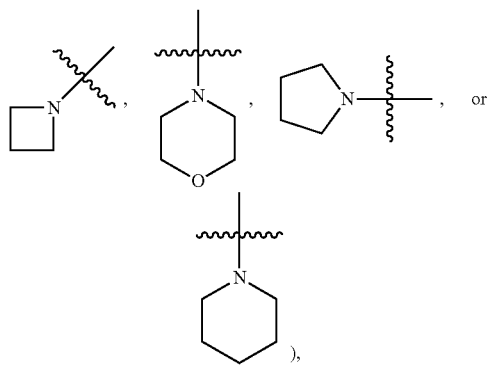

in the case when multiple substituents are present, the substituents are the same or different; $R^{13}$ is a hydrogen or an alkyl (preferably a $C_{1-4}$ alkyl, such as a methyl);

in the definition of $R^4$, the "substituted" in "a substituted or unsubstituted alkyl" and "a substituted or unsubstituted heterocycloalkyl" means to be substituted with the substituents selected from the group consisting of a hydroxyl, an alkyl (preferably a $C_{1-4}$ alkyl, such as a methyl),

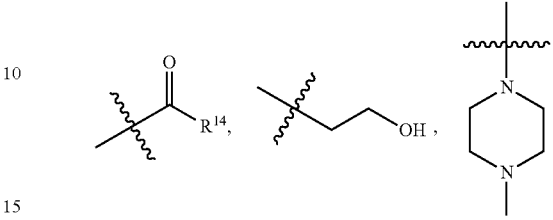

or a heterocycloalkyl (the heterocycloalkyl may be linked to other groups via a carbon atom or a heteroatom thereof; preferably, "a heterocycloalkyl with 1-4 heteroatoms and 3-6 carbon atoms in which the heteroatom is oxygen and/or nitrogen"; more preferably,

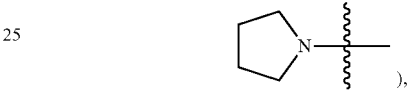

in the case where multiple substituents are present, the substituents are the same or different; $R^{14}$ is a hydrogen, an alkyl (preferably a $C_{1-4}$ alkyl, more preferably a methyl), a hydroxymethyl or an alkoxy (preferably a $C_{1-4}$ methoxy, more preferably a tert-butoxy or an ethoxy);

the "substituted" in "substituted or unsubstituted 5- to 7-membered carbon heterocycle" means to be substituted with one or more than one alkyl (preferably a $C_{1-4}$ alkyl, such as a methyl, an ethyl, a propyl and the like).

In the definitions of $R^1$, $R^2$, $R^3$ and $R^6$, the halogen is fluorine or chlorine; the alkyl in "substituted or unsubstituted alkyl" is preferably a $C_{1-4}$ alkyl, more preferably a methyl; the heterocycloalkyl may be linked to other groups via a carbon atom or a heteroatom thereof; the heterocycloalkyl is preferably "a heterocycloalkyl with 1-4 heteroatoms and 3-8 carbon atoms in which the heteroatom is oxygen and/or nitrogen", more preferably "a heterocycloalkyl with 1-4 (for example 1 or 2) heteroatoms and 3-6 carbon atoms in which the heteroatom is oxygen and/or nitrogen", most preferably

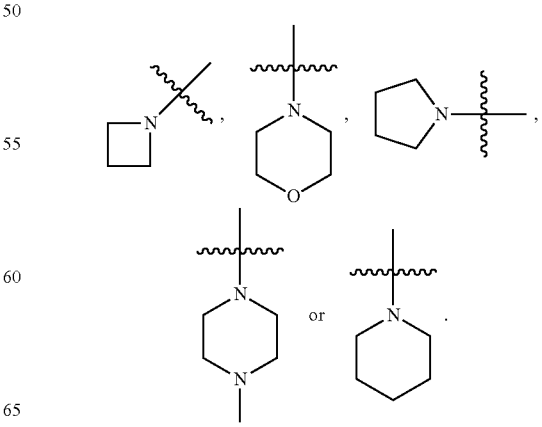

In the definitions of $R^7$, $R^8$, $R^9$, $R^{10}$ and $R^{15}$, the halogen is preferably fluorine; the alkyl in "substituted or unsubstituted alkyl" is preferably a $C_{1-10}$ alkyl, more preferably a $C_{1-4}$ alkyl, most preferably a methyl, a trideuteromethyl, an ethyl, a propyl or an isopropyl; the alkoxy is preferably a $C_{1-10}$ alkoxy, more preferably a $C_{1-4}$ alkoxy, most preferably a methoxy; the heterocycloalkyl may be linked to other groups via a carbon atom or a heteroatom thereof; the heterocycloalkyl is preferably "a heterocycloalkyl with 1-4 heteroatoms and 3-8 carbon atoms in which the heteroatom is oxygen and/or nitrogen", more preferably "a heterocycloalkyl with 1-4 (for example 1 or 2) heteroatoms and 3-6 carbon atoms in which the heteroatom is oxygen and/or nitrogen", most preferably

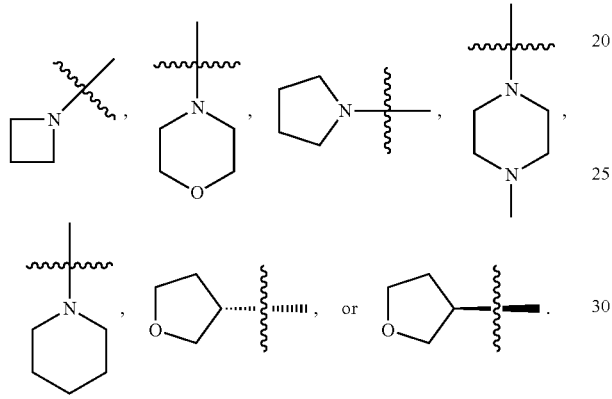

In the definition of $R^4$, the alkyl in "substituted or unsubstituted alkyl" is preferably a $C_{1-4}$ alkyl, more preferably a methyl, an ethyl, a propyl or an isopropyl; the alkoxy is preferably a $C_{1-4}$ alkoxy; the heterocycloalkyl in "substituted or unsubstituted heterocycloalkyl" may be linked to other groups via a carbon atom or a heteroatom thereof; the heterocycloalkyl in "substituted or unsubstituted heterocycloalkyl" is preferably "a heterocycloalkyl with 1-4 heteroatoms and 3-8 carbon atoms in which the heteroatom is oxygen and/or nitrogen", more preferably "a heterocycloalkyl with 1-2 heteroatoms and 3-6 carbon atoms in which the heteroatom is oxygen or nitrogen", such as

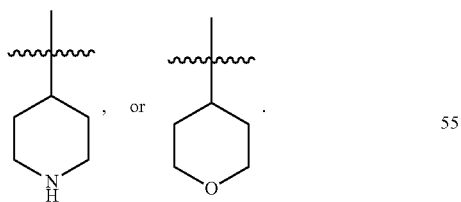

In the definition of $R^5$, the halogen is preferably fluorine; the alkyl is preferably a $C_{1-4}$ alkyl, more preferably a methyl.

The "5- to 7-membered carbon heterocycle" in "substituted or unsubstituted 5- to 7-membered carbon heterocycle" is preferably "a 5- to 7-membered carbon heterocycle with 1-4 heteroatoms and 2-6 carbon atoms in which the heteroatom is oxygen and/or nitrogen", more preferably

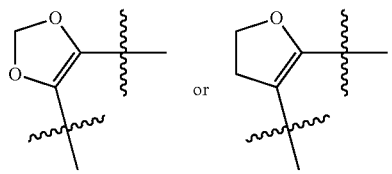

The compound I is preferably of a structure shown as formula I-1 or I-2,

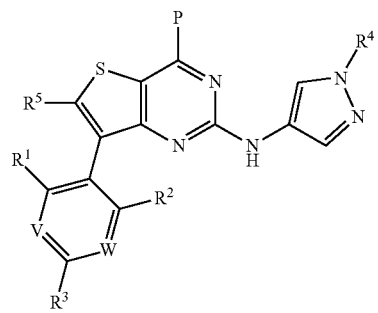

I-1

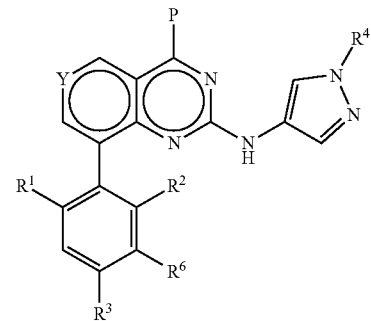

I-2 wherein, each of $R^1$, $R^2$, $R^3$, $R^4$, $R^5$, $R^6$, Y, V, W and P is independently defined as above.

The compound I-1 is preferably of a structure shown as I-1-1 or I-1-2,

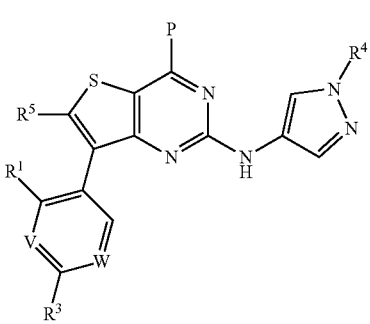

I-1-1

-continued

I-1-2

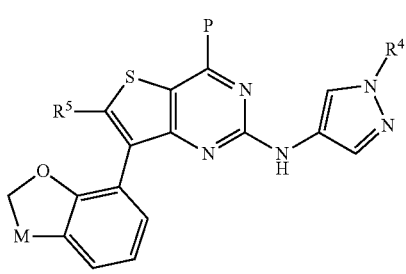

wherein, M is CH$_2$ or O; each of R$^1$, R$^3$, R$^4$, R$^5$, P, V, and W is independently defined as above.

The compound I-2 is preferably of a structure shown as I-2-1 or I-2-2,

I-2-1

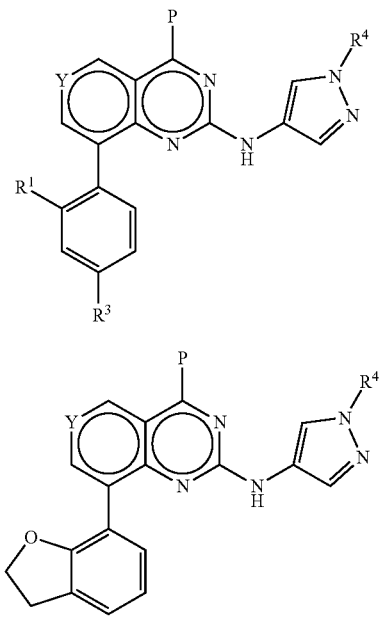

I-2-2 wherein, each of R$^1$, R$^3$, R$^4$, Y and P is independently defined as above.

In the definition of compound I, Y is preferably CR$^5$.

In the definition of compound I, R$^5$ is preferably a hydrogen or an alkyl.

In the definition of compound I, W is preferably CR$^6$.

In the definition of compound I, R$^6$ is preferably a hydrogen.

In the definition of compound I, preferably, R$^6$ and R$^2$ together with two atoms on the ring to which they are attached form "a substituted or unsubstituted 5- to 7-membered carbon heterocycle".

In the definition of compound I, preferably, R$^1$ and R$^2$ are independently a hydrogen or

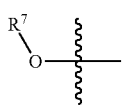

In the definition of compound I, preferably, R$^1$ or R$^2$ is a hydrogen.

In the definition of compound I, R$^3$ is preferably a hydrogen,

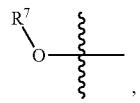

a halogen, or

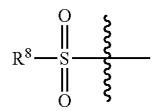

In the definition of compound I, R$^4$ is preferably "a substituted or unsubstituted alkyl", or "a substituted or unsubstituted heterocycloalkyl".

For the target of JAK1, each of the substituents mentioned above is preferably as follows:

In the definition of compound I, Y is preferably CR$^5$.

In the definition of compound I, R$^5$ is preferably a hydrogen or an alkyl.

In the definition of compound I, W is preferably CR$^6$.

In the definition of compound I, R$^6$ is preferably a hydrogen.

In the definition of compound I, preferably, R$^6$ and R$^2$ together with two atoms on the ring to which they are attached form "a substituted or unsubstituted 5- to 7-membered carbon heterocycle".

In the definition of compound I, preferably, each of R$^1$ and R$^2$ is independently a hydrogen or

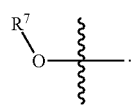

In the definition of compound I, preferably, R$^1$ or R$^2$ is a hydrogen.

In the definition of compound I, R$^3$ is preferably a hydrogen,

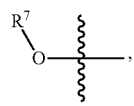

a halogen, or

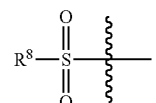

In the definition of compound I, R$^4$ is preferably "a substituted or unsubstituted alkyl", or "a substituted or unsubstituted heterocycloalkyl".

For the target of JAK2, each of the substituents mentioned above is preferably as follows:

In the definition of compound I, X is preferably S.
In the definition of compound I, Y is preferably CR⁵.
In the definition of compound I, R⁵ is preferably an alkyl.
In the definition of compound I, U is preferably a chemical bond.
In the definition of compound I, W is preferably CR⁶.
In the definition of compound I, R⁶ is preferably a hydrogen.
In the definition of compound I, preferably, R⁶ and R² together with two atoms on the ring to which they are attached form "a substituted or unsubstituted 5- to 7-membered carbon heterocycle".
In the definition of compound I, preferably, each of R¹ and R² is independently a hydrogen or

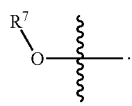

In the definition of compound I, preferably, R¹ or R² is a hydrogen.
In the definition of compound I, R³ is preferably a hydrogen,

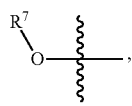

a halogen, or

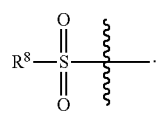

In the definition of compound I, R⁴ is preferably "a substituted or unsubstituted alkyl", or "a substituted or unsubstituted heterocycloalkyl".

For the target of JAK3, each of the substituents mentioned above is preferably as follows:
In the definition of compound I, X is preferably S.
In the definition of compound I, Y is preferably CR⁵.
In the definition of compound I, R⁵ is preferably an alkyl.
In the definition of compound I, W is preferably CR⁶.
In the definition of compound I, R⁶ is preferably a hydrogen.
In the definition of compound I, preferably, R⁶ and R² together with two atoms on the ring to which they are attached form "a substituted or unsubstituted 5- to 7-membered carbon heterocycle".
In the definition of compound I, preferably, each of R¹ and R² is independently a hydrogen or

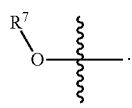

In the definition of compound I, preferably, R¹ or R² is a hydrogen.

In the definition of compound I, R³ is preferably a hydrogen or

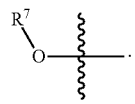

In the definition of compound I, R⁴ is preferably "a substituted or unsubstituted alkyl", or "a substituted or unsubstituted heterocycloalkyl". Preferably, the compound I of the present invention is selected from the group consisting of

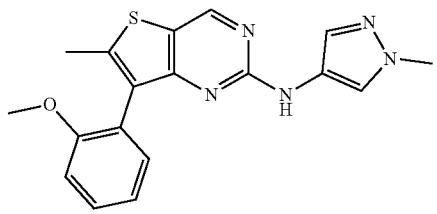

1

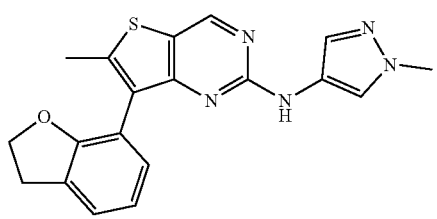

2

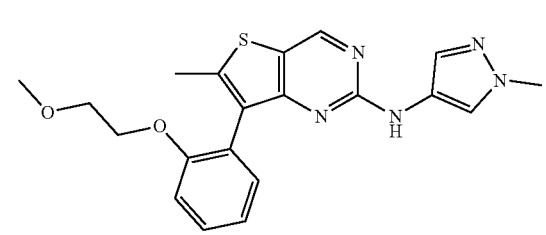

3

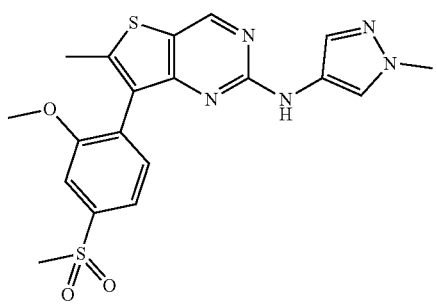

4

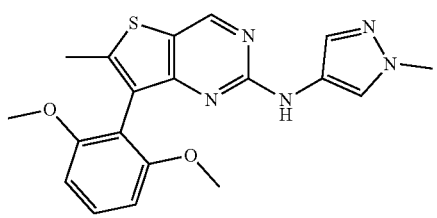

5

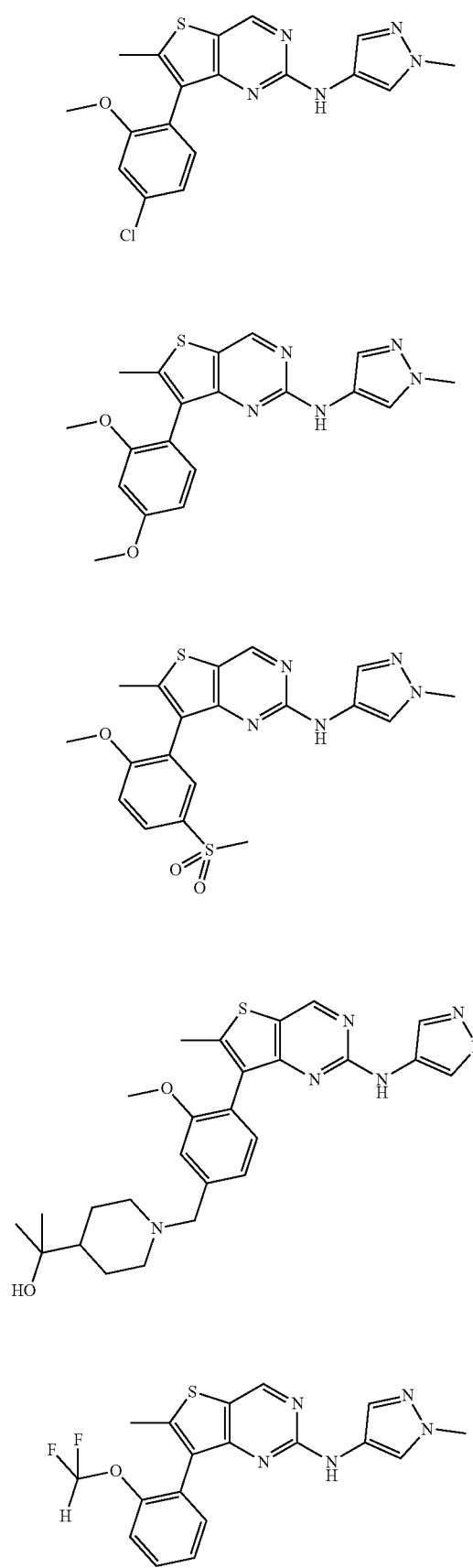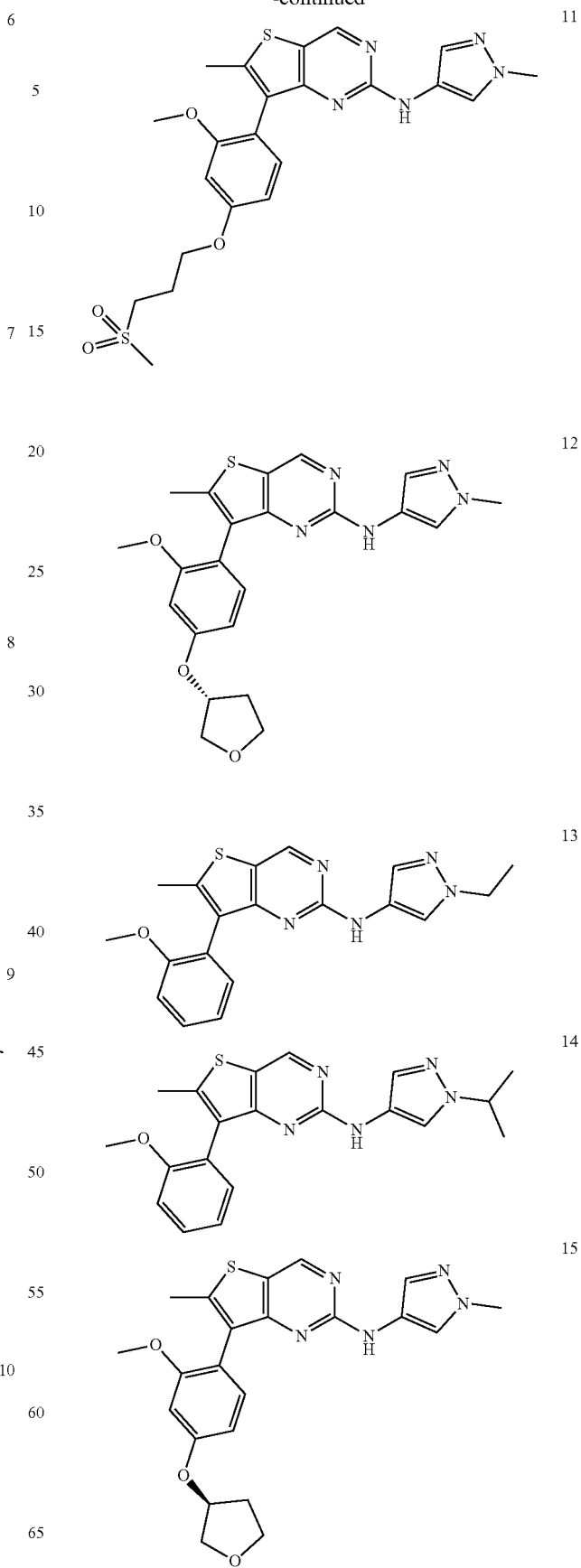

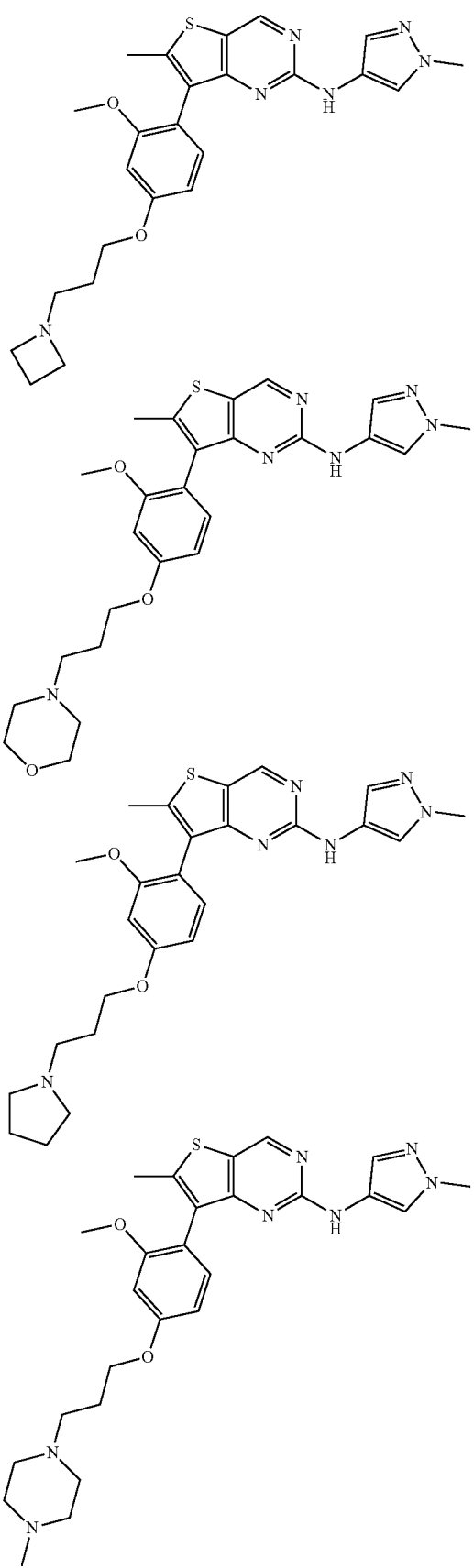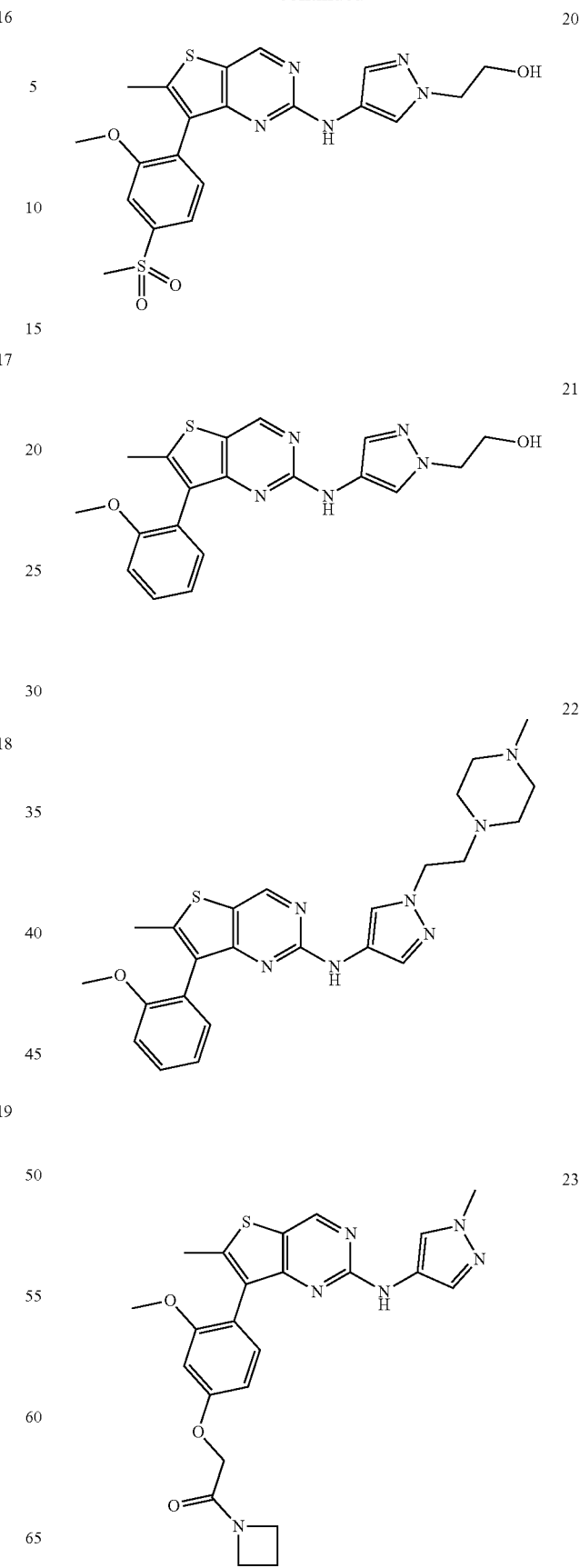

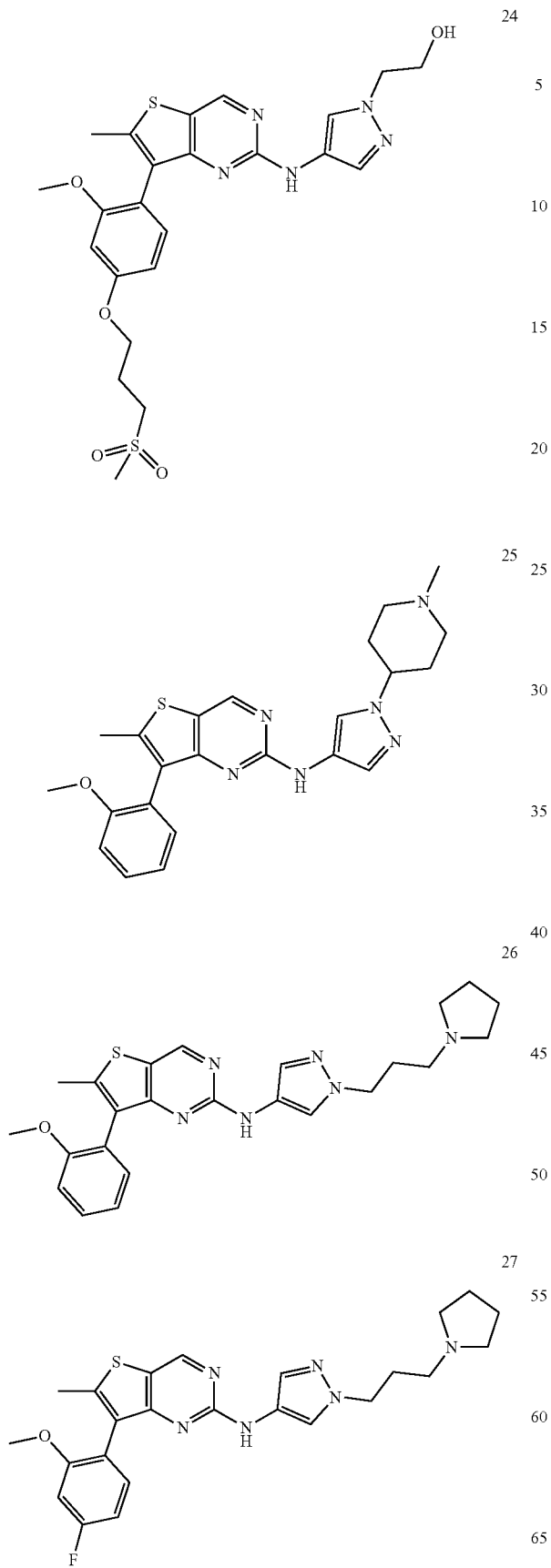
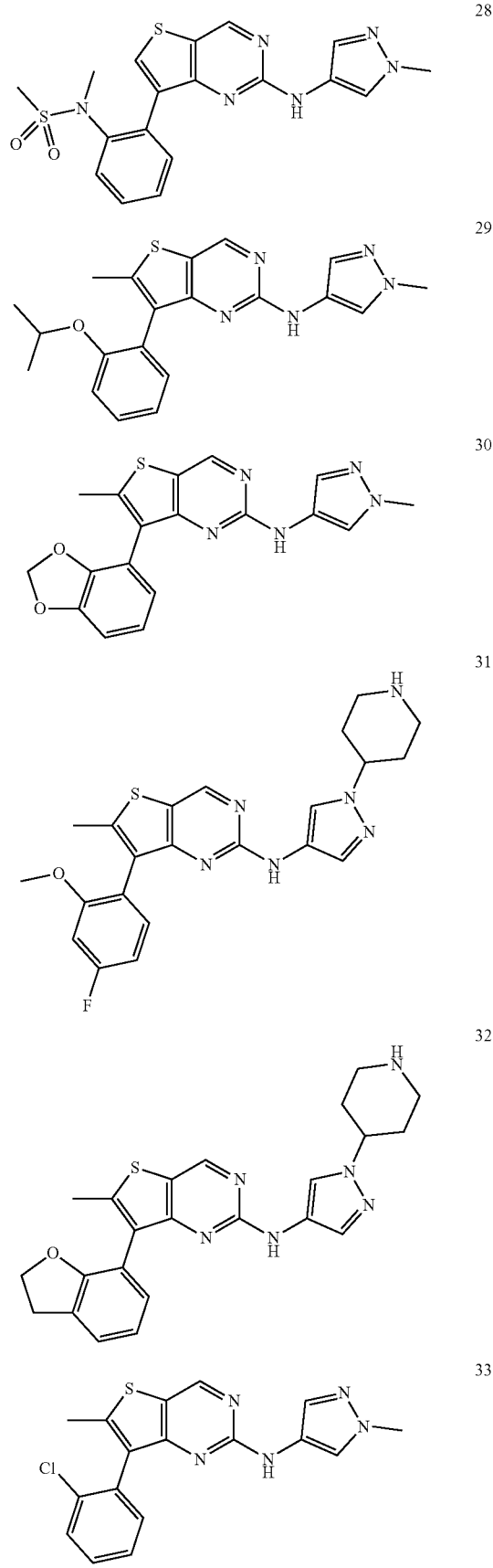

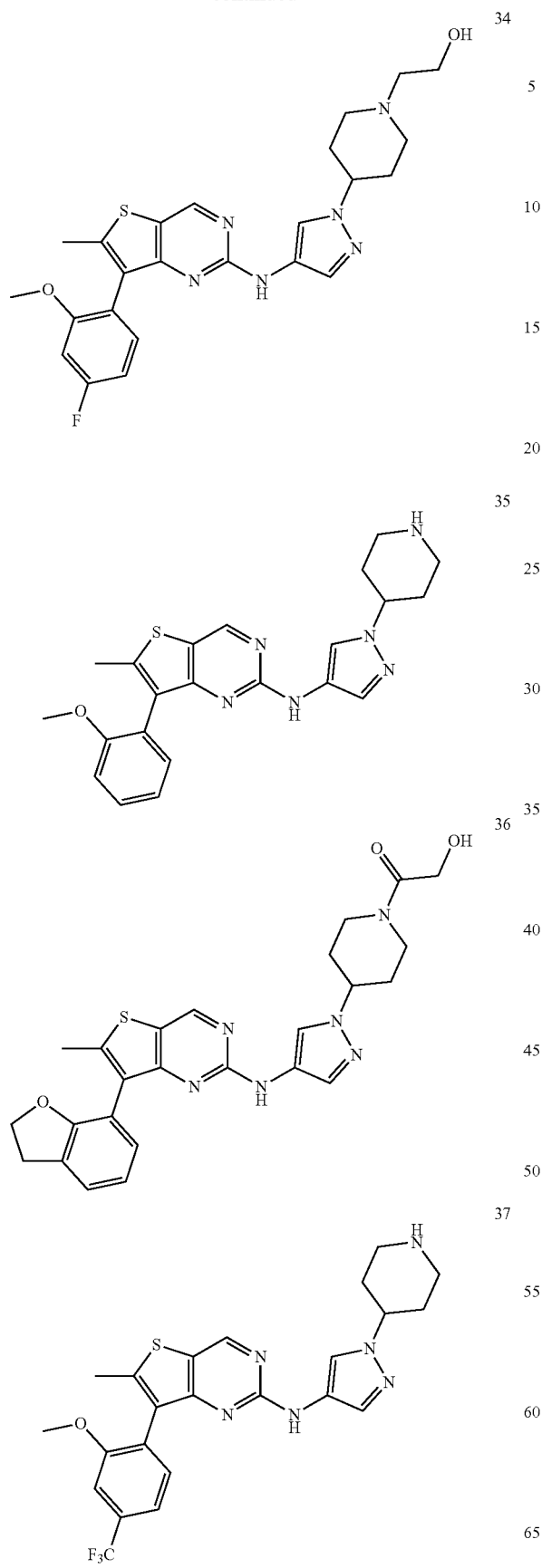
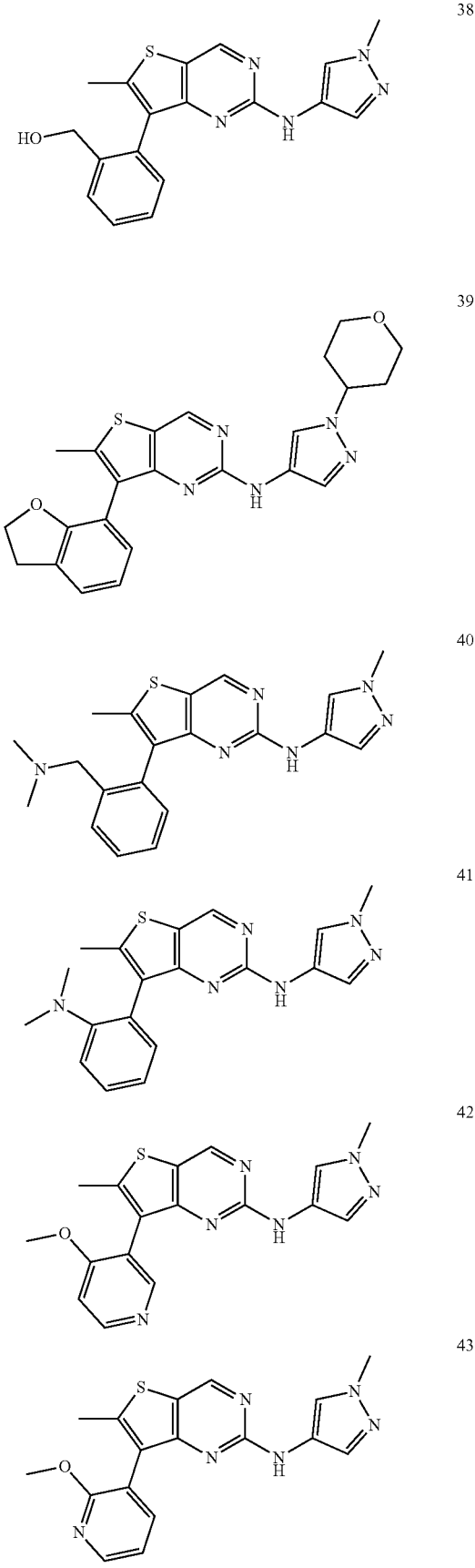

44
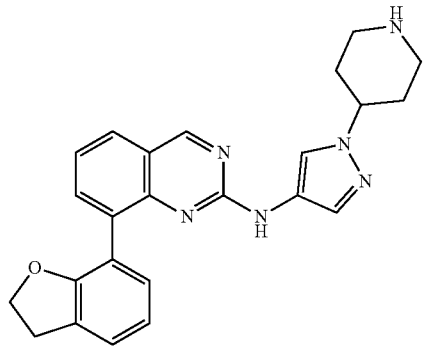
45
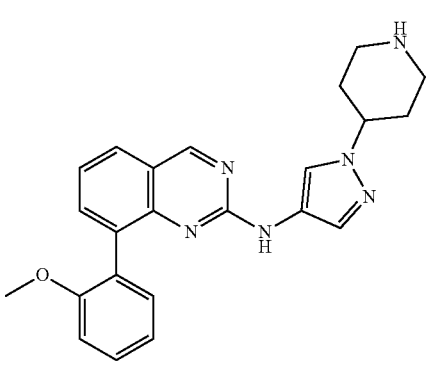
46
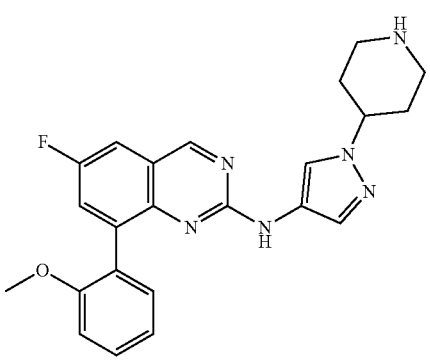
47
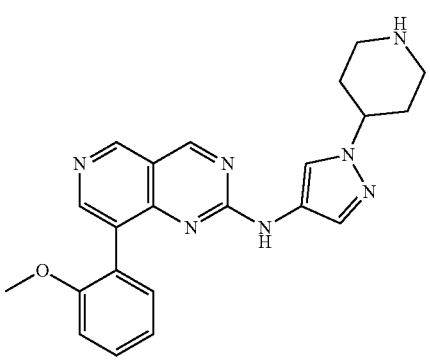
48
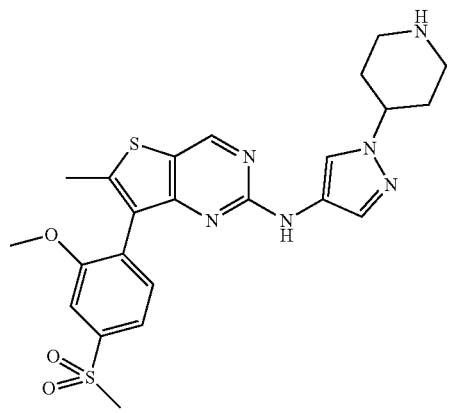
49
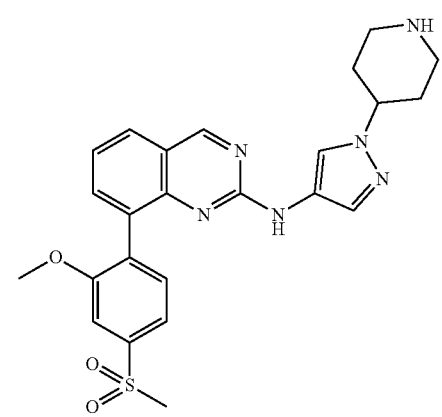
50
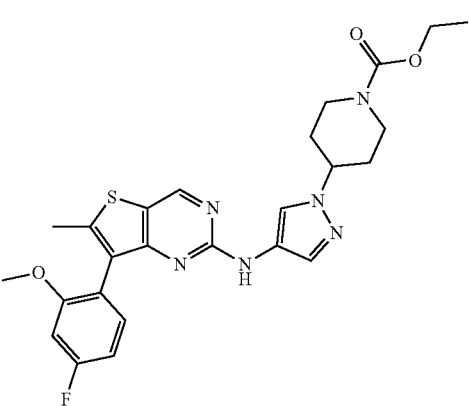
and
51
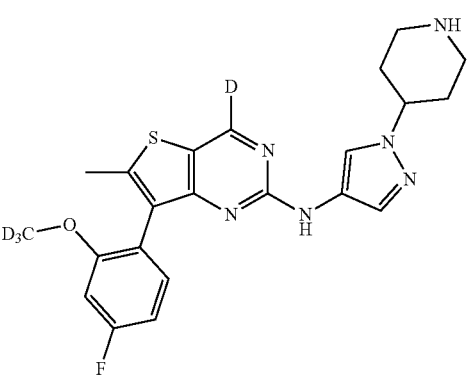
The compound I of the present invention may exhibit tautomerism, structural isomerism and stereoisomerism. The present invention includes any tautomeric or structural or stereoisomeric forms thereof and mixtures thereof that have the ability to modulate kinase activity and this ability is not limited to any one of the isomeric forms or mixtures thereof; the kinases are preferably JAK, FGFR kinase, FLT3 kinase and Src family kinase.

In the present invention, the isotopes of the atoms contained in the fused ring pyrimidine compound of formula I, the tautomer, the enantiomer, the diastereoisomer, the pharmaceutically acceptable salt, the metabolite, the metabolic precursor or the prodrug thereof usually present according to the distribution of each isotopic abundance in nature. The isotopic abundance, also known as the relative isotopic abundance, refers to relative contents (in atomic percent) of various isotopes of an element existing in nature, for example, the isotopic abundance of hydrogen atom: $^1H=99.985\%$, $D=0.015\%$; the isotopic abundance of oxygen atom: $^{16}O=99.76\%$, $^{17}O=0.04\%$, $^{18}O=0.20\%$.

In the present invention, one or more than one isotopes of the atoms contained in the fused ring pyrimidine compound of formula I, the tautomer, the enantiomer, the diastereoisomer, the pharmaceutically acceptable salt, the metabolite, the metabolic precursor or the prodrug thereof may be arbitrarily replaced, for example, $^1H$ is replaced by D, and the isotope-replaced compound can be prepared by reference to the preparation method of the pre-replacement compound and has the same biological activity as the pre-replacement compound. In the present invention, the isotopes may be those existing in nature or those artificially produced.

The present invention also provides a process for preparing the compound of formula I, which is any one of processes 1-13, process 1 comprising the steps of carrying out a substitution reaction with compound 1-a and a methylation reagent in an organic solvent (preferably acetone) and in the presence of a base (preferably potassium carbonate) to give the compound of formula I; the conditions for the substitution reaction may be conventional conditions for this type of reaction in the art;

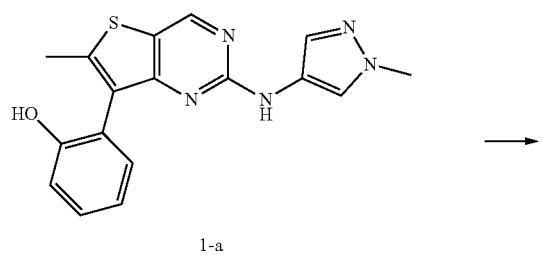

process 2 comprising the steps of carrying out a substitution reaction with compound II and compound VI in an organic solvent (preferably n-butanol and/or N, N-dimethylformamide) and in the presence of a catalyst (preferably selected from the group consisting of p-toluenesulfonic acid, p-toluenesulfonic acid monohydrate and tris(dibenzylidene-indan-acetone)dipalladium)) to give the compound of formula I; the conditions for the substitution reaction may be conventionally used in the art; when the catalyst is tris (dibenzylidene-indanacetone)dipalladium, preferably, the reaction further includes a base (preferably potassium carbonate) and a ligand (preferably 2-dicyclohexylphosphino-2',6'-diisopropoxy-1,1'-biphenyl), and is carried out under inert gas atmosphere;

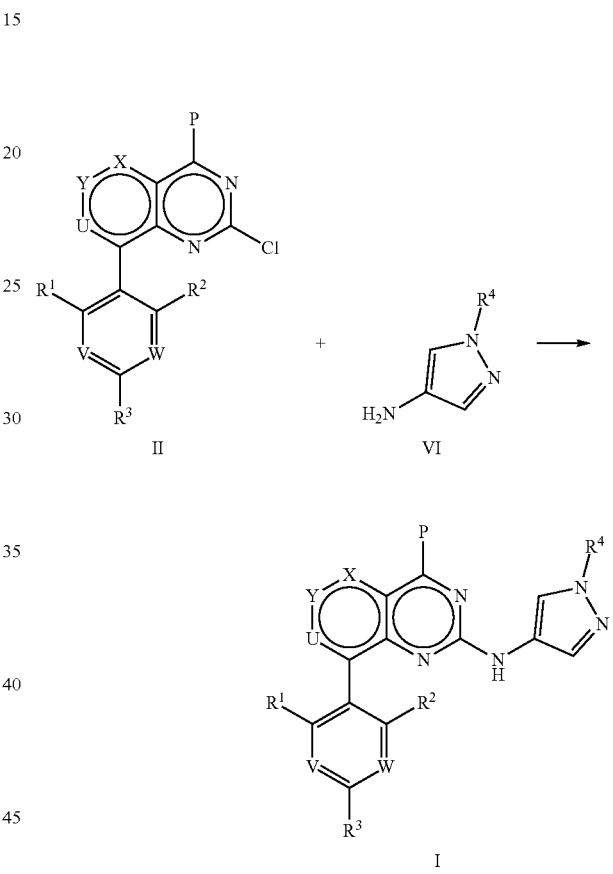

process 3 comprising the steps of under inert gas atmosphere, carrying out a coupling reaction with compound III and compound VII in an organic solvent (preferably selected from the group consisting of 1,4-dioxane, toluene and N, N-dimethylformamide) and in the presence of a base (preferably selected from the group consisting of sodium carbonate, potassium phosphate and potassium carbonate) and a palladium catalyst (preferably selected from the group consisting of [1,1'-bis (diphenylphosphino)ferrocene]dichloropalladium.dichloromethane, palladium acetate, [1,1'-bis(diphenylphosphino)ferrocene]dichloropalladium and tetrakis(triphenylphosphine)palladium) to give the compound of formula I; wherein, A is Br or I; the conditions for the coupling reaction may be conventionally used in the art; when the organic solvent is 1,4-dioxane, preferably, the reaction system may further comprise water; when the palladium catalyst is palladium acetate, preferably, the reaction system may further comprise 2-dicyclohexylphosphine-2,4,6-triisopropylbiphenyl;

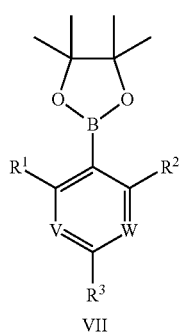

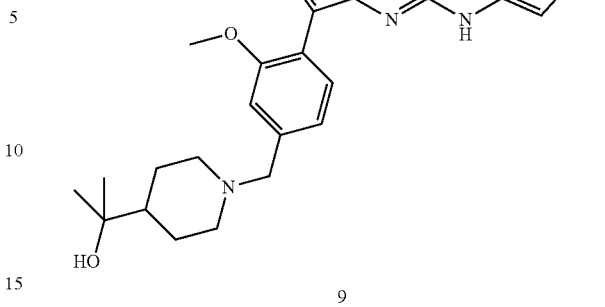

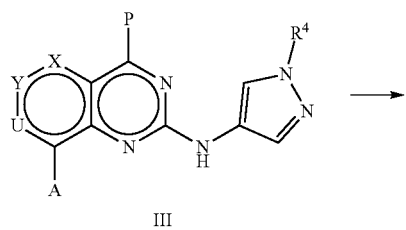

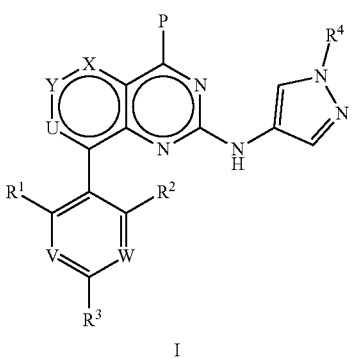

process 4 comprising the steps of carrying out a substitution reaction with compound 9-a and 2-(4-piperidyl)-2-propanol in an organic solvent (preferably dichloromethane) and in the presence of a base (preferably diisopropylethylamine) to give compound 9; the conditions for the substitution reaction may be conventionally used in the art;

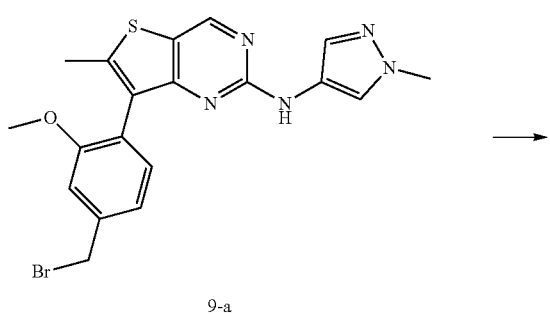

process 5 comprising the steps of carrying out a substitution reaction with compound 17-a and morpholine in an organic solvent (preferably acetonitrile) and in the presence of a base (preferably potassium carbonate) to give compound 17; the conditions for the substitution reaction may be conventionally used in the art;

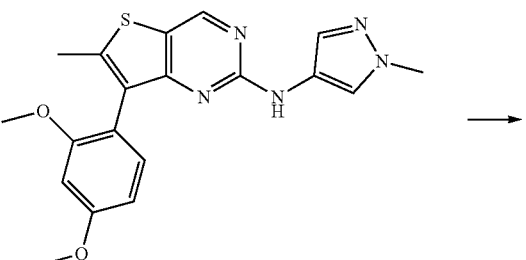

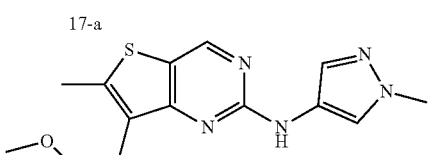

process 6 comprising the steps of carrying out a substitution reaction with compound 17-a and pyrrolidine in an organic solvent (preferably acetonitrile) and in the presence of a base (preferably potassium carbonate) to give compound 18; the conditions for the substitution reaction may be conventionally used in the art;

27

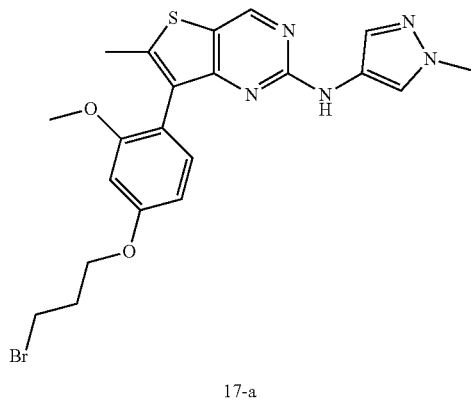

17-a

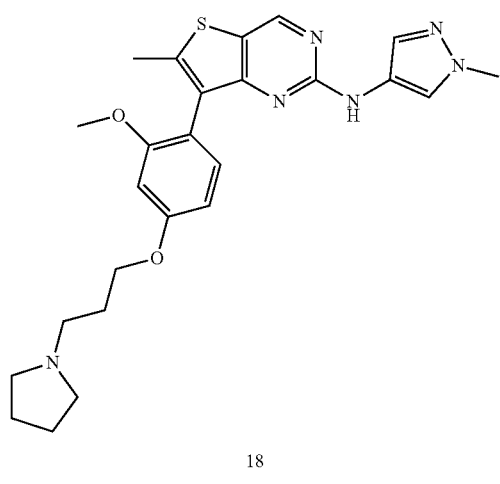

18 process 7 comprising the steps of carrying out a substitution reaction with compound 17-a and N-methylpiperazine in an organic solvent (preferably acetonitrile) and in the presence of a base (preferably potassium carbonate) to give compound 19; the conditions for the substitution reaction may be conventionally used in the art;

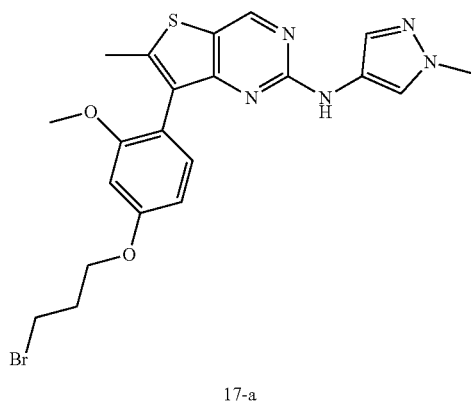

17-a

28

-continued

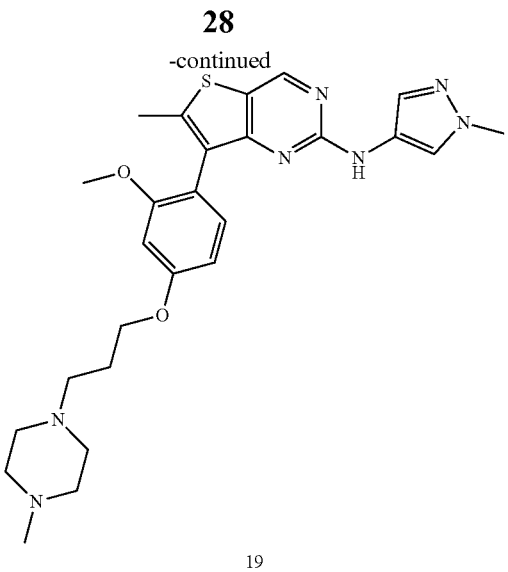

19 process 8 comprising the steps of carrying out a condensation reaction with compound 23-b and azetidine in an organic solvent (preferably dichloromethane) and in the presence of a base (preferably N,N-diisopropylethylamine), N-hydroxybenzotriazole and 1-ethyl-(3-dimethylaminopropyl)carbodiimide hydrochloride to give compound 23; the conditions for the condensation reaction may be conventionally used in the art;

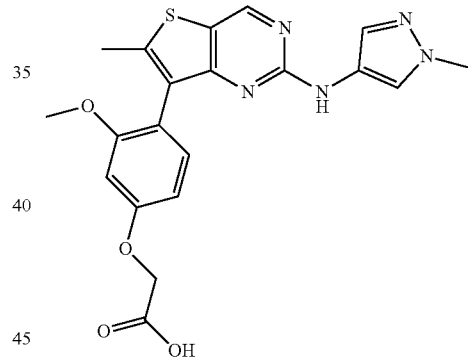

23-a process 9 comprising the steps of deprotecting compound IV in an organic solvent (preferably dichloromethane) and in the presence of an acid (preferably trifluoroacetic acid) to give compound I; wherein $R^4$ is

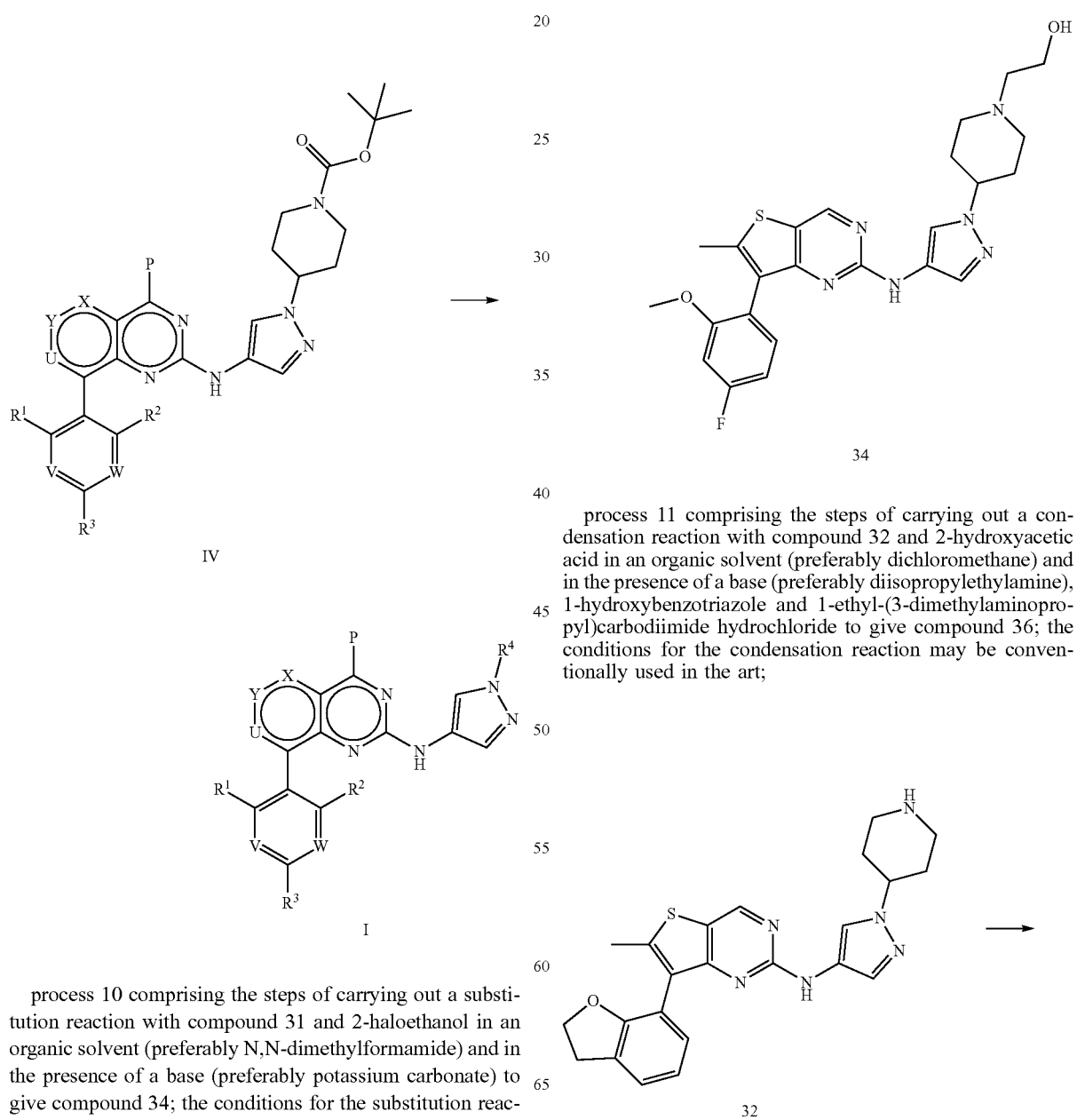

the conditions for the deprotection reaction may be conventionally used in the art;

process 10 comprising the steps of carrying out a substitution reaction with compound 31 and 2-haloethanol in an organic solvent (preferably N,N-dimethylformamide) and in the presence of a base (preferably potassium carbonate) to give compound 34; the conditions for the substitution reaction may be conventionally used in the art;

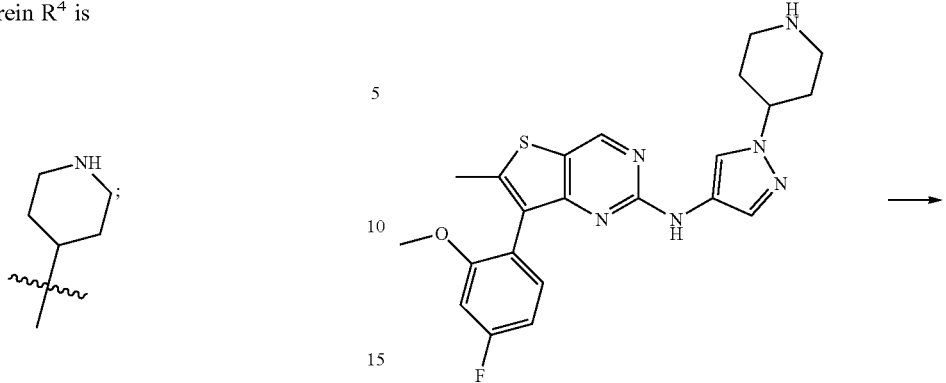

process 11 comprising the steps of carrying out a condensation reaction with compound 32 and 2-hydroxyacetic acid in an organic solvent (preferably dichloromethane) and in the presence of a base (preferably diisopropylethylamine), 1-hydroxybenzotriazole and 1-ethyl-(3-dimethylaminopropyl)carbodiimide hydrochloride to give compound 36; the conditions for the condensation reaction may be conventionally used in the art;

-continued

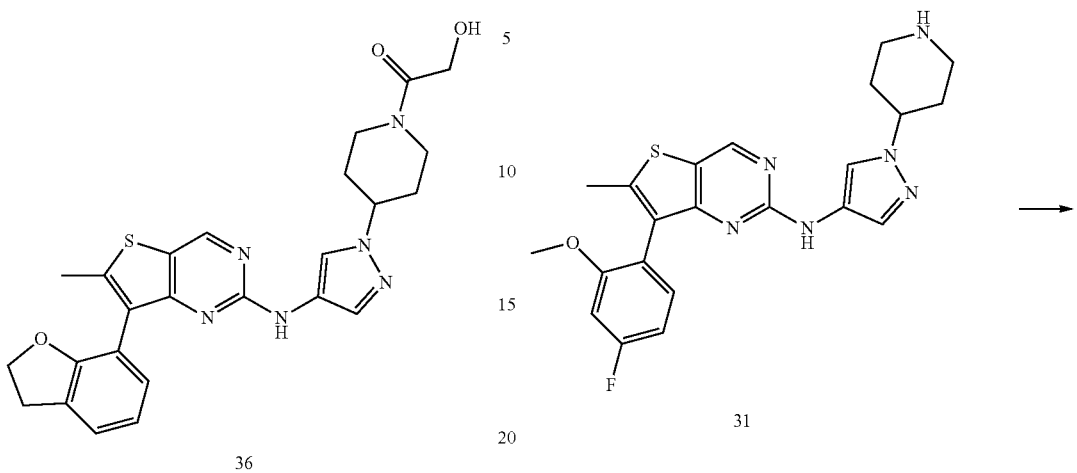

36

31 process 12 comprising the steps of carrying out a reductive amination reaction with compound 40-a, dimethylamine and sodium triacetoxyborohydride in an organic solvent (preferably dichloromethane) and in the presence of an acid (preferably acetic acid) to give compound 40; the conditions for the reductive amination reaction may be conventionally used in the art;

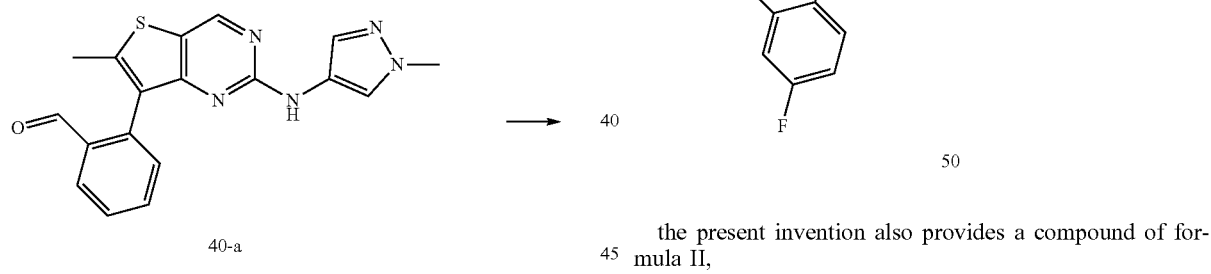

40-a

40 process 13 comprising the steps of carrying out a condensation reaction with compound 31 and ethyl chloroformate in an organic solvent (preferably dichloromethane) and in the presence of a base (preferably triethylamine) to give compound 50; the conditions for the condensation reaction may be conventionally used in the art;

50 the present invention also provides a compound of formula II,

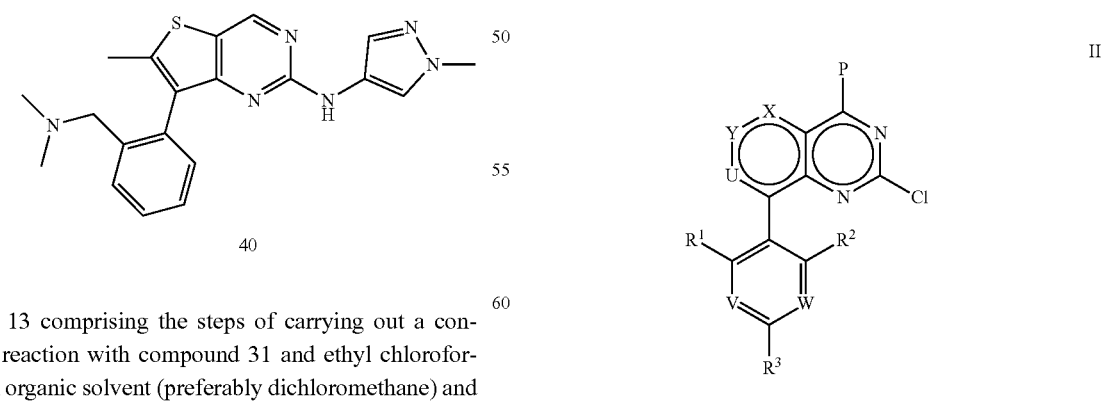

II wherein, each of $R^1$, $R^2$, $R^3$, X, Y, U, P, V and W is as defined above. Preferably, the compound of formula II is selected from the group consisting of

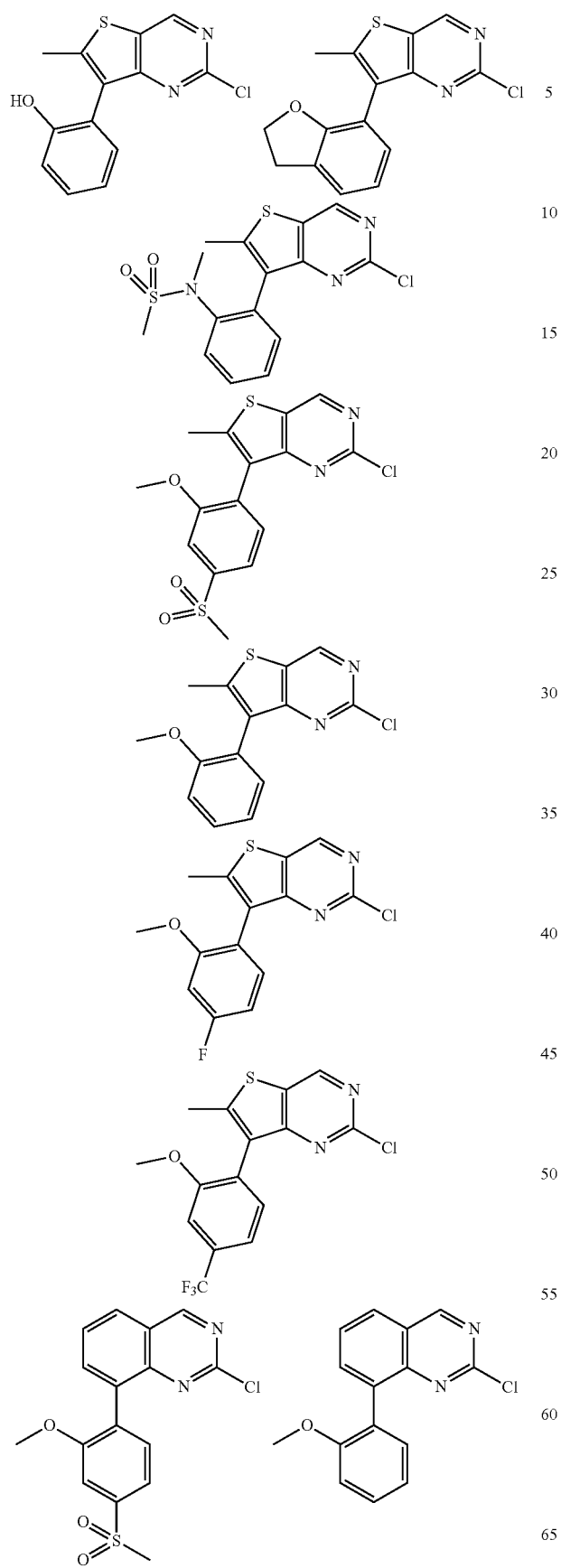
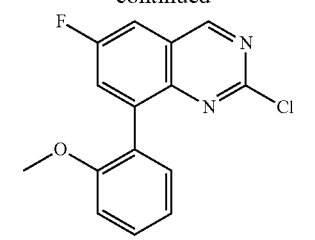
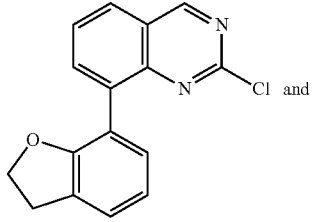
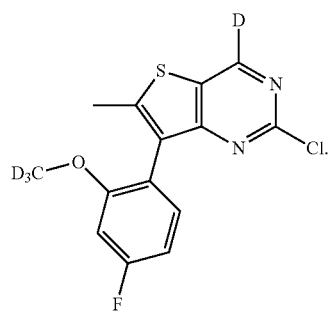
The present invention also provides a compound of formula III,
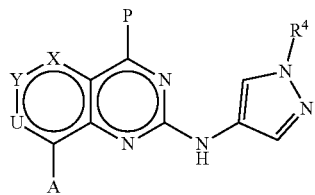
wherein, A is Br or I; each of $R^4$, X, Y, U and P is as defined above. Preferably, the compound of formula III is selected from the group consisting of
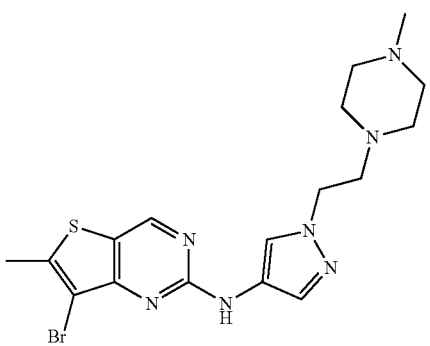

-continued
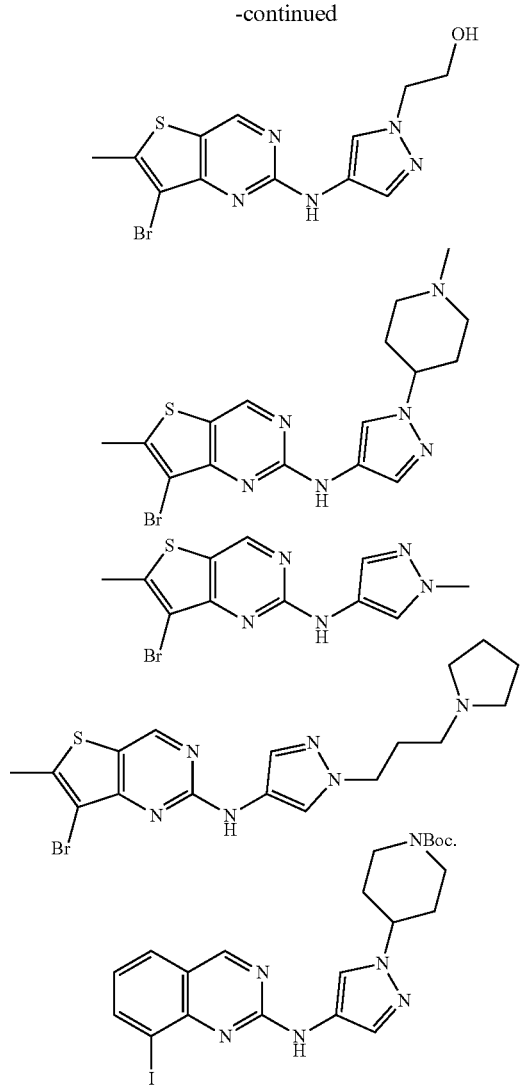
The present invention also provides a compound of formula IV,
wherein, each of $R^1$, $R^2$, $R^3$, X, Y, U, V, W and P is as defined above. Preferably, the compound of formula IV is selected from the group consisting of
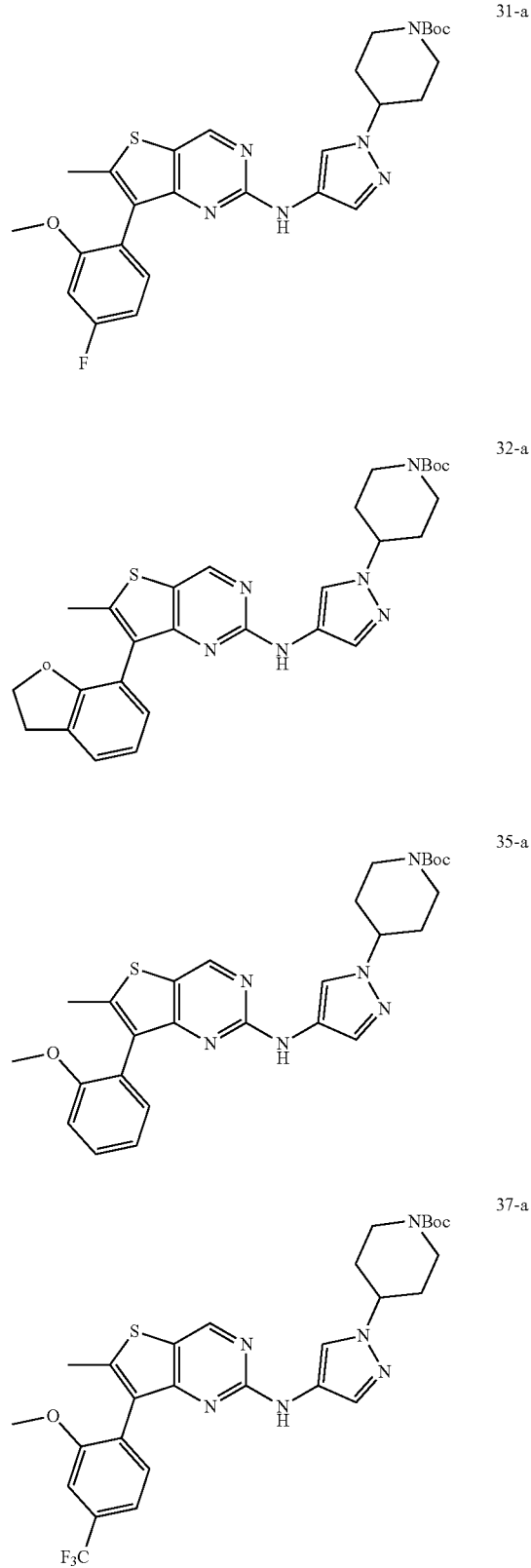

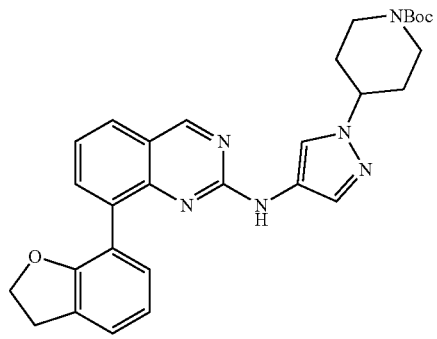
44-a
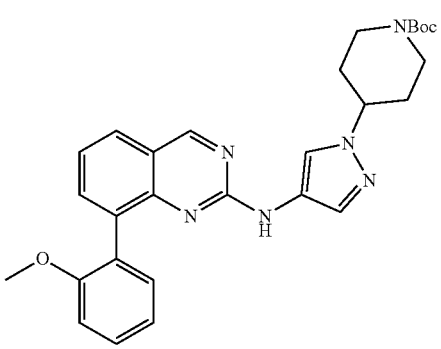
45-a
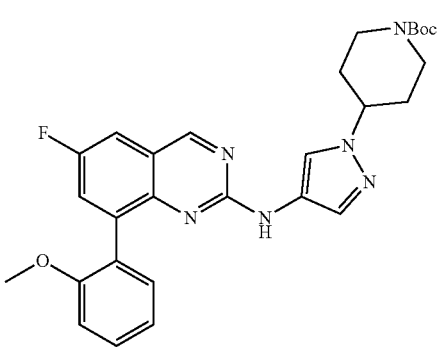
46-a
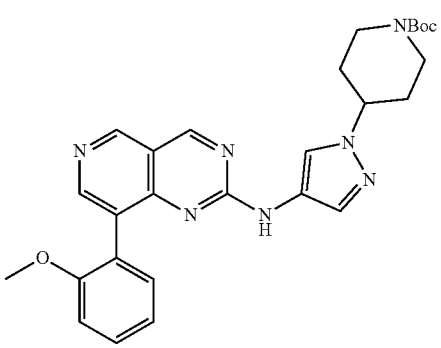
47-a
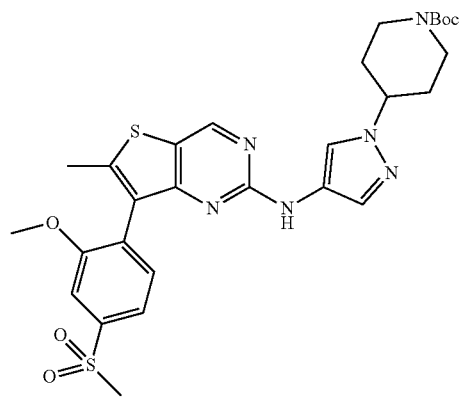
48-a
and
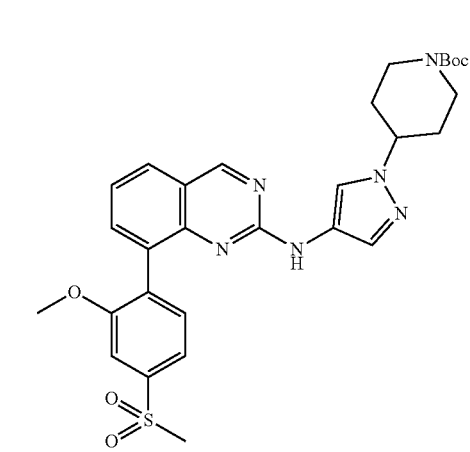
49-a
The present invention also provides a compound V, which is selected from the group consisting of
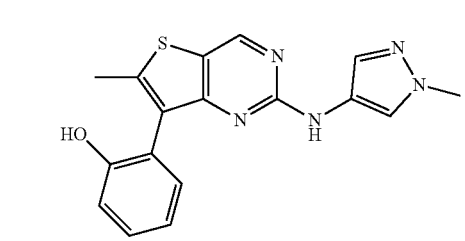
1-a
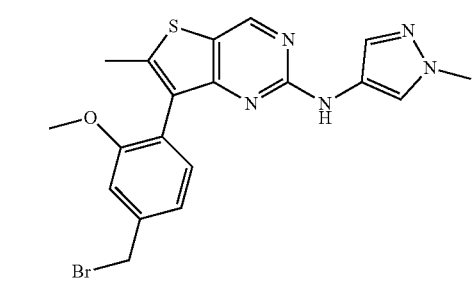
9-a

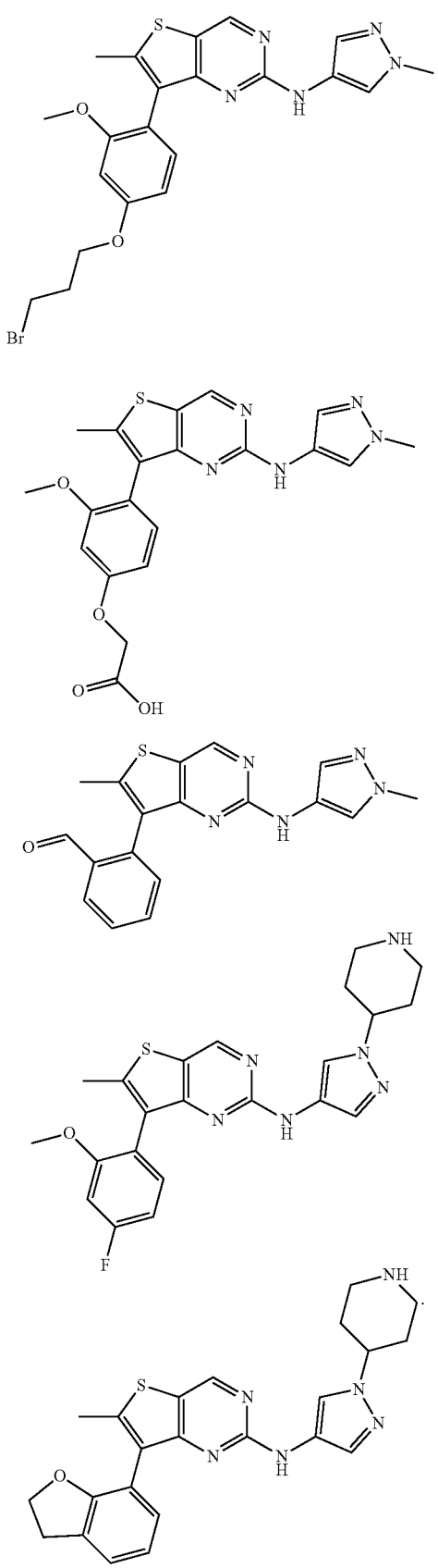

The present invention: and further relates to a use of the fused ring pyrimidine compound, the tautomer, the enantiomer, the diastereoisomer, the pharmaceutically acceptable salt, the metabolite, the metabolic precursor or the prodrug thereof in manufacturing drugs, which are used for prevention, alleviation or treatment of a disease selected from the group consisting of immune system disease, autoimmune disease, cell proliferative disease, allergic disorder and cardiovascular disease; one example of the immune system disease is organ transplant rejection; examples of the autoimmune disease are rheumatoid arthritis, psoriasis, Crohn's disease, multiple sclerosis and the like; examples of the cell proliferative disease are myelofibrosis, hematological tumor (such as leukemia, lymphoma etc.) and solid tumor (such as renal cancer, liver cancer, stomach cancer, lung cancer, breast cancer, prostate cancer, pancreatic cancer, thyroid cancer, ovarian cancer, glioblastoma, skin cancer and melanoma etc.); one example of the allergic disorder is bronchial asthma; examples of the cardiovascular disease are ischemic cardiomyopathy, heart failure, myocardial infarction and the like.

The present invention further relates to a use of the fused ring pyrimidine compound, the tautomer, the enantiomer, the diastereoisomer, the pharmaceutically acceptable salt, the metabolite, the metabolic precursor or the prodrug thereof in manufacturing drugs, which are used for inhibiting Janus kinase, FGFR kinase, FLT3 kinase and Src family kinase; the Janus kinase is preferably selected from the group consisting of JAK1, JAK2 and JAK3; the FGFR kinase is preferably selected from the group consisting of FGFR1, FGFR2 and FGFR3; the FLT3 kinase is preferably selected from FLT3-WT, FLT3-ITD and FLT3-D835Y; the Src family kinase is preferably selected from c-Src, Lyn, Fyn, Lck, Hck, Fgr, Blk, Yes and Yrk; inhibiting Janus kinase, FGFR kinase, FLT3 kinase and/or Src family kinase can prevent, alleviate or treat the disease selected from the group consisting of immune system disease, autoimmune disease, cell proliferative disease, allergic disorder and cardiovascular disease; one example of the immune system disease is organ transplant rejection; examples of the autoimmune disease are rheumatoid arthritis, psoriasis, Crohn's disease, multiple sclerosis and the like; examples of the cell proliferative disease are myelofibrosis, hematological tumor (such as leukemia, lymphoma etc.) and solid tumor (such as renal cancer, liver cancer, stomach cancer, lung cancer, breast cancer, prostate cancer, pancreatic cancer, thyroid cancer, ovarian cancer, glioblastoma, skin cancer and melanoma); one example of the allergic disorder is bronchial asthma; examples of the cardiovascular disease are ischemic cardiomyopathy, heart failure, myocardial infarction and the like.

The present invention relates to a pharmaceutical composition, which comprises the fused ring pyrimidine compound, the tautomer, the enantiomer, the diastereoisomer, the pharmaceutically acceptable salt, the metabolite, the metabolic precursor or the prodrug thereof, and one or more than one pharmaceutically acceptable carrier(s) and/or diluent(s); preferably, the dose of the fused ring pyrimidine compound, the tautomer, the enantiomer, the diastereoisomer, the pharmaceutically acceptable salt, the metabolite, the metabolic precursor or the prodrug thereof is a therapeutically effective amount.

The pharmaceutical composition of the present invention may be in a form suitable for oral use or in the form of a sterile injectable aqueous solution. Oral or injectable compositions may be prepared according to any method known in the art for preparing pharmaceutical compositions.

The pharmaceutical composition of the present invention may be used in combination with one or more than one clinically used chemotherapeutic agents in any suitable ratio to produce a single dosage form, in particular a liposomal dosage form, according to conventional methods in the art, to treat various oncological diseases.

Unless otherwise indicated, the following terms when used in the description and the claims of the present invention have the following meanings:

The term "alkyl" (used alone or included in other groups) refers to branched and straight-chain saturated aliphatic hydrocarbon groups comprising 1 to 20 carbon atoms, preferably 1 to 10 carbon atoms, more preferably 1 to 8 carbon atoms, such as a methyl, an ethyl, a n-propyl, an isopropyl, a n-butyl, a t-butyl, an isobutyl, a pentyl, a hexyl, a heptyl, an octyl, a nonyl, a decyl, 4,4-dimethylpentyl, 2,2,4-trimethylpentyl, an undecyl, a dodecyl and various isomers thereof.

The term "alicyclic" or "cycloalkyl" (used alone or included in other groups) refers to saturated or partially unsaturated (containing 1 or 2 double bonds, but none of the rings has a completely conjugated π electron system) cyclic hydrocarbon groups comprising 1 to 3 rings, including monocycloalkyl, bicycloalkyl and tricycloalkyl groups, containing 3 to 20 carbons enabling to form a ring, preferably 3 to 10 carbons, for example, cyclopropyl, cyclobutyl, cyclopentyl, cyclohexyl, cycloheptyl, cyclooctyl, cyclodecane, cyclododecyl, cyclohexenyl and the like.

The term "heterocycloalkyl" (used alone or included in other groups) refers to 4-12 membered monocyclic or polycyclic groups containing 1-4 heteroatoms (such as selected from the group consisting of nitrogen, oxygen and sulfur), wherein each ring may contain one or more than one double bonds, but none of the rings has a completely conjugated π electron system. Heterocycloalkyl within the scope of this definition include, but is not limited to oxazoline, oxycyclobutyl, pyranyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuryl, dihydroimidazolyl, indolinyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl dihydrothiophenyl, dihydrotriazolyl, dihydroazetidinyl, tetrahydrofuryl and tetrahydrothiophenyl and N-oxides thereof. Heterocycloalkyl may be linked to other groups via carbon atoms or heteroatoms thereof. In addition, any heterocycloalkyl ring can be fused to a cycloalkyl, an aryl, a heteroaryl or a heterocycloalkyl ring to form a fused, a bridged, or a spiro ring.

The term "alkoxy" (used alone or included in other groups) refers to a cyclic or acyclic alkyl having indicated number of carbon atoms attached through an oxygen bridge. Thus, "alkoxy" embraces the definitions of alkyl and cycloalkyl.

The term "aryl" (used alone or included in other groups) refers to any stable monocyclic or bicyclic carbocyclic rings with up to 7 atoms in each ring, at least one of which is an aromatic ring. Examples of the aryl include phenyl, naphthyl, tetrahydronaphthyl, indanyl, biphenylyl, phenanthryl, anthryl or acenaphthyl. It is to be understood that where the aryl is bicyclic and one of the rings is a non-aromatic ring, the attachment is made through an aromatic ring.

The term "aryl hetero" or "heteroaryl" (used alone or included in other groups) refers to stable monocyclic or bicyclic rings with up to 7 atoms in each ring, at least one of which is an aromatic ring and contains 1-4 heteroatoms selected from O, N and S. The heteroaryl within the scope of the definition includes, but is not limited to acridinyl, carbazolyl, cinnolinyl, quinoxalinyl, pyrazolyl, indolyl, benzotriazolyl, furanyl, thienyl, benzothienyl, benzofuranyl, quinolinyl isoquinolyl, oxazolyl, isoxazolyl, indolyl, pyrazinyl, pyridazinyl, pyridinyl, pyrimidinyl, pyrrolyl, tetrahydroquinoline. As the definition of "heterocycloalkyl", "heteroaryl" should also be understood to include N-oxide derivatives of any nitrogen-containing heteroaryl. In the case where the heteroaryl is a bicyclic substituent and one ring is non-aromatic or contains no heteroatoms, it is understood that the attachment is made through the aromatic ring or through the heteroatom on the ring, respectively.

The term "halogen" refers to fluorine, chlorine, bromine, iodine or astatine.

The term "hydroxyl" refers to —OH.

The term "amino" refers to —NH$_2$.

The term "cyano" refers to —CN.

The term "sulfonyl" refers to

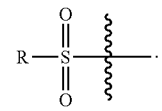

R— may include the definitions of the terms above.

The term "acyl" refers to

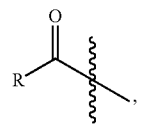

i.e. the remaining monovalent atomic group after removing the hydroxyl of an organic or inorganic oxo acid. R— may contain the definitions of the terms above.

The term "—BOC" refers to

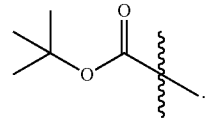 [SMILES: *C(=O)OC(C)(C)C]

In the present invention, "pharmaceutically acceptable salts" refer to conventional acid addition salts or base addition salts which retain the biological effectiveness and properties of compound A, which are formed from suitable non-toxic organic or inorganic acids, or organic or inorganic bases. Examples of acid addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, maleic acid, lactic acid, fumaric acid and the like. Examples of base addition salts include those derived from ammonium, potassium, sodium and quaternary ammonium hydroxides, such as tetramethyl ammonium hydroxide. Chemical modification of pharmaceutical compounds (i.e. drugs) into salts is well-known technique for pharmacists to obtain the compounds with improved physical and chemical stability, hygroscopicity, flowability and solubility.

In the present invention, "pharmaceutically acceptable" in "one or more than one pharmaceutically acceptable carrier(s) and/or diluent(s)" means to be pharmaceutically acceptable and substantially non-toxic to the administered subject for a particular compound.

The above preferred conditions of the present invention may be arbitrarily combined without departing from the general knowledge in the art to obtain the preferred examples of the present invention.

The reagents and raw materials used in the present invention are commercially available.

The advantages of the present invention lie in that this compound has a strong inhibitory effect on Janus kinase (JAK), FGFR kinase, FLT3 kinase and Src family kinase.

DETAILED DESCRIPTION OF THE INVENTION

The following examples further illustrate the present invention, but the present invention is not limited thereto. In the following examples, experimental methods for which specific conditions are not specified are selected according to conventional methods and conditions, or according to the product specification.

The structure of the compound was confirmed by nuclear magnetic resonance (NMR) or mass spectrometry (MS). The nuclear magnetic resonance spectrum was obtained by a Bruker Avance-500 instrument with deuterated dimethylsulfoxide, deuterated chloroform and deuterated methanol etc. as solvents and silane (TMS) as internal standard. Mass spectra was obtained using a Liquid Chromatography-Mass Spectrometry (LC-MS) instrument Agilent Technologies 6110 with ESI source.

The microwave reaction was carried out in the Explorer automatic microwave synthesizer manufactured by CEM Company of the United States. The magnetron frequency was 2450 MHz and the continuous microwave output power was 300 W.

The instrument used for high performance liquid preparation was Gilson 281 and the preparative column used was Shimadazu Shim-Pack, PRC-ODS, 20×250 mm, 15 μm.

Example 1

N-[7-(2-methoxyphenyl)-6-methylthieno[3,2-d]pyrimidinyl-2-yl]-1-methyl-1H-pyrazol-4-amine (Compound 1)

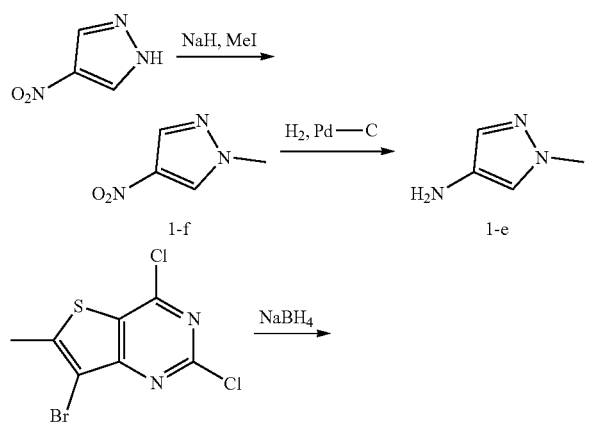

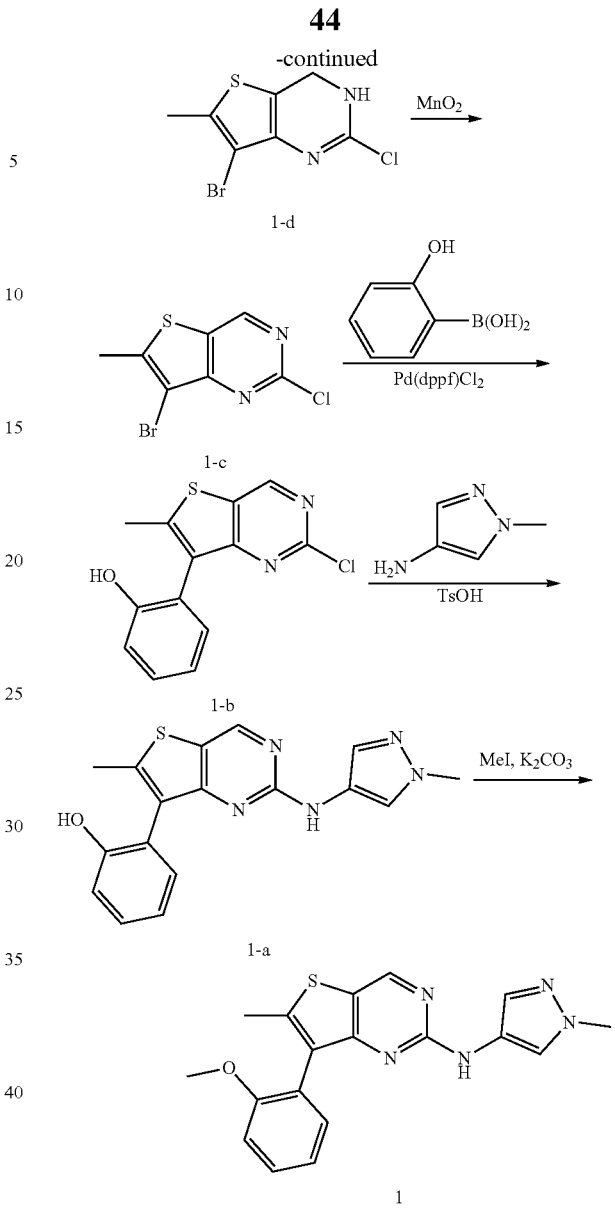

Synthesis of Compound 1-f

Sodium hydride (1.3 g, 32.1 mmol) was added to a solution of 4-nitropyrazole (3.3 g, 29.2 mmol) in dry tetrahydrofuran (30 mL) at 0° C. After stirring for 1 hour, methyl iodide (20 mL) was added and the mixture was stirred for another 2 hours at room temperature. The mixture was poured into ice water (100 mL) and extracted with ethyl acetate (50 mL×3). The organic phase was dried over anhydrous sodium sulfate, filtered and the filtrate was concentrated under reduced pressure. The residue was added to a mixed solvent (20 mL) of petroleum ether and ethyl acetate (20:1), and stirred, solid was precipitated out. The solid was filtered out and dried in vacuo for 8 hours to give 1-f as a white solid (2.6 g, yield 70%). The product was directly used in the next reaction without further purification. LC-MS (ESI): m/z=128[M+H]$^+$.

Synthesis of Compound 1-e

Palladium 10% on carbon (0.2 g) was added to a solution of compound 1-f (1.0 g, 7.87 mmol) in ethanol (15 mL) under hydrogen atmosphere (1 atm). The mixture was reacted at 25° C. for 18 hours, filtered and the filtrate was concentrated under reduced pressure. The residue was purified by silica gel column chromatography (petroleum ether:ethyl acetate=1:1) to give 1-e as a red oil (700 mg, yield 92%). The product was used without further purification.

Synthesis of Compound 1-d

7-Bromo-2,4-dichloro-6-methylthieno[3,2-d]pyrimidine (5.0 g, 16.89 mmol) was dissolved in tetrahydrofuran (50 mL) and ethanol (50 mL). The reaction solution was cooled to 0° C. and sodium borohydride (3.19 g, 84.5 mmol) was added in portions. The reaction solution was warmed to room temperature and further stirred for 3 hours, then added with water (500 mL) and extracted with dichloromethane (300 mL×3). The combined organic phases were dried over anhydrous sodium sulfate, filtered and the filtrate was concentrated under reduced pressure to give 1-d as a yellow liquid (4 g, yield 90%) which was used without further purification. LC-MS (ESI): m/z=265[M+H]+.

Synthesis of Compound 1-c

Compound 1-d (4.0 g, 15.15 mmol) was dissolved in dichloromethane (100 mL), activated manganese dioxide (6.6 g, 75.8 mmol) was added and the mixture was stirred at room temperature for 16 hours. The reaction solution was filtered through celite and the filter cake was washed with dichloromethane (50 mL×5). The combined filtrate was concentrated under reduced pressure to give 1-c as a yellow solid (3.8 g, yield 96%) which was used without further purification. LC-MS (ESI): m/z=263[M+H]+.

Synthesis of Compound 1-b

Compound 1-c (500 mg, 1.91 mmol), 2-hydroxybenzeneboronic acid (267 mg, 1.91 mmol) and sodium carbonate (619 mg, 5.73 mmol) were suspended in dioxane/water (5 mL/5 mL), and [1,1'-bis(diphenylphosphino)ferrocene]dichloro-palladium.dichloromethane (163 mg, 0.2 mmol) was added. The reaction solution was purged with nitrogen gas for three times and heated to 80° C. to react overnight. After removing the solvent by rotary evaporation, the mixture was partitioned with dichloromethane (150 mL) and water (150 mL). The organic phase was separated, dried over anhydrous sodium sulfate, filtered, concentrated and purified by silica gel column chromatography (methylene chloride:methanol=100:1) to give 1-b as a pale brown solid (610 mg). LC-MS (ESI): m/z=277[M+H]+.

Synthesis of Compound 1-a

Compound 1-b (610 mg, 2.21 mmol) and 1-methyl-4-aminopyrazole (643 mg, 6.63 mmol) were dissolved in n-butanol (15 mL) and p-toluenesulfonic acid monohydrate (1.3 g, 6.63 mmol) was added. The mixture was heated to 110° C. to react overnight, then concentrated to remove the solvent, and partitioned between dichloromethane (150 mL) and saturated sodium carbonate (150 mL). The organic phase was separated and dried, filtered, concentrated and purified by silica gel column chromatography (dichloromethane:methanol=50:1) to give 1-a as a yellow solid (250 mg, yield 39%). LC-MS (ESI): m/z=338[M+H]+.

¹H-NMR (400 MHz, CDCl₃) δ: 8.78 (s, 1H), 8.20 (br, 1H), 7.77 (s, 1H), 7.42 (s, 1H), 7.39 (t, J=8 Hz, 1H), 7.28 (d, J=8 Hz, 1H), 7.18 (d, J=8 Hz, 1H), 7.08 (t, J=8 Hz, 1H), 6.99 (br, 1H), 3.85 (s, 3H), 2.69 (s, 3H) ppm Synthesis of Compound 1

Compound 1-a (120 mg, 0.36 mmol) was dissolved in acetone (2 mL), and anhydrous potassium carbonate (74 mg, 0.54 mmol) was added, then methyl iodide (77 mg, 0.54 mmol) was added slowly and the mixture was stirred at room temperature overnight. The mixture was filtered and washed with acetone (20 mL). The combined filtrate was concentrated under reduced pressure and purified by prep-HPLC (mobile phase: 0.05% aqueous trifluoroacetic acid:acetonitrile=30% to 62%) to give 1 as a pale yellow solid (40 mg, yield 32%). LC-MS (ESI): m/z=352[M+H]+.

¹H-NMR (400 MHz, CDCl₃) δ: 8.73 (s, 1H), 7.79 (s, 1H), 7.42 (m, 2H), 7.37 (s, 1H), 7.05-7.14 (m, 3H), 3.77 (s, 1H), 3.76 (s, 3H), 2.49 (s, 3H) ppm Example 2

N-[7-(2,3-dihydro-1-benzofuran-7-yl)-6-methylthieno[3,2-d]pyrimidinyl-2-yl]-1-methyl-1H-pyrazol-4-amine (Compound 2)

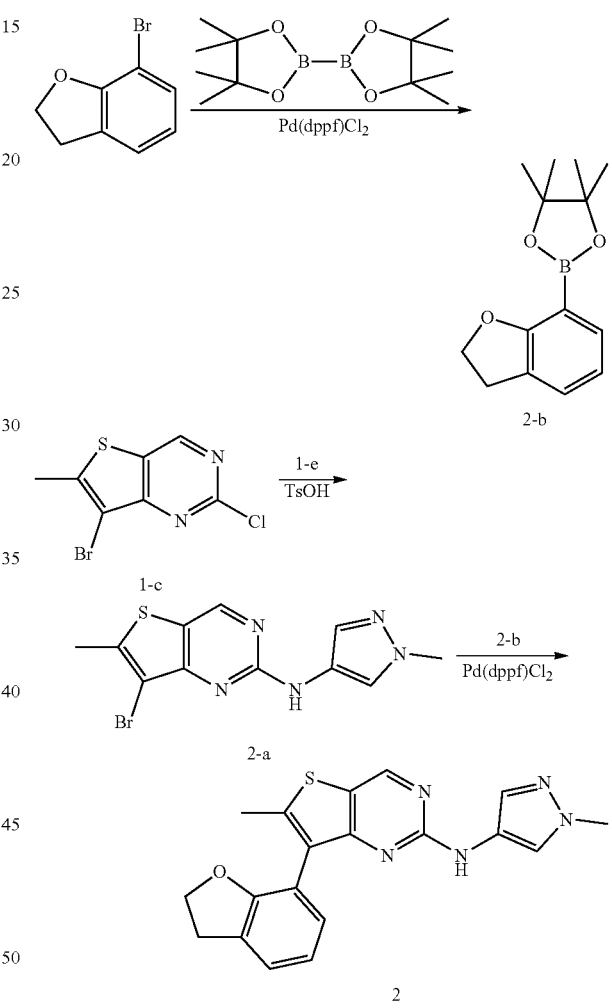

Synthesis of Compound 2-b

The compound 7-bromobenzodihydrofuran (0.4 g, 2 mmol), bis(pinacolato)diboron (0.78 g, 3 mmol) and anhydrous potassium acetate (0.4 g, 4 mmol) were suspended in dimethyl sulfoxide (5 mL), and [1,1'-bis (diphenylphosphino)ferrocene]dichloropalladium (0.16 g, 0.2 mmol) was added. The reaction solution was purged with nitrogen gas for three times to remove the oxygen contained in the system and heated at 80° C. for 8 hours. The reaction was cooled to room temperature, diluted with ice water (100 mL) and extracted with ethyl acetate (50 mL×3). The combined organic phase was washed with water (50 mL×3) and brine (50 mL) successively, dried over anhydrous sodium sulfate, filtered and the filtrate was concentrated under reduced pressure. The residue was purified by silica gel column chromatography (petroleum ether:ethyl acetate=30:1) to give compound 2-b (0.29 g, yield 56%).

$^1$H-NMR (400 MHz, CDCl3) δ: 7.53 (d, J=8 Hz, 1H), 7.27 (d, J=8 Hz, 1H), 6.83 (t, J=8 Hz, 1H), 4.63 (t, J=8.8 Hz, 1H), 3.16 (t, J=8.8 Hz, 1H), 1.36 (s, 12H) ppm Synthesis of Compound 2-a 4-Amino-1-methylpyrazole 1-e (0.9 g, 9 mmol), p-toluenesulfonic acid (2.26 g, 12 mmol) and compound 1-c (1.5 g, 6 mmol) were added to n-butanol (10 mL). The solution was heated to 108° C. and stirred for 6 hours. The reaction solution was concentrated, quenched with saturated aqueous sodium bicarbonate (80 mL), extracted with dichloromethane (100 mL×5), dried over anhydrous sodium sulfate and filtered and the filtrate was concentrated under reduced pressure. The residue was purified by silica gel TLC preparative plate (petroleum ether:ethyl acetate=1:1) to give 2-a as a yellow solid (1660 mg, yield 86.7%). LC-MS (ESI): m/z=324[M+H]$^+$.

Synthesis of Compound 2

Compound 2-a (180 mg, 0.75 mmol), compound 2-b (164 mg, 0.5 mmol), [1,1'-bis (diphenylphosphino)ferrocene]dichloropalladium (36 mg, 0.05 mmol) and sodium carbonate (106 mg, 1 mmol) were dissolved in 1,4-dioxane (8 mL) and water (2 mL). The reaction solution was purged with nitrogen gas for three times to remove the oxygen contained in the system and heated at 90° C. for 8 hours. The reaction solution was cooled to room temperature, diluted with ice water (10 mL) and extracted with dichloromethane (50 mL×3). The combined organic phase was washed with water (20 mL×3) and brine (20 mL) successively, dried over anhydrous sodium sulfate, filtered and the filtrate was concentrated under reduced pressure. The residue was purified by silica gel TLC preparative plate (petroleum ether:ethyl acetate=10:1) to give 2 as a yellow solid (41 mg, yield 22.6%). LC-MS (ESI): m/z=364[M+H]$^+$.

$^1$H-NMR (400 MHz, MeOD) δ: 8.79 (s, 1H), 7.91 (s, 1H), 7.60 (d, J=8 Hz, 1H), 7.52 (s, 1H), 7.36 (d, J=2 Hz, 1H), 7.06 (t, J=8 Hz, 1H), 4.88 (t, J=8 Hz, 2H), 4.58 (t, J=8 Hz, 2H), 3.77 (s, 3H), 2.55 (s, 3H) ppm Example 3

N-[7-[2-(2-methoxyethoxy)phenyl]-6-methylthieno[3,2-d]pyrimidinyl-2-yl]-1-methyl-1H-pyrazole-4-amine (Compound 3)

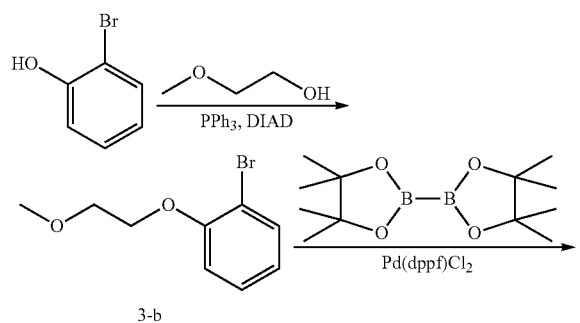

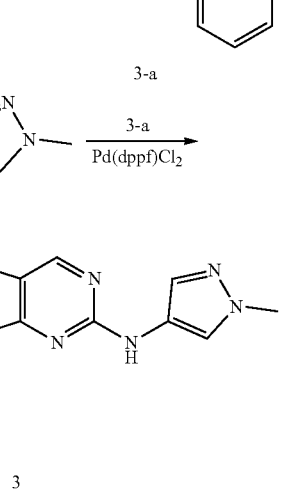

Synthesis of Compound 3-b

2-Bromophenol (5 g, 29.07 mmol), ethylene glycol monomethyl ether (3.3 g, 43.61 mmol) and triphenylphosphine (11.4 g, 43.61 mmol) were dissolved in anhydrous tetrahydrofuran (100 mL). The solution was cooled to 0° C. and diisopropylazodicarboxylate (8.9 g, 43.61 mmol) was slowly added dropwise. After the addition, the mixture was stirred at room temperature for 3 hours. After concentration, a mixed solvent (100 mL) of petroleum ether and ethyl acetate (10:1) was added and the mixture was stirred for 30 minutes, filtered and the filtrate was concentrated under reduced pressure. The residue was purified by silica gel column chromatography (petroleum ether:ethyl acetate=10:1) to give 3-b as a pale yellow oil (5 g, yield 75%).

Synthesis of Compound 3-a

Compound 3-b (1 g, 4.44 mmol) and bis(pinacol)borate (1.7 g, 6.67 mmol) were dissolved in dioxane (10 mL) and anhydrous potassium acetate (1.1 g, 13.32 mmol) and [1,1'-bis(diphenylphosphino)ferrocene]dichloropalladium (370 mg, 0.45 mmol) were added. The reaction solution was heated to 80° C. to react overnight under nitrogen gas atmosphere, and then concentrated under reduced pressure, the residue was purified by silica gel column chromatography (petroleum ether:ethyl acetate=20:1) to give 3-a as a yellow oil (630 mg, yield 51%).

Synthesis of Compound 3

Compound 3-a (51 mg, 0.06 mmol), compound 2-b (30 mg, 0.03 mmol) and sodium carbonate (42 mg, 0.39 mmol) were suspended in dioxane (0.5 mL) and water (0.5 mL), and [1,1'-bis(diphenylphosphino)ferrocene]dichloro-palladium.dichloromethane (13 mg, 0.016 mmol) was added. The mixture was purged with nitrogen gas for three times, and heated to 90° C. with microwave and reacted for 40 minutes. After the reaction solution was cooled to room temperature, the solvent was distilled off under reduced pressure. The residue was purified by silica gel TLC preparative plate (ethyl acetate) to give 3 as a yellow solid (10 mg, yield 27%). LC-MS (ESI): m/z=396[M+H]$^+$.

$^1$H-NMR (400 MHz, CDCl3) δ: 8.72 (s, 2H), 7.79 (s, 1H), 7.41-7.744 (m, 2H), 7.38 (s, 1H), 7.13 (t, J=8 Hz, 1H), 7.06 (d, J=8 Hz, 1H), 6.94 (br, 1H), 4.13 (m, 1H), 4.01 (m, 1H), 3.77 (s, 3H), 3.54 (m, 2H), 3.23 (s, 3H), 2.53 (s, 3H) ppm Example 4

N-[7-(4-methylsulfanyl-2-methoxyphenyl)-6-methylthieno[3,2-d]pyrimidinyl-2-yl]-1-methyl-1H-pyrazol-4-amine (Compound 4)

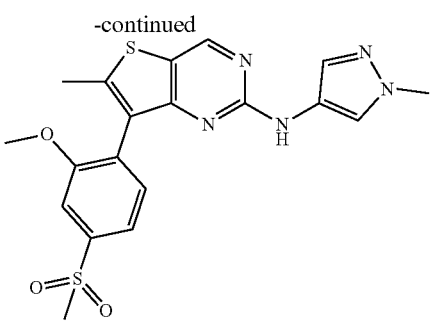

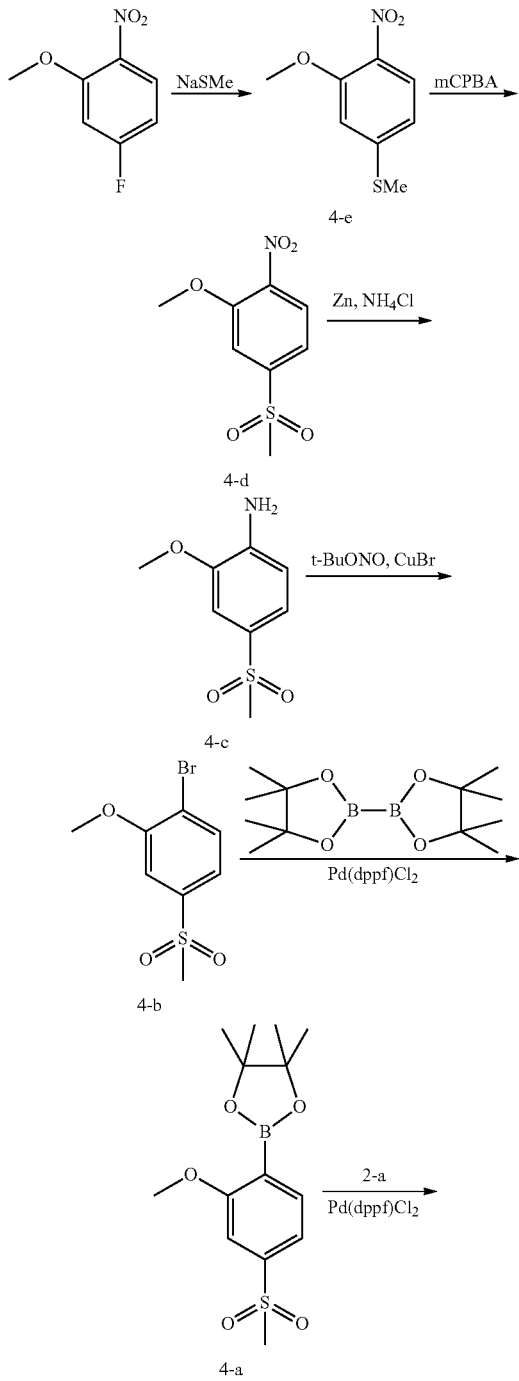

Synthesis of Compound 4-e

2-Methoxy-4-fluoronitrobenzene (5 g, 29.24 mmol) was dissolved in N,N-dimethylformamide (35 mL), 50% sodium methanethiolate (6.1 g, 43.86 mmol) was added and the mixture was stirred overnight at room temperature. The mixture was poured into water (200 mL) and extracted with ethyl acetate (200 mL). The separated organic phase was dried over anhydrous sodium sulfate and filtered. The filtrate was concentrated under reduced pressure and the residue was washed with a mixed solvent of petroleum ether and ethyl acetate (10:1, 50 mL) to give 4-e as a yellow solid (2.8 g, yield 48%).

$^1$H-NMR (400 MHz, CDCl$_3$) δ: 7.89 (d, J=9 Hz, 1H), 6.86 (s, 1H), 6.83 (d, J=9 Hz, 1H), 3.97 (s, 3H), 2.54 (s, 3H) ppm Synthesis of Compound 4-d Compound 4-e (3 g, 15.09 mmol) was dissolved in dichloromethane (10 mL), m-chloroperbenzoic acid (7.8 g, 37.74 mmol) was added and the reaction was stirred at room temperature for 16 hours. After cooling to 0° C., the reaction mixture was filtered and the filter cake was washed with cold dichloromethane. The combined filtrate was concentrated under reduced pressure and the residue was purified by silica gel column chromatography (petroleum ether:ethyl acetate=1:2) to give 4-d as a yellow solid (1.7 g, yield 49%). LC-MS (ESI): m/z=232[M+H]$^+$.

Synthesis of Compound 4-c

Compound 4-d (1.7 g, 7.36 mmol) was dissolved in ethanol (20 mL) and water (20 mL) and ammonium chloride (2 g, 36.79 mmol) and zinc dust (2.4 g, 36.79 mmol) were added. The mixture was heated to 80° C. to react for 2 hours. After cooling to room temperature, the mixture was concentrated under reduced pressure. The residue was partitioned between ethyl acetate (200 mL) and water (200 mL). The organic phase was separated, dried over anhydrous sodium sulfate, filtered, and the filtrate was concentrated under reduced pressure to give 4-c as a brown oil (1 g, yield 68%), which was used without further purification. LC-MS (ESI): m/z=202[M+H]$^+$.

Synthesis of Compound 4-b

Compound 4-c (1 g, 4.98 mmol) was dissolved in acetonitrile (10 mL) and copper bromide (1.9 g, 7.50 mmol) was added, followed by slowly adding tert-butyl nitrite (0.73 mL). The mixture was heated to 80° C. and reacted for 1 hour, cooled to room temperature and then concentrated under reduced pressure. The residue was diluted with ethyl acetate (100 mL) and water (50 mL) and filtered through celite. The combined organic phase was dried over anhydrous sodium sulfate, filtered and the filtrate was concentrated under reduced pressure. The residue was purified by silica gel column chromatography (petroleum ether:ethyl acetate=1:1) to give 4-b as a pale yellow solid (540 mg, yield 41%). LC-MS (ESI): m/z=265[M+H]$^+$.

Synthesis of Compound 4-a

Compound 4-b (300 mg, 1.14 mmol) and bis(pinacolato)diboron (433 mg, 1.71 mmol) were dissolved in dioxane (5 mL) and anhydrous potassium acetate (281 mg, 3.42 mmol) and [1,1'-bis(diphenylphosphino)ferrocene]dichloro-palladium.dichloromethane (98 mg, 0.15 mmol) were added. Under nitrogen gas atmosphere, the mixture was heated to 85° C. and reacted for 16 hours. After cooling to room temperature, the mixture was diluted with ethyl acetate (20 mL) and filtered through celite. The filtrate was concentrated to dryness to give 4-a as a black oil (350 mg) which was used in the next reaction without further purification.

Synthesis of Compound 4

Compound 4-a (72 mg, 0.23 mmol), compound 2-a (50 mg, 0.16 mmol) and sodium carbonate (50 mg, 0.47 mmol) were suspended in dioxane (0.5 mL) and water (0.5 mL), [1,1'-bis(diphenylphosphino)ferrocene]dichloropalladium-.dichloromethane (14 mg, 0.02 mmol) was added. The mixture was purged with nitrogen gas for three times, and heated to 90° C. with microwave, reacted for 40 minutes. After the solvent was evaporated under reduced pressure, the residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 4 as a pale yellow solid (15 mg, yield 23%). LC-MS (ESI): m/z=430[M+H]$^+$.

$^1$H-NMR (400 MHz, CDCl$_3$) δ: 8.76 (s, 1H), 7.68-7.69 (m, 2H), 7.65 (d, J=8 Hz, 1H), 7.59 (d, J=2 Hz, 1H), 7.36 (s, 1H), 7.26 (br, 1H), 3.87 (s, 3H), 3.79 (s, 3H), 3.16 (s, 3H), 2.50 (s, 4H) ppm Example 5

N-[7-(2,6-dimethoxyphenyl)-6-methylthieno[3,2-d]pyrimidinyl-2-yl]-1-methyl-1H-pyrazol-4-amine (Compound 5)

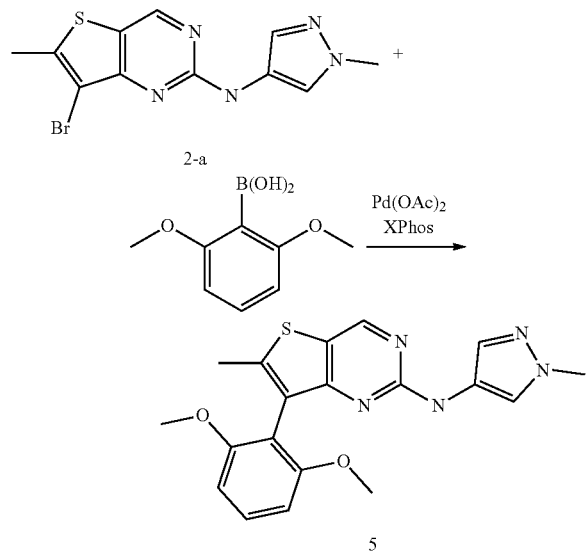

The compound 2,6-dimethoxyphenylboronic acid (136 mg, 0.75 mmol), compound 2-a (164 mg, 0.5 mmol), 2-dicyclohexylphosphino-2,4,6-triisopropylbiphenyl (36 mg, 0.05 mmol) and palladium acetate (0.112 g, 0.5 mmol) and potassium phosphate (0.422 g, 2 mmol) were dissolved in toluene (2 mL). The reaction mixture was purged with nitrogen gas for three times to remove the oxygen contained in the system, and then the mixture was heated at 90° C. for 8 hours. The reaction was cooled to room temperature, diluted with ice water (10 mL) and extracted with dichloromethane (50 mL×3). The combined organic phase was washed with water (20 mL×3) and brine (20 mL) successively, dried over anhydrous sodium sulfate, filtered and the filtrate was concentrated under reduced pressure. The residue was purified by silica gel TLC preparative plate (petroleum ether:ethyl acetate=5:1) to give 5 as a yellow solid (53 mg, yield 27.8%). LC-MS (ESI): m/z=382[M+H]$^+$.

$^1$H-NMR (400 MHz, MeOD) δ: 8.75 (s, 1H), 7.72 (s, 1H), 7.49 (d, J=8 Hz, 1H), 7.46 (s, 1H), 6.84 (d, J=2 Hz, 1H), 3.93 (s, 3H), 3.74 (s, 6H), 2.41 (s, 3H) ppm Example 6

N-[7-(4-chloro-2-dimethoxyphenyl)-6-methylthieno[3,2-d]pyrimidinyl-2-yl]-1-methyl-1H-pyrazol-4-amine (Compound 6)

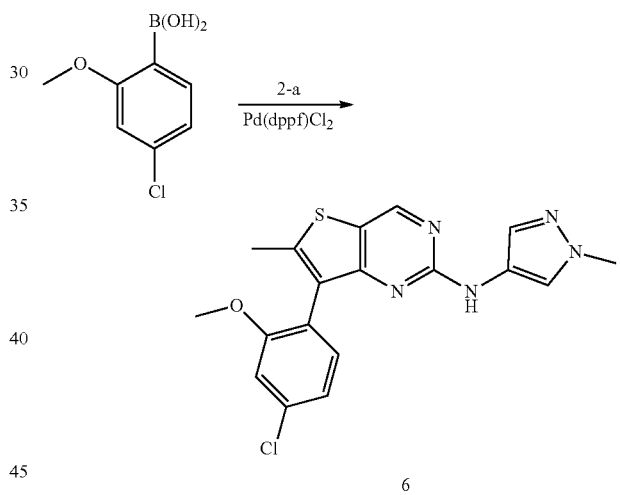

Synthesis of Compound 6

4-chloro-2-methoxybenzeneboronic acid (52 mg, 0.27 mmol), compound 2-a (75 mg, 0.23 mmol) and sodium carbonate (73 mg, 0.69 mmol) were suspended in dioxane (1.2 mL) and water (0.3 mL), and [1,1'-bis (diphenylphosphino)ferrocene]dichloropalladium.dichloromethane (17 mg, 0.02 mmol) was added. The mixture was purged with nitrogen gas for three times and heated at 90° C. under microwave for 1 hour. After cooling to room temperature, the reaction solution was added with water (30 mL) and extracted with dichloromethane (50 mL×2). The combined organic phase was dried over anhydrous sodium sulfate, filtered and the filtrate was concentrated under reduced pressure. The residue was purified by silica gel TLC preparative plate (ethyl acetate) to give 6 as a pale yellow solid (30 mg, yield 23%). LC-MS (ESI): m/z=385[M+H]$^+$.

$^1$H NMR (400 MHz, DMSO-d$_6$) δ: 9.43 (s, 1H), 8.95 (s, 1H), 7.657 (s, 1H), 7.19-7.38 (m, 4H), 3.76 (s, 3H), 3.70 (s, 3H), 2.42 (s, 3H) ppm

Example 7

N-[7-(2,4-dimethoxyphenyl)-6-methylthieno[3,2-d]pyrimidinyl-2-yl]-1-methyl-1H-pyrazol-4-amine (Compound 7)

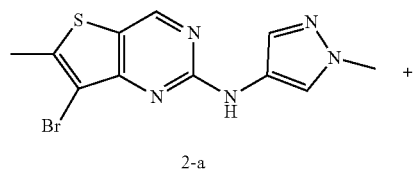

2-a

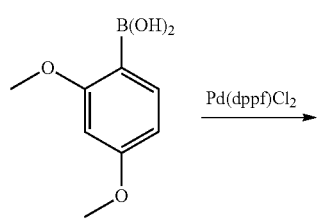

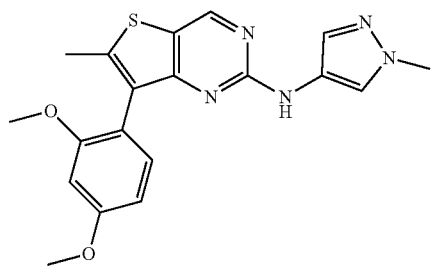

7

Synthesis of Compound 7

2,4-Dimethoxyphenylboronic acid (43 mg, 0.23 mmol), compound 2-a (50 mg, 0.16 mmol) and sodium carbonate (51 mg, 0.47 mmol) were suspended in dioxane (0.5 mL) and water (0.5 mL), and [1,1'-bis(diphenylphosphino)ferrocene]dichloropalladium.dichloromethane (13 mg, 0.02 mmol) was added. The reaction solution was purged with nitrogen gas for three times and heated at 90° C. under microwave for 40 minutes. After cooling to room temperature, the solvent was evaporated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 7 as a pale yellow solid (15 mg, yield 25%). LC-MS (ESI): m/z=381[M+H]⁺.

¹H-NMR (400 MHz, CDCl₃) δ: 8.72 (s, 1H), 7.83 (s, 1H), 7.39 (s, 1H), 7.31 (d, J=8 Hz, 1H), 7.07 (br, 1H), 6.63-6.68 (m, 2H), 3.89 (s, 3H), 3.79 (s, 3H), 3.76 (s, 3H), 2.49 (s, 3H) ppm

Example 8

N-[7-(5-methylsulfonyl-2-dimethoxyphenyl)-6-methylthieno[3,2-d]pyrimidinyl-2-yl]-1-methyl-1H-pyrazol-4-amine (Compound 8)

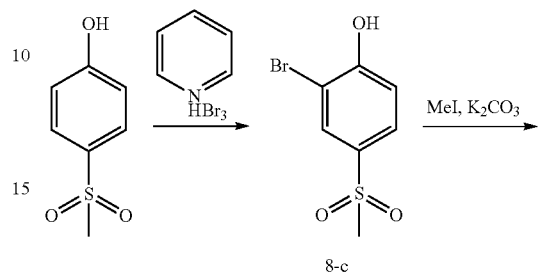

8-c

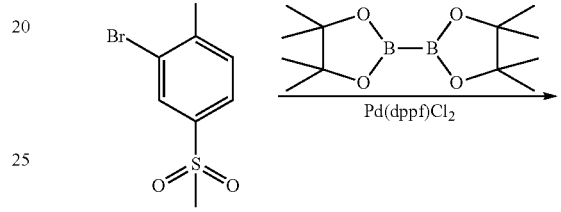

8-b

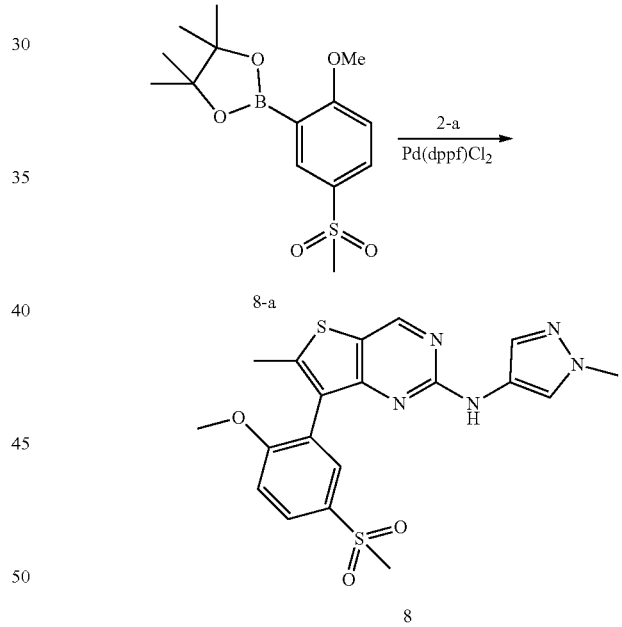

8

Synthesis of Compound 8-c

4-Hydroxyphenyl methyl sulfone (4.5 g, 26.16 mmol) was dissolved in dichloromethane (50 mL) and methanol (50 mL), pyridinium tribromide (8.3 g, 26.16 mmol) was added at room temperature and the mixture was stirred at room temperature for 2 days. The reaction solution was concentrated under reduced pressure. The residue was partitioned between dichloromethane (100 mL) and water (100 mL). The organic phase was dried over anhydrous sodium sulfate, filtered and the filtrate was concentrated under reduced pressure. The residue was added to a mixed solvent (50 mL) of petroleum ether and ethyl acetate (3:1), solid was precipitated out, and filtered to obtain 8-c as a white solid (1.2 g, yield 19%).

Synthesis of Compound 8-b

Compound 8-c (150 mg, 0.57 mmol) and potassium carbonate (236 mg, 1.71 mmol) were suspended in acetone (10 mL) and methyl iodide (809 mg, 5.71 mmol) was added. The reaction mixture was stirred at room temperature for 16 hours, filtered and the filter cake was washed with ethyl acetate (10 mL). The filtrate was concentrated under reduced pressure and the residue was washed with ethyl acetate (50 mL) and water (50 mL). The organic phase was dried over anhydrous sodium sulfate, filtered, and the filtrate was concentrated under reduced pressure to give 8-b as a pale yellow solid (150 mg, yield 95%).

Synthesis of Compound 8-a

Compound 8-b (150 mg, 0.57 mmol) and bis(pinacolato)diboron (160 mg, 0.63 mmol) were dissolved in dioxane (3 mL) and anhydrous potassium acetate (141 mg, 1.71 mmol) and [1,1'-bis(diphenylphosphino)ferrocene]dichloro-palladium.dichloromethane (130 mg, 0.17 mmol) were added. Under nitrogen gas atmosphere, the mixture was heated to 85° C. and reacted overnight. After cooling to room temperature, the mixture was diluted with ethyl acetate (20 mL) and filtered through celite. The filtrate was concentrated under reduced pressure to give 8-a as a black oil (185 mg), which was used directly in the next reaction without further purification.

Synthesis of Compound 8

Compound 8-a (150 mg, 0.46 mmol), compound 2-a (100 mg, 0.31 mmol) and sodium carbonate (100 mg, 0.93 mmol) were suspended in dioxane (0.5 mL) and water (0.5 mL), [1,1'-bis(diphenylphosphino)ferrocene]dichloropalladium-.dichloromethane (26 mg, 0.03 mmol) was added. The reaction solution was purged with nitrogen gas for three times, heated to 80° C. and reacted for 18 hours. After cooling to room temperature, the solvent was removed by rotary evaporation. The residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 8 as a white solid (25 mg, yield 19%). LC-MS (ESI): m/z=430[M+H]$^+$.

$^1$H-NMR (400 MHz, CDCl$_3$) δ: 8.73 (s, 1H), 8.04 (s, 1H), 8.02 (d, J=9 Hz, 1H), 7.71 (s, 1H), 7.39 (s, 1H), 7.19 (d, J=9 Hz, 1H), 6.85 (br, 1H), 3.88 (s, 3H), 3.81 (s, 3H), 3.10 (s, 3H), 2.49 (s, 3H) ppm Example 9

2-{1-[(3-methoxy-4-{6-methyl-2-[(1-methyl-1H-pyrazol-4-yl) amino]thieno[3,2-d]pyrimidinyl-7-yl}phenyl)methyl]piperidinyl-4-yl}propan-2-ol (Compound 9)

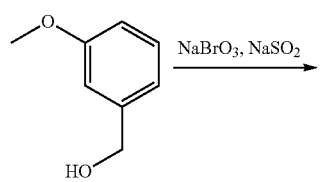

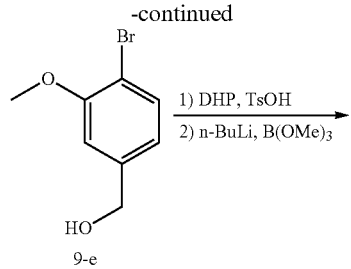

9-e

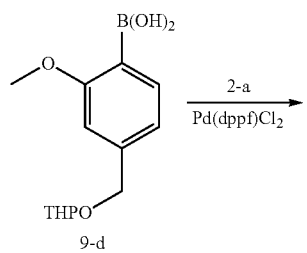

9-d

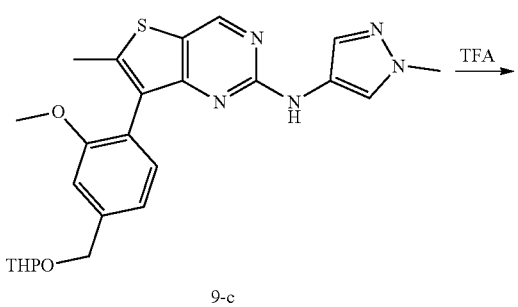

9-c

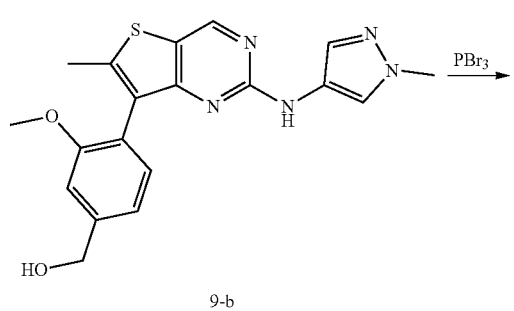

9-b

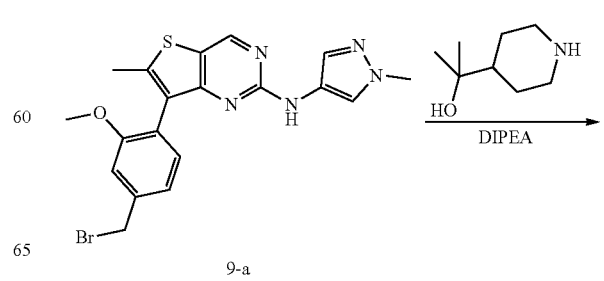

9-a

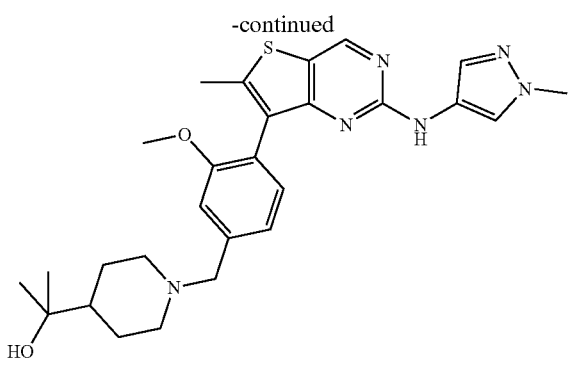

9

Synthesis of Compound 9-e

The compound 3-methoxybenzyl alcohol (10 g, 72.4 mmol) was dissolved in a mixture of acetonitrile (250 mL) and water (250 mL) and then sodium bromate (19.1 g, 127 mmol) and sodium bisulfite (13.2 g, 127 mmol) were added. The reaction solution was stirred at room temperature for 1.5 hours, quenched with a saturated aqueous solution of sodium thiosulfate (250 mL) and then extracted with dichloromethane (200 mL×3). The combined organic phase was washed with water (200 mL×3) and brine (20 mL) sequentially, dried over anhydrous sodium sulfate and filtered. The filtrate was concentrated under reduced pressure, the residue was purified by silica gel TLC preparative plate (petroleum ether:ethyl acetate=3:1) to give 9-e as a yellow solid (1.39 g, yield 88%).

$^1$H-NMR (400 MHz, MeOD) δ: 7.41 (d, J=12 Hz, 1H), 7.06 (d, J=4 Hz, 1H), 6.71 (dd, J=4 Hz, J=8 Hz, 1H), 4.70 (d, J=8 Hz, 2H), 3.81 (s, 3H) ppm Synthesis of Compound 9-d Compound 9-e (2.16 g, 10 mmol) and p-toluenesulfonic acid (1.72 g, 1 mmol) were added to dichloromethane (50 mL), followed by slow addition of 3,4-dihydropyran (1.64 g, 20 mmol) and the resultant was stirred at room temperature for 3 hours. The reaction solution was concentrated under reduced pressure, quenched with saturated aqueous sodium bicarbonate solution (50 mL) and the mixture was extracted with dichloromethane (50 mL×3). The combined organic phase was dried over sodium sulfate, filtered and the filtrate was concentrated under reduced pressure. The residue was added directly to anhydrous tetrahydrofuran (10 mL) pre-cooled to −78° C., followed by the dropwise addition of n-butyllithium in n-hexane (5 mL, 12.5 mmol). After stirring for 2 hours, trimethyl borate (1.3 g, 12.5 mmol) was added to the reaction solution. The reaction mixture was slowly warmed to room temperature and further stirred for 2 hours. The reaction was quenched with water (50 mL) and sodium hydroxide (0.8 g, 20 mmol) and extracted with ethyl acetate (50 mL×3). The aqueous phase is adjusted to pH=7 with 1M aqueous hydrochloric acid solution and then extracted with ethyl acetate (50 mL×3). The organic phase was concentrated under reduced pressure to give 9-d as a yellow solid (2.1 g, yield 72.7%). LC-MS (ESI): m/z=289[M+H]$^+$.

Synthesis of Compound 9-c

Compound 9-d (486 mg, 10 mmol), compound 2-a (480 mg, 15 mmol), [1,1'-bis (diphenylphosphino)ferrocene]dichloropalladium (36 mg, 0.05 mmol) and 2M aqueous sodium carbonate solution (8 mL, 16 mmol) were dissolved in 1,4-dioxane (13 mL). The reaction solution was purged with nitrogen gas for three times to remove the oxygen contained in the system and then heated at 90° C. for 6 hours. The reaction was cooled to room temperature, diluted with ice water (100 mL) and extracted with dichloromethane (100 mL×3). The combined organic phase was washed with water (50 mL×3) and brine (50 mL) successively, dried over anhydrous sodium sulfate, filtered and the filtrate was concentrated under reduced pressure. The residue was purified by silica gel TCL preparative plate (petroleum ether:ethyl acetate=1:1) to give 9-c as a yellow solid (610 mg, yield 87%). LC-MS (ESI): m/z=466[M+H]$^+$.

Synthesis of Compound 9-b

Compound 9-c (468 mg, 1 mmol) was dissolved in dichloromethane (5 mL). The reaction solution was cooled to 0° C., trifluoroacetic acid (1 mL) was added and the mixture was stirred at room temperature for 2 hours. The reaction solution was concentrated under reduced pressure and the residue was dissolved in dichloromethane (50 mL) and diluted with saturated sodium carbonate solution (50 mL). The separated organic phase was dried over anhydrous sodium sulfate, filtered and the filtrate was concentrated under reduced pressure. The residue was purified by preparative HPLC (mobile phase: 10 mM aqueous ammonium bicarbonate solution:acetonitrile=40%-50%) to give 9-b (310 mg, yield 81%) as a yellow solid. LC-MS (ESI): m/z=382[M+H]$^+$.

Synthesis of Compound 9-a

Phosphorus tribromide (1 mL) was slowly added dropwise to a solution of compound 9-b (310 mg, 0.81 mmol) in dichloromethane (5 mL), the mixture was stirred at room temperature for 3 hours and then quenched with saturated aqueous sodium bicarbonate solution (10 mL). The mixture was extracted with dichloromethane (50 mL×3). The combined organic phase was dried over sodium sulfate, filtered and the filtrate was concentrated under reduced pressure to give compound 9-a (280 mg, yield 78%), which was used without further purification. LC-MS (ESI): m/z=444[M+H]$^+$.

Synthesis of Compound 9

Compound 9-a (140 mg, 0.316 mmol), 2-(4-piperidinyl)-2-propanol (54 mg, 0.38 mmol) and diisopropylethylamine (0.082 g, 0.632 mmol) were added to dichloromethane (5 mL), and the reaction solution was stirred at room temperature for 3 hours, and then concentrated under reduced pressure, the residue was purified by silica gel TLC preparative plate (dichloromethane:methanol=10:1) to give 9 as a yellow solid (100 mg, yield 62.5%). LC-MS (ESI): m/z=507[M+H]$^+$.

$^1$H-NMR (400 MHz, DMSO-d6) δ: 9.37 (s, 1H), 8.94 (s, 1H), 7.33 (s, 1H), 7.13 (s, 1H), 7.11 (m, 1H), 6.95 (m, 1H), 3.95 (s, 1H), 3.83 (s, 3H), 3.65 (s, 3H), 3.17 (s, 2H), 2.60 (t, J=8 Hz, 2H), 2.41 (t, J=8 Hz, 2H), 2.38 (s, 3H), 1.56 (t, J=8 Hz, 2H), 1.41 (t, J=8 Hz, 2H), 0.91 (s, 6H) ppm Example 10

N-{7-[2-(difluoromethoxy)phenyl]-6-methylthieno[3,2-d]pyrimidinyl-2-yl}-1-methyl-1H-pyrazol-4-amine (Compound 10)

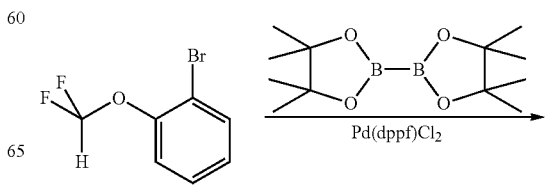

Example 11

N-{7-[4-(3-methylsulfonylpropoxy)-2-methoxyphenyl]-6-methylthieno[3,2-d]pyrimidinyl-2-yl]-1-methyl-1H-pyrazol-4-amine (Compound 11)

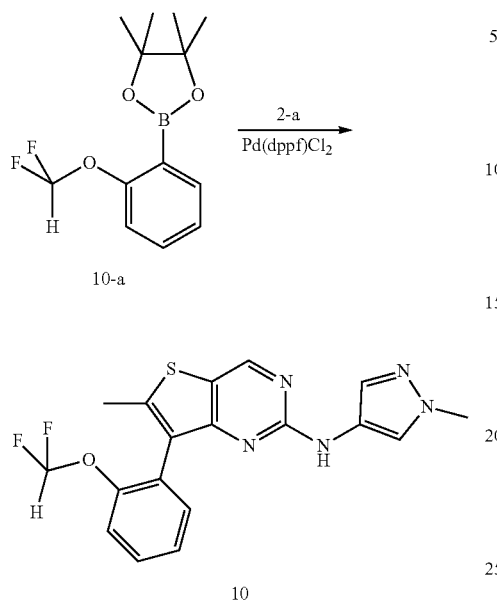

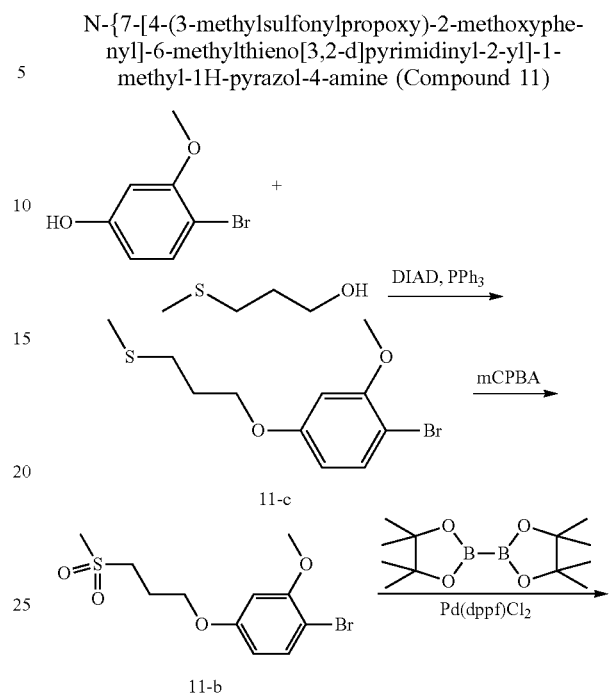

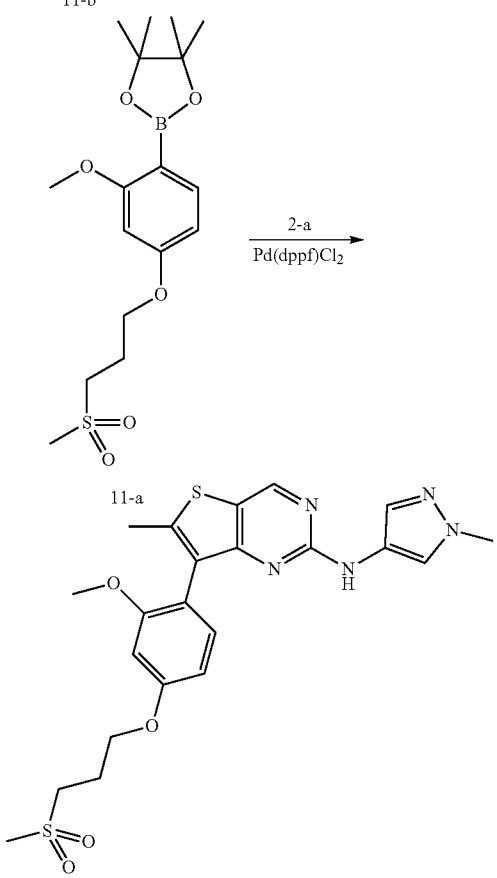

Synthesis of Compound 10-a

2-Bromodifluoromethylphenylether (1 g, 4.5 mmol) and bis(pinacolato)diboron (1.71 g, 6.75 mmol) were dissolved in dioxane (10 mL), and anhydrous potassium acetate (1.1 g, 13.53 mmol) and [1,1'-bis (diphenylphosphino)ferrocene]dichloropalladium.dichloromethane (369 mg, 0.45 mmol) were added. Under nitrogen gas atmosphere, the mixture was heated to 85° C. and stirred for 16 hours. After cooling to room temperature, the reaction was concentrated under reduced pressure. The residue was purified by silica gel column chromatography (petroleum ether:ethyl acetate=10:1) to give 10-a as a pale yellow oil (1.1 g, yield 90.2%).

Synthesis of Compound 10

Compound 10-a (126 mg, 0.465 mmol), compound 2-a (100 mg, 0.31 mmol) and sodium carbonate (99 mg, 0.93 mmol) were suspended in dioxane (0.5 mL) and water (0.5 mL), [1,1'-bis(diphenylphosphino)ferrocene]dichloropalladium.dichloromethane (25 mg, 0.03 mmol) was added. The reaction solution was purged with nitrogen gas for three times and heated at 90° C. under microwave for 50 minutes. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 10 as a pale yellow solid (35 mg, yield 30%). LC-MS (ESI): m/z=389[M+H]$^+$.

$^1$H-NMR (400 MHz, CDCl$_3$) δ: 8.75 (s, 1H), 7.68 (s, 1H), 7.47-7.51 (m, 2H), 7.37-7.41 (m, 1H), 7.32-7.34 (m, 1H), 6.81 (br, 1H), 6.13-6.50 (t, J$_{H-F}$=74 Hz, 1H), 3.77 (s, 3H), 2.53 (s, 3H) ppm

Synthesis of Compound 11-c

3-Methylthiopropanol (830 mg, 7.83 mmol) and 3-methoxy-4-bromophenol (1.44 g, 7.13 mmol) were dissolved in anhydrous tetrahydrofuran (50 mL) and triphenylphosphine (2.8 g, 10.68 mmol). The reaction solution was cooled to 0° C. and diisopropyl azodicarboxylate (2.24 g, 7.13 mmol) was added dropwise. After the addition was complete, the temperature was raised to room temperature and stirring continued for 18 hours. The reaction mixture was concentrated under reduced pressure and the residue was purified by silica gel column chromatography (petroleum ether:ethyl acetate=10:1) to give 11-c as a yellow oil (250 mg, yield 12%).

Synthesis of Compound 11-b

Compound 11-c (610 mg, 2.10 mmol) was dissolved in dichloromethane (15 mL), m-chloroperbenzoic acid (907 mg, 5.26 mmol) was added and the mixture was stirred at room temperature for 16 hours. The reaction mixture was cooled to 0° C., filtered, the filter cake was washed with cold dichloromethane and the filtrate was concentrated under reduced pressure. The residue was purified by silica gel column chromatography (petroleum ether:ethyl acetate=1:1) to give 11-b as a white solid (210 mg, yield 31%).

$^1$H-NMR (400 MHz, CDCl$_3$) δ: 7.40 (d, J=9 Hz, 1H), 6.47 (d, J=2 Hz, 1H), 6.38 (dd, J=9 Hz, J=2 Hz, 1H), 4.11 (t, J=6 Hz, 2H), 3.87 (s, 3H), 3.26 (t, J=6 Hz, 2H), 2.96 (s, 3H), 2.35 (m, 2H) ppm Synthesis of Compound 11-a Compound 11-b (100 mg, 0.31 mmol) and bis(pinacolato)diboron (120 mg, 0.46 mmol) were dissolved in dioxane (5 mL) and anhydrous potassium acetate (77 mg, 0.93 mmol) and [1,1'-bis(diphenylphosphino)ferrocene]dichloro-palladium.dichloromethane (25 mg, 0.03 mmol) were added. Under nitrogen gas atmosphere, the reaction solution was heated to 85° C. and stirred for 16 hours. After cooling to room temperature, the reaction mixture was diluted with ethyl acetate (20 mL), filtered through celite and the filtrate was concentrated under reduced pressure. The residue was purified by silica gel TLC preparative plate (petroleum ether:ethyl acetate=1:1) to give 11-a as a pale yellow solid (45 mg, yield 39%).

Synthesis of Compound 11

Compound 11-a (40 mg, 0.11 mmol), compound 2-a (35 mg, 0.11 mmol) and sodium carbonate (35 mg, 0.33 mmol) were suspended in dioxane (0.5 mL) and water (0.5 mL), and [1,1'-bis (diphenylphosphino)ferrocene]dichloropalladium.dichloromethane (16 mg, 0.02 mmol) was added. The reaction solution was purged with nitrogen gas for three times and was heated at 90° C. under microwave for 40 minutes. After cooling to room temperature, the reaction solution was concentrated under reduced pressure to remove the solvent. The residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (dichloromethane:methanol=10:1) to give 11 as a pale yellow solid (15 mg, yield 29%). LC-MS (ESI): m/z=488[M+H]$^+$.

$^1$H-NMR (400 MHz, CDCl$_3$) δ: 8.72 (s, 1H), 7.77 (s, 1H), 7.44 (s, 1H), 7.31 (d, J=8 Hz, 1H), 6.90 (br, 1H), 6.61-6.64 (m, 2H), 4.20 (t, J=6 Hz, 1H), 3.81 (s, 3H), 3.76 (s, 3H), 3.31 (t, J=6 Hz, 2H), 2.99 (s, 3H), 2.47 (s, 3H), 2.38-2.42 (m, 2H) ppm Example 12

N-(7-{2-methoxy-4-[(3R)-3-tetrahydrofuranoxyl]phenyl]-6-methylthieno[3,2-d]pyrimidinyl-2-yl]-1-methyl-1H-pyrazol-4-amine (Compound 12)

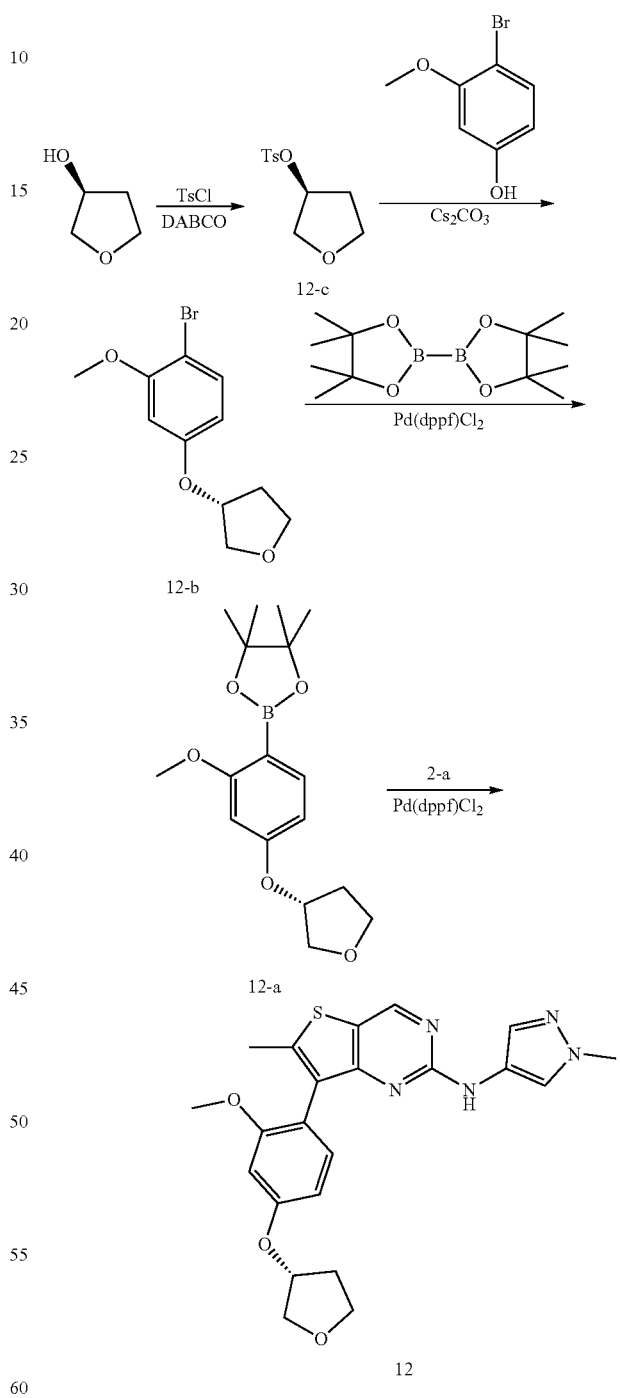

Synthesis of Compound 12-c

In an ice bath, 1,4-diazabicyclo[2.2.2]octane (4.76 g, 42.43 mmol) and p-toluenesulfonyl chloride (3.09 g, 16.2 mmol) were added into a solution of (S)-tetrahydrofuran-3-methanol (1 mL, 12.48 mmol) in dichloromethane (10 mL) respectively. After the addition, the reaction solution was warmed to room temperature and stirred for 1 hour. Additional p-toluenesulfonyl chloride (1 g, 5.25 mmol) was added and the reaction solution was stirred at 28° C. for another 16 hours. The reaction solution was diluted with dichloromethane (30 mL) and washed with water (30 mL). The organic phase was dried over anhydrous sodium sulfate and the filtrate was concentrated under reduced pressure. The residue was purified by silica gel column chromatography (petroleum ether:ethyl acetate=30:1) to give 12-c as an oil (2.1 g, yield 70%).

Synthesis of Compound 12-b

At room temperature, 3-methoxy-4-bromophenol (0.4 g, 1.97 mmol) and cesium carbonate (0.96 g, 2.96 mmol) were added into a solution of compound 12-c (0.57 g, 2.36 mmol) in N,N-dimethylformamide (5 mL) respectively. After the addition, the reaction solution was stirred at 75° C. for 16 hours. The reaction solution was diluted with ethyl acetate (10 mL), washed sequentially with water (10 mL×3) and brine (10 mL×3). The organic phase was dried over anhydrous sodium sulfate and the filtrate was concentrated under reduced pressure. The residue was purified by silica gel column chromatography (petroleum ether:ethyl acetate=10:1) to give compound 12-b (0.55 mg, yield 86%).

Synthesis of Compound 12-a

Compound 12-b (615 mg, 2.25 mmol) and bis(pinacolato)diboron (860 mg, 3.38 mmol) were dissolved in dioxane (10 mL), and anhydrous potassium acetate (662 mg, 6.75 mmol) and [1,1'-bis (diphenylphosphino)ferrocene]dichloropalladium.dichloromethane (183 mg, 0.23 mmol) were added. Under nitrogen gas atmosphere, the reaction was heated to 100° C. and stirred for 16 hours. After cooling to room temperature, the reaction mixture was diluted with ethyl acetate (20 mL), filtered through celite and the filtrate was concentrated under reduced pressure. The residue was purified by silica gel column chromatography (petroleum ether: ethyl acetate=10:1) to give compound 12-a (550 mg, yield 53%). LC-MS (ESI): m/z=321[M+H]$^+$.

Synthesis of Compound 12

Compound 12-a (70 mg, 0.22 mmol), compound 2-a (72 mg, 0.22 mmol) and sodium carbonate (70 mg, 0.66 mmol) were suspended in dioxane (3 mL) and water (3 mL), [1,1'-bis(diphenylphosphino)ferrocene]dichloropalladium-.dichloromethane (20 mg, 0.025 mmol) was added. The reaction solution was purged replaced with nitrogen gas for three times, and stirred at 80° C. for 16 hours. After cooling to room temperature, the reaction mixture was filtered through celite, the filter cake was washed with ethyl acetate (20 mL), the filtrate was washed with brine (20 mL), the organic phase was dried over anhydrous sodium sulfate, filtered and the filtrate was concentrated under reduced pressure, and the residue was purified by silica gel TLC preparative plate (dichloromethane:methanol=10:1) to give compound 12 (10 mg, yield 10%). LC-MS (ESI): m/z=438 [M+H]$^+$.

$^1$H-NMR (400 MHz, CDCl$_3$) δ: 8.73 (s, 1H), 7.80 (s, 1H), 7.40 (s, 1H), 7.30 (d, J=8.4 Hz, 1H), 7.27 (brs, 1H), 6.61 (d, J=2.4 Hz, 1H), 6.58 (dd, J=2.4, 5.4 Hz, 1H), 4.96-5.07 (m, 1H), 3.99-4.11 (m, 3H), 3.88-3.99 (m, 1H), 3.80 (s, 3H), 3.74 (s, 3H), 2.48 (s, 3H), 2.17-2.33 (m, 2H) ppm Example 13

N-[7-(2-methoxyphenyl)-6-methylthieno[3,2-d]pyrimidinyl-2-yl]-1-ethyl-1H-pyrazol-4-amine (Compound 13)

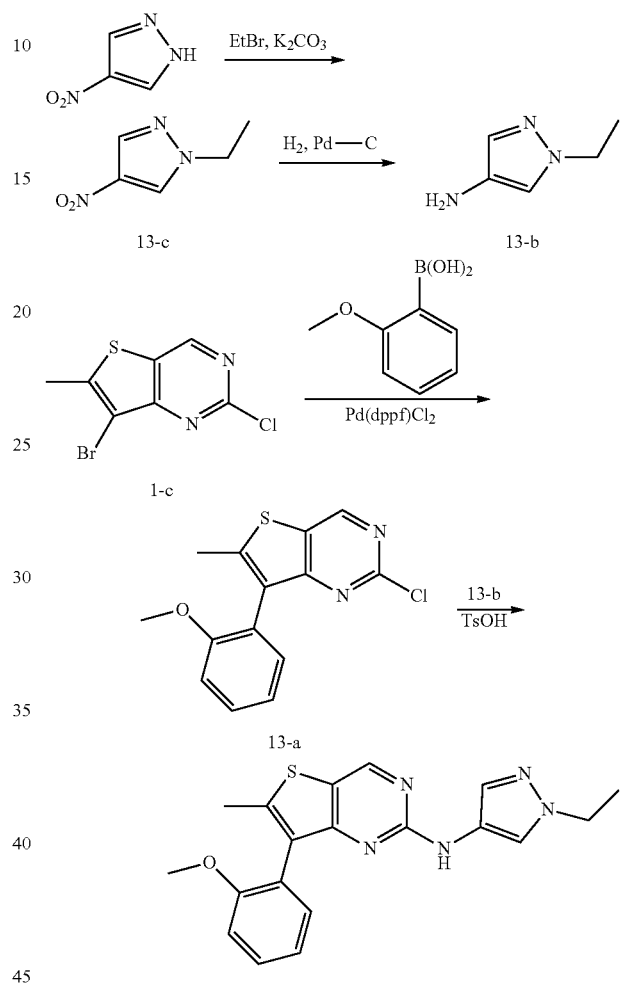

Synthesis of Compound 13-c

Bromoethane (1.1 g, 10 mmol) and potassium carbonate (2.76 g, 20 mmol) were added to a solution of 4-nitropyrazole (1.13 g, 10 mmol) in N,N-dimethylformamide (15 mL), the mixture was heated to 90° C. and stirred for 12 hours. After cooling to room temperature, the reaction solution was added with water (60 mL) and extracted with ethyl acetate (20 mL×3). The organic phases were combined, dried over anhydrous sodium sulfate, filtered and the filtrate was concentrated under reduced pressure. The residue was purified by silica gel column chromatography (petroleum ether:ethyl acetate=5:1) to give compound 13-c (1.2 g, yield 85%). LC-MS (ESI): m/z=142[M+H]$^+$.

Synthesis of Compound 13-b

Palladium 10% on carbon (0.1 g) was added to a solution of compound 13-c (1.0 g, 7.1 mmol) in methanol (10 mL) under hydrogen gas atmosphere (1 atm). The mixture was reacted at 25° C. for 12 hours, then filtered and the filtrate was concentrated under reduced pressure to give compound 13-b (760 mg, yield 96%), which was directly used for the next step without purification. LC-MS (ESI): m/z=112[M+H]⁺.

Synthesis of Compound 13-a

2-Methoxyphenylboronic acid (150 mg, 1 mmol), compound 1-c (380 mg, 1.5 mmol), [1,1'-bis(diphenylphosphino)ferrocene]dichloropalladium (36 mg, 0.05 mmol) and 2M aqueous sodium carbonate solution (2 mL, 4 mmol) were dissolved in 1,4-dioxane (8 mL). The reaction solution was purged with nitrogen gas for three times to remove oxygen contained in the system, and then heated at 110° C. for 6 hours. The reaction was cooled to room temperature, diluted with ice water (100 mL) and extracted with dichloromethane (100 mL×3). The combined organic phase was washed with water (50 mL×3) and brine (50 mL) successively, dried over anhydrous sodium sulfate, filtered and the filtrate was concentrated under reduced pressure. The residue was purified by silica gel TLC preparative plate (petroleum ether:ethyl acetate=10:1) to give 13-a as a yellow solid (239 mg, yield 87%). LC-MS (ESI): m/z=291[M+H]⁺.

Synthesis of Compound 13

Compound 13-b (83 mg, 0.75 mmol), p-toluenesulfonic acid (150 mg, 0.75 mmol) and compound 13-a (145 mg, 0.5 mmol) were added to n-butanol (10 mL), the mixture was heated to 108° C. and stirred for 6 hours. After cooling to room temperature, the reaction solution was concentrated, the residue was added to a saturated aqueous sodium bicarbonate solution (80 mL) and extracted with dichloromethane (100 mL×3). The combined organic phase was dried over anhydrous sodium sulfate, filtered and the filtrate was concentrated under reduced pressure. The residue was purified by silica gel TLC preparative plate (petroleum ether:ethyl acetate=1:1) to give 13 as a yellow solid (67 mg, yield 38%). LC-MS (ESI): m/z=366[M+H]⁺.

¹H-NMR (400 MHz, MeOD) δ: 8.67 (s, 1H), 7.72 (s, 1H), 7.40 (t, J=8 Hz, 1H), 7.34 (s, 1H), 7.26 (d, J=8 Hz, 1H), 7.08 (d, J=8 Hz, 1H), 7.03 (t, J=8 Hz, 1H), 3.90 (q, J=8 Hz, 2H), 3.67 (s, 3H), 2.37 (s, 3H), 1.23 (t, J=8 Hz, 3H) ppm Example 14

N-[7-(2-methoxyphenyl)-6-methylthieno[3,2-d]pyrimidinyl-2-yl]-1-isopropyl-1H-pyrazol-4-amine (Compound 14)

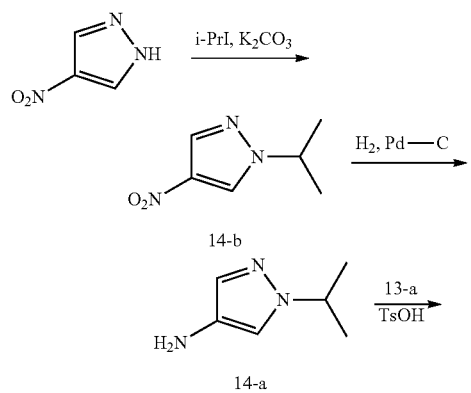

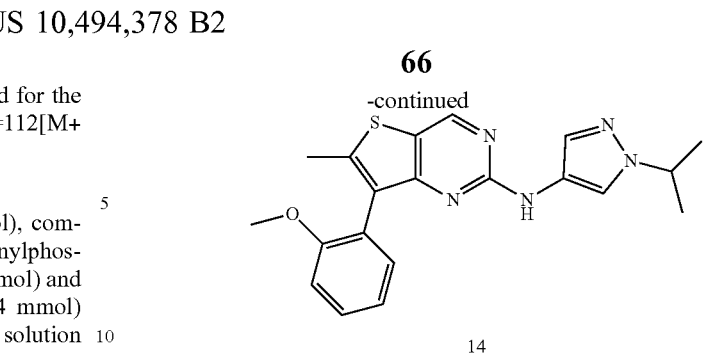

Synthesis of Compound 14-b

2-Iodopropane (2.3 g, 13.27 mmol) and potassium carbonate (1.81 g, 13.27 mmol) were sequentially added to a solution of 4-nitropyrazole (1.0 g, 8.85 mmol) in N,N-dimethylformamide (10 mL) and the mixture was heated to 60° C. for 3 hours. The mixture was poured into ice water (100 mL) and extracted with ethyl acetate (100 mL×3). The organic phases were combined, dried over anhydrous sodium sulfate, filtered and the filtrate was concentrated under reduced pressure to give 14-b as a yellow oil (1.1 g, yield 81%), which was directly used for the next reaction without purification.

Synthesis of Compound 14-a

Palladium 10% on carbon (0.2 g) was added to a solution of compound 14-b (1.0 g, 8.8 mmol) in ethanol (20 mL) under hydrogen gas atmosphere (1 atm). The mixture was reacted at 25° C. for 12 hours, filtered and the filtrate was concentrated under reduced pressure to give compound 14-a (830 mg, yield 94%), which was directly used for the next reaction without purification. LC-MS (ESI): m/z=126[M+H]⁺.

Synthesis of Compound 14

Compound 14-a (94 mg, 0.75 mmol), p-toluenesulfonic acid (150 mg, 0.75 mmol) and compound 13-a (145 mg, 0.5 mmol) were added to n-butanol (10 mL), the mixture was heated to 108° C. and stirred for 6 hours. After cooling to room temperature, the reaction solution was concentrated, the residue was added to a saturated aqueous sodium bicarbonate solution (80 mL) and extracted with dichloromethane (100 mL×3). The combined organic phase was dried over anhydrous sodium sulfate, filtered and the filtrate was concentrated under reduced pressure. The residue was purified by silica gel TLC preparative plate (petroleum ether:ethyl acetate=1:1) to give 14 as a yellow solid (87 mg, yield 46%). LC-MS (ESI): m/z=380[M+H]⁺.

¹H-NMR (400 MHz, DMSO-d6) δ: 8.67 (s, 1H), 7.74 (s, 1H), 7.36 (t, J=8 Hz, 1H), 7.32 (s, 1H), 7.25 (d, J=8 Hz, 1H), 7.08 (d, J=8 Hz, 1H), 7.03 (t, J=8 Hz, 1H), 4.20 (m, 1H), 3.67 (s, 3H), 2.35 (s, 3H), 1.25 (d, J=8 Hz, 6H) ppm Example 15

N-(7-{2-methoxy-4-[(3S)-3-tetrahydrofuranoxy]phenyl}-6-methylthieno[3,2-d]pyrimidinyl-2-yl]-1-methyl-1H-pyrazol-4-amine (Compound 15)

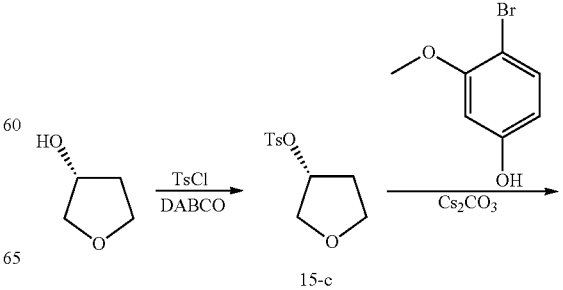

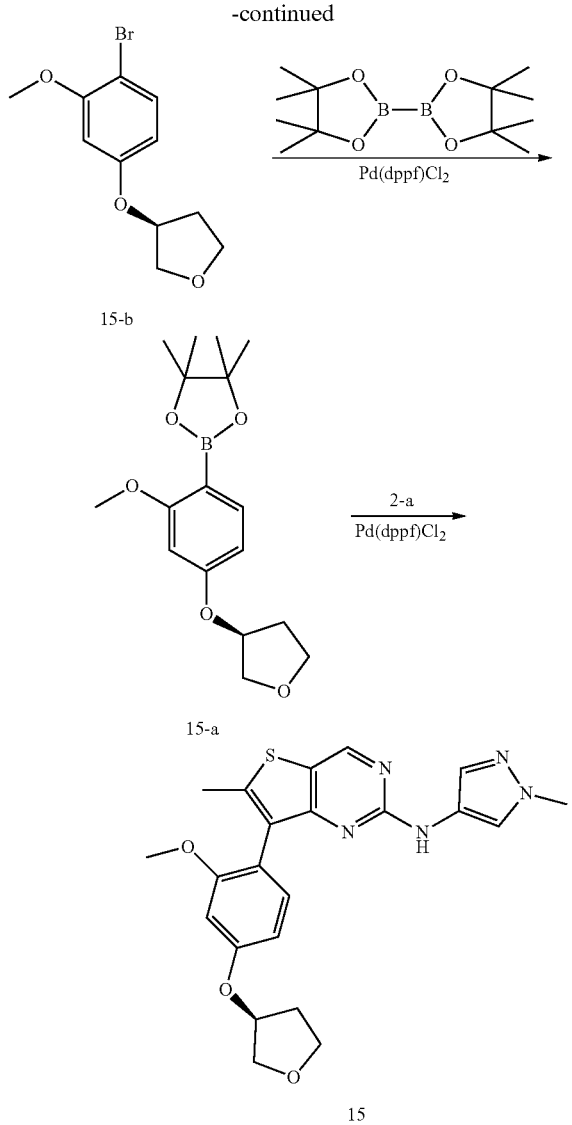

Synthesis of Compound 15-c

In an ice bath, 1,4-diazabicyclo[2.2.2]octane (2.52 g, 22.47 mmol) and p-toluenesulfonyl chloride (4.28 g, 22.45 mmol) were added to a solution of (R)-tetrahydrofuran-3-methanol (0.9 mL, 11.24 mmol) in dichloromethane (10 mL) respectively. After the addition, the reaction solution was warmed to room temperature and stirred for 1 hour. The reaction solution was diluted with dichloromethane (30 mL) and washed with water (30 mL). The organic phase was dried over anhydrous sodium sulfate and the filtrate was concentrated under reduced pressure. The residue was purified by silica gel column chromatography (petroleum ether:ethyl acetate=30:1) to give 15-c (2.17 g, yield 80%).

Synthesis of Compound 15-b

At room temperature, 3-methoxy-4-bromophenol (0.4 g, 1.97 mmol) and cesium carbonate (0.96 g, 2.96 mmol) were added to a solution of compound 15-c (0.43 g, 1.78 mmol) in N,N-dimethylformamide (4 mL) respectively. After the addition, the reaction solution was stirred at 80° C. for 16 hours. The reaction solution was diluted with ethyl acetate (10 mL), washed sequentially with water (10 mL×3) and brine (10 mL×3). The organic phase was dried over anhydrous sodium sulfate and the filtrate was concentrated under reduced pressure. The residue was purified by silica gel column chromatography (petroleum ether:ethyl acetate=10:1) to give compound 15-b (0.31 mg, yield 64%).

$^1$H-NMR (400 MHz, CDCl$_3$) δ: 7.40 (d, J=8.4 Hz, 1H), 6.48 (d, J=2.8 Hz, 1H), 6.33 (dd, J=2.8, 8.8 Hz, 1H), 4.85-4.94 (m, 1H), 3.94-4.05 (m, 3H), 3.87-3.94 (m, 1H), 3.86 (s, 3H), 2.07-2.29 (m, 2H) ppm Synthesis of Compound 15-a Compound 15-b (309 mg, 1.13 mmol) and bis(pinacolato)diboron (430 mg, 1.7 mmol) were dissolved in dioxane (10 mL), and anhydrous potassium acetate (333 mg, 3.39 mmol) and [1,1'-bis (diphenylphosphino)ferrocene]dichloropalladium.dichloromethane (90 mg, 0.1 mmol) were added. Under nitrogen gas atmosphere, the reaction solution was heated to 100° C. and stirred for 16 hours. After cooling to room temperature, the reaction mixture was diluted with ethyl acetate (20 mL), filtered through celite and the filtrate was concentrated under reduced pressure. The residue was purified by silica gel column chromatography (petroleum ether:ethyl acetate=10:1) to give compound 15-a (170 mg, yield 47%). LC-MS (ESI): m/z=321[M+H]$^+$.

Synthesis of Compound 15

Compound 15-a (92 mg, 0.28 mmol), compound 2-a (100 mg, 0.31 mmol) and sodium carbonate (92 mg, 0.86 mmol) were suspended in dioxane (2.5 mL) and water (2.5 mL), [1,1'-bis(diphenylphosphino)ferrocene]dichloropalladium-.dichloromethane (15 mg, 0.018 mmol) was added. The reaction solution was purged with nitrogen gas for three times, and stirred at 80° C. for 16 hours. After cooling to room temperature, the reaction mixture was filtered through celite, the filter cake was washed with ethyl acetate (20 mL), the filtrate was washed with brine (20 mL), the organic phase was dried over anhydrous sodium sulfate, filtered and the filtrate was concentrated under reduced pressure, and the residue was purified by silica gel TLC preparative plate (dichloromethane:methanol=10:1) to give compound 15 (16 mg, yield 13%). LC-MS (ESI): m/z=438[M+H]$^+$.

$^1$H-NMR (400 MHz, CDCl$_3$) δ: 8.73 (s, 1H), 7.80 (s, 1H), 7.40 (s, 1H), 7.30 (d, J=8.4 Hz, 1H), 7.17 (brs, 1H), 6.52-6.66 (m, 2H), 4.96-5.07 (m, 1H), 3.99-4.11 (m, 3H), 3.88-3.99 (m, 1H), 3.80 (s, 3H), 3.74 (s, 3H), 2.48 (s, 3H), 2.17-2.31 (m, 2H) ppm Example 16

N-(7-{4-[3-(1-azetidinyl)propoxy-2-methoxyphenyl}-6-methylthieno[3,2-d]pyrimidinyl-2-yl)-1-methyl-1H-pyrazol-4-amine (Compound 16)

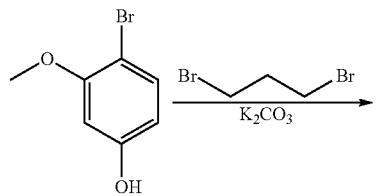

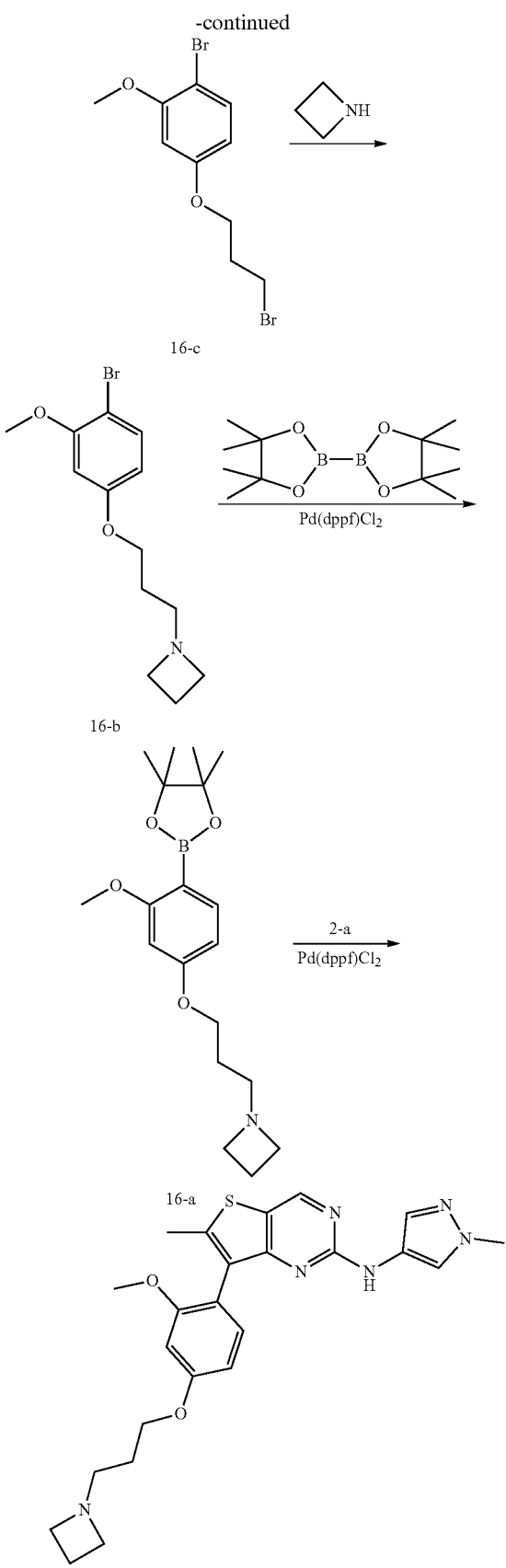

Synthesis of Compound 16-c

3-Methoxy-4-bromophenol (350 mg, 1.73 mmol) and potassium carbonate (716 mg, 5.19 mmol) were suspended in acetonitrile (10 mL), 1,3-dibromopropane (700 mg, 3.46 mmol) was added. The reaction solution was heated to 80° C. for 6 hours. After cooling to room temperature, the reaction solution was filtered, the filter cake was washed with ethyl acetate (50 mL), and the filtrate was concentrated under reduced pressure. The residue was partitioned between ethyl acetate (50 mL) and water (50 mL). The organic phase was dried over anhydrous sodium sulfate, filtered and the filtrate was concentrated under reduced pressure. The residue was purified by silica gel column chromatography (petroleum ether:ethyl acetate=10:1) to give 16-c as a colorless oil (310 mg, yield 56%).

$^1$H-NMR (400 MHz, CDCl$_3$) δ: 7.40 (d, J=9 Hz, 1H), 6.49 (d, J=3 Hz, 1H), 6.40 (dd, J=9 Hz, J=3 Hz, 1H), 4.11 (t, J=6 Hz, 2H), 3.87 (s, 3H), 3.61 (t, J=6 Hz, 2H), 2.31 (m, 2H) ppm Synthesis of Compound 16-b Compound 16-c (150 mg, 0.47 mmol) was dissolved in N,N-dimethylacetamide (1 mL), and azetidine (0.5 mL) was added. The reaction solution was heated to 80° C. and reacted for 2 hours, then diluted with water (20 mL), followed by extraction with ethyl acetate (20 mL×2). The combined organic phase was dried over anhydrous sodium sulfate, filtered and the filtrate was concentrated under reduced pressure to give 16-b as a pale yellow oil (310 mg), which was directly used for the next step without purification. LC-MS (ESI): m/z=300[M+H]$^+$.

Synthesis of Compound 16-a

Compound 16-b (310 mg, 1.03 mmol) and bis(pinacolato)diboron (177 mg, 0.69 mmol) were dissolved in dioxane (5 mL), anhydrous potassium acetate (114 mg, 1.39 mmol) and [1,1'-bis(diphenylphosphino)ferrocene]dichloro-palladium-.dichloromethane (41 mg, 0.05 mmol) were added. Under nitrogen gas atmosphere, the mixture was heated to 85° C. and stirred for 16 hours. After cooling to room temperature, the mixture was diluted with ethyl acetate (20 mL) and filtered through celite. The filtrate was concentrated to dryness to give 16-a as a black oil (190 mg), which was directly used for the next step without purification. LC-MS (ESI): m/z=348[M+H]$^+$.

Synthesis of Compound 16

Compound 16-a (190 mg, 0.54 mmol), compound 2-a (90 mg, 0.28 mmol) and sodium carbonate (88 mg, 0.84 mmol) were suspended in dioxane (0.5 mL) and water (0.5 mL), [1,1'-bis(diphenylphosphino)ferrocene]dichloropalladium-.dichloromethane (25 mg, 0.03 mmol) was added. The mixture was purged with nitrogen gas for three times, and heated to 90° C. under microwave to react for 40 minutes. After cooling to the room temperature, the reaction was concentrated under reduced pressure to remove solvent, the residue was partitioned between dichloromethane (50 mL) and water (50 mL). The combined organic phase was dried over anhydrous sodium sulfate, filtered and the filtrate was concentrated under reduced pressure. The residue was purified by preparative HPLC (mobile phase: 10 mM aqueous ammonium bicarbonate solution:acetonitrile=35%-45%) to give 16 as a white solid (12 mg, yield 7%). LC-MS (ESI): m/z=465[M+H]$^+$.

$^1$H-NMR (400 MHz, CDCl$_3$) δ: 8.72 (s, 2H), 7.82 (s, 1H), 7.39 (s, 1H), 7.28-7.39 (m, 1H), 6.94 (br, 1H), 6.62-6.65 (m, 2H), 4.08 (t, J=6 Hz, 2H), 3.86 (s, 3H), 3.80 (s, 3H), 3.20-3.27 (m, 4H), 2.60-2.64 (m, 2H), 2.48 (s, 3H), 2.11 (m, 2H), 1.84 (m, 2H) ppm

Example 17

N-(7-{2-methoxy-4-[3-(4-morpholinyl)propoxy]phenyl}-6-methylthieno[3,2-d]pyrimidinyl-2-yl)-1-methyl-1H-pyrazol-4-amine (Compound 17)

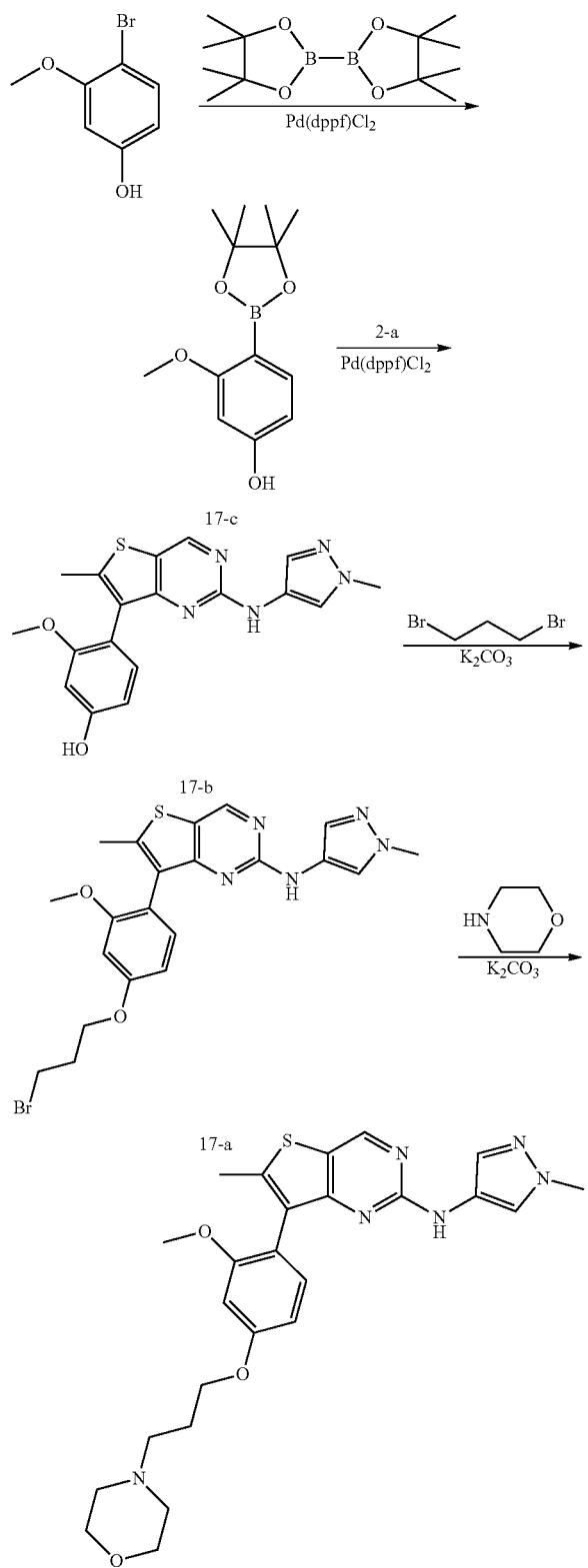

Synthesis of Compound 17-c

3-Methoxy-4-bromophenol (5 g, 24.75 mmol) and bis(pinacolato)diboron (9.43 g, 37.13 mmol) were dissolved in dioxane (50 mL), anhydrous potassium acetate (6.1 g, 74.25 mmol) and [1,1'-bis (diphenylphosphino)ferrocene]dichloro-palladium.dichloromethane (2 g, 2.47 mmol) were added. Under nitrogen gas atmosphere, the mixture was heated to 80° C. and stirred for 16 hours. After cooling to room temperature, the mixture was diluted with ethyl acetate (50 mL) and filtered through celite, the filtrate was concentrated under reduced pressure. The residue was purified by silica gel column chromatography (petroleum ether:ethyl acetate=1:1) to give 17-c as a pale yellow solid (2.8 g, yield 45%). LC-MS (ESI): m/z=251[M+H]$^+$.

Synthesis of Compound 17-b

Compound 17-c (900 mg, 3.6 mmol), compound 2-a (969 mg, 3.0 mmol) and sodium carbonate (980 mg, 9.0 mmol) were suspended in dioxane (5 mL) and water (5 mL), [1,1'-bis(diphenylphosphino)ferrocene]dichloropalladium-.dichloromethane (245 mg, 0.3 mmol) was added. The reaction solution was purged with nitrogen gas for three times and heated to 90° C. under microwave for 40 minutes. After cooling to room temperature, the reaction solution was concentrated under reduced pressure to remove the solvent. The residue was partitioned between ethyl acetate (50 mL) and water (50 mL). The organic phase was dried over anhydrous sodium sulfate, filtered and the filtrate was concentrated under reduced pressure. The residue was purified by silica gel column chromatography (dichloromethane:methanol=20:1) to give 17-b as a pale yellow solid (350 mg, yield 32%). LC-MS (ESI): m/z=368[M+H]$^+$.

Synthesis of Compound 17-a

Compound 17-b (90 mg, 0.25 mmol) and potassium carbonate (51 mg, 0.37 mmol) were suspended in acetonitrile (10 mL), and 1,3-dibromopropane (72 mg, 0.36 mmol) was added. The reaction mixture was heated to 60° C. and stirred for 3 hours. After cooling to room temperature, the mixture was filtered and the filter cake was washed with ethyl acetate (50 mL). The filtrate was concentrated under reduced pressure and the residue was partitioned between ethyl acetate (50 mL) and water (50 mL). The organic phase was dried over anhydrous sodium sulfate, filtered, and the filtrate was concentrated under reduced pressure to give 17-a as a pale yellow oil (120 mg), which was directly used for the next step without purification.

Synthesis of Compound 17

Compound 17-a (35 mg, 0.072 mmol) and potassium carbonate (30 mg, 0.22 mmol) were suspended in acetonitrile (2 mL), and morpholine (19 mg, 0.22 mmol) was added. The reaction mixture was heated to 60° C. and stirred for 3 hours. After cooling to room temperature, the mixture was filtered and the filter cake was washed with acetonitrile (10 mL). The filtrate was concentrated under reduced pressure and the residue was purified by preparative HPLC (mobile phase: 0.05% aqueous trifluoroacetic acid:acetonitrile=20% to 50%) to give 17 as a pale yellow solid (20 mg, yield 56%). LC-MS (ESI): m/z=495[M+H]$^+$.

$^1$H-NMR (400 MHz, CDCl$_3$) δ: 8.72 (s, 1H), 7.81 (s, 1H), 7.41 (s, 1H), 7.29 (d, J=8 Hz, 1H), 6.87 (br, 1H), 6.61-6.67 (m, 2H), 4.10 (t, J=6 Hz, 2H), 3.93 (s, 3H), 3.75 (s, 3H), 3.74 (br, 4H), 2.59 (t, J=6 Hz, 2H), 2.51 (br, 4H), 2.48 (s, 3H), 2.03 (m, 2H) ppm

Example 18

N-(7-{2-methoxy-4-[3-(1-pyrrolidinyl)propoxy]phenyl}-6-methylthieno[3,2-d]pyrimidinyl-2-yl)-1-methyl-1H-pyrazol-4-amine (Compound 18)

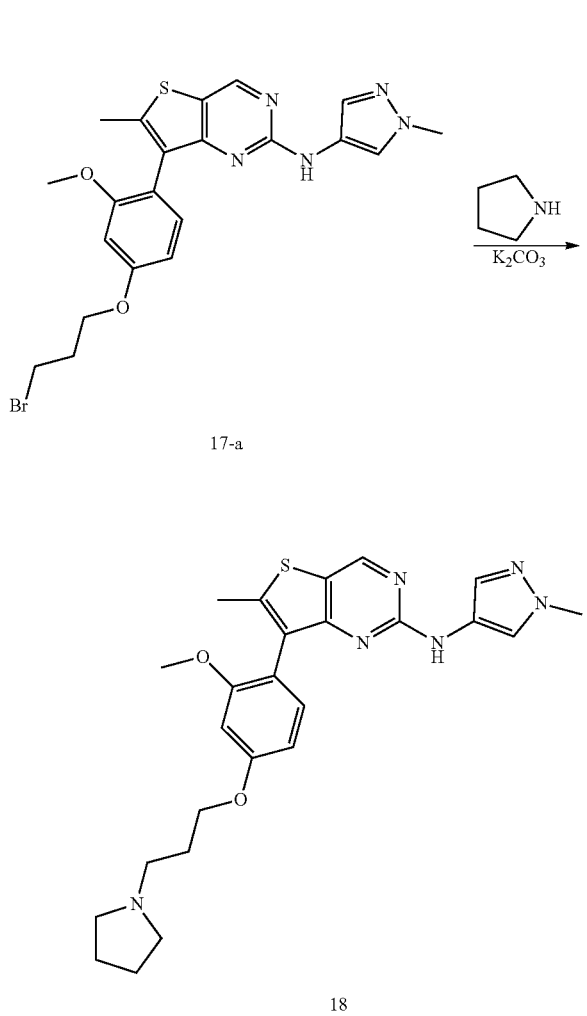

Synthesis of Compound 18

Compound 17-a (35 mg, 0.072 mmol) and potassium carbonate (15 mg, 0.11 mmol) were suspended in acetonitrile (2 mL), and pyrrolidine (8 mg, 0.11 mmol) was added. The reaction mixture was heated to 80° C. and stirred for 3 hours. After cooling to room temperature, the mixture was filtered and the filter cake was washed with acetonitrile (10 mL). The filtrate was concentrated under reduced pressure and the residue was purified by preparative HPLC (mobile phase: 0.05% aqueous ammonium bicarbonate solution:acetonitrile=45% to 75%) to give 18 as a pale yellow solid (8 mg, yield 28%). LC-MS (ESI): m/z=408[M+H]+.

$^1$H-NMR (400 MHz, CDCl$_3$) δ: 8.72 (s, 1H), 7.82 (s, 1H), 7.39 (s, 1H), 7.29 (d, J=8 Hz, 1H), 7.13 (br, 1H), 6.62-6.66 (m, 2H), 4.10 (t, J=6 Hz, 2H), 3.79 (s, 3H), 3.75 (s, 3H), 2.69 (t, J=6 Hz, 2H), 2.56 (m, 4H), 2.48 (s, 3H), 2.07 (m, 2H), 1.81 (m, 4H) ppm

Example 19

N-(7-{2-methoxy-4-[3-(4-methylpiperazin-1-yl)propoxy]phenyl}-6-methylthieno[3,2-d]pyrimidinyl-2-yl)-1-methyl-1H-pyrazol-4-amine (Compound 19)

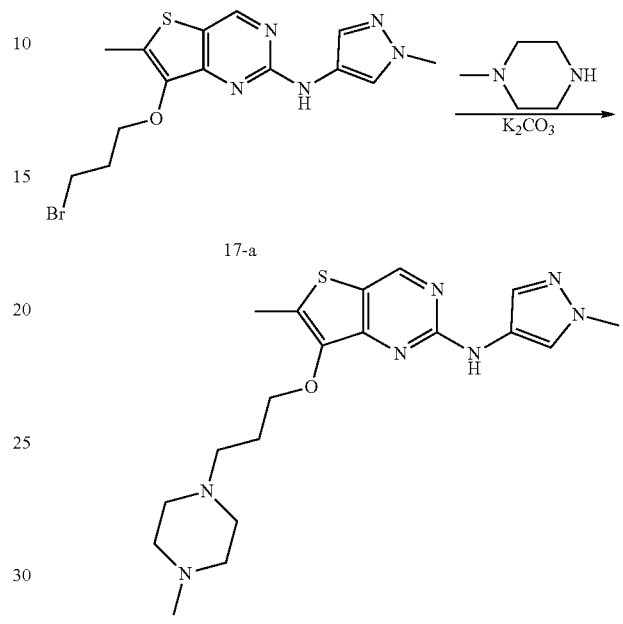

Synthesis of Compound 19

Compound 17-a (35 mg, 0.072 mmol) and potassium carbonate (15 mg, 0.11 mmol) were suspended in acetonitrile (2 mL), and N-methylpiperazine (11 mg, 0.11 mmol) was added. The reaction mixture was heated to 80° C. and stirred for 3 hours. After cooling to room temperature, the mixture was filtered and the filter cake was washed with acetonitrile (10 mL). The filtrate was concentrated under reduced pressure and the residue was purified by preparative HPLC (mobile phase: 0.05% aqueous ammonium bicarbonate solution:acetonitrile=20% to 50%) to give 19 as a pale yellow solid (8 mg, yield 28%). LC-MS (ESI): m/z=508 [M+H]+.

$^1$H-NMR (400 MHz, CDCl$_3$) δ: 8.72 (s, 1H), 7.82 (s, 1H), 7.39 (s, 1H), 7.29 (d, J=8 Hz, 1H), 6.83 (br, 1H), 6.61-6.66 (m, 2H), 4.10 (t, J=6 Hz, 2H), 3.79 (s, 3H), 3.75 (s, 3H), 2.59 (t, J=6 Hz, 2H), 2.52 (br, 4H), 2.47 (s, 3H), 2.32 (s, 3H), 2.07 (m, 2H), 1.67 (br, 4H) ppm

Example 20

2-(4-{[7-(4-methylsulfonyl-2-methoxyphenyl)-6-methylthieno[3,2-d]pyrimidinyl-2-yl]amino}-1H-pyrazol-1-yl)-1-ethanol (Compound 20)

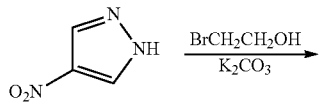

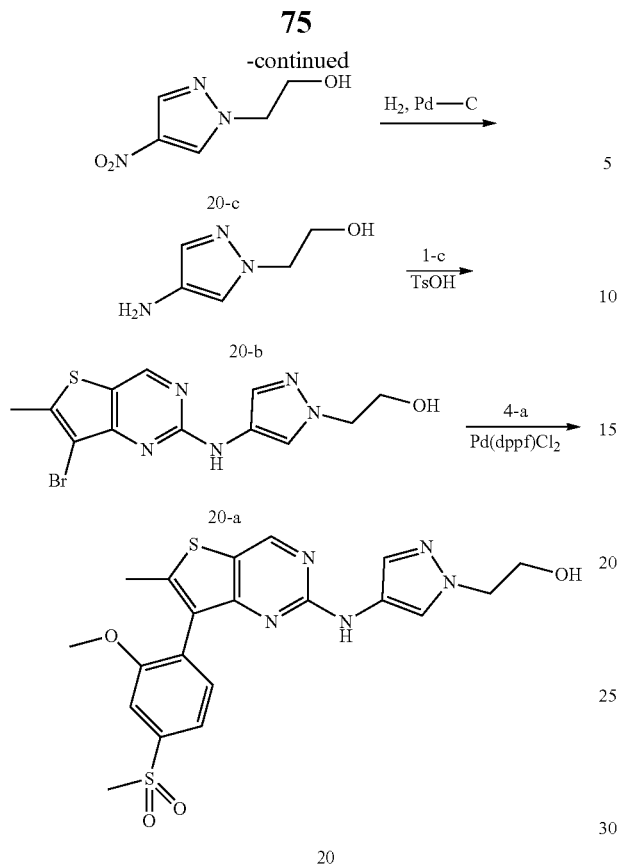

Synthesis of Compound 20-c

Bromoethanol (1.9 g, 15.57 mmol) and potassium carbonate (2.9 g, 21.12 mmol) were sequentially added to a solution of 4-nitropyrazole (1.6 g, 14.16 mmol) in acetonitrile (20 mL). The suspension was stirred at 60° C. for 16 hours. After cooling to room temperature, the mixture was filtered and the filter cake was washed with acetonitrile (10 mL). The filtrate was concentrated under reduced pressure to give 20-c as a yellow oil (1.1 g, yield 49.5%), which was directly used for the next step without purification.

Synthesis of Compound 20-b

Palladium 10% on carbon (0.2 g) was added to a solution of compound 20-c (1.1 g, 7 mmol) in ethanol (20 mL) under hydrogen gas atmosphere (1 atm). The mixture was reacted at 25° C. for 16 hours, filtered and the filtrate was concentrated under reduced pressure to give 20-b as a red oil (740 mg, yield 83%), which was directly used for the next step without purification. LC-MS (ESI): m/z=128[M+H]$^+$.

Synthesis of Compound 20-a

Compound 1-c (1 g, 3.82 mmol) and compound 20-b (1.45 g, 11.45 mmol) were dissolved in n-butanol (15 mL), and p-toluenesulfonic acid monohydrate (2.17 g, 11.45 mmol) was added. The mixture was heated to 110° C. and stirred for 16 hours, then cooled to 0° C. filtered and the filter cake was washed with saturated sodium bicarbonate solution (50 mL) to give 20-a as a pale yellow solid (950 mg, yield 71%), which was used without purification. LC-MS (ESI): m/z=354[M+H]$^+$.

Synthesis of Compound 20

Compound 20-a (102 mg, 0.29 mmol), compound 4-a (136 mg, 0.43 mmol) and sodium carbonate (93 mg, 0.86 mmol) were suspended in dioxane (2 mL) and water (2 mL), and [1,1'-bis(diphenylphosphino)ferrocene]dichloro-palladium.dichloromethane (25 mg, 0.03 mmol) was added. The system was purged with nitrogen gas for three times, and the reaction solution was heated to 90° C. under microwave for 40 minutes. After the reaction solution was cooled to room temperature, the reaction solution was concentrated under reduced pressure, the residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 20 as a pale yellow solid (10 mg, yield 8%). LC-MS (ESI): m/z=460[M+H]$^+$.

$^1$H-NMR (400 MHz, CDCl$_3$) δ: 8.76 (s, 2H), 7.94 (s, 1H), 7.82 (s, 1H), 7.49 (d, J=8 Hz, 1H), 7.44 (s, 1H), 7.36 (d, J=8 Hz, 1H), 6.98 (br, 1H), 4.19 (t, J=6 Hz, 1H), 3.94 (s, 5H), 3.13 (s, 4H), 2.67 (s, 3H) ppm Example 21

2-(4-{[7-(2-methoxyphenyl)-6-methylthieno[3,2-d]pyrimidinyl-2-yl]amino}-1H-pyrazol-1-yl)-1-ethanol (Compound 21)

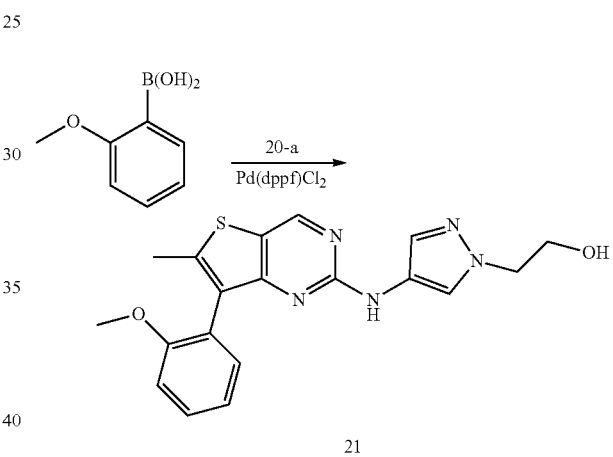

Synthesis of Compound 21

Compound 20-a (100 mg, 0.28 mmol), 2-methoxyphenylboronic acid (65 mg, 0.42 mmol) and sodium carbonate (89 mg, 0.84 mmol) were suspended in dioxane (2 mL) and water (2 mL), and [1,1'-bis(diphenylphosphino)ferrocene] dichloro-palladium.dichloromethane (25 mg, 0.03 mmol) was added. The system was purged with nitrogen gas for three times, and the reaction solution was heated to 90° C. under microwave for 40 minutes. After the reaction solution was cooled to room temperature, the reaction solution was concentrated under reduced pressure, the residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 21 as a pale yellow solid (25 mg, yield 23%). LC-MS (ESI): m/z=382[M+H]$^+$.

$^1$H-NMR (400 MHz, CDCl$_3$) δ: 8.73 (s, 1H), 7.86 (s, 1H), 7.38-7.74 (m, 3H), 7.13 (t, J=8 Hz, 1H), 7.06 (d, J=8 Hz, 2H), 6.88 (br, 1H), 4.08 (t, J=4 Hz, 1H), 3.95 (t, J=4 Hz, 4H), 3.09 (br, 1H), 2.49 (s, 3H) ppm

Example 22

4-[2-(4-{[7-(2-methoxyphenyl)-6-methylthieno[3,2-d]pyrimidinyl-2-yl]amino}-1H-pyrazol-1-yl)ethyl]piperazin-1-amine (Compound 22)

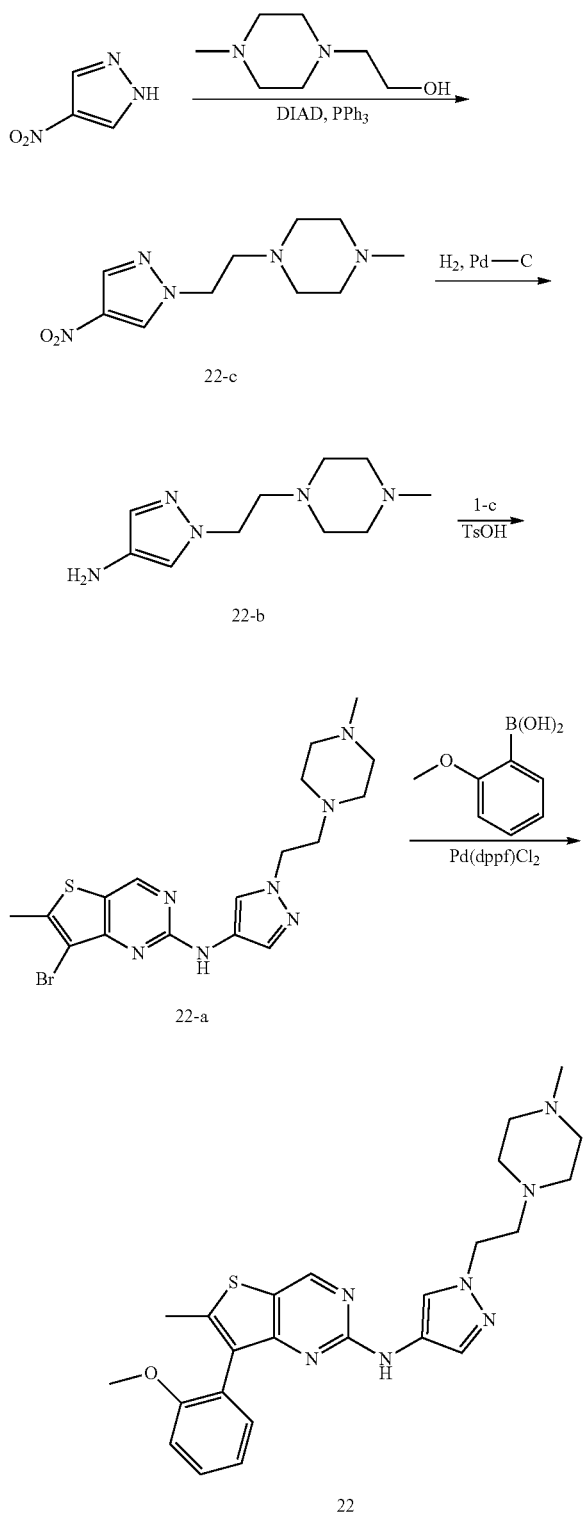

Synthesis of Compound 22-c

4-Nitropyrazole (2.81 g, 13.88 mmol) and 1-hydroxyethyl-4-methylpiperazine (1.0 g, 6.94 mmol) were dissolved in anhydrous tetrahydrofuran (50 mL), and a solution of triphenylphosphine (3.64 g, 13.88 mmol) and diisopropyl azodicarboxylate (2.81 g, 13.88 mmol) in anhydrous tetrahydrofuran (6 mL) was added dropwise under nitrogen gas atmosphere. The reaction solution was stirred at room temperature for 1 hour, and then 1N hydrochloric acid (30 mL) and water (50 mL) was added. The aqueous phase was extracted with ethyl acetate (50 mL×2). The combined organic phase was dried over anhydrous sodium sulfate, filtered and the filtrate was concentrated. The residue was purified by silica gel column chromatography (dichloromethane:methanol=10:1) to give compound 22-c (1.0 g, yield 60.2%). LC-MS (ESI): m/z=240.2[M+H]$^+$.

Synthesis of Compound 22-b

Palladium 10% on carbon (0.2 g) was slowly added to a solution of compound 22-c (1.0 g, 4.18 mmol) in methanol (20 mL) under hydrogen gas atmosphere (1 atm). The mixture was reacted at 25° C. for 16 hours, and dichloromethane (50 mL) was added to the reaction solution. The reaction solution was filtered through celite to remove palladium-carbon, and the filtrate was concentrated under reduced pressure to give 20-b (680 mg, yield 77.8%), which was directly used for the next step without purification.

Synthesis of Compound 22-a

Compound 1-c (200 mg, 0.76 mmol) and compound 22-b (319 mg, 1.53 mmol) were dissolved in iso-butanol (5 mL), and p-toluenesulfonic acid monohydrate (435 mg, 2.29 mmol) was added. The mixture was heated to 108° C. and stirred for 16 hours. After the mixture was cooled to room temperature, a saturated sodium bicarbonate solution (50 mL) was slowly added thereto. The aqueous phase was extracted with a mixed solvent (50 mL×2) of tetrahydrofuran and ethyl acetate (1:1). The combined organic layer was dried over anhydrous sodium sulfate, filtered and the filtrate was concentrated under reduced pressure. The residue was purified by silica gel column chromatography (dichloromethane:methanol:aqueous ammonia=64:8:1) to give compound 22-a (150 mg, yield 45%). LC-MS (ESI): m/z=436[M+H]$^+$.

Synthesis of Compound 22

Compound 22-a (60 mg, 0.138 mmol), 2-methoxyphenylboronic acid (42 mg, 0.275 mmol) and sodium carbonate (44 mg, 0.414 mmol) were suspended in dioxane (1.6 mL) and water (0.4 mL), and [1,1'-bis(diphenylphosphino)ferrocene]dichloro-palladium.dichloromethane (10 mg, 0.0138 mmol) was added. The reaction solution was purged with nitrogen gas for three times, and heated to 90° C. under microwave for 40 minutes. After cooling to room temperature, the reaction solution was concentrated under reduced pressure, the residue was dissolved in dichloromethane (50 mL), filtered through celite and the filtrate was concentrated under reduced pressure. The residue was purified by preparative HPLC (mobile phase: 10 mM aqueous ammonium bicarbonate:acetonitrile=40%-50%) to give 22 as a pale yellow solid (38 mg, yield 59.6%). LC-MS (ESI): m/z=464[M+H]$^+$.

$^1$H NMR (400 MHz, CDCl$_3$) δ: 8.73 (s, 1H), 7.82 (s, 1H), 7.39-7.45 (m, 3H), 7.05-7.14 (m, 2H), 6.85 (s, 1H), 4.10 (t, J=7.2 Hz, 2H), 3.78 (s, 3H), 2.74 (t, J=7.2 Hz, 2H), 2.39-2.56 (m, 11H), 2.29 (s, 3H) ppm

Example 23

1-(azetidinyl)-2-(3-methoxy-4-{6-methyl-2-[(1-methyl-1H-pyrazol-4-yl) amino]thieno[3,2-d]pyrimidinyl-7-yl}phenoxy)-1-ethanol (Compound 23)

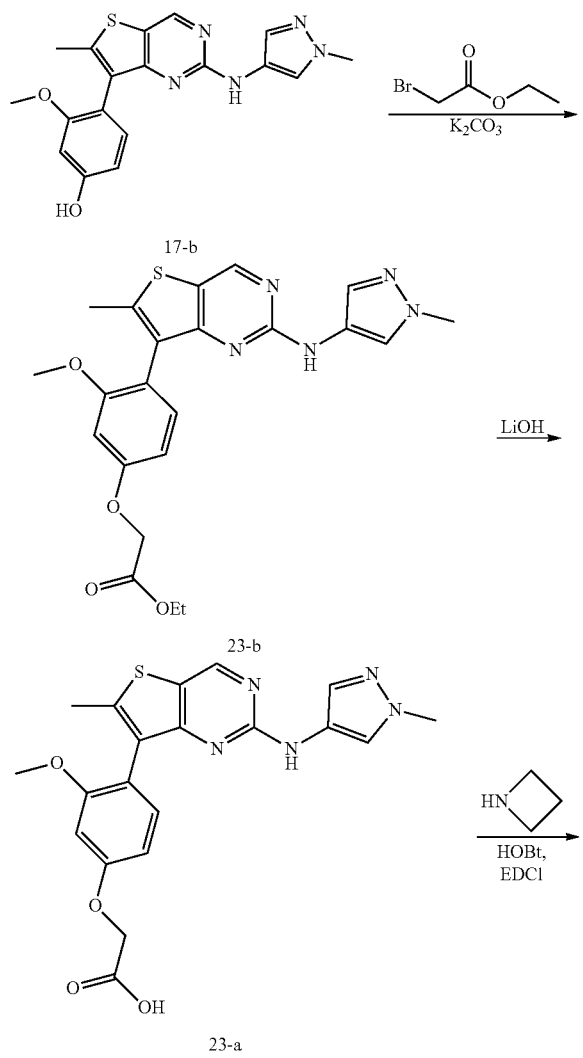

Synthesis of Compound 23-b

Compound 17-b (120 mg, 0.33 mmol) and ethyl bromoacetate (82 mg, 0.49 mmol) were dissolved in acetonitrile (2 mL) and potassium carbonate (69 mg, 0.49 mmol) was added and the reaction mixture was stirred at room temperature for 16 hours, then filtered. The filter cake was washed with dichloromethane (50 mL) and the combined filtrate was concentrated to dryness to give 23-b as a pale yellow syrup (110 mg, yield 74%), which was used directly for the next step without further purification. LC-MS (ESI): m/z=454[M+H]$^+$.

Synthesis of Compound 23-a

Compound 23-b (110 mg, 0.24 mmol) was dissolved in tetrahydrofuran (3 mL) and water (0.5 mL), and lithium hydroxide monohydrate (20 mg, 0.49 mmol) was added and the mixture was stirred overnight at room temperature. The reaction solution was concentrated and the residue was adjusted to pH=3 with 2N hydrochloric acid, then filtered and the filter cake was dried in vacuo to give 23-b as a pale yellow solid (108 mg), which was used directly for the next step without further purification.

Synthesis of Compound 23

23-b (108 mg, 0.25 mmol) was dissolved in dichloromethane (5 mL), and N, N-diisopropylethylamine (0.5 mL), N-hydroxybenzotriazole (7 mg, 0.05 mmol), azetidine (28 mg, 0.49 mmol) and 1-ethyl-(3-dimethylaminopropyl)carbodiimide hydrochloride (139 mg, 0.73 mmol) were added. The reaction solution was stirred at room temperature for 16 hours, diluted with dichloromethane (50 mL), washed sequentially with water (20 mL), 0.1N hydrochloric acid (20 mL) and water (20 mL). The organic phase was separated and dried over anhydrous sodium sulfate, then filtered and the filtrate was concentrated under reduced pressure, the residue was purified by preparative HPLC (mobile phase: 10 mM aqueous ammonium bicarbonate solution:acetonitrile=35% to 45%) to give 23 as a colorless solid (25 mg, yield 23%). LC-MS (ESI): m/z=465[M+H]$^+$.

$^1$H-NMR (400 MHz, CDCl$_3$) δ: 8.73 (s, 1H), 7.80 (s, 1H), 7.41 (s, 1H), 7.32 (d, J=8 Hz, 1H), 6.81 (br, 1H), 6.62-6.65 (m, 2H), 4.64 (s, 2H), 4.41 (t, J=8 Hz, 2H), 4.14 (t, J=8 Hz, 4H), 3.81 (s, 3H), 3.76 (s, 3H), 2.47 (s, 3H), 2.36 (m, 2H) ppm

Example 24

2-(4-{[7-(4-(3-methylsulfonylpropoxy)-2-methoxyphenyl]-6-methylthieno[3,2-d]pyrimidinyl-2-yl}amino)-1H-pyrazol-1-yl]-1-ethanol (Compound 24)

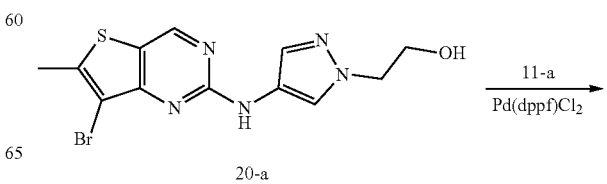

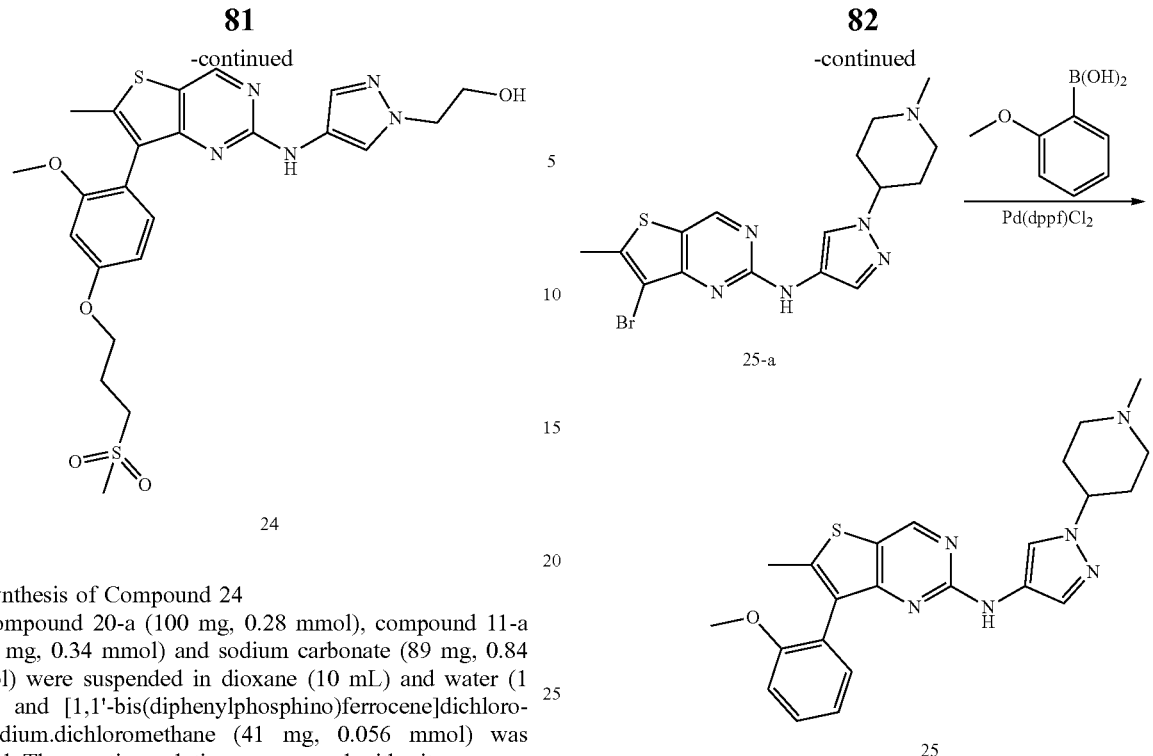

24

Synthesis of Compound 24

Compound 20-a (100 mg, 0.28 mmol), compound 11-a (125 mg, 0.34 mmol) and sodium carbonate (89 mg, 0.84 mmol) were suspended in dioxane (10 mL) and water (1 mL), and [1,1'-bis(diphenylphosphino)ferrocene]dichloropalladium.dichloromethane (41 mg, 0.056 mmol) was added. The reaction solution was purged with nitrogen gas for three times, then heated to 90° C. and stirred for 16 hours. After cooling to room temperature, the reaction solution was separated and concentrated under reduced pressure, the residue was purified by preparative HPLC (mobile phase: 10 mM aqueous ammonium bicarbonate solution:acetonitrile=35% to 45%) to give 19 as a pale yellow solid (41 mg, yield 28%). LC-MS (ESI): m/z=518 [M+H]$^+$.

$^1$H NMR (400 MHz, CDCl$_3$) δ: 8.71 (s, 1H), 7.85 (s, 1H), 7.45 (s, 1H), 7.30 (d, J=8.1 Hz, 1H), 6.97 (s, 1H), 6.66-6.57 (m, 2H), 4.22 (t, J=5.5 Hz, 2H), 4.11 (t, J=4.9 Hz, 2H), 3.95 (s, 2H), 3.76 (s, 3H), 3.37-3.28 (m, 2H), 2.99 (s, 3H), 2.47 (s, 3H), 2.41 (dd, J=13.7, 6.9 Hz, 2H) ppm Example 25

N-[7-(2-methoxyphenyl)-6-methylthieno[3,2-d]pyrimidinyl-2-yl]-1-(1-methylpiperidin-4-yl)-1H-pyrazol-4-amine (Compound 25)

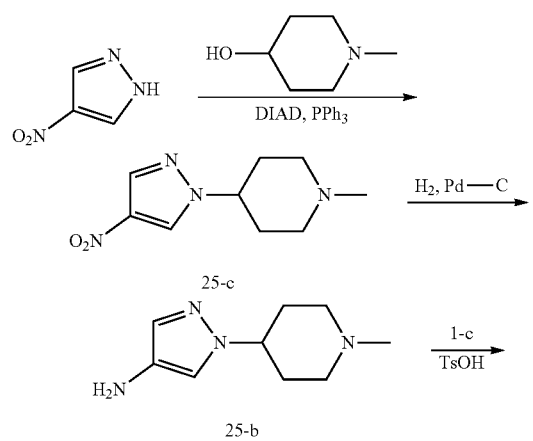

Synthesis of Compound 25-c

4-Nitropyrazole (2 g, 17.69 mmol), triphenylphosphine (6.95 g, 26.54 mmol) and N-methyl-4-hydroxypiperidine (2.4 g, 21.23 mmol) were dissolved in anhydrous tetrahydrofuran (50 mL). The solution was cooled to 0° C. and diisopropylazodicarboxylate (5.4 g, 26.54 mmol) was slowly added dropwise. After the addition, the mixture was warmed to room temperature and stirred for 16 hours. The mixture was concentrated under reduced pressure and the residue was diluted with ethyl acetate (50 mL) and 3N aqueous hydrochloric acid solution (50 mL) was added. The aqueous phase was adjusted to pH=9 with saturated potassium carbonate solution and then extracted with ethyl acetate (50 mL×2). The combined organic phase was dried over anhydrous sodium sulfate, filtered and the filtrate was concentrated under reduced pressure to give 25-c as a yellow oil (2.1 g, yield: 57%).

Synthesis of Compound 25-b

Palladium 10% on carbon (0.1 g) was added to a solution of compound 25-c (1.0 g, 4.18 mmol) in ethanol (10 mL) under hydrogen gas atmosphere (1 atm). The mixture was reacted at 25° C. for 16 hours, then filtered through celite to remove palladium-carbon and the filtrate was concentrated under reduced pressure to give 25-b as a reddish brown oil (420 mg, yield 98%), which was used directly for the next step without further purification. LC-MS (ESI): m/z=181 [M+H]$^+$.

Synthesis of Compound 25-a

Compound 1-c (200 mg, 3.09 mmol) and compound 25-b (334 mg, 9.28 mmol) were dissolved in n-butanol (2 mL), and p-toluenesulfonic acid monohydrate (588 mg, 15.48 mmol) was added. The reaction solution was heated to 110° C. and stirred for 16 hours. After cooling to room temperature, the reaction solution was concentrated under reduced pressure, and the residue was partitioned between dichloromethane (20 mL) and saturated sodium carbonate (20 mL). The organic phase was dried over anhydrous sodium sulfate, filtered and the filtrate was concentrated under reduced pressure, and the residue was purified by TLC preparative plate (dichloromethane:methanol=10:1) to give 25-a as a pale yellow solid (50 mg, yield 20%). LC-MS (ESI): m/z=407[M+H]⁺.

Synthesis of Compound 25

Compound 25-a (50 mg, 0.12 mmol), 2-methoxyphenylboronic acid (28 mg, 0.19 mmol) and sodium carbonate (40 mg, 0.37 mmol) were suspended in dioxane (0.5 mL) and water (0.5 mL), and [1,1'-bis(diphenylphosphino)ferrocene]dichloro-palladium.dichloromethane (11 mg, 0.02 mmol) was added. The reaction solution was purged with nitrogen gas for three times, then heated to 80° C. under microwave for 40 minutes. After cooling to room temperature, the reaction solution was concentrated under reduced pressure to remove solvent, and the residue was partitioned between dichloromethane (50 mL) and water (50 mL). The organic phase was dried over anhydrous sodium sulfate, filtered and the filtrate was concentrated under reduced pressure, and the residue was purified by silica gel TLC preparative plate (dichloromethane:methanol=10:1) to give 25 as a pale yellow solid (21 mg, yield 40%). LC-MS (ESI): m/z=435[M+H]⁺.

¹H-NMR (400 MHz, CDCl₃) δ: 8.71 (s, 1H), 7.86 (s, 1H), 7.36-7.45 (m, 3H), 7.04-7.13 (m, 3H), 3.94 (m, 1H), 3.77 (s, 3H), 2.97 (m, 2H), 2.47 (s, 3H), 2.36 (s, 3H), 2.14 (m, 2H), 2.05 (m, 2H), 1.91 (m, 2H) ppm Example 26

N-[7-(2-methoxyphenyl)-6-methylthieno[3,2-d]pyrimidinyl-2-yl]-1-[3-(1-pyrrolidinyl)propyl]-1H-pyrazol-4-amine (Compound 26)

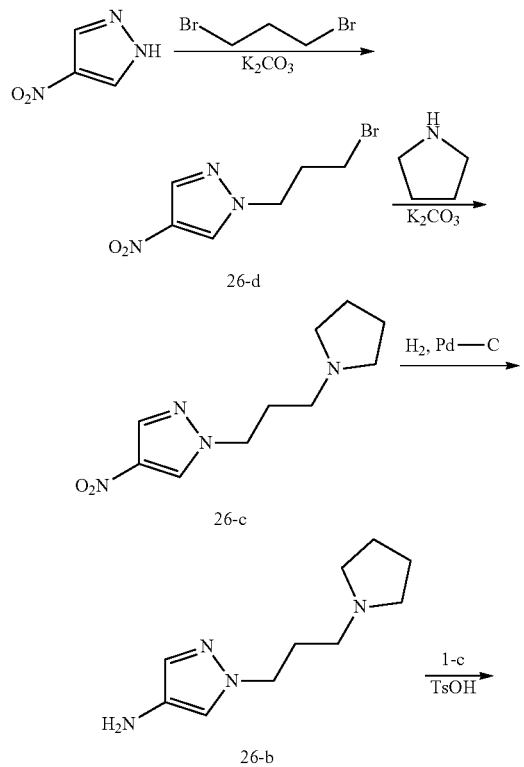

Synthesis of Compound 26-d 1,3-Dibromopropane (8.92 g, 44.2 mmol) and potassium carbonate (6.10 g, 44.2 mmol) were sequentially added to a solution of 4-nitropyrazole (2.5 g, 22.12 mmol) in acetonitrile (50 mL). The suspension was stirred at 60° C. for 8 hours. After cooling to room temperature, the mixture was added with dichloromethane (200 mL), then filtered and the filtrate was concentrated under reduced pressure. The residue was washed with petroleum ether (30 mL×2) to give 26-c (3.6 g, yield 69.6%), which was directly used for the next step without purification.

Synthesis of Compound 26-c

Pyrrolidine (910 mg, 12.82 mmol) and potassium carbonate (1.77 g, 12.82 mmol) were added successively to a solution of compound 26-d (1.5 g, 6.41 mmol) in acetonitrile (25 mL). The suspension was stirred at 60° C. for 16 hours. After cooling to room temperature, the mixture was added with dichloromethane (50 mL), then filtered and the filtrate was concentrated under reduced pressure. The residue was purified by silica gel column chromatography (dichloromethane:methanol:aqueous ammonia=10:1:0 to 80:8:1) to give compound 26-c (750 mg, yield 52.2%). LC-MS (ESI): m/z=225[M+H]⁺.

Synthesis of Compound 26-b

Palladium 10% on carbon (0.2 g) was slowly added to a solution of compound 26-c (750 mg, 3.35 mmol) in methanol (15 mL) under hydrogen gas atmosphere (1 atm). The mixture was reacted at 25° C. for 16 hours, and dichloromethane (50 mL) was added to the reaction solution. The reaction solution was filtered through celite to remove palladium-carbon, and the filtrate was concentrated under reduced pressure to give 26-b (609 mg, yield 93.8%), which was used directly for the next step without further purification.

Synthesis of Compound 26-a

Compound 1-c (311 mg, 1.18 mmol) and compound 26-b (458 mg, 2.36 mmol) were dissolved in iso-butanol (10 mL), and p-toluenesulfonic acid monohydrate (448 mg, 2.36 mmol) was added. The mixture was heated to 108° C. and stirred for 16 hours. After cooling to room temperature, a saturated sodium bicarbonate solution (50 mL) was slowly added thereto. The aqueous phase was extracted with dichloromethane (50 mL×2). The combined organic layer was dried over anhydrous sodium sulfate, filtered and the filtrate was concentrated under reduced pressure. The residue was purified by silica gel column chromatography (dichloromethane:methanol:aqueous ammonia=80:8:1) to give compound 26-a (175 mg, yield 35.2%). LC-MS (ESI): m/z=421[M+H]$^+$.

Synthesis of Compound 26

Compound 26-a (60 mg, 0.142 mmol), 2-methoxyphenylboronic acid (43 mg, 0.285 mmol) and sodium carbonate (45 mg, 0.427 mmol) were suspended in dioxane (1.6 mL) and water (0.4 mL), and [1,1'-bis(diphenylphosphino)ferrocene]dichloro-palladium.dichloromethane (10 mg, 0.014 mmol) was added. The reaction solution was purged with nitrogen gas for three times, and heated to 90° C. under microwave for 40 minutes. After cooling to room temperature, the reaction solution was concentrated under reduced pressure, the residue was dissolved in dichloromethane (40 mL), filtered through celite and the filtrate was concentrated under reduced pressure. The residue was purified by silica gel column chromatography (dichloromethane:methanol: aqueous ammonia=80:8:1) to give 26 (25 mg, yield 39.2%). LC-MS (ESI): m/z=449[M+H]$^+$.

$^1$H-NMR (400 MHz, CDCl3) δ: 8.73 (s, 1H), 7.81 (s, 1H), 7.38-7.46 (m, 3H), 7.05-7.14 (m, 2H), 4.03 (t, J=6.8 Hz, 2H), 3.77 (s, 3H), 2.40-2.49 (m, 9H), 1.96-2.02 (m, 2H), 1.76-1.79 (m, 4H) ppm Example 27

N-[7-(4-fluoro-2-methoxyphenyl)-6-methylthieno[3,2-d]pyrimidinyl-2-yl]-1-[3-(1-pyrrolidinyl)propyl]-1H-pyrazol-4-amine (Compound 27)

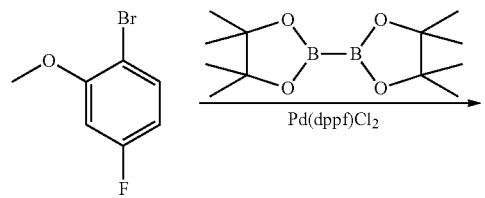

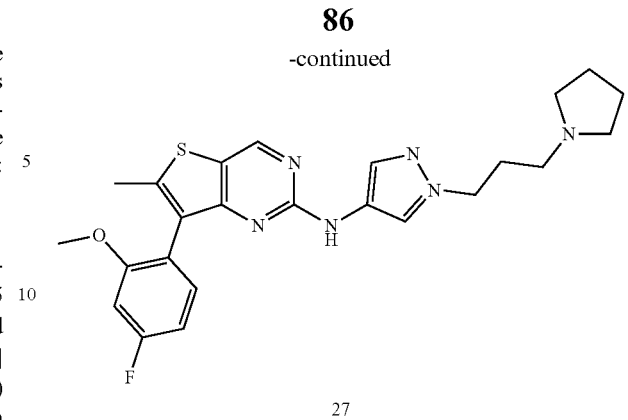

27

Synthesis of Compound 27-a

1-Bromo-4-fluoro-3-methoxybenzene (773 mg, 3.77 mmol) and bis(pinacolato)diboron (1.24 mg, 4.90 mmol) were dissolved in dioxane (10 mL), and anhydrous potassium acetate (1.11 mg, 11.31 mmol) and [1,1'-bis (diphenylphosphino)ferrocene]dichloropalladium.dichloromethane (276 mg, 0.377 mmol) were added. Under nitrogen gas atmosphere, the mixture was heated to 80° C. and stirred for 16 hours. After cooling to room temperature, the mixture was filtered through celite, and the filtrate was concentrated under reduced pressure. The residue was purified by silica gel TLC preparative plate (petroleum ether:ethyl acetate=1:1) to give compound 27-a (600 mg, yield 63%).

$^1$H-NMR (400 MHz, CDCl$_3$) δ: 7.65 (t, J=8.0 Hz, 1H), 6.55-6.66 (m, 2H), 3.82 (s, 3H), 1.34 (s, 12H) ppm Synthesis of Compound 27

Compound 27-a (84 mg, 0.33 mmol), compound 26-a (70 mg, 0.16 mmol) and sodium carbonate (53 mg, 0.5 mmol) were suspended in dioxane (1.6 mL) and water (0.4 mL), [1,1'-bis(diphenylphosphino)ferrocene]dichloropalladium-.dichloromethane (12 mg, 0.016 mmol) was added. The reaction solution was purged with nitrogen gas for three times, heated to 80° C. and stirred for 16 hours. After cooling to the room temperature, the reaction was concentrated under reduced pressure, the residue was dissolved in dichloromethane (40 mL), then filtered through celite, and the filtrate was concentrated under reduced pressure. The residue was purified by preparative HPLC (mobile phase: 0.05% aqueous ammonium bicarbonate solution:acetonitrile=40%-70%) to give 27 (15 mg, yield 19.3%). LC-MS (ESI): m/z=467[M+H]$^+$.

$^1$H-NMR (400 MHz, CDCl3) δ: 8.73 (s, 1H), 7.79 (s, 1H), 7.42 (s, 1H), 7.34-7.40 (m, 1H), 7.12 (s, 1H), 6.77-6.86 (m, 2H), 4.06 (t, J=6.8 Hz, 2H), 3.76 (s, 3H), 2.43-2.51 (m, 9H), 1.98-2.05 (m, 2H), 1.75-1.82 (m, 4H) ppm Example 28

N-methyl-N-(2-{2-[(1-methyl-1H-pyrazol-4-yl)amino]thieno[3,2-d]pyrimidinyl-7-yl}phenyl)methanesulfonamide (Compound 28)

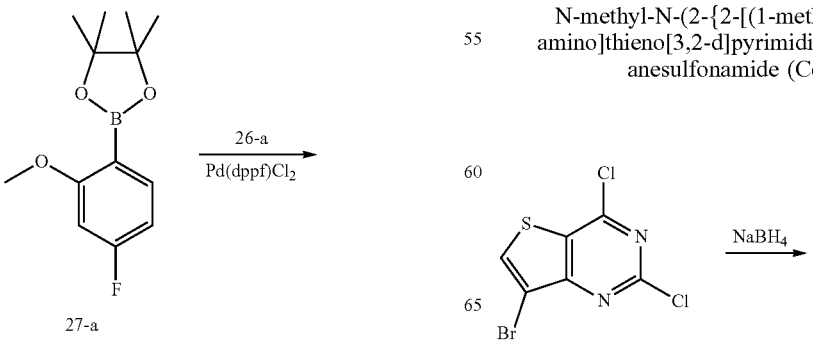

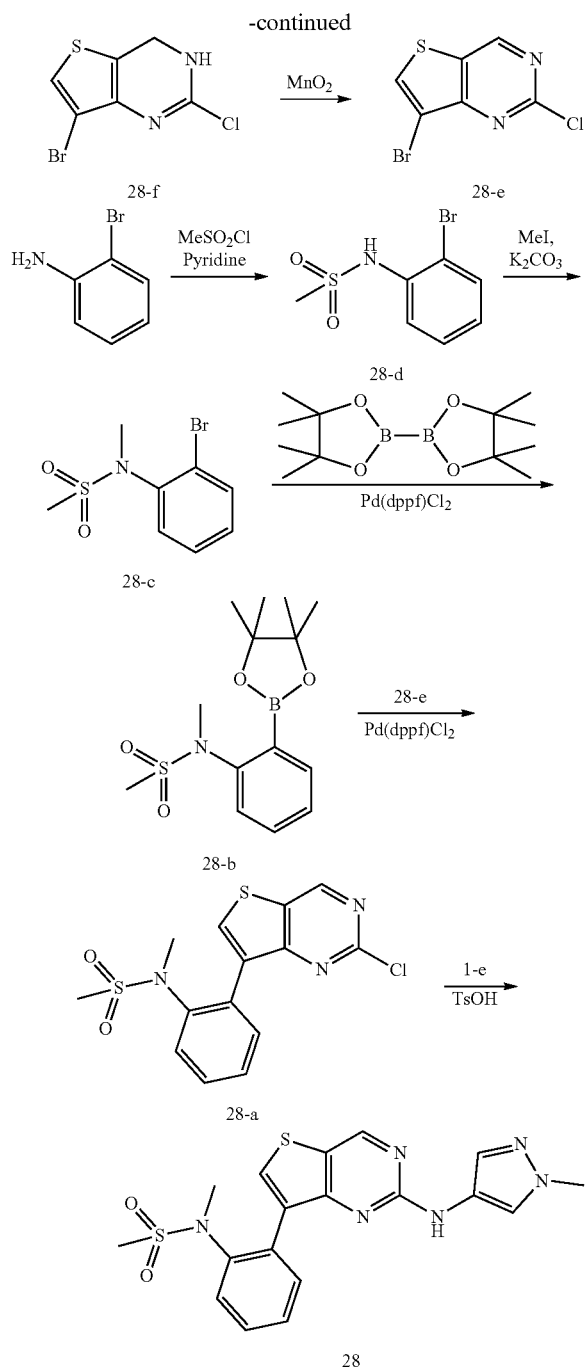

Synthesis of Compound 28-f

7-Bromo-2,4-dichlorothieno[3,2-d]pyrimidine (4.0 g, 14.18 mmol) was dissolved in tetrahydrofuran (60 mL) and ethanol (60 mL). The solution was cooled to 0° C. and sodium borohydride (2.7 g, 71.05 mmol) was added in portions. The reaction solution was warmed to room temperature and stirred for 1 hour, then dichloromethane (500 mL) and water (500 mL) were added. The separated organic phase was dried over anhydrous sodium sulfate, filtered and the filtrate was concentrated under reduced pressure to give 28-f as a yellow solid (2.5 g, yield 71%) which was used without further purification. LC-MS (ESI): m/z=251[M+H]$^+$.

Synthesis of Compound 28-e

Compound 28-f (500 mg, 2.02 mmol) was dissolved in dichloromethane (5 mL), active manganese dioxide (270 mg, 3.04 mmol) was added and the mixture was stirred at room temperature for 3 hours. The reaction solution was filtered through celite and the filter cake was washed with dichloromethane (5 mL×4). The combined filtrate was concentrated under reduced pressure to give 28-e as a white solid (430 mg, yield 86%) which was used without further purification. LC-MS (ESI): m/z=249[M+H]$^+$.

Synthesis of Compound 28-d

2-Bromoaniline (10.0 g, 58.5 mmol) was dissolved in pyridine (50 mL) and acetonitrile (50 mL), and the reaction solution was cooled to 0° C. and methanesulfonyl chloride (10.0 g, 87.7 mmol) was added dropwise. The reaction solution was warmed to room temperature and stirred for 30 minutes, then concentrated under reduced pressure. The residue was dissolved in ethyl acetate (250 mL) and diluted with water (250 mL). The separated organic phase was adjusted to pH=7 with 1M aqueous hydrochloric acid. The organic phase was dried over anhydrous sodium sulfate, filtered and the filtrate was concentrated under reduced pressure to give 28-d as a yellow solid (14 g, yield 96%) which was used without further purification. LC-MS (ESI): m/z=250[M+H]$^+$.

Synthesis of Compound 28-c

Compound 28-d (5.0 g, 20.08 mmol) was dissolved in acetone (100 mL), anhydrous potassium carbonate (4.2 g, 30.12 mmol) was added and then iodomethane (4.3 g, 30.12 mmol) was added slowly. The reaction was stirred at room temperature for 16 hours, then filtered, and the filter cake was washed with acetone (100 mL), the combined filtrate was concentrated under reduced pressure. The residue was dissolved in ethyl acetate (150 mL) and diluted with water (100 mL). The separated organic phase was dried over anhydrous sodium sulfate, filtered and the filtrate was concentrated under reduced pressure to give 28-c as a pale yellow solid (3.1 g, yield 59%), which was used without further purification. LC-MS (ESI): m/z=264[M+H]$^+$.

Synthesis of Compound 28-b

Compound 28-c (4.0 g, 15.21 mmol), bis(pinacolato)diboron (5.6 g, 22.05 mmol) and anhydrous potassium acetate (4.5 g, 45.9 mmol) were suspended in dioxane (60 mL), and [1,1'-bis(diphenylphosphino)ferrocene]dichloropalladium (1.2 g, 1.52 mmol) was added. The mixture was purged with nitrogen gas for three times to remove oxygen contained in the system, then heated at 80° C. for 16 hours. The reaction was cooled to room temperature, diluted with ice water (100 mL) and extracted with ethyl acetate (50 mL×3). The combined organic phase was washed with water (50 mL×3) and brine (50 mL) successively, dried over anhydrous sodium sulfate, filtered and the filtrate was concentrated under reduced pressure. The residue was purified by silica gel column chromatography (petroleum ether:ethyl acetate=5:1) to give 28-b as a pale yellow oil (3.4 g, yield 72%). LC-MS (ESI): m/z=312[M+H]$^+$.

Synthesis of Compound 28-a

Compound 28-b (1.05 g, 3.38 mmol), compound 28-e (840 mg, 3.38 mmol), [1,1'-bis(diphenylphosphino)ferrocene]dichloropalladium (316 mg, 0.38 mmol) and sodium carbonate (1.06 g, 9.92 mmol) were dissolved in 1,4-dioxane (11 mL) and water (11 mL). The reaction solution was purged with nitrogen gas for three times to remove the oxygen contained in the system, then heated at 90° C. for 30 minutes. The reaction was cooled to room temperature, diluted with ice water (10 mL) and extracted with dichloromethane (50 mL×3). The combined organic phase was washed with water (20 mL×3) and brine (20 mL) successively, dried over anhydrous sodium sulfate, filtered and the filtrate was concentrated under reduced pressure. The residue was purified by silica gel column chromatography (dichloromethane:methanol=100:1) to give 28-a as a pale brown solid (610 mg, yield 51%). LC-MS (ESI): m/z=354 [M+H]$^+$.

Synthesis of Compound 28

Compound 28-a (100 mg, 0.28 mmol) and compound 1-e (83 mg, 0.85 mmol) were dissolved in n-butanol (2 mL), and p-toluenesulfonic acid monohydrate (161 mg, 0.85 mmol) was added. The mixture was heated to 110° C. and stirred for 16 hours. After cooling to room temperature, the reaction mixture was concentrated under reduced pressure, and the residue was partitioned between dichloromethane (50 mL) and saturated sodium carbonate (50 mL). The organic phase was dried over anhydrous sodium sulfate, filtered and the filtrate was concentrated under reduced pressure, the residue was purified by preparative HPLC (mobile phase: 0.05% aqueous trifluoroacetic acid solution:acetonitrile=25% to 50%) to give 28 as a yellow solid (14 mg, yield 12%). LC-MS (ESI): m/z=415[M+H]$^+$.

$^1$H-NMR (400 MHz, CDCl$_3$) δ: 8.92 (s, 1H), 8.18 (s, 1H), 7.74 (s, 1H), 7.45-7.53 (m, 3H), 7.44 (s, 2H), 6.94 (br, 1H), 3.80 (s, 3H), 3.06 (s, 3H), 2.82 (s, 3H) ppm Example 29

1-Methyl-N-{6-methyl-7-[2-(isopropoxy)phenyl] thieno[3,2-d]pyrimidinyl-2-yl]-1H-pyrazol-4-amine (Compound 29)

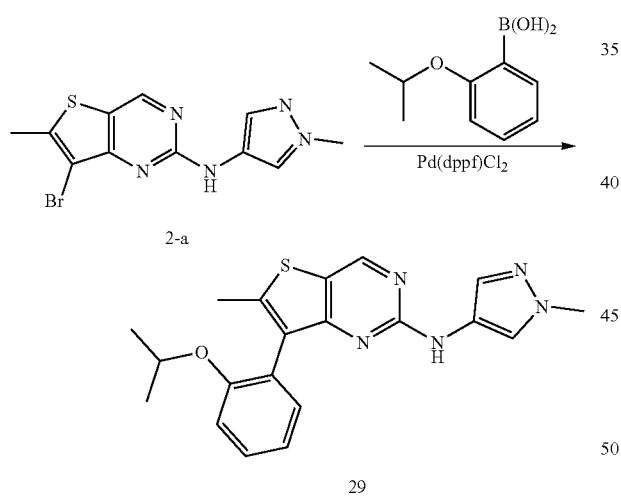

Synthesis of Compound 29

Compound 2-a (50 mg, 0.15 mmol), 2-isopropoxybenzeneboronic acid (42 mg, 0.23 mmol), [1,1'-bis(diphenylphosphino)ferrocene]dichloropalladium (13 mg, 0.12 mmol) and sodium carbonate (66 mg, 0.62 mmol) were dissolved in 1,4-dioxane (2 mL) and water (0.2 mL). The reaction solution was purged with nitrogen gas for three times to remove oxygen contained in the system, and heated at 80° C. under microwave for 1 hour. The reaction was cooled to room temperature, diluted with ice water (10 mL) and extracted with dichloromethane (20 mL×3). The combined organic phase was washed with water (10 mL×3) and brine (10 mL) successively, dried over anhydrous sodium sulfate, filtered and the filtrate was concentrated under reduced pressure. The residue was purified by preparative HPLC (mobile phase: 10 mM aqueous ammonium bicarbonate solution:acetonitrile=50% to 80%) to give 29 as a white solid (14 mg, yield 24%). LC-MS (ESI): m/z=380 [M+H]$^+$.

$^1$H-NMR (400 MHz, CDCl$_3$) δ: 8.73 (s, 1H), 7.83 (s, 1H), 7.45-7.37 (m, 3H), 7.12-7.04 (m, 2H), 6.89 (s, 1H), 4.39-4.35 (m, 1H), 3.77 (s, 3H), 2.51 (s, 3H), 1.25 (d, J=6 Hz, 3H), 1.06 (d, J=6 Hz, 3H) ppm Example 30

N-[7-(2H-1,3-benzodioxol-4-yl)-6-methylthieno[3,2-d]pyrimidinyl-2-yl]-1-methyl-1H-pyrazol-4-amine (Compound 30)

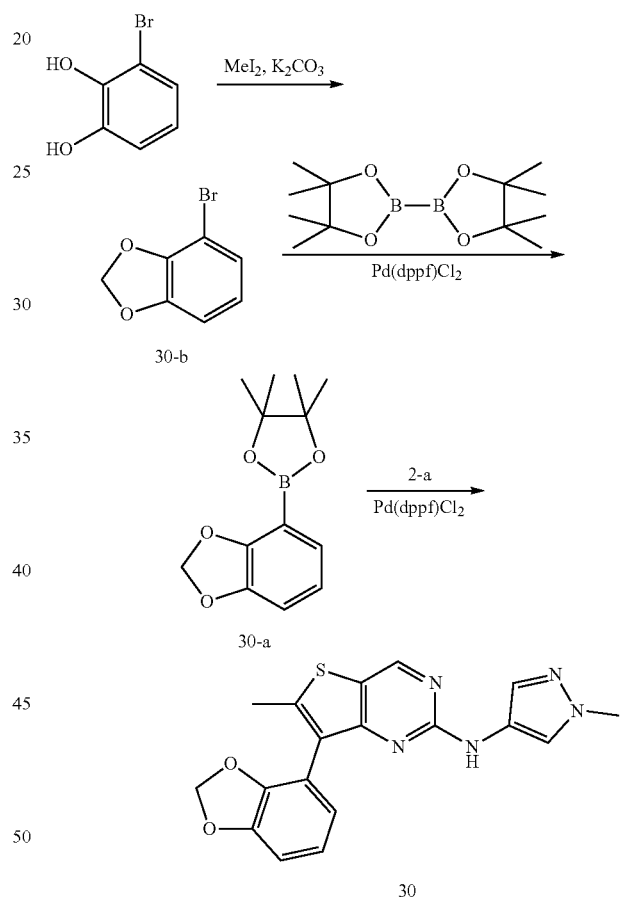

Synthesis of Compound 30-b

3-Bromocatechol (1.88 g, 10 mmol) was added to a reaction solution of N,N-dimethylformamide (10 mL) and potassium carbonate (2.76 mL, 20 mmol), and then diiodomethane (5.4 g, 20 mmol) was added to the mixture and stirred at 60° C. for 3 hours. The reaction was quenched with water (50 mL) and extracted with ethyl acetate (100 mL×5). The reaction mixture was concentrated under reduced pressure and the residue was purified by silica gel TLC preparative plate (petroleum ether) to give 30-b as a solid (1460 mg, yield 73%).

$^1$H-NMR (400 MHz, CDCl3) δ: 6.97 (d, J=8 Hz, 1H), 6.77 (d, J=8 Hz, 1H), 6.71 (d, J=8 Hz, 1H), 6.03 (s, 2H) ppm Synthesis of Compound 30-a Compound 30-b (1 g, 5 mmol) was added to anhydrous tetrahydrofuran (20 mL) at −78° C., and n-butyllithium (3 mL, 7.5 mmol) was then slowly added dropwise and stirred for 2 hours. Trimethylborate (1 g, 10 mmol) was added to the reaction mixture and stirred for 2 hours. After warming to room temperature, the reaction was quenched by the addition of 1N hydrochloric acid (10 mL, 10 mmol) and the mixture was extracted with dichloromethane (100 mL×5). The organic phase was concentrated under reduced pressure to give compound 30-a (530 mg, yield 64%), which was used without further purification.

Synthesis of Compound 30

Compound 30-a (125 mg, 0.75 mmol), 2-a (160 mg, 0.5 mmol), [1,1'-bis (diphenylphosphino)ferrocene]dichloropalladium (36 mg, 0.05 mmol) and 2M aqueous sodium carbonate solution (2 mL, 4 mmol) were dissolved in 1,4-dioxane (13 mL). The reaction solution was purged with nitrogen gas for three times to remove oxygen contained in the system, and heated at 90° C. for 6 hours. The reaction was cooled to room temperature, diluted with ice water (100 mL) and extracted with dichloromethane (100 mL×3). The combined organic phase was washed with water (50 mL×3) and brine (50 mL) successively, dried over anhydrous sodium sulfate, filtered and the filtrate was concentrated under reduced pressure. The residue was purified by silica gel TLC preparative plate (petroleum ether:ethyl acetate=1:1) to give 30 as a yellow solid (71 mg, yield 39%). LC-MS (ESI): m/z=366[M+H]$^+$.

$^1$H-NMR (400 MHz, DMSO-d6) δ: 9.48 (s, 1H), 8.98 (s, 1H), 7.83 (s, 1H), 7.43 (s, 1H), 7.05 (m, 2H), 6.03 (s, 2H), 3.71 (s, 3H), 2.51 (s, 3H) ppm Example 31

N-[7-(4-fluoro-2-methoxyphenyl)-6-methylthieno[3,2-d]pyrimidinyl-2-yl]-1-(piperidinyl-4-yl)-1H-pyrazol-4-amine (Compound 31)

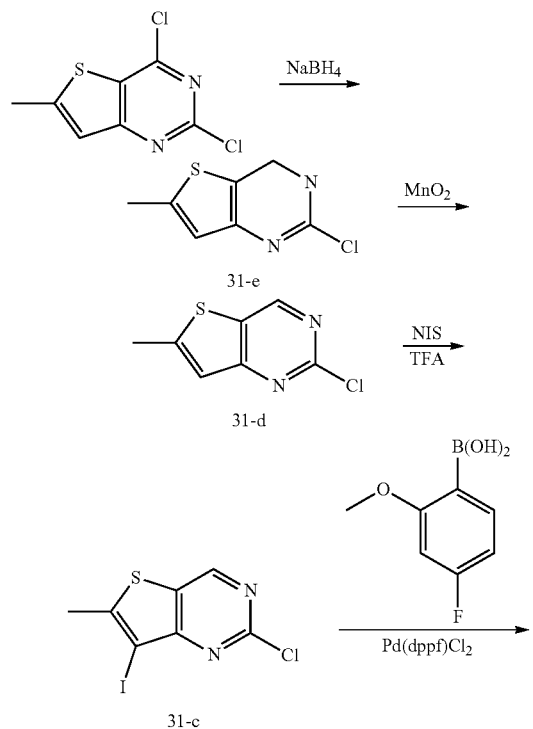

Synthesis of Compound 31-e 2,4-Dichloro-6-methylthieno[3,2-d]pyrimidine (10 g, 45.6 mmol) was dissolved in tetrahydrofuran (100 mL) and ethanol (100 mL). The reaction solution was cooled to 0° C. and sodium borohydride (12.5 g, 198 mmol) was added in portions. The reaction solution was warmed to room temperature and stirred for further 16 hours, then diluted with water (500 mL) and adjusted to pH=7 with 1N aqueous hydrochloric acid solution. The aqueous phase was extracted with ethyl acetate (150 mL×3). The organic phase was washed with water (100 mL×3) and brine (100 mL) successively, dried over anhydrous sodium sulfate, filtered and the filtrate was concentrated under reduced pressure to give 31-e as a white solid (7.5 g, yield 88%) which was used without further purification. LC-MS (ESI): m/z=187[M+H]$^+$.

Synthesis of Compound 31-d

Compound 31-e (7.5 g, 40 mmol) was dissolved in dichloromethane (300 mL) at 0° C., and activated manganese dioxide (35 g, 400 mmol) was added. The reaction solution was warmed to room temperature and stirred at room temperature for 16 hours. The reaction solution was filtered through celite and the filter cake was washed with chloroform (100 mL×3). The combined filtrates were concentrated under reduced pressure to give 31-d as a white solid (6.6 g, yield 89%) which was used without further purification. LC-MS (ESI): m/z=185[M+H]$^+$.

Synthesis of Compound 31-c

Compound 31-d (3.1 g, 16.8 mmol) was dissolved in trifluoroacetic acid (30 mL) at 0° C. and N-iodosuccinimide (5.7 g, 25.3 mmol) was added in portions. The reaction solution was warmed to room temperature and stirred for 1 hour. The reaction solution was quenched by the addition of water (50 mL) and extracted with dichloromethane (50 mL×3). The organic phase was washed with water (50 mL×3) and brine (50 mL) sequentially, dried over anhydrous sodium sulfate and filtered. The filtrate was concentrated under reduced pressure to give 31-c as a white solid (4.9 g, yield 94%), which was used without further purification. LC-MS (ESI): m/z=311[M+H]$^+$.

Synthesis of Compound 31-b

Compound 31-c (615 mg, 1.98 mmol), 2-methoxy-4-fluorobenzeneboronic acid (405 mg, 2.38 mmol) and sodium carbonate (630 mg, 5.94 mmol) were suspended in dioxane (5 mL) and water (5 mL), [1,1'-bis(diphenylphosphino)ferrocene]dichloro-palladium.dichloromethane (163 mg, 0.2 mmol) was added. The reaction solution was purged with nitrogen gas for three times and heated to 80° C. to react for 16 hours. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel column chromatography (petroleum ether:dichloromethane=1:1) to give 31-b as a white solid (240 mg, yield 39%). LC-MS (ESI): m/z=309[M+H]$^+$.

Synthesis of Compound 31-a

Compound 31-b (240 mg, 0.78 mmol) and compound 32-c (208 mg, 0.78 mmol) were dissolved in N,N-dimethylformamide (3 mL), potassium carbonate (323 mg, 2.34 mmol), 2-dicyclohexylphosphino-2',6'-diisopropoxy-1,1'-biphenyl (112 mg, 0.24 mmol) and tris(dibenzylideneacetone)dipalladium (0) (134 mg, 0.24 mmol) were added. Under nitrogen gas atmosphere, the mixture was heated to 110° C. and reacted for 16 hours. After cooling to room temperature, the reaction solution was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (petroleum ether:ethyl acetate=1:1) to give 31-a as a yellow viscous oil (190 mg, yield 45%). LC-MS (ESI): m/z=539 [M+H]$^+$.

Synthesis of Compound 31

31-a (190 mg, 0.35 mmol) was dissolved in dichloromethane (3 mL), trifluoroacetic acid (3 mL) was added and the mixture was stirred at room temperature for 3 hours. The reaction mixture was concentrated under reduced pressure and the residue was partitioned between ethyl acetate (50 mL) and 1N aqueous hydrochloric acid solution (50 mL). The aqueous phase was adjusted to pH=10 with saturated aqueous potassium carbonate solution and solid was precipitated out. The solid was filtered out and the filter cake was washed with water (20 mL×3). The solid was dried under vacuum to give 31 as a pale yellow solid (22 mg, yield 14%). LC-MS (ESI): m/z=439[M+H]$^+$.

$^1$H-NMR (400 MHz, MeOD) δ: 8.78 (d, J=5 Hz, 1H), 7.87 (s, 1H), 7.48 (s, 1H), 7.35 (m, 1H), 7.05 (dd, J=11 Hz, J=2 Hz, 1H), 6.91 (m, 1H), 4.10 (m, 1H), 3.79 (s, 3H), 3.22 (m, 2H), 2.77 (m, 2H), 2.47 (s, 3H), 2.03 (m, 2H), 1.73 (m, 2H) ppm Example 32

N-[7-(2,3-dihyro-1-benzofuran-7-yl)-6-methylthieno[3,2-d]pyrimidinyl-2-yl]-1-(piperidinyl-4-yl)-1H-pyrazol-4-amine (Compound 32)

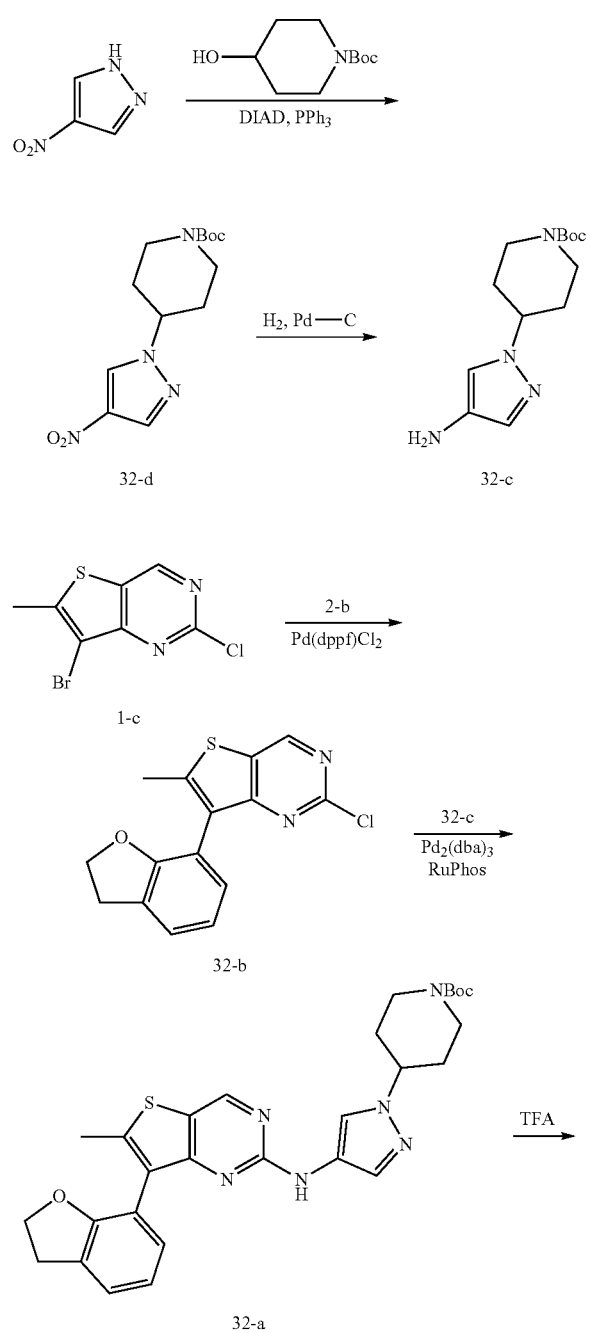

-continued

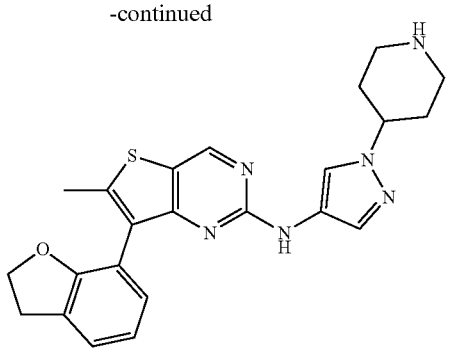

32

Synthesis of Compound 32-d

4-Nitropyrazole (1.14 g, 10 mmol), N-Boc-4-hydroxypiperidine (2.01 g, 10 mmol), diisopropyl azodicarboxylate (3 g, 15 mmol) and triphenylphosphine (3.9 g, 15 mmol) were added to tetrahydrofuran (50 mL), and the reaction solution was stirred at room temperature for 6 hours. The reaction solution was concentrated under reduced pressure and the residue was purified by silica gel TLC preparative plate (petroleum ether:ethyl acetate=1:1-1:2) to give 32-d as a yellow solid (1460 mg, yield 50%). LC-MS (ESI): m/z=241 [M+H-t-Bu]+.

Synthesis of Compound 32-c

Compound 32-d (614 mg, 2 mmol) and palladium-carbon (0.1 g) were added to methanol (10 mL) under hydrogen gas atmosphere (1 atm). The reaction solution was heated to 40° C. and stirred for 3 hours. After cooling to room temperature, the reaction solution was filtered and the filtrate was concentrated under reduced pressure to give 32-c as a purple solid (500 mg, yield 94%), which was used without further purification. LC-MS (ESI): m/z=267[M+H]+.

Synthesis of Compound 32-b

Compound 1-c (1.23 g, 5 mmol), compound 2-b (1.5 g, 5 mmol), [1,1'-bis (diphenylphosphino)ferrocene]dichloropalladium (36 mg, 0.05 mmol) and sodium carbonate (1.06 g, 10 mmol) were dissolved in dioxane (8 mL) and water (2 mL). The mixture was purged with nitrogen gas for three times to remove the oxygen contained in the system, then stirred at 90° C. for 8 hours. The reaction solution was cooled to room temperature, diluted with ice water (10 mL) and extracted with dichloromethane (50 mL×3). The combined organic phases were washed with water (20 mL×3) and brine (20 mL) successively, dried over anhydrous sodium sulfate, filtered and the filtrate was concentrated under reduced pressure. The residue was purified by silica gel TLC preparative plate (petroleum ether:ethyl acetate=10:1) to give 32-b as a yellow solid (860 mg, yield 57%). LC-MS (ESI): m/z=303[M+H]+.

Synthesis of Compound 32-a

Compound 32-b (1.35 g, 5 mmol), compound 32-c (1.5 g, 5 mmol), potassium carbonate (1.38 g, 10 mmol), tris (dibenzylidene indenone)dipalladium (140 mg, 0.1 mmol) and 2-dicyclohexylphosphine-2',6'-diisopropoxy-1,1'-biphenyl (150 mg, 0.2 mmol) were dissolved in N,N-dimethylformamide (150 mL) and the reaction solution was purged with nitrogen gas for three times to remove oxygen contained in the system and then heated at 110° C. for 16 hours. The reaction was cooled to room temperature, and concentrated under reduced pressure. The residue was purified by silica gel column chromatography (dichloromethane:methanol=40:1) to give compound 32-a (1 g, yield 38%). LC-MS (ESI): m/z=533[M+H]+.

Synthesis of Compound 32

Compound 32-a (1.0 g, 1.9 mmol) was dissolved in dichloromethane (6 mL). The reaction solution was cooled to 0° C., trifluoroacetic acid (2 mL) was added and the mixture was stirred at room temperature for 1 hour. The reaction solution was adjusted to pH=8-9 with saturated aqueous sodium carbonate solution and then extracted with dichloromethane (15 mL×3). The combined organic phases were dried over anhydrous sodium sulphate, filtered and the filtrate was concentrated under reduced pressure. The residue was purified by preparative HPLC (mobile phase: 10 mM aqueous ammonium bicarbonate solution:acetonitrile=38% to 46%) to give compound 32 (100 mg, yield 12.3%). LC-MS (ESI): m/z=433[M+H]+.

$^1$H-NMR (400 MHz, MeOD) δ: 8.78 (s, 1H), 7.98 (s, 1H), 7.53 (s, 1H), 7.36 (d, J=8.0 Hz, 1H), 7.27 (d, J=8.0 Hz, 1H), 7.05 (t, J=8 Hz, 1H), 4.56 (t, J=8 Hz, 2H), 4.10 (m, 1H), 3.36 (d, J=12 Hz, 2H), 3.20 (d, J=12 Hz, 2H), 2.75 (t, J=8 Hz, 2H), 2.02 (d, J=12 Hz, 2H), 1.78 (d, J=12 Hz, 2H) ppm Example 33

N-[7-(2-chlorophenyl)-6-methylthieno[3,2-d]pyrimidinyl-2-yl]-1-methyl-1H-pyrazol-4-amine (Compound 33)

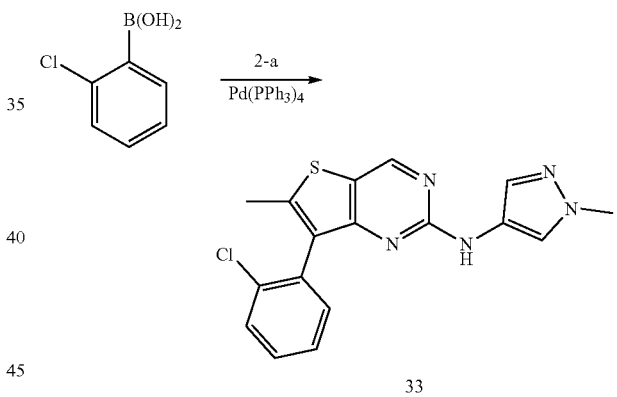

33

Synthesis of Compound 33

2-Chlorobenzeneboronic acid (100 mg, 0.31 mmol), compound 2-a (59 mg, 0.37 mmol), tetrakis(triphenylphosphine) palladium (17 mg, 0.016 mmol) and potassium carbonate (86 mg, 0.62 mmol)) were dissolved in 1,4-dioxane (4 mL) and water (1 mL). The reaction was purged with nitrogen gas for three times to remove the oxygen contained in the system, and then stirred at 80° C. for 16 hours. The reaction solution was cooled to room temperature and concentrated under reduced pressure. The residue was added with water (10 mL) and solid was precipitated out. The solid was filtered out and washed with a mixed solvent (20 mL) of petroleum ether, ethyl acetate and methanol (1:1:1) to give 33 as a white solid (40 mg, yield 37%). LC-MS (ESI): m/z=356[M+H]+.

$^1$H NMR (400 MHz, CDCl$_3$) δ: 8.75 (s, 1H), 7.68 (s, 1H), 7.58 (t, J=3.6 Hz, 1H), 7.42-7.37 (m, 4H), 7.22 (s, 1H), 3.74 (s, 3H), 2.51 (s, 3H) ppm

Example 34

2-[4-(4-{[7-(4-fluoro-2-methoxyphenyl)-6-methylthieno[3,2-d]pyrimidinyl-2-yl]amino}-1H-pyrazol-1-yl)-piperidinyl-1-yl]-1-ethanol (Compound 34)

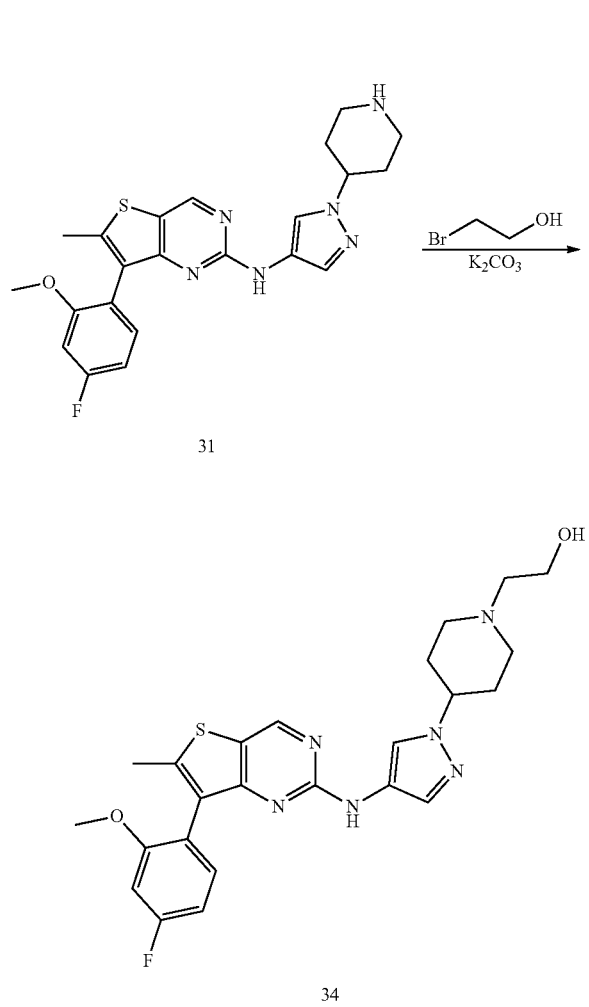

Example 35

N-[7-(2-methoxyphenyl)-6-methylthieno[3,2-d]pyrimidinyl-2-yl]-1-(piperidinyl-4-yl)-1H-pyrazol-4-amine (Compound 35)

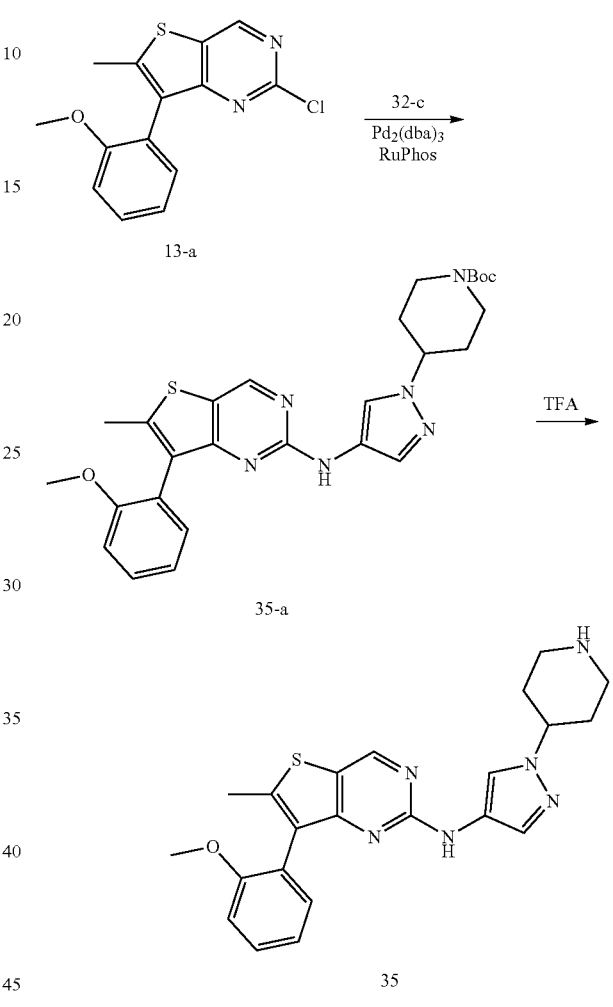

Synthesis of Compound 34

Compound 31 (300 mg, 0.68 mmol), bromoethanol (129 mg, 1.03 mmol) and potassium carbonate (282 mg, 2.04 mmol) were added to N,N-dimethylformamide (10 mL), and the mixture was heated to 70° C. and stirred for 16 hours. After cooling to room temperature, water (30 mL) was added and the mixture was extracted with ethyl acetate (40 mL). The organic phase was washed with brine (40 mL), dried over anhydrous sodium sulfate, filtered and the filtrate was concentrated under reduced pressure. The residue was purified by silica gel column chromatography (dichloromethane:methanol=20:1 to 15:1) to give 34 as a yellow solid (125 mg, yield 38%). LC-MS (ESI): m/z=483[M+H]$^+$.

$^1$H NMR (400 MHz, DMSO) δ: 9.43 (s, 1H), 8.94 (s, 1H), 7.78 (s, 1H), 7.35 (m, 2H), 7.11 (dd, J=11.5, 2.2 Hz, 1H), 6.96 (m, J=7.5 Hz, 1H), 4.39 (t, 1H), 3.88 (m, 1H), 3.74 (s, 3H), 3.55 (dd, J=11.8, 6.1 Hz, 2H), 2.95 (d, J=11.5 Hz, 2H), 2.44 (t, J=6.3 Hz, 2H), 2.40 (s, 3H), 2.11 (t, J=11.3 Hz, 2H), 1.87 (m, J=10.9 Hz, 2H), 1.72 (m, 2H) ppm

Synthesis of Compound 35-a

Compound 13-a (200 mg, 0.67 mmol) and compound 32-c (178 mg, 0.67 mmol) were dissolved in N,N-dimethylformamide (2 mL), potassium carbonate (290 mg, 2.7 mmol), 2-dicyclohexylphosphino-2',6'-diisopropoxy-1,1'-biphenyl (98 mg, 0.21 mmol) and tris(dibenzylideneacetone)dipalladium (115 mg, 0.21 mmol) were added. Under nitrogen gas atmosphere, the mixture was heated to 110° C. and reacted for 16 hours. After cooling to room temperature, the reaction solution was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (petroleum ether:ethyl acetate=1:1) to give 35-a as a yellow compound (190 mg, yield 53%). LC-MS (ESI): m/z=521[M+H]$^+$.

Synthesis of Compound 35

35-a (190 mg, 0.36 mmol) was dissolved in dichloromethane (3 mL), trifluoroacetic acid (3 mL) was added and the mixture was stirred at room temperature for 3 hours. The reaction mixture was concentrated under reduced pressure and the residue was partitioned between ethyl acetate (50 mL) and 1N aqueous hydrochloric acid solution (50 mL). The aqueous phase was adjusted to pH=10 with saturated aqueous potassium carbonate solution and solid was precipitated out. The solid was filtered out and the filter cake was washed with water (20 mL×3). The solid was dried under vacuum to give 35 as a pale yellow solid (102 mg, yield 67%). LC-MS (ESI): m/z=421[M+H]⁺.

¹H-NMR (400 MHz, MeOD) δ: 8.72 (s, 1H), 7.87 (s, 1H), 7.42 (m, 3H), 7.12 (m, 2H), 6.96 (s, 1H), 4.05 (m, 1H), 3.77 (s, 3H), 3.21 (m, 2H), 2.72 (m, 2H), 2.48 (s, 3H), 2.03 (m, 2H), 1.68 (m, 2H) ppm Example 36

1-[4-(4-{[7-(2,3-dihydro-1-benzofuran-7-yl)-6-methylthieno[3,2-d]pyrimidinyl-2-yl]amino}-1H-pyrazol-1-yl)piperidinyl-1-yl]-2-hydroxyacetamide (Compound 36)

was concentrated under reduced pressure. The residue was added with 2N aqueous sodium bicarbonate solution (6 mL) and extracted with dichloromethane (15 mL×3). The organic phase was washed with 2N aqueous hydrochloric acid solution (15 mL×3), dried over anhydrous sodium sulfate, filtered, and the filtrate was concentrated under reduced pressure to give 36 as a yellow solid (51 mg, yield 52%). LC-MS (ESI): m/z=491[M+H]⁺.

¹H-NMR (400 MHz, CDCl3) δ: 8.73 (s, 1H), 7.99 (s, 1H), 7.38 (s, 1H), 7.32 (d, J=8.0 Hz, 1H), 7.27 (d, J=8.0 Hz, 1H), 7.14 (s, 1H), 6.95 (t, J=8 Hz, 1H), 4.67 (d, J=12 Hz, 1H), 4.57 (t, J=8 Hz, 2H), 4.27 (m, 3H), 3.76 (t, J=4 Hz, 2H), 3.61 (d, J=12 Hz, 1H), 3.49 (s, 1H), 3.30 (t, J=8 Hz, 2H), 3.15 (t, J=12 Hz, 1H), 2.91 (t, J=12 Hz, 1H), 2.11 (m, 2H), 1.77 (m, 2H) ppm Example 37

N-{7-[2-methoxy-4-(trifluoromethyl)phenyl]-6-methylthieno[3,2-d]pyrimidinyl-2-yl}-1-(piperidinyl-4-yl)-1H-pyrazol-4-amine (Compound 37)

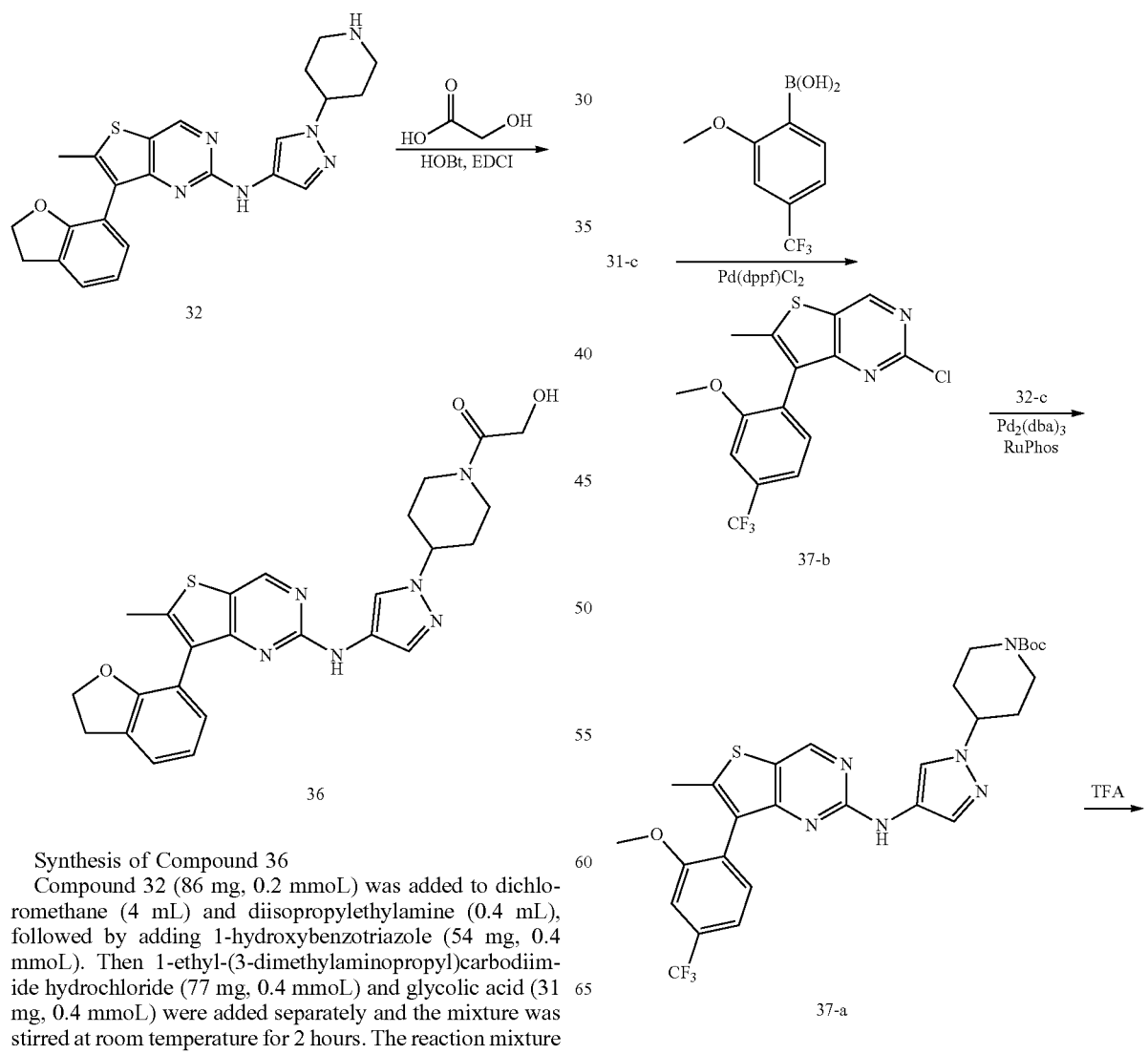

Synthesis of Compound 36

Compound 32 (86 mg, 0.2 mmoL) was added to dichloromethane (4 mL) and diisopropylethylamine (0.4 mL), followed by adding 1-hydroxybenzotriazole (54 mg, 0.4 mmoL). Then 1-ethyl-(3-dimethylaminopropyl)carbodiimide hydrochloride (77 mg, 0.4 mmoL) and glycolic acid (31 mg, 0.4 mmoL) were added separately and the mixture was stirred at room temperature for 2 hours. The reaction mixture

101
-continued

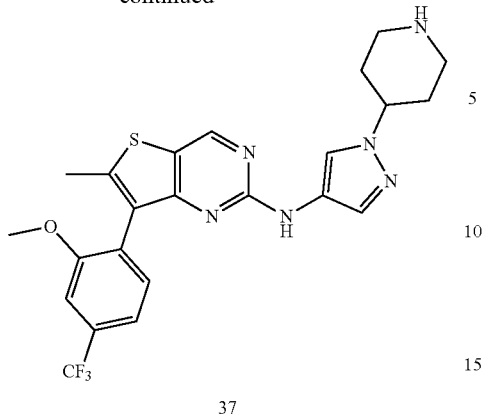

37

Synthesis of Compound 37-b

Compound 31-c (640 mg, 2.07 mmol), 2-methoxy-4-trifluoromethylphenylboronic acid (500 mg, 2.27 mmol) and sodium carbonate (658 mg, 6.21 mmol) were suspended in dioxane (5 mL) and water (5 mL), and [1,1'-bis (diphenylphosphino)ferrocene]dichloropalladium.dichloromethane (171 mg, 0.21 mmol) was added. The reaction solution was purged with nitrogen gas for three times, heated to 80° C. and reacted for 16 hours. After cooling to room temperature, the reaction solution was concentrated under reduced pressure, the residue was partitioned between dichloromethane (50 mL) and water (50 mL). The organic phase was dried over anhydrous sodium sulfate, filtered and the filtrate was concentrated and then purified by silica gel column chromatography (petroleum ether:dichloromethane=1:1) to give 37-b as a white solid (190 mg, yield 26%). LC-MS (ESI): m/z=359[M+H]$^+$.

Synthesis of Compound 37-a

Compound 37-b (200 mg, 0.67 mmol) and compound 32-c (113 mg, 0.42 mmol) were dissolved in N,N-dimethylformamide (3 mL), potassium carbonate (173 mg, 1.25 mmol), 2-dicyclohexylphosphino-2',6'-diisopropoxy-1,1'-biphenyl (98 mg, 0.21 mmol) and tris(dibenzylideneacetone)dipalladium (58 mg, 0.14 mmol) were added. Under nitrogen gas atmosphere, the mixture was heated to 110° C. to react for 16 hours. After cooling to room temperature, the reaction solution was partitioned between ethyl acetate (100 mL) and water (100 mL). The organic phase was dried over anhydrous sodium sulfate, filtered and the filtrate was concentrated under reduced pressure. The residue was purified by silica gel TLC preparative plate (petroleum ether:ethyl acetate=1:1) to give 37-a as a yellow compound (98 mg, yield 40%). LC-MS (ESI): m/z=589[M+H]$^+$.

Synthesis of Compound 37

37-a (98 mg, 0.17 mmol) was dissolved in dichloromethane (3 mL), trifluoroacetic acid (3 mL) was added and the mixture was stirred at room temperature for 3 hours. The reaction mixture was concentrated under reduced pressure and the residue was partitioned between ethyl acetate (50 mL) and 1N aqueous hydrochloric acid solution (50 mL). The aqueous phase was adjusted to pH=10 with saturated aqueous potassium carbonate solution and solid was precipitated out. The solid was filtered out and the filter cake was washed with water (20 mL×3). The solid was dried under vacuum to give 37 as a pale yellow solid (70 mg, yield 86%). LC-MS (ESI): m/z=489[M+H]$^+$.

$^1$H-NMR (400 MHz, CDCl$_3$) δ: 8.74 (s, 1H), 7.80 (s, 1H), 7.54 (d, J=14 Hz, 1H), 7.38 (d, J=14 Hz, 1H), 7.37 (s, 1H), 6.95 (s, 1H), 4.02 (m, 1H), 3.84 (s, 3H), 3.19 (m, 2H), 2.72 (m, 2H), 2.48 (s, 3H), 2.01 (m, 2H), 1.74 (m, 2H) ppm

Example 38

(2-{6-methyl-2-[(1-methyl-1H-pyrazol-4-yl)amino]thieno[3,2-d]pyrimidinyl-7-yl}phenyl)methanol (Compound 38)

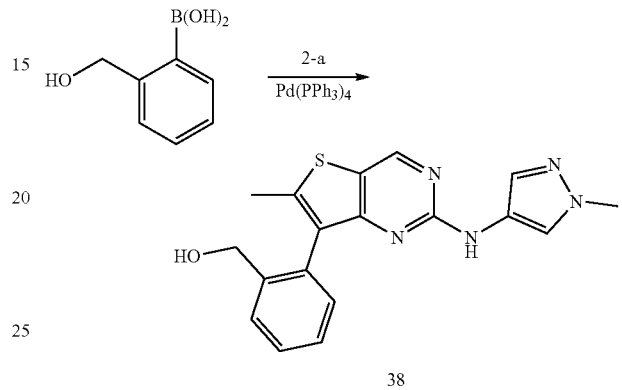

38

Synthesis of Compound 38

2-Hydroxymethylphenylboronic acid (213 mg, 1.395 mmol), compound 2-a (300 mg, 0.93 mmol), tetrakis(triphenylphosphine)palladium (108 mg, 0.093 mmol) and potassium carbonate (257 mg, 1.86 mmol) were dissolved in 1,4-dioxane (8 mL) and water (2 mL). The reaction was purged with nitrogen gas for three times to remove the oxygen contained in the system, and then stirred at 80° C. for 2 hours. The reaction solution was cooled to room temperature and concentrated under reduced pressure. The residue was added with water (20 mL) and solid was precipitated out. The solid was filtered out and washed with a mixed solvent (20 mL) of petroleum ether and ethyl acetate (1:1) to give 38 as an off-white solid (325 mg, yield 100%). LC-MS (ESI): m/z=352[M+H]$^+$.

$^1$H NMR (400 MHz, DMSO-d$_6$) δ: 9.42 (s, 1H), 8.98 (s, 1H), 7.69 (d, J=8.0 Hz, 1H), 7.58 (bs, 1H), 7.51 (t, J=7.6 Hz, 1H), 7.40 (t, J=7.6 Hz, 1H), 7.32 (s, 1H), 7.21 (d, J=7.6 Hz, 1H), 5.03 (t, J=5.2 Hz, 1H), 4.39 (dd, J=13.6, 4.8 Hz, 1H), 4.20 (dd, J=14.0, 5.2 Hz, 1H), 3.65 (s, 3H), 2.41 (s, 3H) ppm

Example 39

N-[7-(2,3-dihydro-1-benzofuran-7-yl)-6-methylthieno[3,2-d]pyrimidin-2-yl]-1-(tetrahydropyran-4-yl)-1H-pyrazol-4-amine (Compound 39)

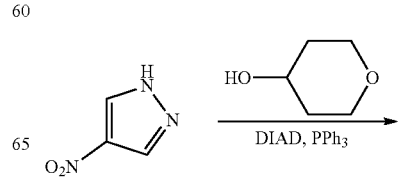

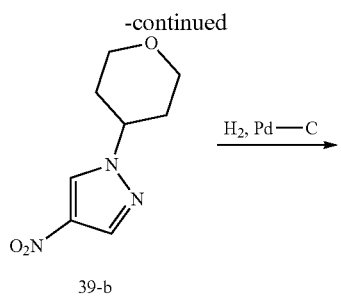

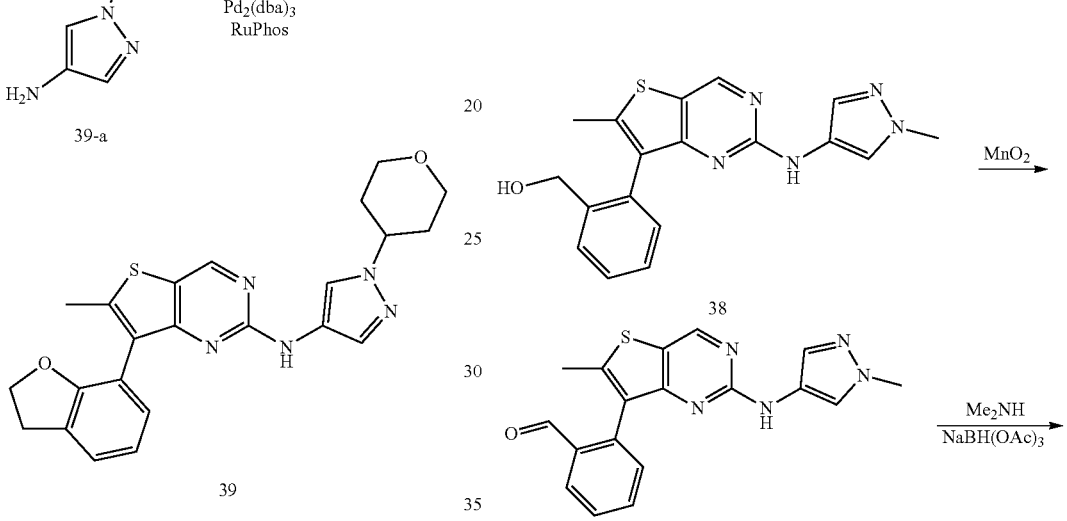

Synthesis of Compound 39-b

4-Nitropyrazole (1.14 g, 10 mmol), 4-hydroxytetrahydropyran (1.01 g, 10 mmol), diisopropyl azodicarboxylate (3 g, 15 mmol) and triphenylphosphine (3.9 g, 15 mmol) were added to tetrahydrofuran (50 mL), and the reaction solution was stirred at room temperature for 6 hours. The reaction solution was concentrated under reduced pressure and the residue was purified by silica gel TLC preparative plate (petroleum ether:ethyl acetate=1:1 to 1:2) to give 39-b as a yellow solid (1460 mg, yield 71%). LC-MS (ESI): m/z=199 [M+H]$^+$.

Synthesis of Compound 39-a

Compound 39-b (1.0 g, 5 mmol) and palladium-carbon (0.1 g) were added to methanol (10 mL) under hydrogen gas atmosphere (1 atm). The reaction solution was heated to 40° C. and stirred for 3 hours. After cooling to room temperature, the reaction solution was filtered and the filtrate was concentrated under reduced pressure to give 39-a as a purple solid (830 mg, yield 100%), which was used without further purification. LC-MS (ESI): m/z=168[M+H]$^+$.

Synthesis of Compound 39

Compound 39-a (135 mg, 0.5 mmol), compound 32-b (150 mg, 0.5 mmol), potassium carbonate (138 mg, 1 mmol), tris(dibenzylidene indenone)dipalladium (14 mg, 0.01 mmol) and 2-dicyclohexylphosphine-2',6'-diisopropoxy-1,1'-biphenyl (15 mg, 0.02 mmol) were dissolved in N,N-dimethylformamide (15 mL) and the reaction solution was purged with nitrogen gas for three times to remove oxygen contained in the system and then heated at 110° C. for 6 hours. The reaction solution was cooled to room temperature, and concentrated under reduced pressure. The residue was purified by silica gel column chromatography (dichloromethane:methanol=40:1) to give compound 39 (31 mg, yield 14%). LC-MS (ESI): m/z=533[M+H]$^+$.

$^1$H-NMR (400 MHz, CDCl3) δ: 8.73 (s, 1H), 8.00 (s, 1H), 7.40 (s, 1H), 7.32 (d, J=8.0 Hz, 1H), 7.27 (d, J=8.0 Hz, 1H), 6.95 (t, J=8 Hz, 1H), 4.58 (t, J=8 Hz, 2H), 4.26 (m, 1H), 4.11 (d, J=8 Hz, 2H), 3.53 (t, J=12 Hz, 2H), 3.35 (t, J=12 Hz, 2H), 2.55 (s, 3H), 1.93 (m, 4H) ppm Example 40

N-[7-{2-[(dimethylamino)methyl]phenyl}-6-methyl-thieno[3,2-d]pyrimidinyl-2-yl]-1-methyl-1H-pyrazol-4-amine (Compound 40)

Synthesis of Compound 40-a

Compound 38 (302 mg, 0.86 mmol) was dissolved in dichloromethane (10 mL), manganese dioxide (225 mg, 2.58 mmol) was added. The reaction mixture was stirred at room temperature for 16 hours, filtered through celite and the filtrate was concentrated under reduced pressure to remove solvent thereby giving 40-a as a pale yellow solid (227 mg, yield 76%). LC-MS (ESI): m/z=350[M+H]$^+$.

Synthesis of Compound 40

Compound 40-a (107 mg, 0.31 mmol) and dimethylamine hydrochloride (76 mg, 0.93 mmol) were dissolved in dichloroethane (10 mL) and a drop of acetic acid was added. The reaction was stirred at room temperature for 2 hours, then sodium triacetoxyborohydride (329 mg, 1.55 mmol) was added and the reaction was further stirred for 16 hours. The reaction was quenched by addition of saturated sodium bicarbonate solution (20 mL) and extracted with dichloromethane (20 mL×3). The organic phase was washed with brine (50 mL), dried over anhydrous sodium sulfate, filtered and the filtrate was concentrated under reduced pressure, and the residue was purified by silica gel TLC preparative plate (dichloromethane:methanol=10:1) to give 40 as a yellow solid (26 mg, yield 23%). LC-MS (ESI): m/z=379[M+H]+.

¹H NMR (400 MHz, CDCl₃) δ: 8.75 (s, 1H), 7.68 (d, J=7.6 Hz, 1H), 7.58 (s, 1H), 7.46 (t, J=7.6 Hz, 1H), 7.37 (t, J=7.6 Hz, 1H), 7.32 (s, 2H), 7.21 (d, J=7.6 Hz, 1H), 3.70 (s, 3H), 3.30 (d, J=13.2 Hz, 1H), 3.14 (d, J=13.2 Hz, 1H), 2.45 (s, 3H), 2.02 (s, 6H) ppm Example 41

N-{7-[2-(dimethylamino)phenyl]-6-methylthieno[3,2-d]pyrimidin-2-yl}-1-methyl-1H-pyrazol-4-amine (Compound 41)

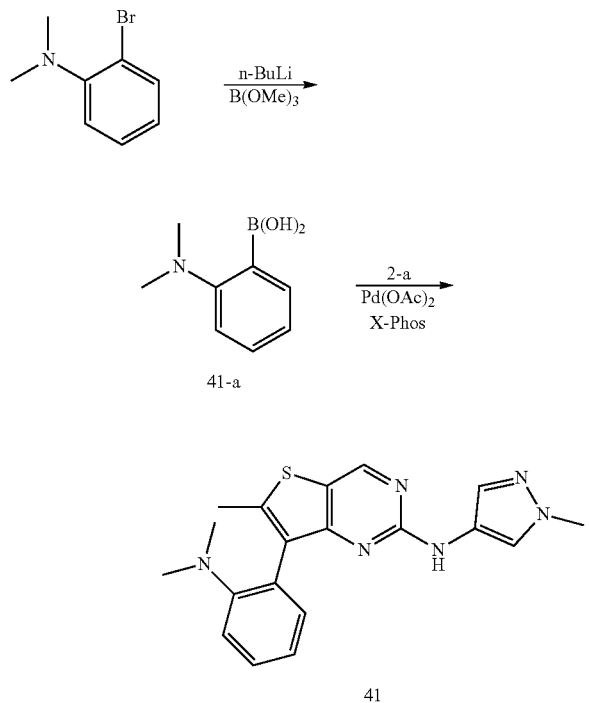

Synthesis of Compound 41-a

N,N-dimethyl-o-bromoaniline (4 g, 20 mmol) was added to anhydrous tetrahydrofuran (100 mL) at −78° C., and 2.5M n-butyllithium (10 mL, 25 mmol) was then slowly added dropwise and stirred for 2 hours. Trimethylborate (2.6 g, 25 mmol) was added to the reaction mixture and stirred for another 2 hours. After warming to room temperature, the reaction was quenched by the addition of 0.1N hydrochloric acid solution (200 mL) and the mixture was extracted with dichloromethane (150 mL×3), then washed with water (150 mL×3). The organic phase was concentrated under reduced pressure to give compound 41-a (3.0 g, yield 91%). LC-MS (ESI): m/z=166[M+H]+.

Synthesis of Compound 41

Compound 2-a (160 mg, 0.5 mmol), compound 41-a (125 mg, 0.75 mmol), palladium acetate (112 mg, 0.5 mmol) were dissolved in toluene (4 mL) and water (1 mL), and 2-dicyclohexylphosphine-2,4,6-triisopropylbiphenyl (24 mg, 0.05 mmol) and potassium phosphate (422 mg, 1 mmol) were added. The reaction mixture was stirred at 90° C. for 8 hours under nitrogen atmosphere. After cooling to room temperature, the reaction mixture was concentrated under reduced pressure to remove toluene. The residue was added with ethyl acetate (150 mL) and filtered through celite, the filtrate was washed with water (150 mL×3), dried over anhydrous sodium sulfate and filtered, and the filtrate was concentrated under reduced pressure. The residue was purified by silica gel column chromatography (ethyl acetate:petroleum ether=1:1) to give compound 41 (80 mg, yield 44%). LC-MS (ESI): m/z=382[M+H]+.

Example 42

N-[7-(4-(methoxypyridin-3-yl)-6-methylthieno[3,2-d]pyrimidin-2-yl]-1-methyl-1H-pyrazol-4-amine (Compound 42)

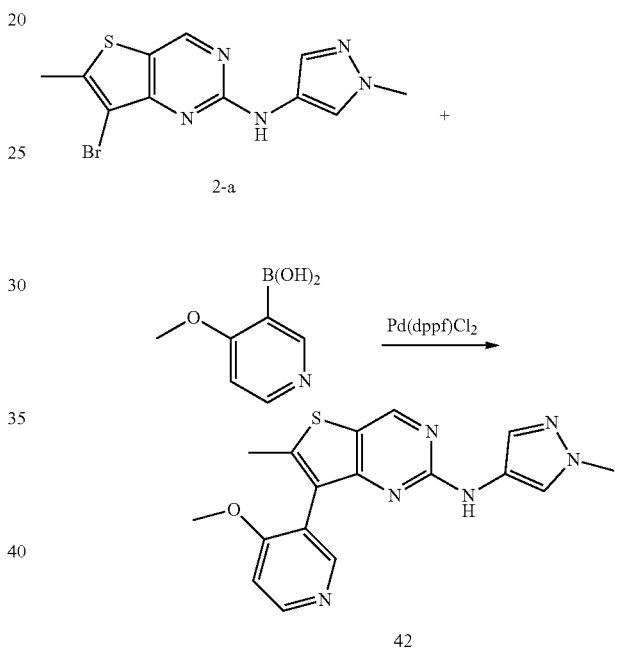

Synthesis of Compound 42

Compound 2-a (100 mg, 0.31 mmol), 4-methoxypyridin-3-boronic acid (71 mg, 0.46 mmol) and sodium carbonate (99 mg, 0.93 mmol) were suspended in dioxane (0.5 mL) and water (0.5 mL), and [1,1'-bis (diphenylphosphino)ferrocene]dichloropalladium.dichloromethane (26 mg, 0.03 mmol) was added. The reaction solution was purged with nitrogen gas for three times and heated to 90° C. under microwave to react for 40 minutes. After cooling to room temperature, the reaction solution was concentrated under reduced pressure, and the residue was partitioned between dichloromethane (50 mL) and water (50 mL). The organic phase was dried over anhydrous sodium sulfate, filtered and the filtrate was concentrated under reduced pressure. The residue was purified by preparative HPLC (mobile phase: 10 mM aqueous ammonium bicarbonate solution:acetonitrile=30% to 40%) to give 42 as a white solid (15 mg, yield 14%). LC-MS (ESI): m/z=353[M+H]+.

¹H-NMR (400 MHz, CDCl₃) δ: 8.75 (s, 1H), 8.59 (d, J=6 Hz, 1H), 8.55 (s, 1H), 7.76 (s, 1H), 7.38 (s, 1H), 7.26 (s, 1H), 6.99 (d, J=6 Hz, 1H), 3.91 (s, 3H), 3.79 (s, 3H), 2.63 (s, 3H) ppm

Example 43

N-[7-(2-(methoxypyridin-3-yl)-6-methylthieno[3,2-d]pyrimidin-2-yl]-1-methyl-1H-pyrazol-4-amine (Compound 43)

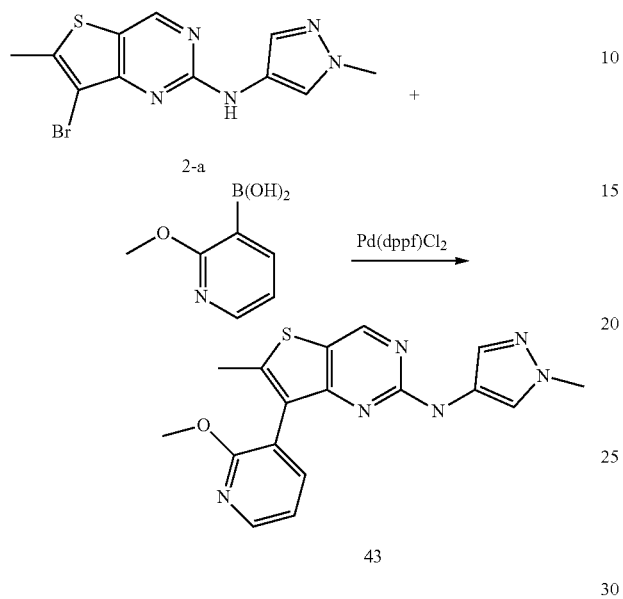

Synthesis of Compound 43

Compound 2-a (180 mg, 0.75 mmol), 2-methoxypyridin-3-boronic acid (153 mg, 1 mmol) and sodium carbonate (106 mg, 1 mmol) were suspended in dioxane (8 mL) and water (2 mL), and [1,1'-bis (diphenylphosphino)ferrocene]dichloropalladium.dichloromethane (36 mg, 0.05 mmol) was added. The reaction solution was purged with nitrogen gas for three times, heated to 90° C. and stirred for 8 hours. After cooling to room temperature, the reaction solution was diluted with ice water (10 mL), and extracted with dichloromethane (50 mL×3). The combined organic phase was washed with water (20 mL×3) and brine (20 mL) successively, dried over anhydrous sodium sulfate, filtered and the filtrate was concentrated under reduced pressure. The residue was purified by silica gel TLC preparative plate (petroleum ether:ethyl acetate=10:1) to give 43 as a yellow solid (61 mg, yield 34%). LC-MS (ESI): m/z=366[M+H]$^+$.

$^1$H-NMR (400 MHz, DMSO-d6) δ: 9.43 (s, 1H), 8.97 (s, 1H), 8.31 (s, 1H), 7.81 (s, 1H), 7.66 (s, 1H), 7.37 (s, 1H), 7.22 (s, 1H), 3.84 (s, 3H), 3.70 (s, 3H), 2.50 (s, 3H) ppm

Example 44

8-(2,3-Dihydro-1-benzofuran-7-yl)-N-[1-(4-piperidin)-1H-pyrazol-4-yl]quinazolin-2-amine (Compound 44)

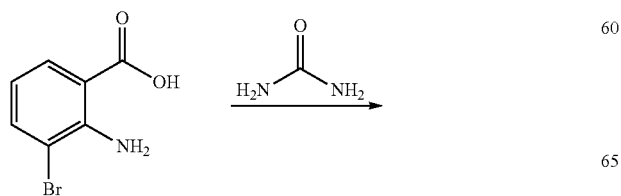

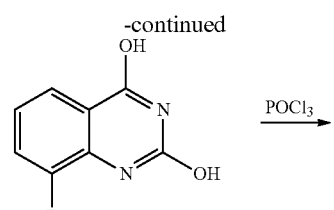

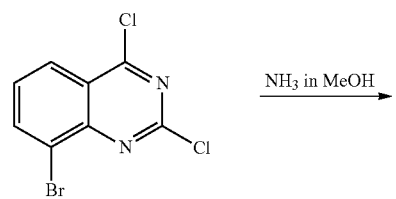

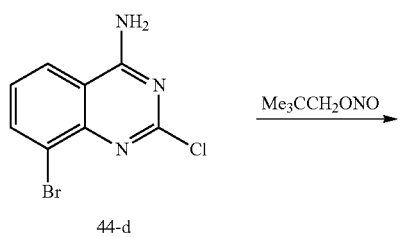

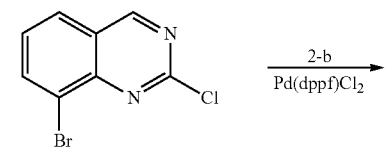

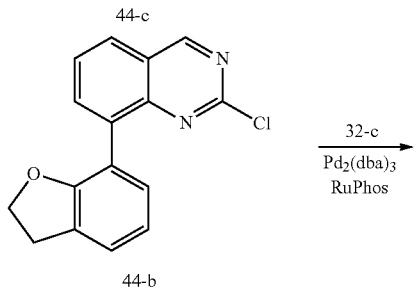

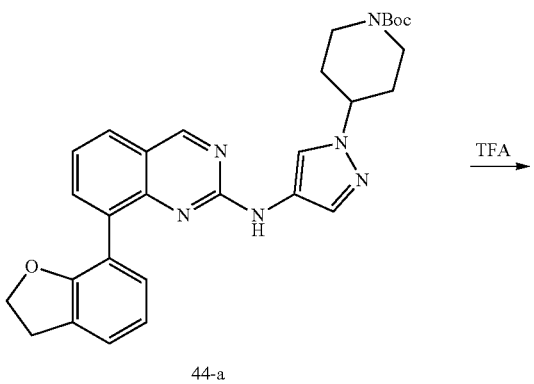

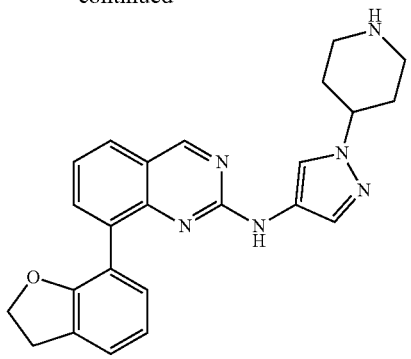

44

Synthesis of Compound 44-f

2-Amino-3-bromobenzoic acid (5.0 g, 23.26 mmol) was mixed with urea (7.0 g, 116.28 mmol) and the mixture was heated at 210° C. for 2 hours. The reaction mixture was cooled to 90° C., then water (50 mL) was added and the mixture was stirred for 30 minutes. The reaction mixture was cooled to room temperature and filtered. The filter cake was dried under vacuum to give 44-f as a yellow solid (5.5 g, yield 98%) which was used without further purification. LC-MS (ESI): m/z=241[M+H]$^+$.

Synthesis of Compound 44-e

Compound 44-f (5.5 g, 22.9 mmol) was dissolved in phosphorus oxychloride (30 mL), N,N-dimethylaniline (5 mL) was added and the reaction solution was heated at 110° C. for 18 hours. The reaction was cooled to room temperature and concentrated under reduced pressure to remove phosphorus oxychloride. The residue was concentrated to dryness and the residue was dissolved in dichloromethane (500 mL) and washed with water (500 mL). The separated organic phase was dried over anhydrous sodium sulfate, filtered and the filtrate was concentrated under reduced pressure. The residue was purified by silica gel column chromatography (petroleum ether:dichloromethane=3:1) to give 44-e as a pale yellow solid (2.5 g, yield 40%). LC-MS (ESI): m/z=277[M+H]$^+$.

Synthesis of Compound 44-d

Compound 44-e (1.2 g, 4.35 mmol) was dissolved in dichloromethane (5 mL), then 7M ammonia in methanol (50 mL) was added and the reaction was stirred at room temperature for 16 hours. The reaction solution was concentrated under reduced pressure. The residue was added with water (50 mL) and solid was precipitated out. The solid was filtered out and the filter cake was washed with water (50 mL) and dried in vacuo to give 44-d as a yellow solid (1.5 g, yield 100%), which was used for the next step without further purification.

Synthesis of Compound 44-c

Compound 44-d (1.5 g, 5.84 mmol) was dissolved in tetrahydrofuran (20 mL) and tert-amyl nitrite (2.7 g, 23.36 mmol) was added. The reaction mixture was heated at 70° C. for 18 hours. The reaction mixture was concentrated under reduced pressure and the residue was purified by silica gel column chromatography (petroleum ether:dichloromethane=3:1) to give 44-c as a light yellow solid (0.79 g, yield 56%). LC-MS (ESI): m/z=243[M+H]$^+$.

Synthesis of Compound 44-b

Compound 44-c (1.2 g, 5 mmol), compound 2-b (1.25 g, 5 mmol), [1,1'-bis (diphenylphosphino)ferrocene]dichloropalladium (36 mg, 0.05 mmol) and sodium carbonate (1.06 g, 10 mmol) were dissolved in 1,4-dioxane (8 mL) and water (2 mL). The reaction mixture was purged with nitrogen gas for three times to remove the oxygen contained in the system, and then heated at 90° C. for 8 hours. The reaction was cooled to room temperature, diluted with ice water (10 mL) and extracted with dichloromethane (50 mL×3). The combined organic phase was washed with water (20 mL×3) and brine (20 mL), dried over anhydrous sodium sulfate, filtered, and the filtrate was concentrated under reduced pressure. The residue was purified by silica gel TLC preparative plate (petroleum ether:ethyl acetate=10:1) to give 44-b as a yellow solid (790 mg, yield 56%). LC-MS (ESI): m/z=283[M+H]$^+$.

Synthesis of Compound 44-a

Compound 32-c (140 mg, 0.5 mmol), compound 44-b (140 mg, 0.5 mmol), potassium carbonate (138 mg, 1 mmol), tris(dibenzylideneindenone)dipalladium (14 mg, 0.01 mmol) and 2-dicyclohexylphosphine-2',6'-diisopropyloxy-1,1'-biphenyl (15 mg, 0.02 mmol) were dissolved in N,N-dimethylformamide (15 mL) and the reaction was purged with nitrogen gas for three times to remove oxygen contained in the system and then heated at 110° C. for 12 hours. The reaction was cooled to room temperature and concentrated under reduced pressure. The residue was purified by silica gel column chromatography (ethyl acetate: petroleum ether=10:1) to give compound 44-a (100 mg, yield 38%). LC-MS (ESI): m/z=513[M+H]$^+$.

Synthesis of Compound 44

Compound 44-a (100 mg, 1.9 mmol) was dissolved in dichloromethane (6 mL). The reaction was cooled to 0° C., trifluoroacetic acid (2 mL) was added and the reaction was stirred at room temperature for 1 hour. The reaction mixture was concentrated under reduced pressure. The residue was adjusted to pH=8-9 with saturated aqueous sodium carbonate solution, and solid was precipitated out. The solid was filtered out and dried in vacuo to give compound 44 (69 mg, yield 88%). LC-MS (ESI): m/z=413[M+H]$^+$.

$^1$H-NMR (400 MHz, DMSO-d6) δ: 9.74 (s, 1H), 9.23 (s, 1H), 7.86 (d, J=8.0 Hz, 1H), 7.70 (d, J=8.0 Hz, 1H), 7.35 (t, J=8 Hz, 1H), 7.24 (m, 3H), 7.0 (s, 1H), 4.42 (t, J=8 Hz, 2H), 3.91 (m, 1H), 3.28 (t, J=8 Hz, 2H), 3.17 (d, J=8 Hz, 2H), 2.55 (t, J=8 Hz, 2H), 1.71 (m, 2H), 1.55 (m, 2H) ppm Example 45

8-(2-Methoxyphenyl)-N-[1-(4-piperidinyl)-1H-pyrazol-4-yl]quinazolin-2-amine (Compound 45)

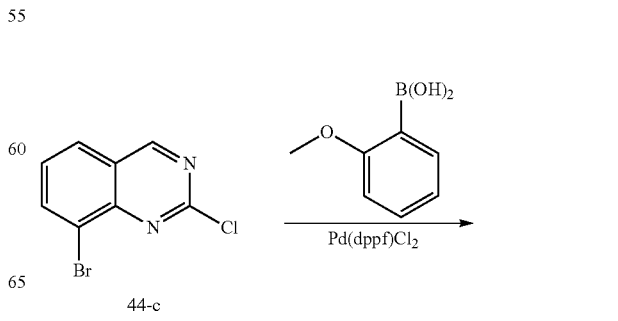

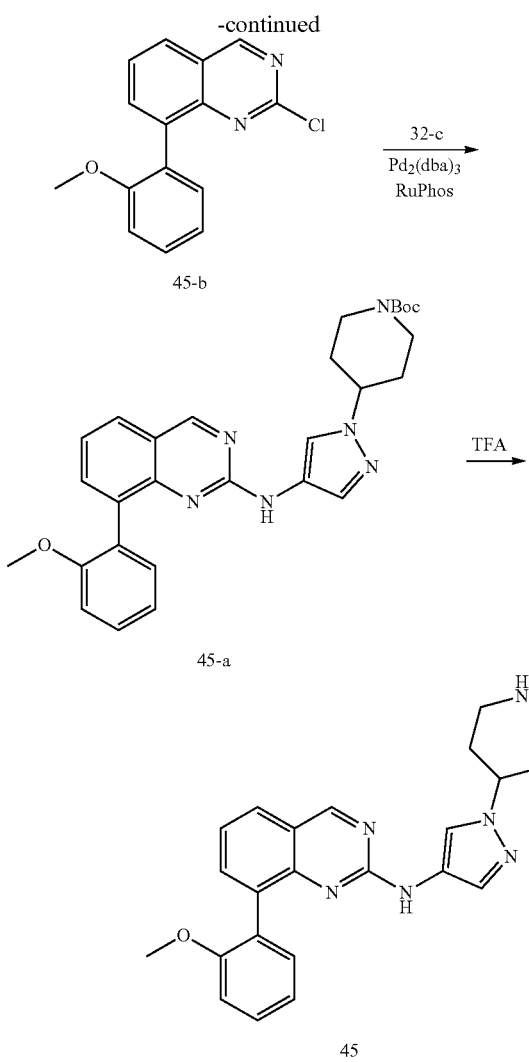

45-b 45-a

45

Synthesis of Compound 45-b

Compound 44-c (600 mg, 2.48 mmol), pinacol 2-methoxyphenylboronate (415 mg, 2.73 mmol), [1,1'-bis(diphenylphosphino)ferrocene]dichloropalladium (204 mg, 0.25 mmol) and sodium carbonate (804 mg, 7.44 mmol) were dissolved in 1,4-dioxane (5 mL) and water (3 mL). The reaction solution was purged with nitrogen gas for three times to remove the oxygen contained in the system and then heated at 80° C. for 16 hours. The reaction was cooled to room temperature, diluted with ice water (10 mL) and extracted with dichloromethane (50 mL×3). The combined organic phase was washed with water (20 mL×3) and brine (20 mL) sequentially, dried over anhydrous sodium sulfate, filtered and the filtrate was concentrated under reduced pressure. The residue was purified by silica gel column chromatography (petroleum ether:dichloromethane=3:1) to give 45-b as a white solid (450 mg, yield 67%). LC-MS (ESI): m/z=271[M+H]$^+$.

Synthesis of Compound 45-a

Compound 32-c (140 mg, 0.5 mmol), compound 45-b (135 mg, 0.5 mmol), potassium carbonate (138 mg, 1 mmol), tris(dibenzylidene indenone)dipalladium (14 mg, 0.01 mmol) and 2-dicyclohexylphosphine-2',6'-diisopropyloxy-1,1'-biphenyl (15 mg, 0.02 mmol) were dissolved in N,N-dimethylformamide (1 mL) and the reaction solution was purged with nitrogen gas for three times to remove oxygen contained in the system and then heated at 110° C. for 12 hours. The reaction was cooled to room temperature and concentrated under reduced pressure. The residue was purified by silica gel column chromatography (ethyl acetate:petroleum ether=10:1) to give compound 45-a (110 mg, yield 44%). LC-MS (ESI): m/z=541[M+H]$^+$.

Synthesis of Compound 45

Compound 45-a (110 mg, 1.9 mmol) was dissolved in dichloromethane (6 mL). The reaction was cooled to 0° C., trifluoroacetic acid (2 mL) was added and the mixture was stirred at room temperature for 1 hour. The reaction mixture was concentrated under reduced pressure and the residue was adjusted to pH=8-9 with saturated aqueous sodium carbonate solution, and solid was precipitated out. The solid was filtered out and dried in vacuo to give compound 45 (60 mg, yield 75%). LC-MS (ESI): m/z=441[M+H]$^+$.

$^1$H-NMR (400 MHz, CD$_3$OD) δ: 9.17 (s, 1H), 7.85 (d, J=8.0 Hz, 1H), 7.83 (d, J=8.0 Hz, 1H), 7.81 (s, 1H), 7.69 (t, J=8 Hz, 1H), 7.37 (m, 3H), 7.20 (m, 2H), 4.42 (m, 1H), 3.68 (s, 3H), 3.56 (t, J=8 Hz, 2H), 3.25 (t, J=8 Hz, 2H), 2.16 (m, 4H) ppm Example 46

6-fluoro-8-(2-methoxyphenyl)-N-[1-(4-piperidinyl)-1H-pyrazol-4-yl]quinazolin-2-amine (Compound 46)

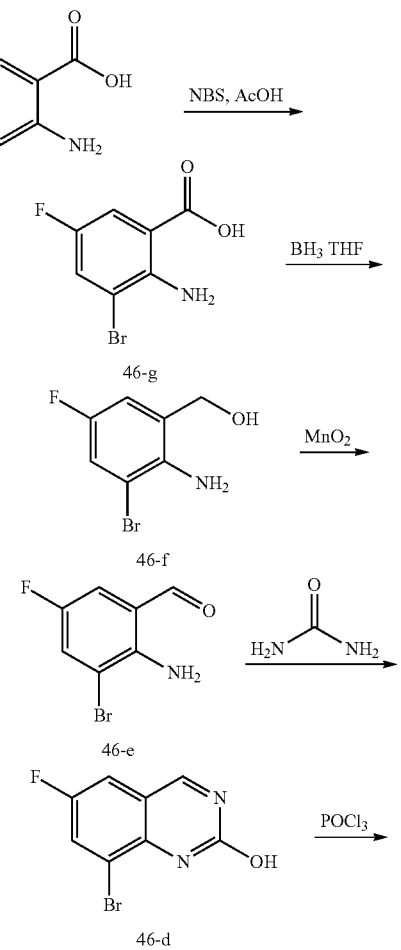

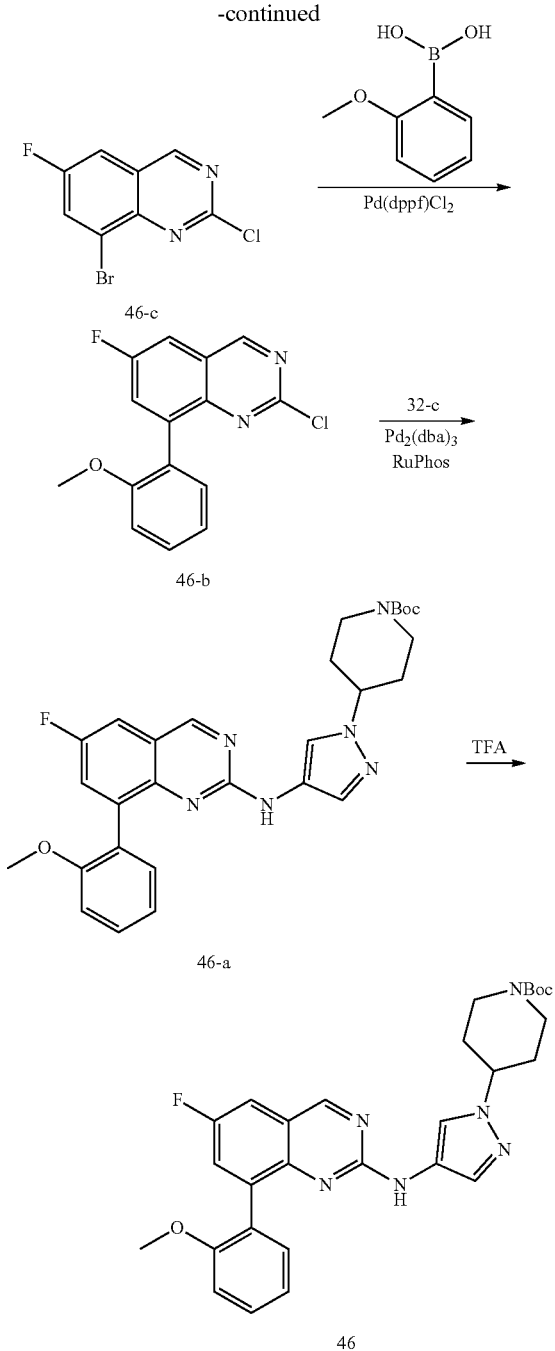

Synthesis of Compound 46-g

At 0° C., 2-amino-5-fluorobenzoic acid (20 g, 129 mmol) was dissolved in glacial acetic acid (250 mL), and N-bromosuccinimide (25 g, 140 mmol) was added thereto in portions. The mixture was filtered after stirring at room temperature for 16 hours and the filter cake was washed with petroleum ether (100 mL×3). The filter cake was dried in vacuo to give 46-g as a white solid (18.8 g, yield 62%) which was used without further purification. LC-MS (ESI): m/z=234[M+H]$^+$.

Synthesis of Compound 46-f

Borane tetrahydrofuran solution (240 mL, 240 mmol) was added dropwise to a solution of compound 21-g (18.8 g, 80 mmol) in tetrahydrofuran (160 mL) at 0° C. and the reaction solution was stirred at room temperature for 16 hours. Methanol (10 mL) was added to quench the reaction, and the reaction solution was concentrated under reduced pressure to remove the organic solvent. The residue was dissolved in ethyl acetate (200 mL). The solution was washed with water (50 mL×3) and brine (50 mL) successively, dried over anhydrous sodium sulfate and filtered. The filtrate was concentrated under reduced pressure to give 46-f as a white solid (17.2 g, yield 97%). LC-MS (ESI): m/z=220[M+H]$^+$.

Synthesis of Compound 46-e

Manganese dioxide (34 g, 390 mmol) was added in portions to a solution of compound 21-f (17.2 g, 78 mmol) in chloroform (300 mL) at 0° C. and the reaction solution was stirred at room temperature for 16 hours. The reaction solution was filtered and the filtrate was concentrated under reduced pressure to give 46-e as a white solid (16.5 g, yield 95%) which was used without further purification. LC-MS (ESI): m/z=218[M+H]$^+$.

Synthesis of Compound 46-d

Compound 46-f (16.5 g, 76 mmol) was mixed with urea (64 g, 1070 mmol), the mixture was heated at 185° C. for 30 minutes. The reaction mixture was cooled to room temperature and then water (200 mL) was added, the mixture was stirred for 30 minutes. The reaction mixture was filtered and the filter cake was dried in vacuo to give 46-d as a white solid (18 g, yield 97%) which was used without further purification. LC-MS (ESI): m/z=243[M+H]$^+$.

Synthesis of Compound 46-c

Compound 46-d (18 g, 74 mmol) was dissolved in phosphorus oxychloride (120 mL, 860 mmol) at 0° C. and the reaction was heated at 105° C. for 16 hours. The reaction solution was cooled to room temperature, concentrated under reduced pressure to remove phosphorus oxychloride, and the residue was added with water (100 mL) and stirred. The reaction mixture was filtered and the filter cake was dried under vacuum to give 46-c as a white solid (5 g, yield 26%) which was used without further purification. LC-MS (ESI): m/z=261[M+H]$^+$.

Synthesis of Compound 46-b

Compound 46-c (1.03 g, 3.93 mmol), o-methoxyphenylboronic acid (600 mg, 3.95 mmol), [1,1'-bis(diphenylphosphino)ferrocene]dichloropalladium (150 mg, 0.2 mmol) and sodium carbonate (1.2 g, 11.3 mmol) were dissolved in 1,4-dioxane (30 mL) and water (10 mL). The reaction solution was purged with nitrogen gas for three times to remove the oxygen contained in the system, and then heated at 120° C. for 16 hours. The reaction was cooled to room temperature, diluted with ice water (10 mL) and extracted with dichloromethane (50 mL×3). The combined organic phase was washed with water (20 mL×3) and brine (20 mL) sequentially, dried over anhydrous sodium sulfate, filtered and the filtrate was concentrated under reduced pressure. The residue was purified by silica gel column chromatography (petroleum ether:ethyl acetate=5:1) to give 46-b as a white solid (0.49 g, yield 43%). LC-MS (ESI): m/z=599 [M+H]$^+$.

Synthesis of Compound 46-a

Compound 46-b (140 mg, 0.48 mmol), compound 32-c (108 mg, 0.41 mmol), potassium carbonate (220 mg, 1.6 mmol), tris(dibenzylidene indenone)dipalladium (20 mg, 0.028 mmol) and 2-dicyclohexylphosphine-2',6'-diisopropoxy-1,1'-biphenyl (20 mg, 0.042 mmol) were dissolved in N,N-dimethylformamide (20 mL). The reaction solution was purged with nitrogen gas for three times to remove oxygen contained in the system, and then heated at 130° C. for 16 hours. The reaction was cooled to room temperature, diluted with ice water (10 mL) and extracted with dichloromethane (50 mL×3). The combined organic phase was washed with water (20 mL×3) and brine (20 mL), dried over anhydrous sodium sulfate, filtered and the filtrate was concentrated under reduced pressure. The residue was purified by silica gel column chromatography (petroleum ether:ethyl acetate=5:1) to give 46-a as a yellow solid (140 mg, yield 56%). LC-MS (ESI): m/z=517[M+H]$^+$.

Synthesis of Compound 46

Compound 46-a (140 mg, 0.27 mmol) was dissolved in dichloromethane (10 mL). The reaction was cooled to 0° C., trifluoroacetic acid (8 mL, 70 mmol) was added and the mixture was stirred at room temperature for 30 minutes. The reaction mixture was concentrated under reduced pressure. The residue was diluted with water (30 mL), adjusted to pH=10 with potassium carbonate solution and the aqueous phase was extracted with dichloromethane (50 mL×3). The combined organic phase was washed with water (20 mL×3) and brine (20 mL), dried over anhydrous sodium sulfate, filtered and the filtrate was concentrated under reduced pressure. The residue was purified by silica gel column chromatography (petroleum ether:ethyl acetate=2:1) to give 46 a yellow solid (27 mg, yield 24%). LC-MS (ESI): m/z=417[M+H]$^+$.

$^1$H-NMR (400 MHz, CD$_3$OD) δ: 9.11 (s, 1H), 7.64 (s, 1H), 7.56-7.48 (m, 3H), 7.42 (s, 1H), 7.18 (d, J=8.4 Hz, 1H), 7.17 (t, J=7.4 Hz, 1H), 3.98-4.00 (m, 1H), 3.70 (s, 3H), 3.36-3.27 (m, 2H), 2.89-2.82 (m, 2H), 1.97-1.94 (m, 2H), 1.86-1.82 (m, 2H) ppm Example 47

N-[8-(2-methoxyphenyl)pyridino[4,3-d]pyrimidin-2-yl]-1-(4-piperidin)-1H-pyrazol-4-amine (Compound 47)

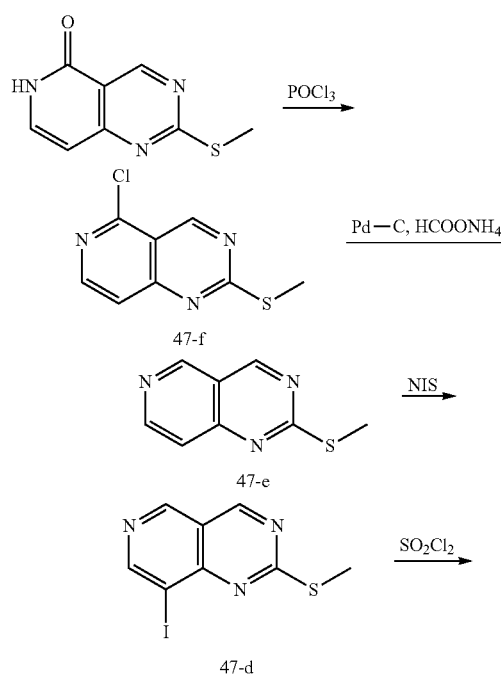

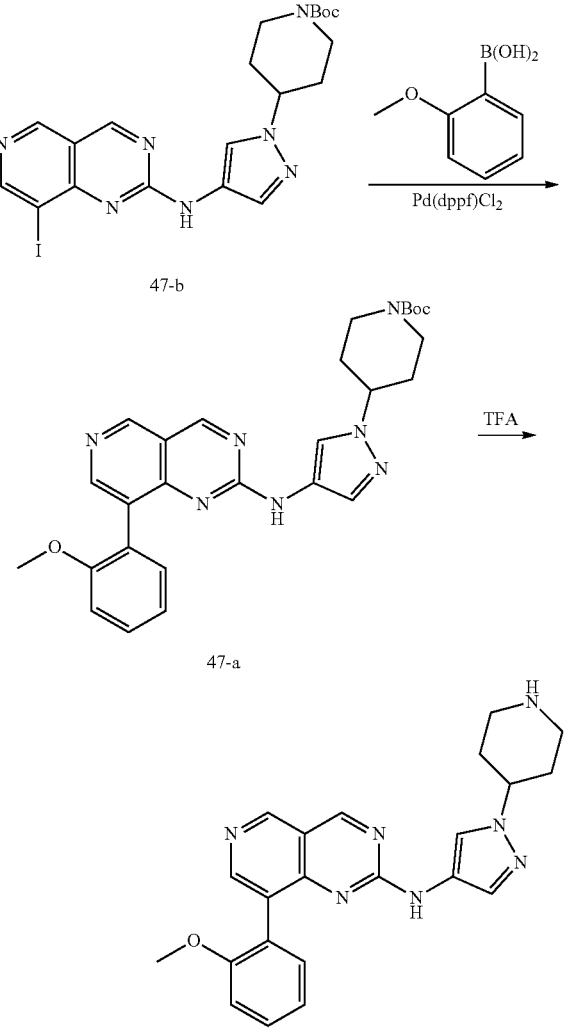

Synthesis of Compound 47-f

Phosphorus oxychloride (150 mL) was added to a 500 mL three necked flask, and 2-methylthio-5H-6H-pyrido[4,3-d]pyrimidin-5-one (25 g, 0.13 mol) was added at room temperature. The reaction solution was heated to reflux overnight and most of the phosphorus oxychloride was removed by distillation. After cooling to room temperature, the residue was poured into ice water (3 L) and adjusted to pH=7 with solid potassium carbonate. The aqueous phase was extracted with dichloromethane (1 L×2) and the combined organic phase was dried over anhydrous sodium sulphate, filtered and the filtrate was concentrated under reduced pressure to give a yellow solid which was washed with a mixed solvent (150 mL) of petroleum ether and ethyl acetate (5:1) and then dried in vacuo to give compound 47-f (17 g, yield: 63%) which was used without further purification. LC-MS (ESI): m/z=212[M+H]$^+$.

Synthesis of Compound 47-e

Compound 47-f (10 g, 47.4 mmol), palladium 10% on carbon (50% aq., 4.5 g) and absolute ethanol (100 mL) were added to a 250 mL three necked flask followed by the addition of solid ammonium formate (6.1 g, 94.8 mmol). The mixture was heated to reflux for 16 hours. After cooling to room temperature, the reaction mixture was filtered through celite and the filter cake was washed with absolute ethanol (50 mL×2). The combined filtrate was concentrated under reduced pressure and the residue was partitioned between dichloromethane (200 mL) and water (200 mL). The organic phase was dried over anhydrous sodium sulfate, filtered and the filtrate was concentrated. The residue was washed with a mixed solvent (100 mL) of petroleum ether and ethyl acetate (5:1) and the solid was dried under vacuum to give compound 47-e (3.3 g, yield 39%) which was used without further purification. LC-MS (ESI): m/z=178[M+H]$^+$.

Synthesis of Compound 47-d

Compound 47-e (1.7 g, 9.6 mmol) was dissolved in N,N-dimethylformamide (10 mL) and trifluoroacetic acid (1.32 g, 11.52 mmol) and N-iodosuccinimide (2.37 g, 10.56 mmol) were added, the resulting brown solution was heated to 50° C. and stirred for 16 hours. After cooling to room temperature, the reaction solution was poured into ice water (150 mL), extracted with dichloromethane (250 mL). The organic phase was washed with saturated sodium thiosulfate solution (100 mL), dried over anhydrous sodium sulfate, filtered, and the filtrate was concentrated under reduced pressure. The residue was washed with a mixed solvent (20 mL) of petroleum ether and ethyl acetate (3:1). The solid was dried in vacuo to give 47-d as a yellow solid (1.3 g, yield 45%), which was used without further purification. LC-MS (ESI): m/z=304[M+H]$^+$.

Synthesis of Compound 47-c

Compound 47-d (450 mg, 1.49 mmol) was dissolved in a mixed solvent of acetonitrile (10 mL) and dichloromethane (10 mL), the reaction solution was cooled to 0° C. and sulfonyl chloride (2 g, 14.9 mmol) was added and the mixture was stirred for further 3 hours. After warming to room temperature, the reaction solution was concentrated under reduced pressure and the residue was washed with a mixed solvent (10 mL) of petroleum ether and ethyl acetate (1:1). The solid was dried in vacuo to give 47-c as a yellow solid (380 mg, yield 78%), which was used without further purification. LC-MS (ESI): m/z=292[M+H]$^+$.

Synthesis of Compound 47-b

Compound 47-c (380 mg, 1.31 mmol) and compound 32-c (278 mg, 1.04 mmol) were dissolved in N,N-dimethylformamide (3 mL), cesium carbonate (426 mg, 1.31 mmol) was added and the mixture was stirred at room temperature for 16 hours. The reaction mixture was poured into ice-water (50 mL) and extracted with ethyl acetate (50 mL). The organic phase was dried over anhydrous sodium sulfate, filtered and the filtrate was concentrated under reduced pressure. The residue was purified by silica gel column chromatography (petroleum ether:ethyl acetate=1:2) to give 47-b as a yellow solid (150 mg, yield 28%).

Synthesis of Compound 47-a

Compound 47-b (150 mg, 0.29 mmol), 2-methoxybenzeneboronic acid (66 mg, 0.43 mmol) and sodium carbonate (92 mg, 0.86 mmol) were suspended in dioxane (3 mL) and water (3 mL), and [1,1'-bis(diphenylphosphino)ferrocene]dichloro-palladium.dichloromethane (25 mg, 0.03 mmol) was added. The reaction solution was purged with nitrogen gas for three times, then heated to 80° C. and stirred for 16 hours. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel TLC preparative plate (ethyl acetate) to give 47-a as a yellow solid (60 mg, yield 42%). LC-MS (ESI): m/z=502 [M+H]$^+$.

Synthesis of Compound 47

Compound 47-a (60 mg, 0.12 mmol) was dissolved in dichloromethane (2 mL), trifluoroacetic acid (2 mL) was added and the mixture was stirred at room temperature for 3 hours. The reaction mixture was concentrated under reduced pressure and the residue was partitioned between ethyl acetate (50 mL) and 1N aqueous hydrochloric acid solution (50 mL). The aqueous phase was adjusted to pH=10 with saturated aqueous potassium carbonate solution and solid was precipitated out. The solid was filtered out, and the filter cake was washed with water (20 mL×3) and dried under vacuum to give 47 as a pale yellow solid (12 mg, yield 25%). LC-MS (ESI): m/z=402[M+H]$^+$.

$^1$H-NMR (400 MHz, MeOD) δ: 9.31 (s, 1H), 9.04 (s, 1H), 8.48 (s, 1H), 7.77 (s, 1H), 7.58 (m, 1H), 7.49 (s, 1H), 7.27 (d, J=8 Hz, 1H), 7.20 (d, J=8 Hz, 1H), 7.18 (m, 1H), 3.99 (m, 1H), 3.73 (s, 3H), 3.23 (m, 2H), 2.78 (m, 2H), 1.93 (m, 2H), 1.73 (m, 2H) ppm Example 48

N-[7-(4-methylsulfonyl-2-methoxyphenyl)-6-methylthieno[3,2-d]pyrimidin-2-yl]-1-(4-piperidin)-1H-pyrazol-4-amine (Compound 48)

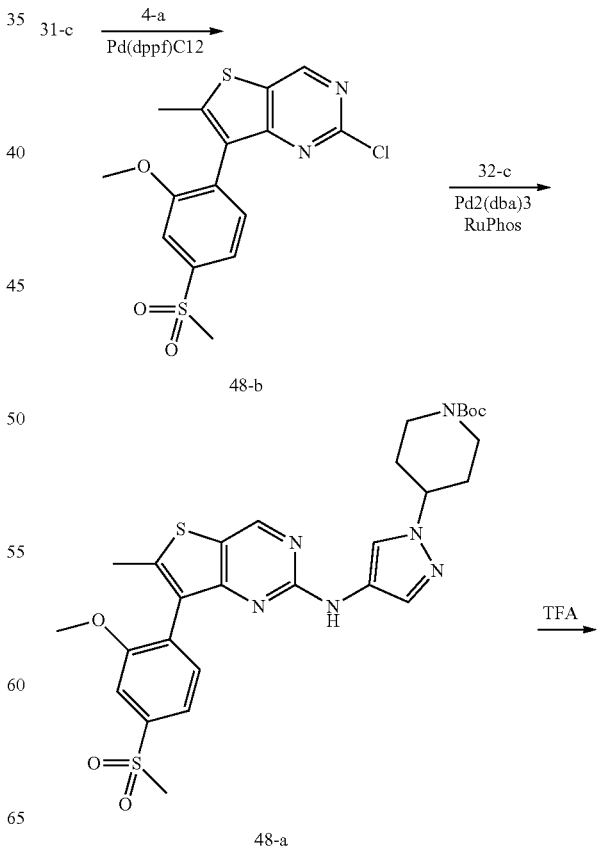

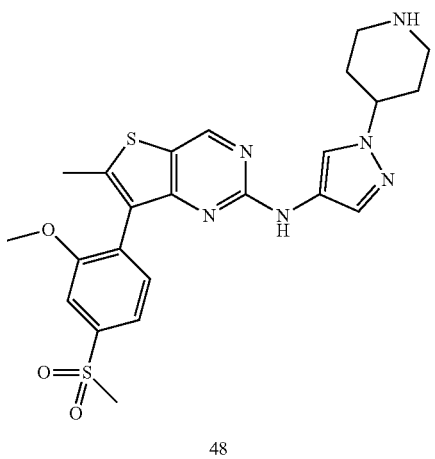

48

Synthesis of Compound 48-b

Compound 31-c (598 mg, 1.92 mmol), compound 4-a (600 mg, 1.92 mmol) and sodium carbonate (610 mg, 5.76 mmol) were suspended in dioxane (5 mL) and water (5 mL), [1,1'-bis(diphenylphosphino)ferrocene]dichloropalladium-·dichloromethane (473 mg, 0.58 mmol) was added. The reaction solution was purged with nitrogen gas for three times, then heated to 80° C. and reacted overnight. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel column chromatography (petroleum ether:dichloromethane=1:1) to give 48-b as a white solid (250 mg, yield 35%). LC-MS (ESI): m/z=369[M+H]⁺.

Synthesis of Compound 48-a

Compound 48-b (250 mg, 0.68 mmol) and compound 32-c (181 mg, 0.68 mmol) were dissolved in N,N-dimethylformamide (3 mL), and potassium carbonate (281 mg, 2.37 mmol), 2-dicyclohexylphosphino-2',6'-diisopropoxy-1,1'-biphenyl (58 mg, 0.13 mmol) and tris(dibenzylideneacetone)dipalladium (136 mg, 0.24 mmol) were added. The reaction solution was heated to 110° C. and stirred for 16 hours under nitrogen gas atmosphere. After cooling to room temperature, the reaction mixture was partitioned between ethyl acetate (100 mL) and water (100 mL). The organic phase was dried over anhydrous sodium sulfate, filtered and the filtrate was concentrated under reduced pressure. The residue was purified by silica gel TLC preparative plate (petroleum ether:ethyl acetate=1:1) to give 48-a as a pale yellow solid (75 mg, yield 18%). LC-MS (ESI): m/z=599 [M+H]⁺.

Synthesis of Compound 48

48-a (70 mg, 0.12 mmol) was dissolved in dichloromethane (3 mL), trifluoroacetic acid (3 mL) was added, and the mixture was stirred at room temperature for 3 hours. The reaction solution was concentrated under reduced pressure. The residue was partitioned between dichloromethane (100 mL) and saturated aqueous potassium carbonate solution (50 mL). The organic phase was dried over anhydrous sodium sulfate, filtered and the filtrate was concentrated under reduced pressure. The residue was purified by silica gel TLC preparative plate (dichloromethane:methanol=10:1) to give 48 as a white solid (18 mg, yield 31%). LC-MS (ESI): m/z=499[M+H]⁺.

¹H-NMR (400 MHz, CDCl₃) δ: 8.75 (s, 1H), 7.75 (s, 1H), 7.70 (dd, J=8 Hz, J=2 Hz, 1H), 7.64 (d, J=8 Hz, 1H), 7.59 (d, J=2 Hz, 1H), 7.38 (s, 1H), 6.89 (s, 1H), 4.12 (m, 1H), 3.94 (s, 3H), 3.25 (m, 2H), 3.18 (s, 3H), 2.78 (m, 2H), 2.47 (s, 3H), 2.04 (m, 2H), 1.63 (m, 2H) ppm Example 49

8-(4-methylsulfonyl-2-methoxyphenyl)-N-[1-(4-piperidin)-1H-pyrazol-4-yl]quinazolin-2-amine (Compound 49)

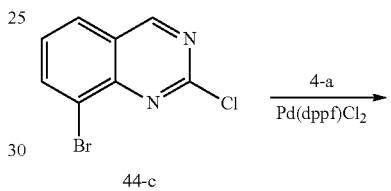

44-c

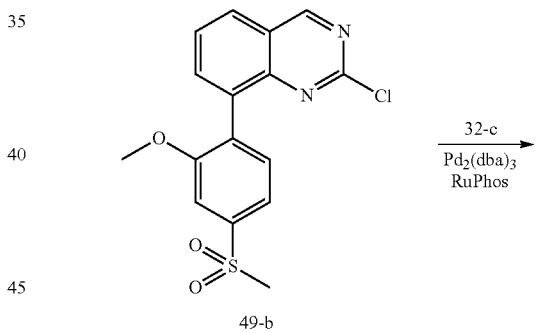

49-b

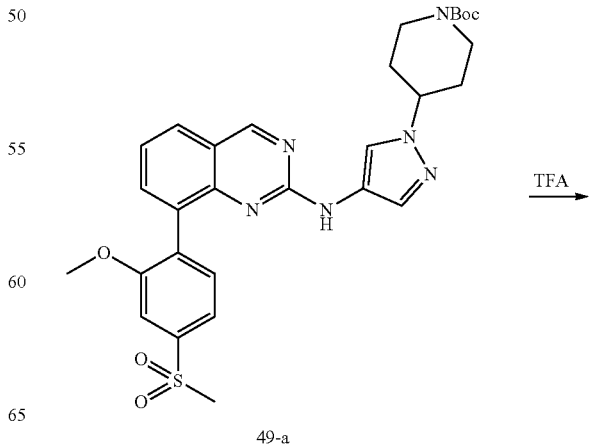

49-a

-continued

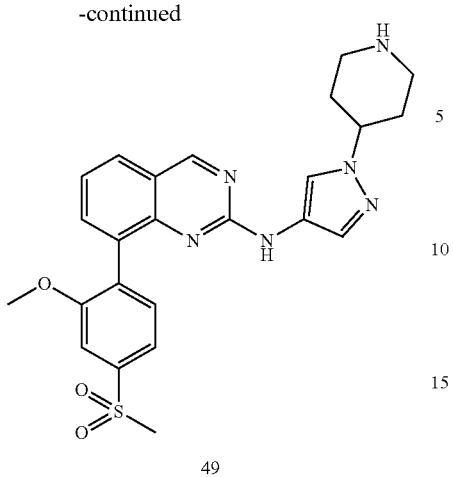

49

Synthesis of Compound 49-b

Compound 44-c (930 mg, 3.84 mmol), compound 4-a (1.2 g, 3.84 mmol) and sodium carbonate (1.2 g, 11.52 mmol) were suspended in dioxane (5 mL) and water (5 mL), [1,1'-bis(diphenylphosphino)ferrocene]dichloropalladium-.dichloromethane (937 mg, 1.15 mmol) was added. The reaction solution was purged with nitrogen gas for three times, then heated to 80° C. and reacted overnight. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated under reduced pressure. The residue was purified by silica gel column chromatography (petroleum ether:dichloromethane=1:2) to give 49-b as a white solid (150 mg, yield 12%). LC-MS (ESI): m/z=349[M+H]$^+$.

Synthesis of Compound 49-a

Compound 49-b (150 mg, 0.43 mmol) and compound 32-c (114 mg, 0.43 mmol) were dissolved in N,N-dimethylformamide (3 mL), and potassium carbonate (178 mg, 1.29 mmol), 2-dicyclohexylphosphino-2',6'-diisopropoxy-1,1'-biphenyl (61 mg, 0.13 mmol) and tris(dibenzylideneacetone)dipalladium (75 mg, 0.13 mmol) were added. The reaction solution was heated to 110° C. and stirred for 16 hours under nitrogen gas atmosphere. After cooling to room temperature, the reaction mixture was partitioned between ethyl acetate (50 mL) and water (50 mL). The organic phase was dried over anhydrous sodium sulfate, filtered and the filtrate was concentrated under reduced pressure. The residue was purified by silica gel TLC preparative plate (petroleum ether:ethyl acetate=1:1) to give 49-a as a pale yellow solid (130 mg, yield 52%). LC-MS (ESI): m/z=579[M+H]$^+$.

Synthesis of Compound 49

49-a (130 mg, 0.23 mmol) was dissolved in dichloromethane (3 mL), trifluoroacetic acid (3 mL) was added and the mixture was stirred at room temperature for 3 hours. The reaction mixture was concentrated under reduced pressure and the residue was partitioned between dichloromethane (50 mL) and saturated aqueous potassium carbonate solution (50 mL). The aqueous phase was adjusted to pH=10 with saturated aqueous potassium carbonate solution and solid was precipitated out. The solid was washed with water (20 mL×3) and dried in vacuo to give 49 as a white solid (85 mg, yield 79%). LC-MS (ESI): m/z=479[M+H]$^+$.

$^1$H-NMR (400 MHz, CDCl$_3$) δ: 9.07 (s, 1H), 7.77 (d, J=8 Hz, 1H), 7.61-7.71 (m, 4H), 7.49 (s, 1H), 7.38 (m, 2H), 7.09 (s, 1H), 4.01 (m, 1H), 3.78 (s, 3H), 3.22 (m, 2H), 3.19 (s, 3H), 2.80 (m, 2H), 1.94 (m, 2H), 1.71 (m, 2H) ppm Example 50

Ethyl 4-(4-{[7-(4-fluoro-2-methoxyphenyl)-6-methylthieno[3,2-d]pyrimidin-2-yl]amino}-1H-pyrazol-1-yl)piperidin-1-yl)-1-carboxylate (Compound 50)

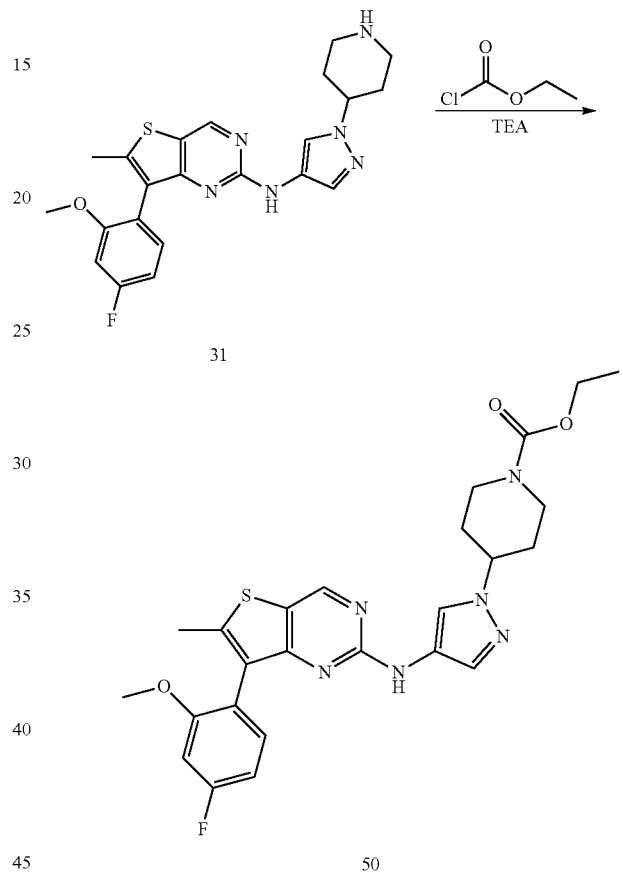

Synthesis of Compound 50

Ethyl chloroformate (163 mg, 1.5 mmol) was slowly added to a solution of compound 31 (438 mg, 1 mmol) and triethylamine (304 mg, 3 mmol) in dichloromethane (10 mL) at 0° C., and stirred for 1 hour. After warming to room temperature, the reaction mixture was added with water (20 mL) and extracted with dichloromethane (50 mL). The organic phase was washed with brine (50 mL), dried over anhydrous sodium sulfate, filtered and the filtrate was concentrated under reduced pressure. The residue was purified by preparative HPLC (mobile phase: 10 mM aqueous ammonium bicarbonate solution:acetonitrile=45% to 60%) to give 50 as a yellow solid (275 mg, yield 54%). LC-MS (ESI): m/z=511[M+H]$^+$.

$^1$H-NMR (400 MHz, DMSO-d6) δ: 9.44 (s, 1H), 8.94 (s, 1H), 7.75 (s, 1H), 7.40-7.33 (m, 2H), 7.10 (d, J=9.3 Hz, 1H), 6.94 (t, J=8.4 Hz, 1H), 4.15 (s, 1H), 4.08 (dd, J=14.1, 7.0 Hz, 4H), 3.73 (s, 3H), 2.95 (m, 2H), 2.40 (s, 3H), 1.93 (d, J=11.8 Hz, 2H), 1.59 (m, 2H), 1.22 (t, J=7.1 Hz, 3H) ppm

Example 51

N-[7-(4-fluoro-2-trideuteromethoxyphenyl)-3-deutero-6-methylthieno[3,2-d]pyrimidin-2-yl]-1-(piperidin-4-yl)-1H-pyrazol-4-amine (Compound 51)

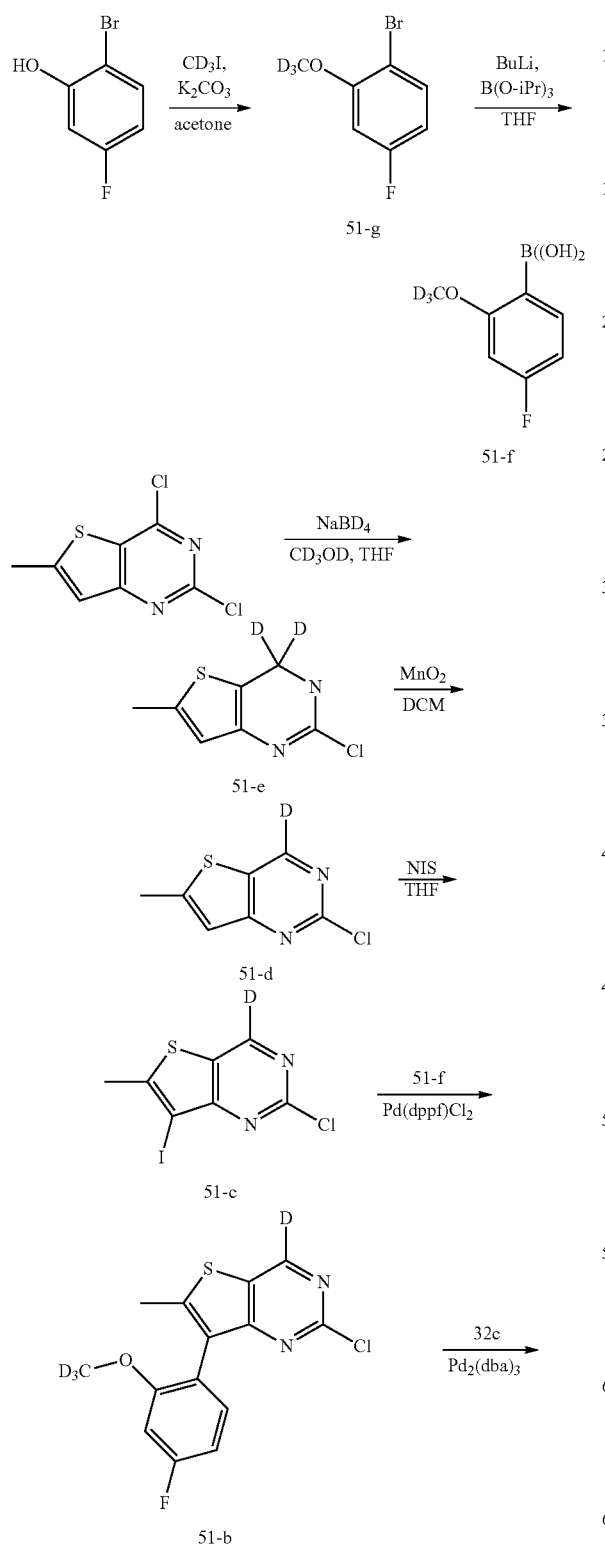

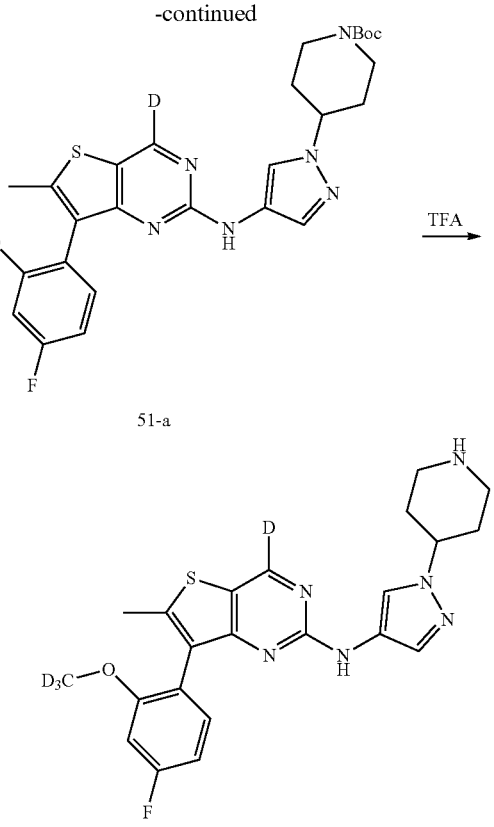

Synthesis of Compound 51-g

The compound 2-bromo-5-fluorophenol (2.56 g, 13.4 mmol) was dissolved in acetone (80 mL), and potassium carbonate (3.70 g, 26.8 mmol) and deuterated iodomethane (0.83 mL, 13.4 mmol) were added sequentially to the solution, and the reaction mixture was stirred for 16 hours at room temperature. After completion of the reaction, a 20% aqueous sodium hydroxide solution (80 mL) was added to the reaction solution and the mixture was extracted with ethyl acetate (50 mL×2). The organic layers were combined, dried over anhydrous sodium sulfate, filtered and the filtrate was concentrated under reduced pressure. The residue was purified by silica gel column chromatography (ethyl acetate) to give compound 51-g (1.22 g, yield 44%).

Synthesis of Compound 51-f

Compound 51-g (1.22 g, 5.89 mmol) was dissolved in tetrahydrofuran (30 mL), then the reaction solution was cooled to −78° C., a 2.5M solution of n-butyllithium in tetrahydrofuran (5.9 mL, 14.72 mmol) was added dropwise slowly, and the mixture was stirred at −78° C. for 1.5 hours, and triisopropylborate (4.1 mL, 17.67 mmol) was added slowly, then the mixture was stirred at −78° C. for another 1 hour, and then slowly warmed to room temperature, followed by further stirring for 1.5 hours at room temperature. After the reaction was completed, the reaction solution was diluted with 3M hydrochloric acid (60 mL) and extracted with ethyl acetate (80 mL×2). The organic layers were combined, dried over anhydrous sodium sulfate and filtered. The filtrate was concentrated under reduced pressure and the residue was purified by silica gel TLC preparative plate (petroleum ether:ethyl acetate=1:1) to give compound 51-f (220 mg, yield 21.6%).

Synthesis of Compound 51-e 2,4-Dichloro-6-methylthieno[3,2-d]pyrimidine (820 mg, 3.76 mmol) was dissolved in tetrahydrofuran (20 mL) and deuterium methanol (2 mL), and the reaction solution was cooled to 0° C., deuterium sodium borohydride (632 mg, 15.04 mmol) was added in portions. The reaction solution was warmed to room temperature and stirred for another 16 hours. The reaction solution was diluted with saturated ammonium chloride solution (40 mL) and the aqueous phase was extracted with ethyl acetate (80 mL×2). The organic layers were combined, dried over anhydrous sodium sulfate, filtered, and the filtrate was concentrated to give compound 51-e (660 mg, yield 93.4%) which was used for the next step without further purification. LC-MS (ESI): m/z=189.1[M+H]$^+$.

Synthesis of Compound 51-d

Compound 51-e (660 mg, 3.51 mmol) was dissolved in dichloromethane (20 mL) at 0° C. and active manganese dioxide (3.05 g, 35.1 mmol) was added, and the reaction solution was allowed to warm to room temperature and further stirred for 16 hours. The reaction solution was filtered through celite and the filter cake was washed with dichloromethane (10 mL×3). The combined filtrate was concentrated under reduced pressure to give 51-d as a white solid (635 mg, yield 97.8%) which was used without further purification. LC-MS (ESI): m/z=186[M+H]$^+$.

Synthesis of Compound 51-c

Compound 51-d (635 mg, 3.43 mmol) was dissolved in trifluoroacetic acid (10 mL) at 0° C., and N-iodosuccinimide (927 mg, 4.12 mmol) was added in portions, and the reaction solution was warmed to room temperature and stirred for another 16 hours. The reaction solution was concentrated under reduced pressure, saturated aqueous sodium bicarbonate solution (50 mL) was added and the mixture was stirred for 30 minutes. The mixture was filtered and the solid was washed with water (30 mL) and dried to give 51-c as a white solid (320 mg, yield 30%) which was used without further purification. LC-MS (ESI): m/z=312[M+H]$^+$.

Synthesis of Compound 51-b

Compound 51-c (235 mg, 0.755 mmol), compound 51-f (220 mg, 1.06 mmol) and sodium carbonate (240 mg, 2.265 mmol) were suspended in dioxane (8 mL) and water (4 mL), [1,1'-bis(diphenylphosphino)ferrocene]dichloropalladium-.dichloromethane (55 mg, 0.076 mmol) was added. The reaction solution was purged with nitrogen gas for three times and heated to 80° C. and reacted for 16 hours. After cooling to room temperature, the reaction mixture was concentrated under reduced pressure. The residue was partitioned between dichloromethane (50 mL) and water (50 mL). The organic phase was dried over anhydrous sodium sulfate, filtered and the filtrate was concentrated and purified by silica gel column chromatography (petroleum ether:dichloromethane=1:1) to give 51-b as a yellow solid (150 mg, yield 63.8%). LC-MS (ESI): m/z=313[M+H]$^+$.

Synthesis of Compound 51-a

Compound 51-b (150 mg, 0.48 mmol) and compound 32-c (128 mg, 0.48 mmol) were dissolved in N,N-dimethylformamide (15 mL), and potassium carbonate (198 mg, 1.44 mmol), 2-dicyclohexylphosphino-2',6'-diisopropoxy-1,1'-biphenyl (67 mg, 0.144 mmol) and tris(dibenzylideneacetone)dipalladium (82 mg, 0.144 mmol) were added. Under nitrogen gas atmosphere, the reaction solution was heated to 110° C. and reacted for 16 hours. After cooling to room temperature, the reaction solution was partitioned between dichloromethane (50 mL) and water (50 mL). The organic phase was dried over anhydrous sodium sulfate, filtered and the filtrate was concentrated under reduced pressure. The residue was purified by silica gel column chromatography (petroleum ether:dichloromethane:ethyl acetate=1:1:2) to give 51-a as a yellow solid (170 mg, yield 65.4%). LC-MS (ESI): m/z=543[M+H]$^+$.

Synthesis of Compound 51

51-a (170 mg, 0.314 mmol) was dissolved in dichloromethane (4 mL), trifluoroacetic acid (1 mL) was added and the mixture was stirred at room temperature for 1 hour. Saturated sodium bicarbonate solution (30 mL) was slowly added to the reaction and the aqueous phase was extracted with dichloromethane (30 mL×2). The organic phases were combined, dried over anhydrous sodium sulfate, filtered and the filtrate was concentrated under reduced pressure. The residue was purified by preparative HPLC (mobile phase: 10 mM ammonium bicarbonate+0.01% aqueous ammonia:acetonitrile=40% to 70%) to give 51 (45 mg, yield 32.5%). LC-MS (ESI): m/z=443[M+H]$^+$.
$^1$H-NMR (400 MHz, CDCl$_3$) δ: 9.43 (s, 1H), 7.75 (s, 1H), 7.37-7.34 (m, 2H), 7.14 (d, J=11.2 Hz, 1H), 6.98 (t, J=8.0 Hz, 1H), 3.96 (s, br., 1H), 3.03 (d, J=12.4 Hz, 2H), 2.56 (t, J=10.8 Hz, 2H), 2.40 (s, 3H), 1.83 (d, J=11.2 Hz, 2H), 1.54-1.49 (m, 2H) ppm Effect Example 1:IC50 Evaluation Assay on Cytoplasmic Tyrosine Kinase JAK1,2,3 Inhibition Experiment Steps 1. The compound was dissolved in 100% DMSO, diluted into solutions with appropriate concentration gradients with water according to experimental requirement, and added to a 384-well plate.

2. JAK2 kinase (Carna, Cat. No. 08-045, Lot. No. 07CBS-1927) and JAK3 kinase (Carna, Cat. No. 08-046, Lot. No. 08CBS-0371) were diluted to the optimum concentration with the following buffer solution: 50 mM HEPES, pH 7.5, 0.0015% Brij-35, 2 mM DTT. JAK1 kinase (Carna, Cat. No. 08-144, Lot. No. 11CBS-0144D) was diluted to the optimum concentration with the following buffer solution: 25 mM HEPES pH 7.5, 0.01% Brij-35, 2 mM DTT, 0.01M Triton. Transfer to the 384-well plate and incubated with the compound for a period of time.

3. The substrates of JAK2,3 were diluted to the optimum concentration with the following buffer: 50 mM HEPES, pH 7.5, 0.0015% Brij-35, 10 mM MgCl$_2$, adenosine triphosphate at Km. The substrate of JAK1 was diluted to the optimum concentration with the following buffer: 25 mM HEPES, pH 7.5, 0.01% Brij-35, 10 mM MgCl$_2$, 0.01M Triton, adenosine triphosphate at Km. Add to the 384-well plate to initiate there action and react for 1 hour at 28° C.

4. 1 Eq. of sulfuric acid solution was added to terminate the reaction, the conversion rate was read with Caliper Reader. The inhibition rate was calculated as the average of two tests.

Experiment Results

The biological activity of some of the compounds of the present invention was determined by the above assay. The results obtained are shown in Table 1:

TABLE 1

IC50 (nM) of some compounds of the present invention inhibiting JAK 1, 2, 3 kinase

| Compound | JAK 1 | JAK 2 | JAK 3 |
| --- | --- | --- | --- |
| 1 | 6.8 | 1.7 | 1.7 |
| 2 | 14 | 1.8 | 0.99 |

TABLE 1-continued

IC50 (nM) of some compounds of the present
invention inhibiting JAK 1, 2, 3 kinase

| Compound | JAK 1 | JAK 2 | JAK 3 |
|---|---|---|---|
| 4 | 16 | 1.3 | 3.1 |
| 6 | 12 | 1.4 | 1.4 |
| 7 | 13 | 1.2 | 1.8 |
| 10 | 10.6 | 1.1 | 3.6 |
| 11 | 5.1 | 0.94 | 0.73 |
| 12 | 12 | 1.8 | 1.4 |
| 15 | 13 | 1.8 | 2.1 |
| 16 | 34 | 6.1 | 6.4 |
| 17 | 16 | 2.3 | 1.3 |
| 18 | 20 | 4.3 | 4.5 |
| 21 | 1.3 | 0.31 | 0.39 |
| 22 | 43 | 1.7 | 1.5 |
| 23 | 1.1 | 0.37 | 0.64 |
| 24 | 9 | 0.94 | 1.3 |
| 25 | 3.6 | 0.6 | 1.3 |
| 26 | 12 | 1.6 | 1.6 |
| 27 | 10 | 2.3 | 1.6 |
| 28 | 75.8 | 23 | 1.3 |
| 29 | 30.4 | 0.8 | 15.9 |
| 30 | 8.5 | 1.9 | 5.1 |
| 32 | 6.6 | 0.79 | 0.42 |
| 33 | 18.5 | 8.9 | 12.9 |
| 34 | 5.6 | 0.71 | 1.1 |
| 35 | 3.8 | 0.70 | 0.84 |
| 36 | 13 | 0.82 | 0.41 |
| 39 | 18 | 1.6 | 0.71 |
| 41 | 41 | 36 | 33.7 |
| 42 | 47 | 13 | 29 |
| 43 | 7.2 | 1.7 | 1.0 |
| 44 | 54 | 7.7 | 16 |
| 45 | 2.4 | 5.8 | 1.0 |
| 47 | 58 | 9.6 | 3.0 |
| 48 | 4.2 | 0.51 | 1.3 |
| 49 | 58 | 2.1 | 9.8 |

Effect Example 2: IC50 Evaluation Assay of FGFR1,2,3 Kinase Inhibition

Experiment Steps

1. The compound was dissolved in 100% DMSO, diluted into solutions with appropriate concentration gradients with water according to experimental requirement, and added to a 96-well plate.

2. FGFR1 kinase (Carna, Cat. No. 08-133, Lot. No. 09CBS-0989) and FGFR2 kinase (Carna, Cat. No. 08-134, Lot. No. 07CBS-2468), JAK3 kinase (Carna, Cat. No. 08-135, Lot. No. 06CBS-3177) were diluted to the optimum concentration with the following buffer solution: 50 mM HEPES, pH 7.5, 0.0015% Brij-35, 2 mM DTT. Transfer to the 96-well plate and incubate with the compound at 28° C. for a period of time.

3. The buffer solution (100 mM HEPES, pH 7.5, 0.0015% Brij-35, 0.2% Coating Reagent and 50 nM EDTA) was added to terminate the reaction.

4. The conversion rate was read with Caliper Reader. The inhibition rate was calculated as the average of two tests.

Experiment Results

The biological activity of some of the compounds of the present invention was determined by the above assay. The results obtained are shown in Table 2:

TABLE 2

IC50 (nM) of some compounds of the present
invention inhibiting FGFR1, 2, 3 kinase

| Compound | FGFR 1 | FGFR 2 | FGFR 3 |
|---|---|---|---|
| 31 | 5.1 | 10 | 16 |
| 34 | 3.8 | 8.9 | 15 |

Effect Example 3: IC50 Evaluation Assay of FLT3, FLT3-ITD, FLT3-D835Y Kinase Inhibition Experiment Steps 1. The compound was dissolved in 100% DMSO, diluted into solutions with appropriate concentration gradients with water according to experimental requirement, and added to a 96-well plate.

2. FLT3 kinase (Carna, Cat. No. 08-154, Lot. No. 07CBS-2350), FLT3-ITD kinase (Invitrogen, Cat. No. PV6191, Lot. No. 1753453) and FLT3-D835Y kinase (Invitrogen, Cat. No. PR7450A, Lot. No. 1629729C) were diluted to the optimum concentration with the following buffer solution: 50 mM HEPES, pH 7.5, 0.0015% Brij-35, 10 mM $MgCl_2$, 2 mM DTT. Transfer to the 96-well plate and incubate with the compound at 28° C. for a period of time.

3. The buffer solution (100 mM HEPES, pH 7.5, 0.0015% Brij-35, 0.2% Coating Reagent and 50 nM EDTA) was added to terminate the reaction.

4. The conversion rate was read with Caliper Reader. The inhibition rate was calculated as the average of two tests.

Experiment Results

The biological activity of some of the compounds of the present invention was determined by the above assay. The results obtained are shown in Table 3:

TABLE 3

IC50 (nM) of some compounds of the present
invention inhibiting FLT3 kinase

| Compound | FLT3-WT | FLT3-ITD | FLT3-D835Y |
|---|---|---|---|
| 31 | 0.28 | 0.34 | 0.20 |
| 34 | <5 | 0.33 | 0.23 |

Effect Example 4: IC50 Evaluation Assay of Src Family Kinase Inhibition

Experiment Steps

1. The compound was dissolved in 100% DMSO, diluted into solutions with appropriate concentration gradients with water according to experimental requirement, and added to a 96-well plate.

2. c-Src kinase (Carna, Cat. No. 08-173, Lot. No. 05CBS-1367), LYNαkinase (Carna, Cat. No. 08-171, Lot. No. 06CBS-3296D), FYN kinase (Carna, Cat. No. 08-068, Lot. No. 05CBS-1032), LCK kinase (Carna, Cat. No. 08-170, Lot. No. 07CBS-2482), HCK kinase (BPS, Cat. No. 40440, Lot. No. 1001), FGR kinase (Carna, Cat. No. 08-166, Lot. No. 05CBS-2781), YES kinase (Carna, Cat. No. 08-175, Lot. No. 06CBS-3247) were diluted to the optimum concentration with the following buffer solution: 50 mM HEPES, pH 7.5, 0.0015% Brij-35, 10 mM $MgCl_2$, 2 mM DTT. Transfer to the 96-well plate and incubate with the compound at 28° C. for a period of time.

3. The buffer solution (100 mM HEPES, pH 7.5, 0.0015% Brij-35, 0.2% Coating Reagent and 50 nM EDTA) was added to terminate the reaction.

4. The conversion rate was read with Caliper Reader. The inhibition rate was calculated as the average of two tests.

Experiment Results

The biological activity of some of the compounds of the present invention was determined by the above assay. The results obtained are shown in Table 4:

TABLE 4

| IC50 (nM) of some compounds of the present invention inhibiting Src family kinase | | | | | | | |
|---|---|---|---|---|---|---|---|
| Compound | c-Src | LYNα | FYN | LCK | HCK | FGR | YES |
| 31 | 6.0 | 1.3 | 3.7 | 5.5 | 30 | 14 | 5.8 |
| 34 | 6.3 | <5 | <5 | <5 | 27 | 11 | 6.8 |

What is claimed is:

1. A fused ring pyrimidine compound of formula I, a tautomer, an enantiomer, a diastereoisomer or a pharmaceutically acceptable salt thereof;

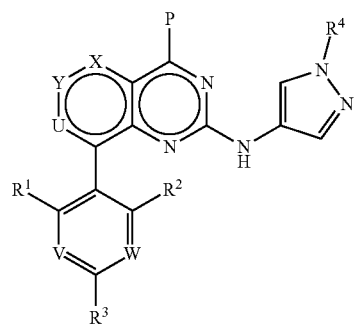

wherein, P is selected from a hydrogen or a deuterium;
X is selected from CH or S;
Y is selected from N or $CR^5$;
U is selected from a chemical bond or CH;
V is selected from N or CH;
W is selected from N or $CR^6$;
each of $R^1$, $R^2$, $R^3$ and $R^6$ is independently selected from the group consisting of a hydrogen, a deuterium, a halogen, a substituted or unsubstituted alkyl,

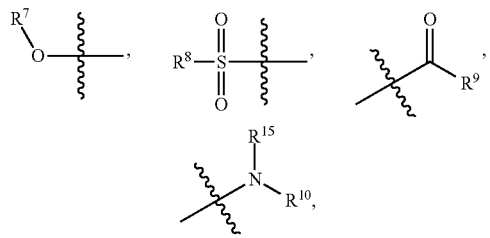

a cycloalkyl and a heterocycloalkyl; each of $R^7$, $R^8$, $R^9$, $R^{10}$ and $R^{15}$ is independently selected from the group consisting of a hydrogen, a deuterium, a halogen, a hydroxyl, an amino, a substituted or unsubstituted alkyl, an alkoxy,

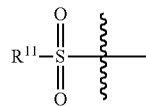

and a heterocycloalkyl; $R^{11}$ is a hydrogen, a deuterium or an alkyl; or $R^6$, $R^2$ and the two atoms on the ring to which they are attached form a "substituted or unsubstituted 5- to 7-membered carbon heterocycle"; or, $R^6$, $R^3$ and the two atoms on the ring to which they are attached form a "substituted or unsubstituted 5- to 7-membered carbon heterocycle"; the heteroatom in "substituted or unsubstituted 5- to 7-membered carbon heterocycle" is selected from the group consisting of nitrogen, oxygen and sulfur;

$R^4$ is a hydrogen, a deuterium, a substituted or unsubstituted alkyl, an alkoxy, a cycloalkyl, or a substituted or unsubstituted heterocycloalkyl;

$R^5$ is a hydrogen, a deuterium, a halogen, or an alkyl;

in the definitions of $R^1$, $R^2$, $R^3$ and $R^6$, the "substituted" in "a substituted or unsubstituted alkyl" means to be substituted with the substituents selected from the group consisting of a halogen, a hydroxyl, an amino, an alkyl, an alkoxy,

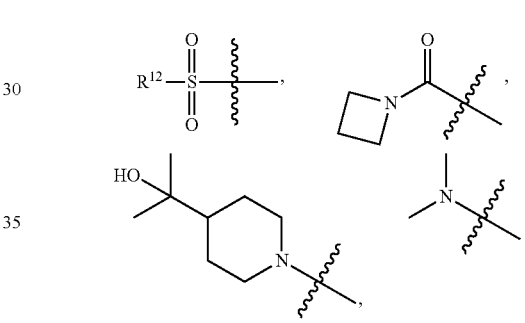

and a heterocycloalkyl, in the case when multiple substituents are present, the substituents are the same or different;

$R^{12}$ is a hydrogen, a deuterium, or an alkyl;

in the definitions of $R^7$, $R^8$, $R^9$, $R^{10}$ and $R^{15}$, the "substituted" in "a substituted or unsubstituted alkyl" means to be substituted with the substituents selected from the group consisting of a deuterium, a halogen, a hydroxyl, an amino, an alkyl, an alkoxy,

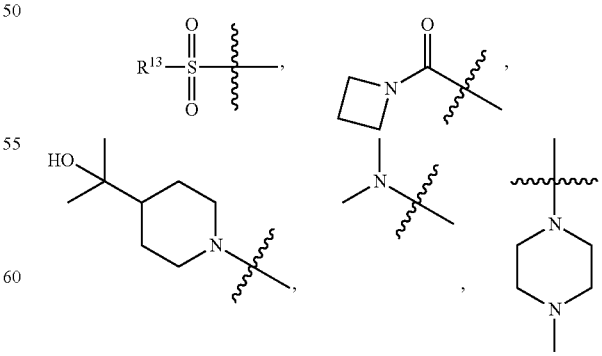

and a heterocycloalkyl, in the case when multiple substituents are present, the substituents are the same or different;

$R^{13}$ is a hydrogen or an alkyl;

in the definition of $R^4$, the "substituted" in "a substituted or unsubstituted alkyl" and "a substituted or unsubstituted heterocycloalkyl" means to be substituted with the substituents selected from the group consisting of a hydroxyl, an alkyl,

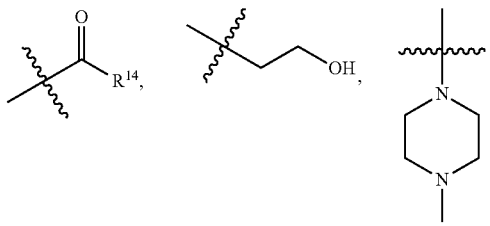

and heterocycloalkyl, in the case when multiple substituents are present, the substituents are the same or different; $R^{14}$ is a hydrogen, an alkyl, a hydroxymethyl or an alkoxy;

the "substituted" in "substituted or unsubstituted 5- to 7-membered carbon heterocycle" means to be substituted with one or more than one alkyl.

2. The fused ring pyrimidine compound, the tautomer, the enantiomer, the diastereoisomer or the pharmaceutically acceptable salt thereof according to claim 1, wherein, in the case where each of $R^1$, $R^2$, $R^3$ and $R^6$ is independently a halogen, the halogen is fluorine or chlorine;

and/or, in the case where each of $R^1$, $R^2$, $R^3$ and $R^6$ is independently "a substituted or unsubstituted alkyl", the alkyl is a $C_{1-4}$ alkyl;

and/or, in the case where each of $R^1$, $R^2$, $R^3$ and $R^6$ is independently a heterocycloalkyl, the heterocycloalkyl is linked to other groups via a carbon atom or a heteroatom thereof;

and/or, in the case where each of $R^1$, $R^2$, $R^3$ and $R^6$ is independently a heterocycloalkyl, the heterocycloalkyl is "a heterocycloalkyl with 1-4 heteroatoms and 3-8 carbon atoms in which the heteroatom is oxygen and/or nitrogen";

and/or, in the case where each of $R^7$, $R^8$, $R^9$, $R^{10}$ and $R^{15}$ is independently a halogen, the halogen is fluorine;

and/or, in the case where each of $R^7$, $R^8$, $R^9$, $R^{10}$ and $R^{15}$ is independently "a substituted or unsubstituted alkyl", the alkyl is a $C_{1-10}$ alkyl;

and/or, in the case where each of $R^7$, $R^8$, $R^9$, $R^{10}$ and $R^{15}$ is independently an alkoxy, the alkoxy is a $C_{1-10}$ alkoxy;

and/or, in the case where each of $R^7$, $R^8$, $R^9$, $R^{10}$ and $R^{15}$ is independently a heterocycloalkyl, the heterocycloalkyl is linked to other groups via a carbon atom or a heteroatom thereof;

and/or, in the case where each of $R^7$, $R^8$, $R^9$, $R^{10}$ and $R^{15}$ is independently a heterocycloalkyl, the heterocycloalkyl is "a heterocycloalkyl with 1-4 heteroatoms and 3-8 carbon atoms in which the heteroatom is oxygen and/or nitrogen";

and/or, in the case where each of $R^7$, $R^8$, $R^{9'}$ $R^{19}$ and $R^{15}$ is independently

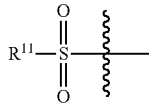

wherein $R^{11}$ is a $C_{1-4}$ alkyl;

and/or, in the case where $R^4$ is "a substituted or unsubstituted alkyl", the alkyl is a $C_{1-4}$ alkyl;

and/or, in the case where $R^4$ is an alkoxy, the alkoxy is a $C_{1-4}$ alkoxy;

and/or, in the case where $R^4$ is "a substituted or unsubstituted heterocycloalkyl", the heterocycloalkyl is linked to other groups via a carbon atom or a heteroatom thereof;

and/or, in the case where $R^4$ is "a substituted or unsubstituted heterocycloalkyl", the heterocycloalkyl is "a heterocycloalkyl with 1-4 heteroatoms and 3-8 carbon atoms in which the heteroatom is oxygen and/or nitrogen";

and/or, in the case where $R^5$ is a halogen, the halogen is fluorine;

and/or, in the case where $R^5$ is an alkyl, the alkyl is a $C_{1-4}$ alkyl;

and/or, in the case where the "5- to 7-membered carbon heterocycle" in "a substituted or unsubstituted 5- to 7-membered carbon heterocycle" is "a carbon heterocycle with 1-4 heteroatoms and 2-6 carbon atoms in which the heteroatom is oxygen and/or nitrogen";

and/or, in the case where each of $R^1$, $R^2$, $R^3$ and $R^6$ is independently "a substituted or unsubstituted alkyl", the substituent in "a substituted or unsubstituted alkyl" is fluorine;

and/or, in the case where each of $R^1$, $R^2$, $R^3$ and $R^6$ is independently "a substituted or unsubstituted alkyl", the substituent in "a substituted or unsubstituted alkyl" is a $C_{1-10}$ alkyl;

and/or, in the case where each of $R^1$, $R^2$, $R^3$ and $R^6$ is independently "a substituted or unsubstituted alkyl", the substituent in "a substituted or unsubstituted alkyl" is a $C_{1-10}$ alkoxy;

and/or, in the case where each of $R^1$, $R^2$, $R^3$ and $R^6$ is independently "a substituted or unsubstituted alkyl" and the substituent in "a substituted or unsubstituted alkyl" is a heterocycloalkyl, the heterocycloalkyl is linked to other groups via a carbon atom or a heteroatom thereof;

and/or, in the case where each of $R^1$, $R^2$, $R^3$ and $R^6$ is independently "a substituted or unsubstituted alkyl" and the substituent in "a substituted or unsubstituted alkyl" is "a heterocycloalkyl with 1-4 heteroatoms and 3-8 carbon atoms in which the heteroatom is oxygen and/or nitrogen";

and/or, in the case where each of $R^1$, $R^2$, $R^3$ and $R^6$ is independently "a substituted or unsubstituted alkyl", the substituent in "a substituted or unsubstituted alkyl" is

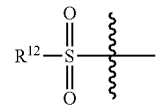

wherein $R^{12}$ is a $C_{1-4}$ alkyl;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is fluorine;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a $C_{1-10}$ alkyl;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a $C_{1-10}$ alkoxy;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a heterocycloalkyl, the heterocycloalkyl is linked to other groups via a carbon atom or a heteroatom thereof;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is "a heterocycloalkyl with 1-4 heteroatoms and 3-8 carbon atoms in which the heteroatom is oxygen and/or nitrogen";

and/or, in the case where each of $R^7$, $R^8$, $R^9$, $R^{10}$ and $R^{15}$ is independently "a substituted or unsubstituted alkyl", the substituent in "a substituted or unsubstituted alkyl" is

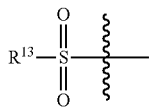

wherein $R^{13}$ is a $C_{1-4}$ alkyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is a $C_{1-4}$ alkyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is a heterocycloalkyl, the heterocycloalkyl is linked to other groups via a carbon atom or a heteroatom thereof;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is "a heterocycloalkyl with 1-4 heteroatoms and 3-6 carbon atoms in which the heteroatom is oxygen and/or nitrogen";

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is

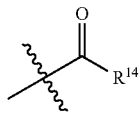

wherein $R^{14}$ is a $C_{1-4}$ alkyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is

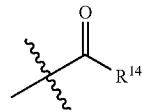

wherein $R^{14}$ is a $C_{1-4}$ alkoxy;

and/or, in the case where the substituent in "a substituent and unsubstituent 5- to 7-membered carbon heterocycle" is a $C_{1-4}$ alkyl.

3. The fused ring pyrimidine compound, the tautomer, the enantiomer, the diastereoisomer or the pharmaceutically acceptable salt thereof according to claim 2, wherein, in the case where each of $R^1$, $R^2$, $R^3$ and $R^6$ is independently "a substituted or unsubstituted alkyl", the alkyl is a methyl;

and/or, in the case where each of $R^1$, $R^2$, $R^3$ and $R^6$ is independently a heterocycloalkyl, the heterocycloalkyl is "a heterocycloalkyl with 1-4 heteroatoms and 3-6 carbon atoms in which the heteroatom is oxygen and/or nitrogen";

and/or, in the case where each of $R^7$, $R^8$, $R^9$, $R^{10}$ and $R^{15}$ is independently "a substituted or unsubstituted alkyl", the alkyl is a $C_{1-4}$ alkyl;

and/or, in the case where each of $R^7$, $R^8$, $R^9$, $R^{10}$ and $R^{15}$ is independently an alkoxy, the alkoxy is a $C_{1-4}$ alkoxy;

and/or, in the case where each of $R^7$, $R^8$, $R^9$, $R^{10}$ and $R^{15}$ is independently a heterocycloalkyl, the heterocycloalkyl is "a heterocycloalkyl with 1-4 heteroatoms and 3-6 carbon atoms in which the heteroatom is oxygen and/or nitrogen";

and/or, in the case where each of $R^7$, $R^8$, $R^9$, $R^{10}$ and $R^{15}$ is independently

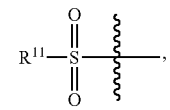

$R^{11}$ is a methyl;

and/or, in the case where $R^4$ is "a substituted or unsubstituted alkyl", the alkyl is a methyl, an ethyl, a propyl or an isopropyl;

and/or, in the case where $R^4$ is "a substituted or unsubstituted heterocycloalkyl", the heterocycloalkyl is "a heterocycloalkyl with 1-4 heteroatoms and 3-6 carbon atoms in which the heteroatom is oxygen and/or nitrogen";

and/or, in the case where $R^5$ is an alkyl, the alkyl is a methyl;

and/or, the "5- to 7-membered carbon heterocycle" in "substituted or unsubstituted 5- to 7-membered carbon heterocycle" is

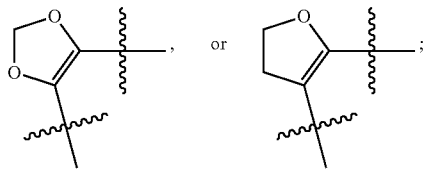 [SMILES: *C1=C(*)OCO1 ; *C1=C(*)OCC1]

and/or, in the case where each of $R^1$, $R^2$, $R^3$ and $R^6$ is independently "a substituted or unsubstituted alkyl", the substituent in "a substituted or unsubstituted alkyl" is a $C_{1-4}$ alkyl;

and/or, in the case where each of $R^1$, $R^2$, $R^3$ and $R^6$ is independently "a substituted or unsubstituted alkyl", the substituent in "a substituted or unsubstituted alkyl" is a $C_{1-4}$ alkoxy;

and/or, in the case where each of $R^1$, $R^2$, $R^3$ and $R^6$ is independently "a substituted or unsubstituted alkyl", the substituent in "a substituted or unsubstituted alkyl" is "a heterocycloalkyl with 1-4 heteroatoms and 3-6 carbon atoms in which the heteroatom is oxygen and/or nitrogen";

and/or, in the case where each of $R^1$, $R^2$, $R^3$ and $R^6$ is independently "substituted or unsubstituted alkyl", the substituent in "substituted or unsubstituted alkyl" is

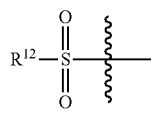

wherein $R^{12}$ is a methyl;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a $C_{1-4}$ alkyl;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a $C_{1-4}$ alkoxy;

and/or, in the case where each of $R^7$, $R^8$, $R^9$, $R^{10}$ and $R^{15}$ is independently "a substituted or unsubstituted alkyl", the substituent in "a substituted or unsubstituted alkyl" is "a heterocycloalkyl with 1-4 heteroatoms and 3-6 carbon atoms in which the heteroatom is oxygen and/or nitrogen";

and/or, in the case where each of $R^1$, $R^2$, $R^3$ and $R^6$ is independently "a substituted or unsubstituted alkyl", the substituent in "a substituted or unsubstituted alkyl" is

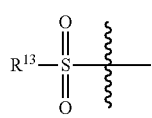

wherein $R^{13}$ is a methyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is a methyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is

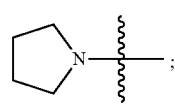 [SMILES: *N1CCCC1]

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is

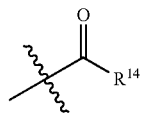

wherein $R^{14}$ is a methyl;

and/or, in the case where $R^4$ is "a substituted or unsubstituted alkyl" or "a substituted or unsubstituted heterocycloalkyl", the substituent in "a substituted or unsubstituted alkyl" or "a substituted or unsubstituted heterocycloalkyl" is

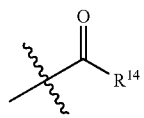

wherein $R^{14}$ is a tert-butoxy or an ethoxy;

and/or, in the case where the alkyl substituent in "substituted or unsubstituted 5- to 7-membered carbon heterocycle" is a methyl, an ethyl or a propyl.

4. The fused ring pyrimidine compound, the tautomer, the enantiomer, the diastereoisomer or the pharmaceutically acceptable salt thereof according to claim 3, wherein, in the case where each of $R^1$, $R^2$, $R^3$ and $R^6$ is independently a heterocycloalkyl, the heterocycloalkyl is

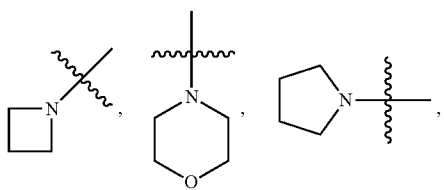

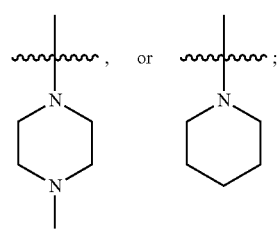

and/or, in the case where each of $R^7$, $R^8$, $R^9$, $R^{10}$ and $R^{15}$ is independently "a substituted or unsubstituted alkyl", the alkyl is a methyl, a trideuteromethyl, an ethyl, a propyl or an isopropyl;

and/or, in the case where each of $R^7$, $R^8$, $R^9$, $R^{10}$ and $R^{15}$ is independently an alkoxy, the alkoxy is a methoxy;

and/or, in the case where each of $R^7$, $R^8$, $R^9$, $R^{10}$ and $R^{15}$ is independently a heterocycloalkyl, the heterocycloalkyl is

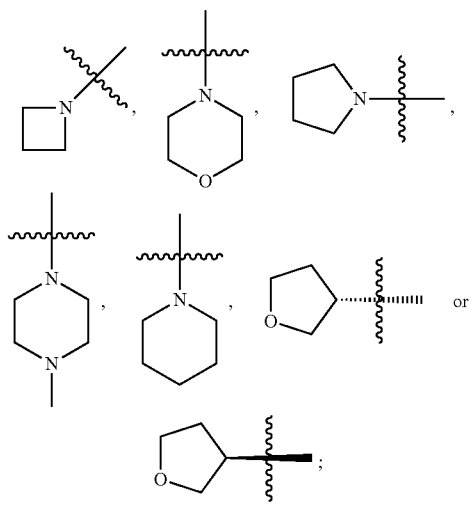

and/or, in the case where R⁴ is "a substituted or unsubstituted heterocycloalkyl", the heterocycloalkyl in "a substituted or unsubstituted heterocycloalkyl" is

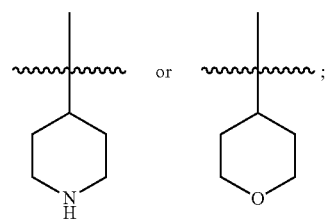 [SMILES: *C1CCNCC1 ; *C1CCOCC1]

and/or, in the case where each of $R^1$, $R^2$, $R^3$ and $R^6$ is independently "a substituted or unsubstituted alkyl", the substituent in "a substituted or unsubstituted alkyl" is a methyl;
and/or, in the case where each of $R^1$, $R^2$, $R^3$ and $R^6$ is independently "a substituted or unsubstituted alkyl", the substituent in "a substituted or unsubstituted alkyl" is a methoxy;
and/or, in the case where each of $R^1$, $R^2$, $R^3$ and $R^6$ is independently "a substituted or unsubstituted alkyl", the substituent in "a substituted or unsubstituted alkyl" is

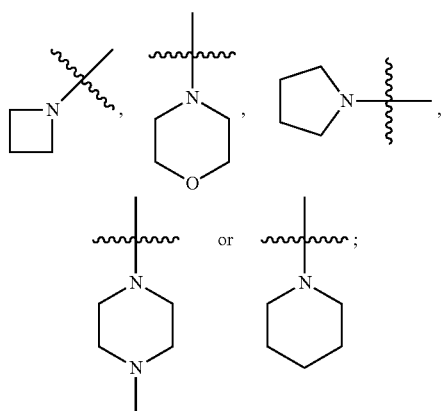

and/or, in the case where each of $R^7$, $R^8$, $R^9$, $R^{10}$ and $R^{15}$ is independently "a substituted or unsubstituted alkyl", the substituent in "a substituted or unsubstituted alkyl" is a methyl;
and/or, in the case where each of $R^7$, $R^8$, $R^9$, $R^{10}$ and $R^{15}$ is independently "a substituted or unsubstituted alkyl", the substituent in "a substituted or unsubstituted alkyl" is a methoxy;
and/or, in the case where each of $R^7$, $R^8$, $R^9$, $R^{10}$ and $R^{15}$ is independently "a substituted or unsubstituted alkyl", the substituent in "a substituted or unsubstituted alkyl" is

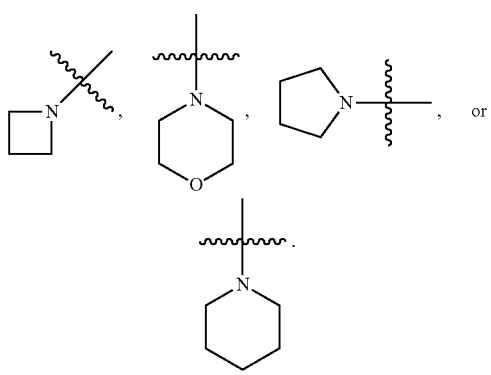

5. The fused ring pyrimidine compound, the tautomer, the enantiomer, the diastereoisomer or the pharmaceutically acceptable salt thereof according to claim 1, wherein the compound I is shown as formula I-1 or I-2,

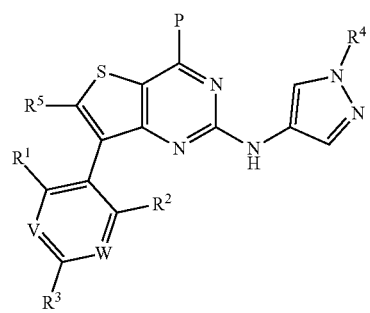

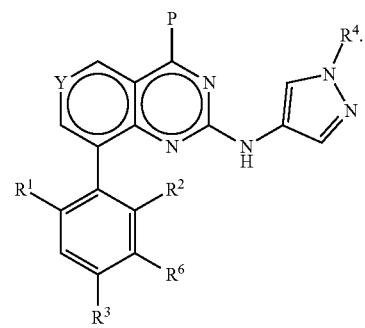

6. The fused ring pyrimidine compound, the tautomer, the enantiomer, the diastereoisomer or the pharmaceutically acceptable salt thereof according to claim 5, wherein, the compound I-1 is shown as formula I-1-1 or I-1-2,

I-1-1

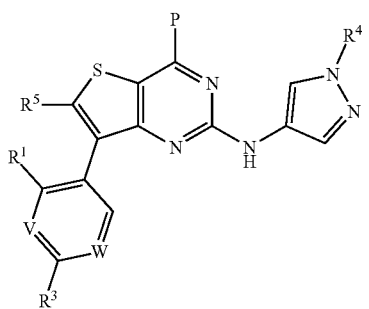

I-1-2

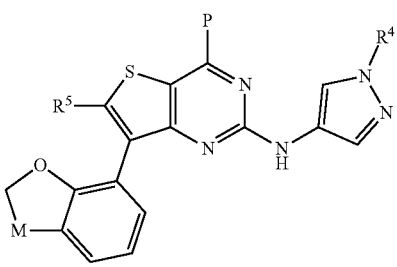

wherein, M is CH₂ or O;
the compound I-2 is shown as formula I-2-1 or I-2-2,

I-2-1

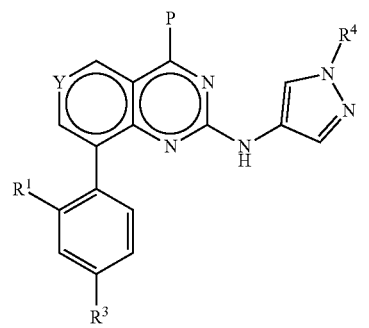

I-2-2

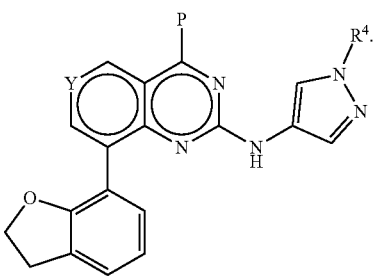

7. The fused ring pyrimidine compound, the tautomer, the enantiomer, the diastereoisomer or the pharmaceutically acceptable salt thereof according to claim 1, wherein, in compound I, Y is $CR^5$;

and/or, in compound I, $R^5$ is a hydrogen or an alkyl;
and/or, in compound I, W is $CR^6$;
and/or, in compound I, $R^6$ is a hydrogen;
and/or, in compound I, $R^6$ and $R^2$ together with two atoms on the ring to which they are attached form "a substituted or unsubstituted 5- to 7-membered carbon heterocycle";

and/or, in compound I, each of $R^1$ and $R^2$ is independently a hydrogen or

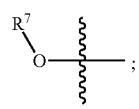

and/or, in compound I, $R^1$ or $R^2$ is a hydrogen;
and/or, in compound I, $R^3$ is a hydrogen,

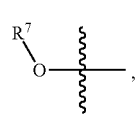

a halogen, or

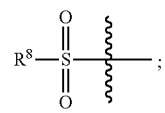

and/or, in compound I, $R^4$ is "a substituted or unsubstituted alkyl", or "a substituted or unsubstituted heterocycloalkyl".

8. The fused ring pyrimidine compound, the tautomer, the enantiomer, the diastereoisomer or the pharmaceutically acceptable salt thereof according to claim 1, which is selected from the group consisting of

1

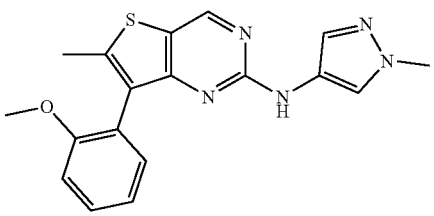

2

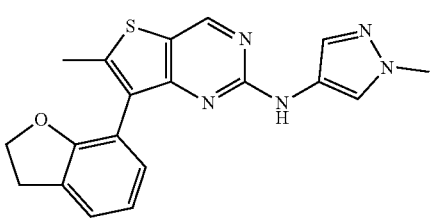

3

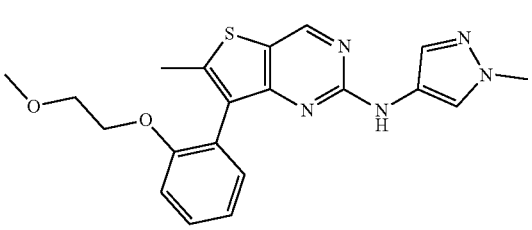

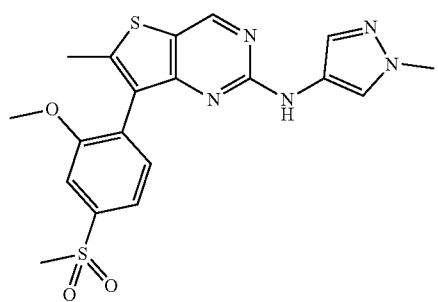
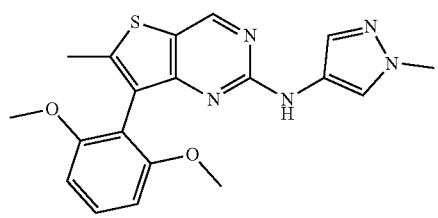
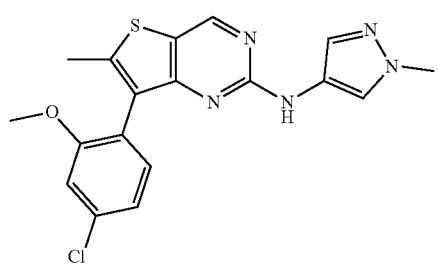
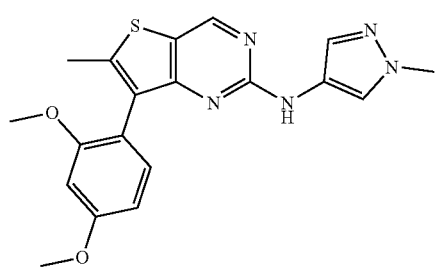
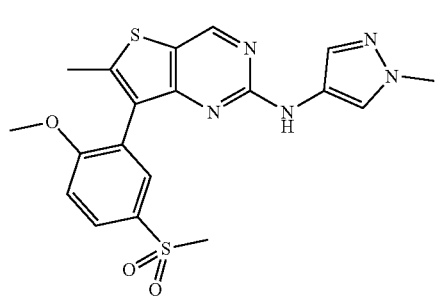
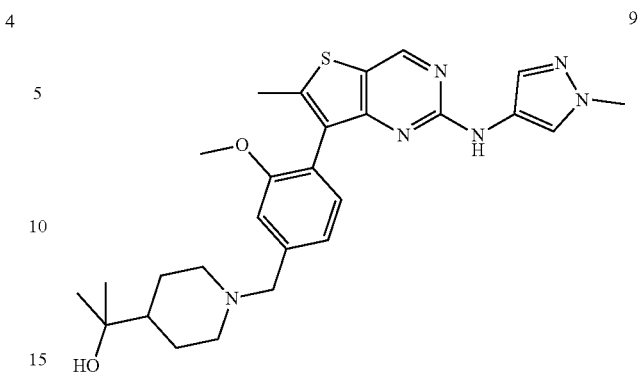
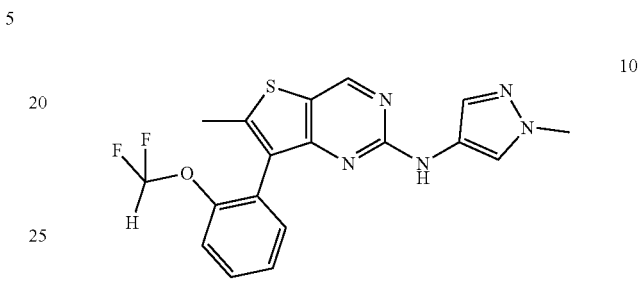
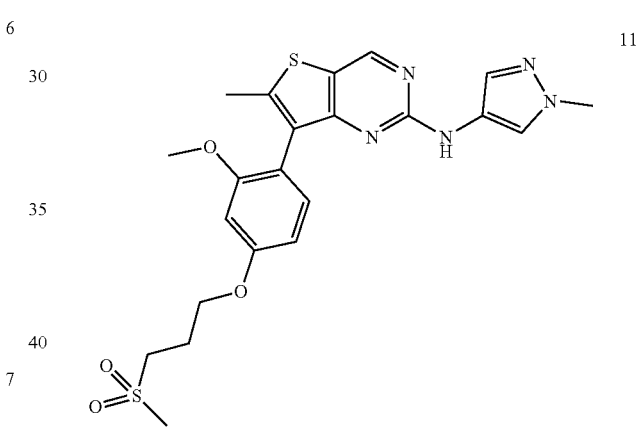
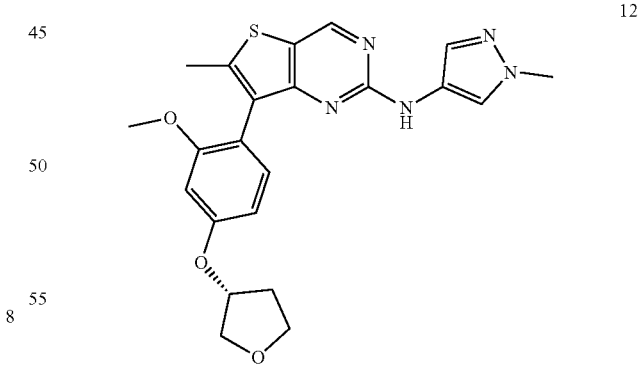
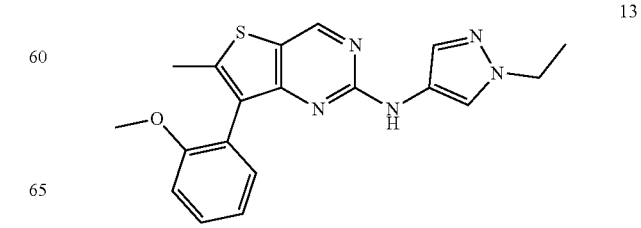

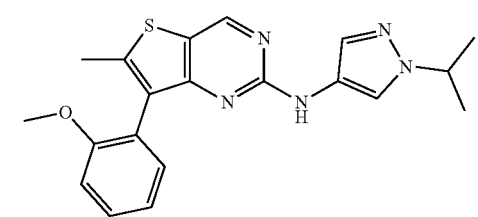
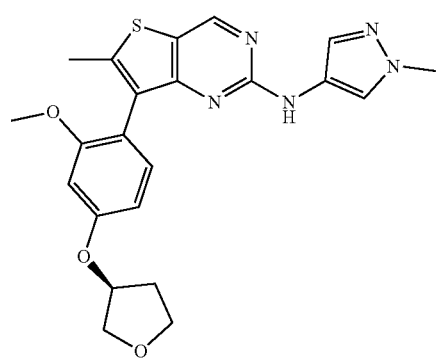
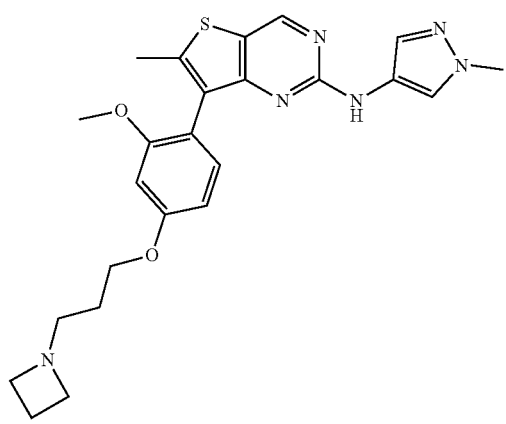
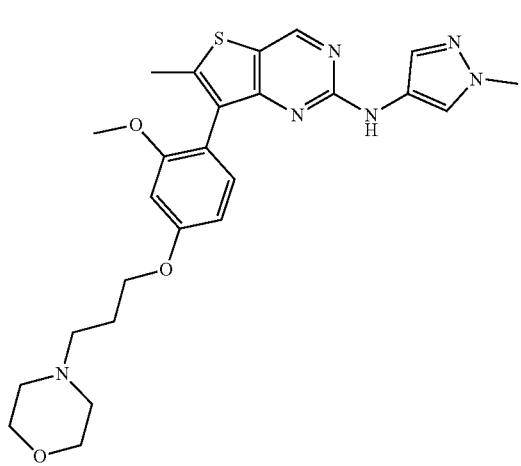
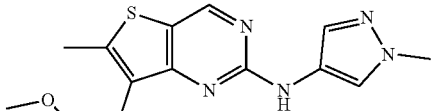

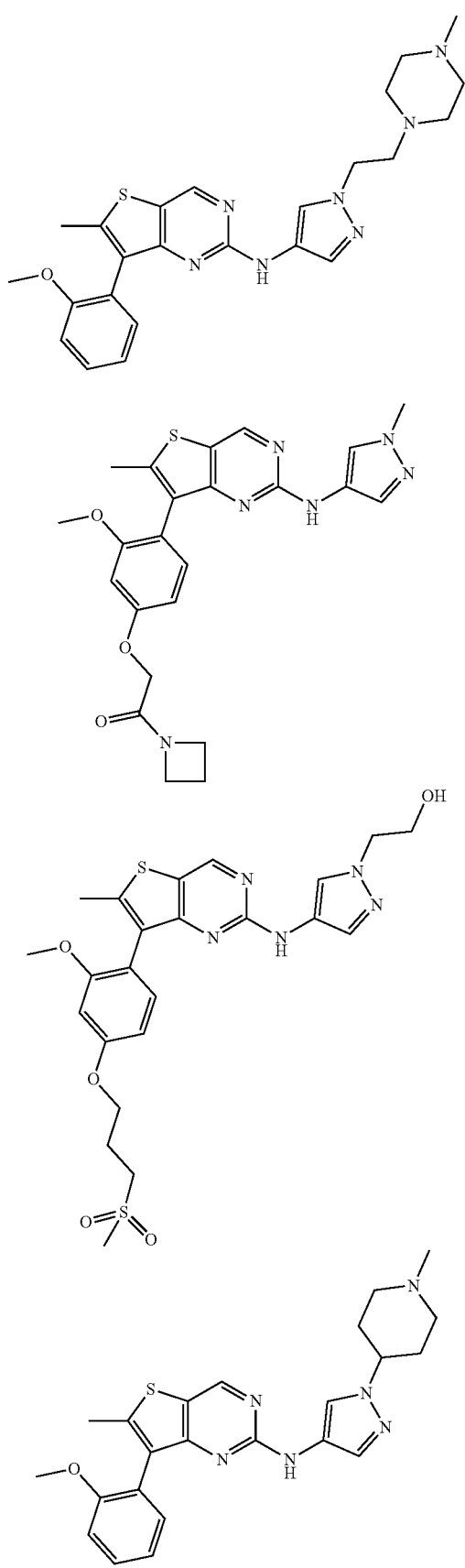
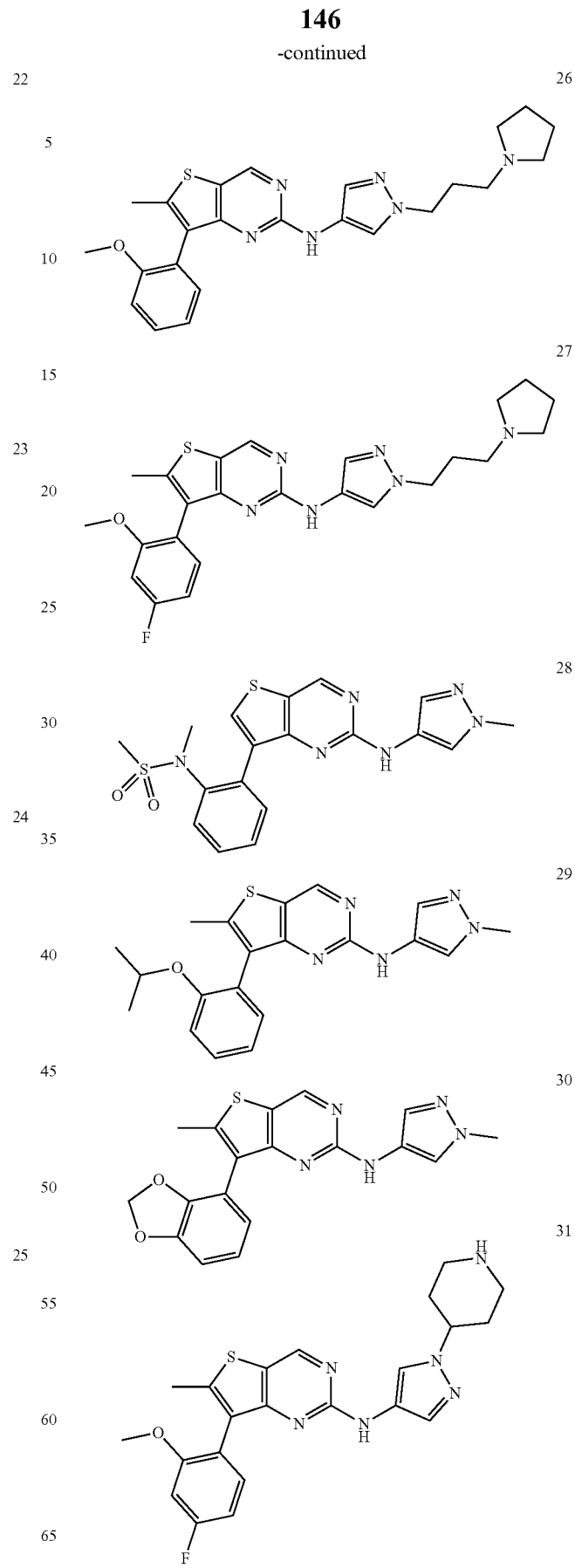

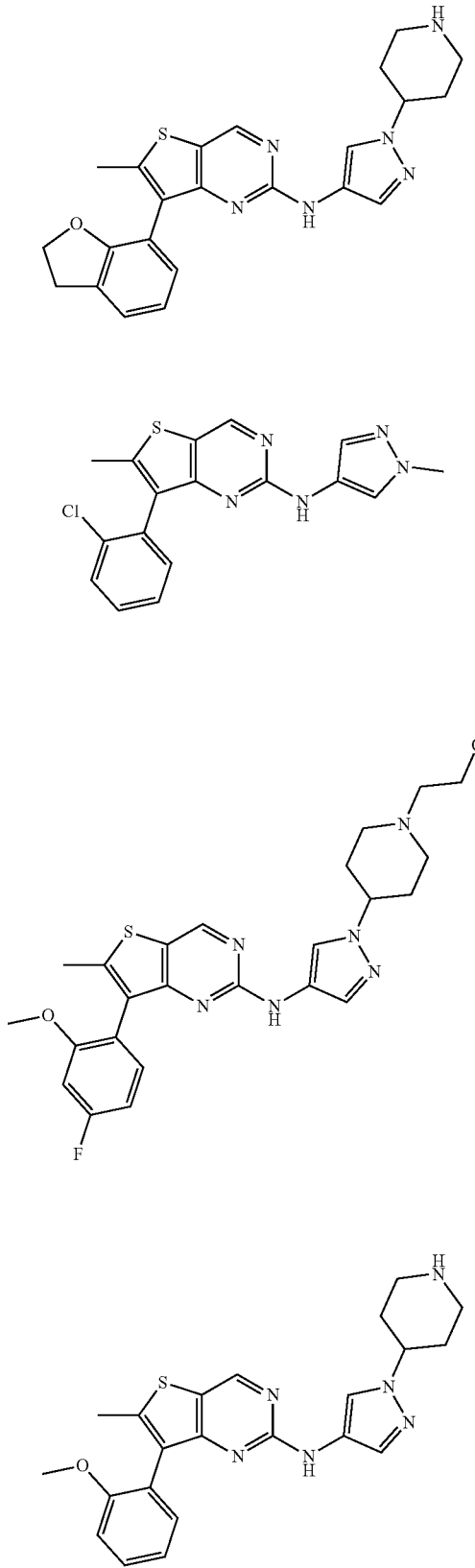
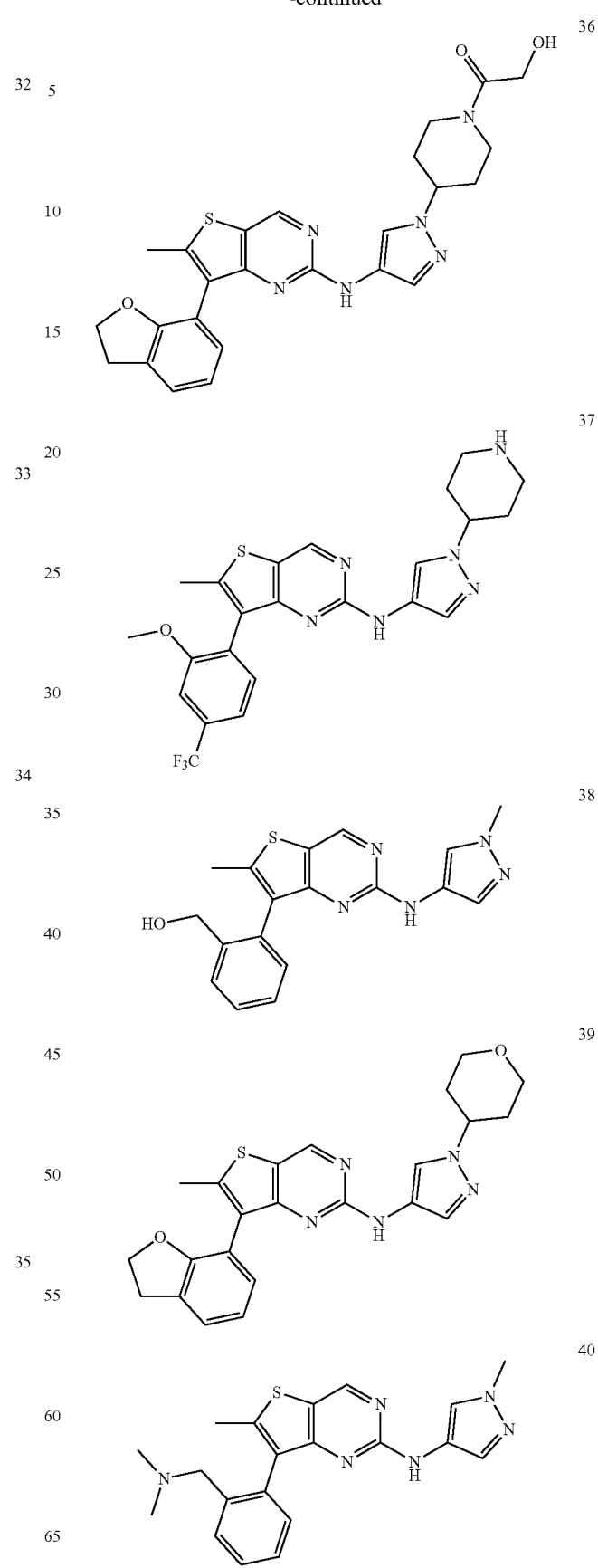

41
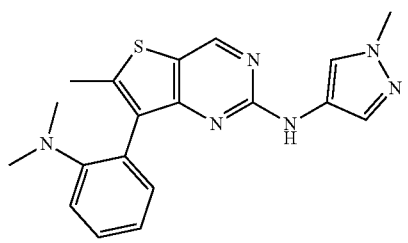
42
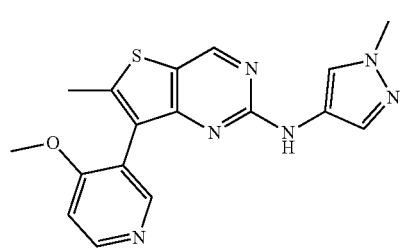
43
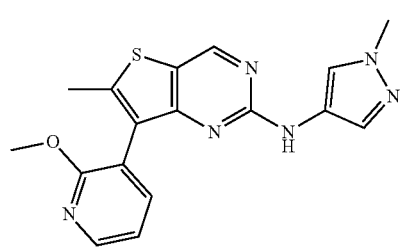
44
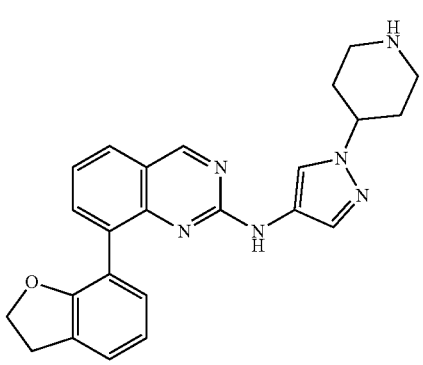
45
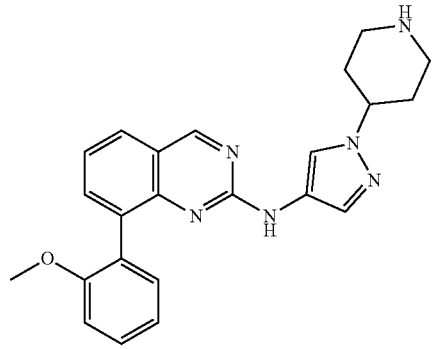
46
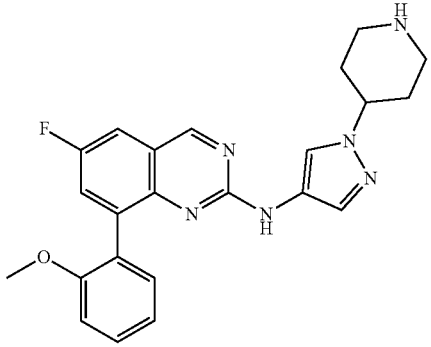
47
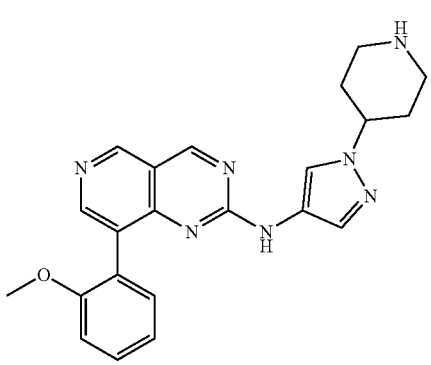
48
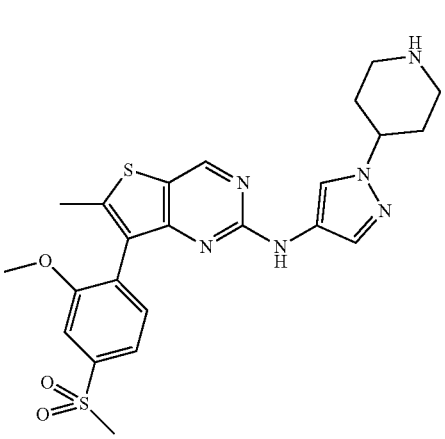
49
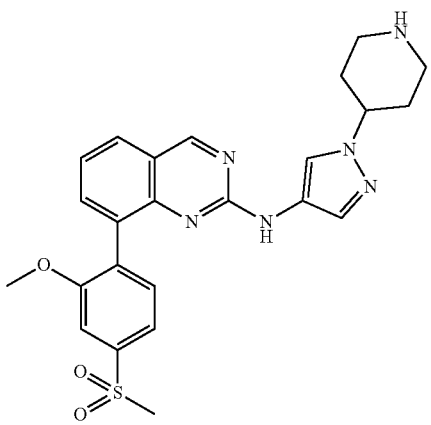

-continued

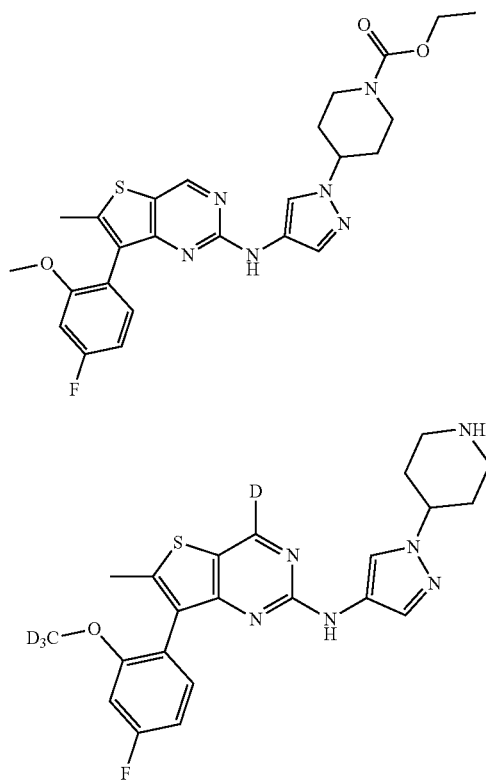

9. A process for preparing the fused ring pyrimidine compound according to claim 1, which is any one of processes 1-13, process 1 comprises carrying out a substitution reaction with compound 1-a and a methylation reagent in an organic solvent and in the presence of a base to give compound I;

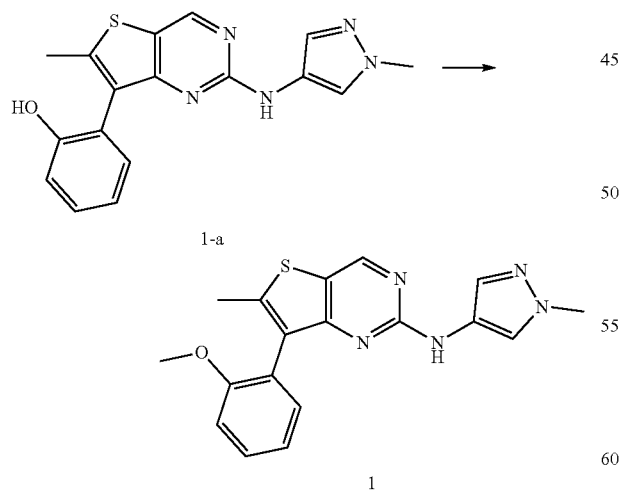

process 2 comprises carrying out a substitution reaction with compound II and compound VI in an organic solvent and in the presence of a catalyst to give compound I;

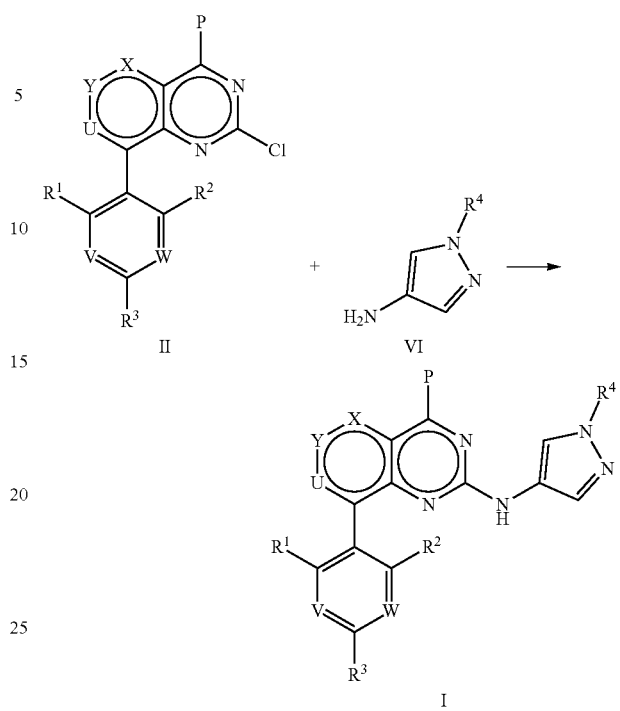

process 3 comprises carrying out a coupling reaction with compound III and compound VII in an organic solvent and water and in the presence of a base and a palladium catalyst to give compound I; wherein, A is Br or I;

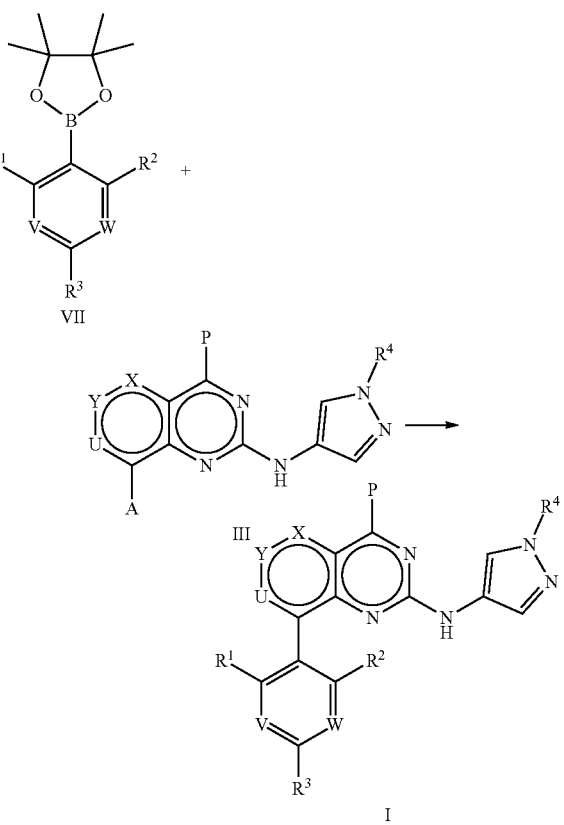

process 4 comprises carrying out a substitution reaction with compound 9-a and 2-(4-piperidyl)-2-propanol in an organic solvent and in the presence of a base to give compound 9;

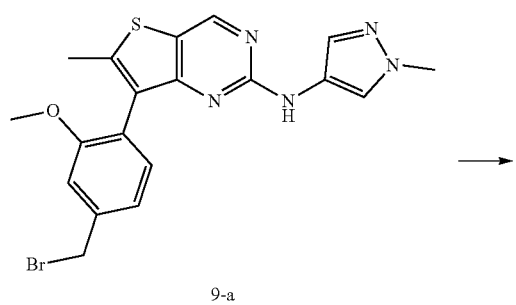

9-a

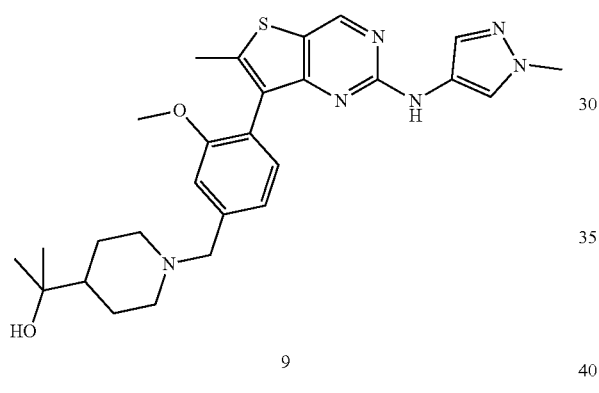

9 process 5 comprises carrying out a substitution reaction with compound 17-a and morpholine in an organic solvent and in the presence of a base to give compound 17;

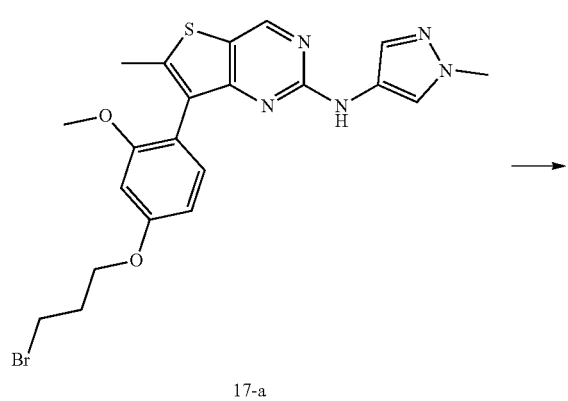

17-a

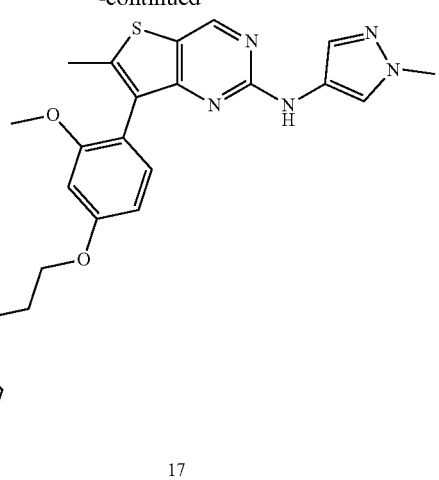

17 process 6 comprises carrying out a substitution reaction with compound 17-a and pyrrolidine in an organic solvent and in the presence of a base to give compound 18;

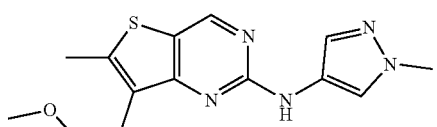

17-a

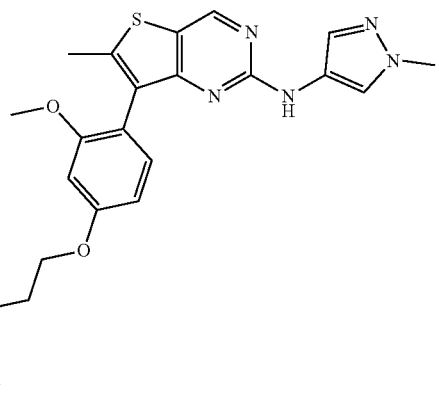

18 process 7 comprises carrying out a substitution reaction with compound 17-a and N-methylpiperazine in an organic solvent and in the presence of a base to give compound 19;

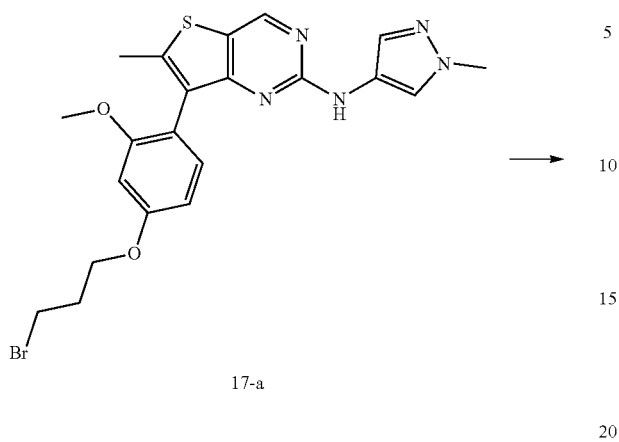

17-a

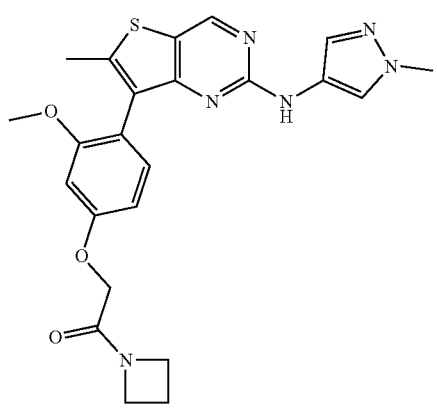

23 process 9 comprises deprotecting compound IV in an organic solvent and in the presence of an acid to give compound I; wherein R⁴ is

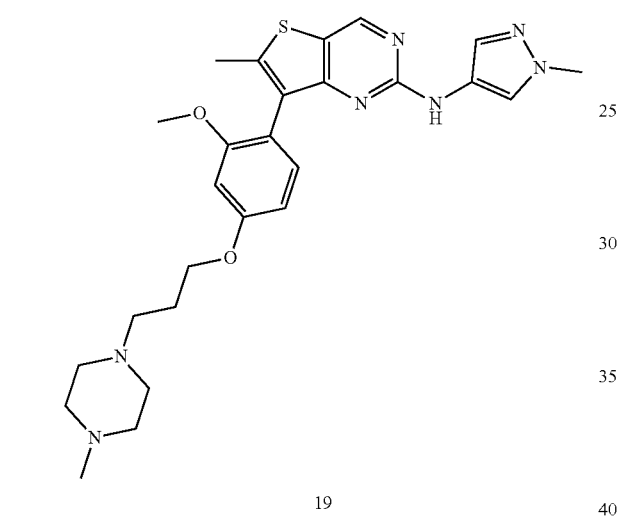

19

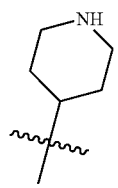

process 8 comprises carrying out a condensation reaction with compound 23-b and azetidine in an organic solvent and in the presence of a base, N-hydroxybenzotriazole and 1-ethyl-(3-dimethylaminopropyl)carbodiimide hydrochloride to give compound 23;

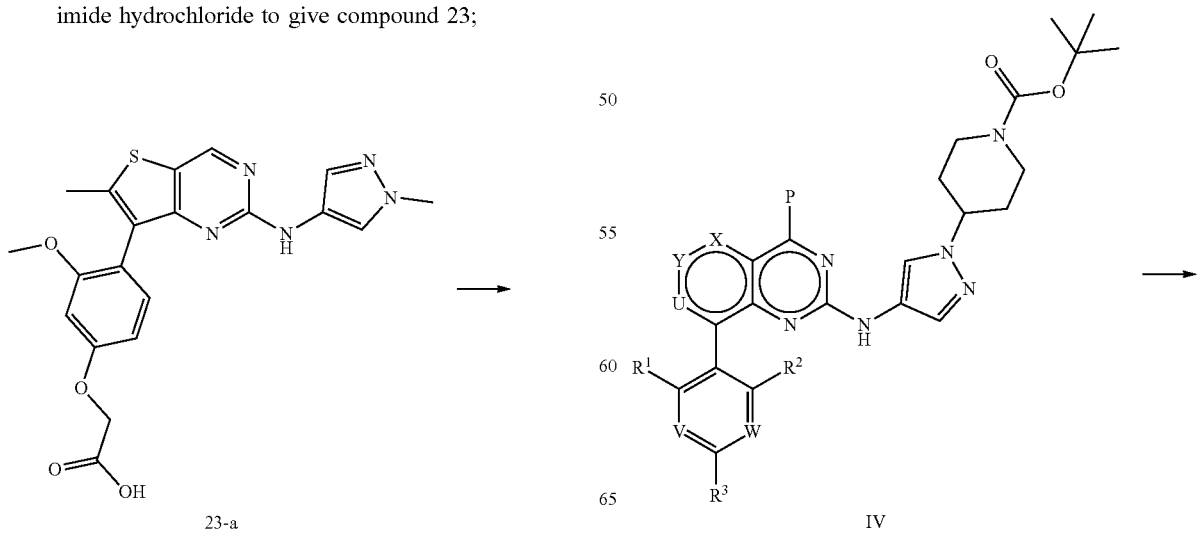

23-a

IV

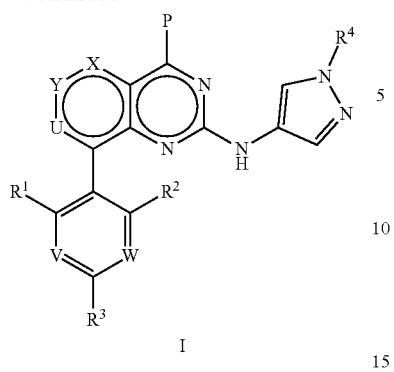

I

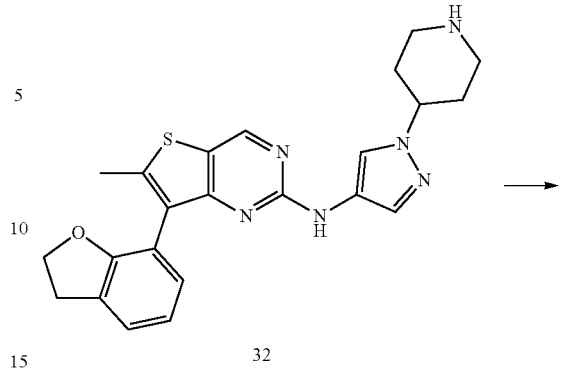

32 process 10 comprises carrying out a substitution reaction with compound 31 and 2-haloethanol in an organic solvent and in the presence of a base to give compound 34;

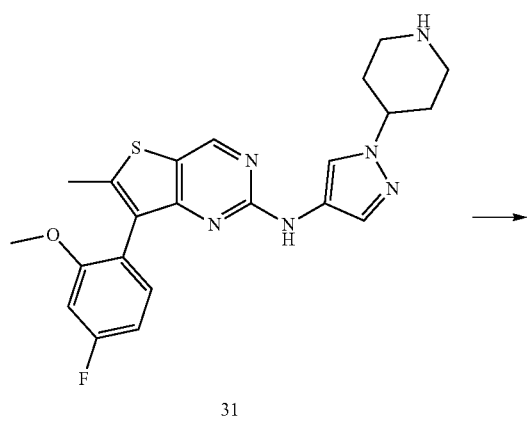

31

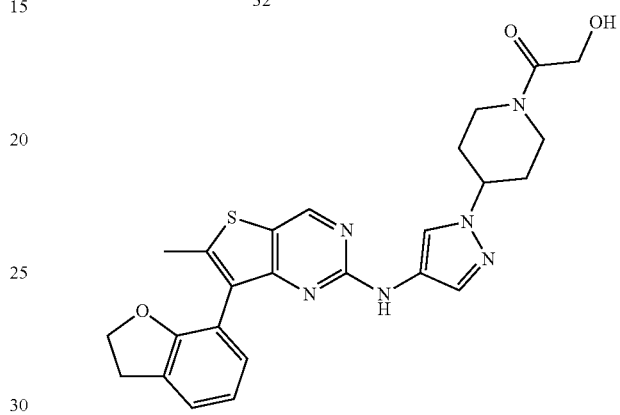

36 process 12 comprises carrying out a reduction amination reaction with compound 40-a, dimethylamine and sodium triacetoxyborohydride in an organic solvent and in the presence of an acid to give compound 40;

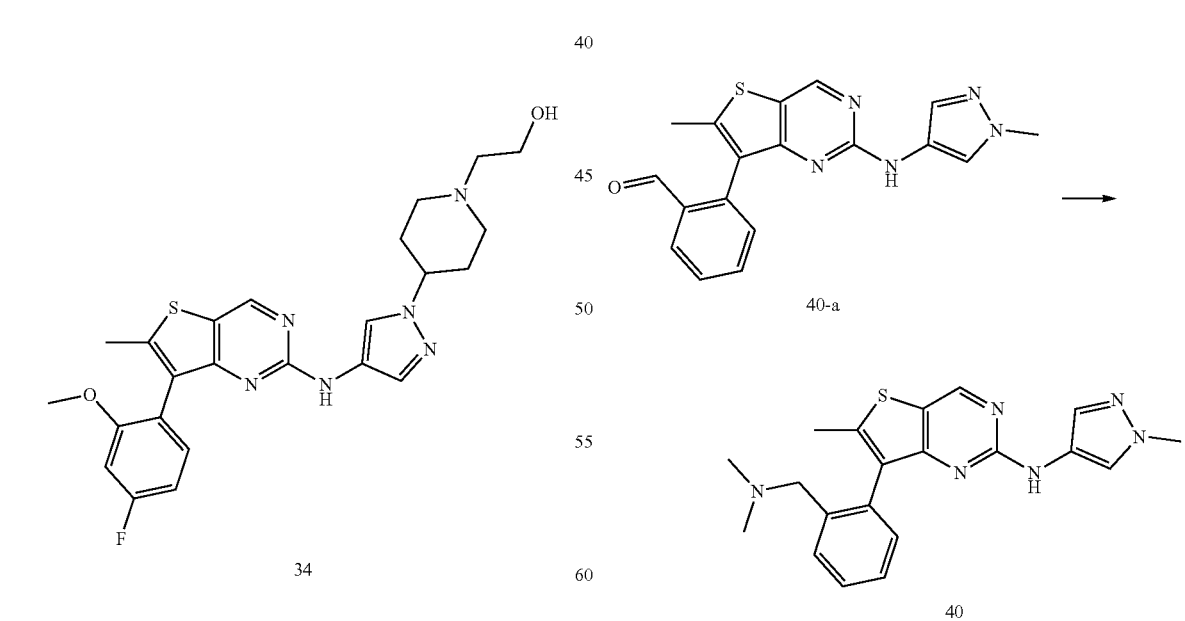

34

40-a

40 process 11 comprises carrying out a condensation reaction with compound 32 and 2-hydroxyacetic acidin an organic solvent and in the presence of a base, 1-hydroxybenzotriazole and 1-ethyl-(3-dimethylaminopropyl)carbodiimide hydrochloride to give compound 36;

process 13 comprises carrying out a condensation reaction with compound 31 and ethyl chloroformate in an organic solvent and in the presence of a base to give compound 50;

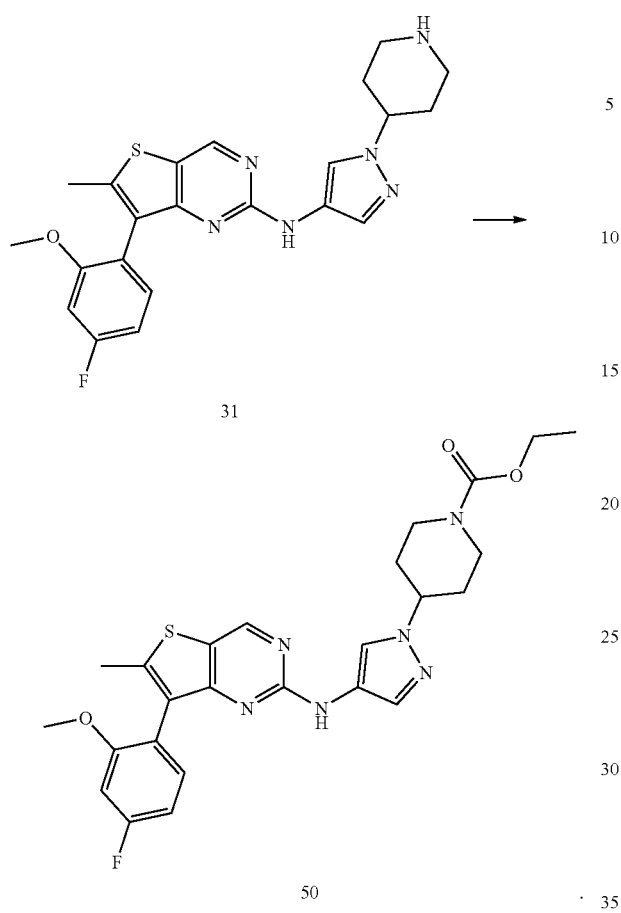
10. A compound having a structure of formula III or formula IV,
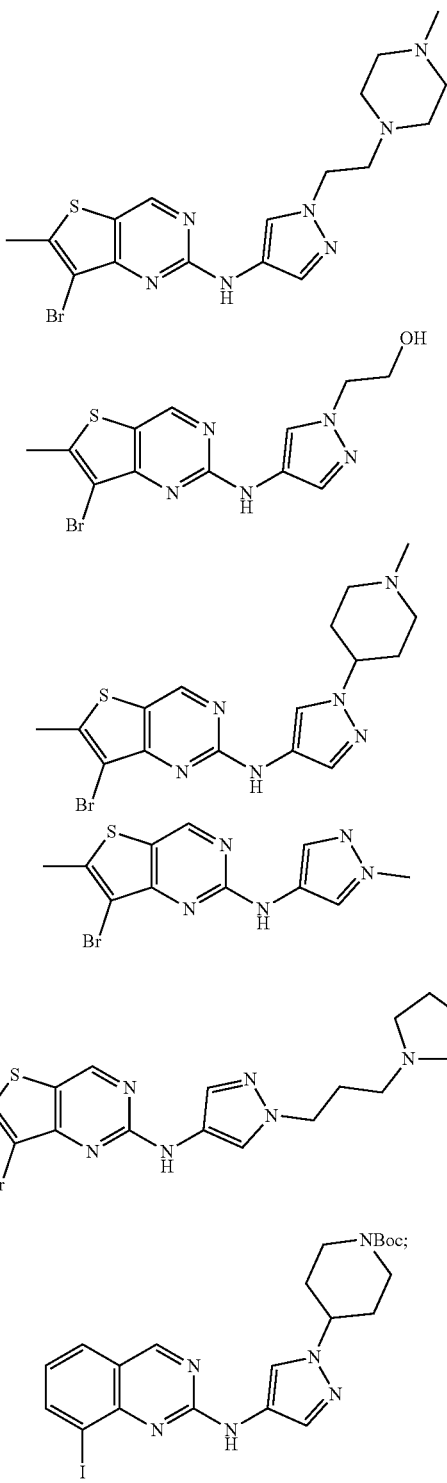
wherein, each of R¹, R², R³, X, Y, U, P, V and W is as defined in claim 1;
wherein, A is Br or I; each of $R^4$, X, Y, U and P is as defined in claim 1.
11. The compound according to claim 10, wherein, the compound of formula III is selected from the group consisting of:
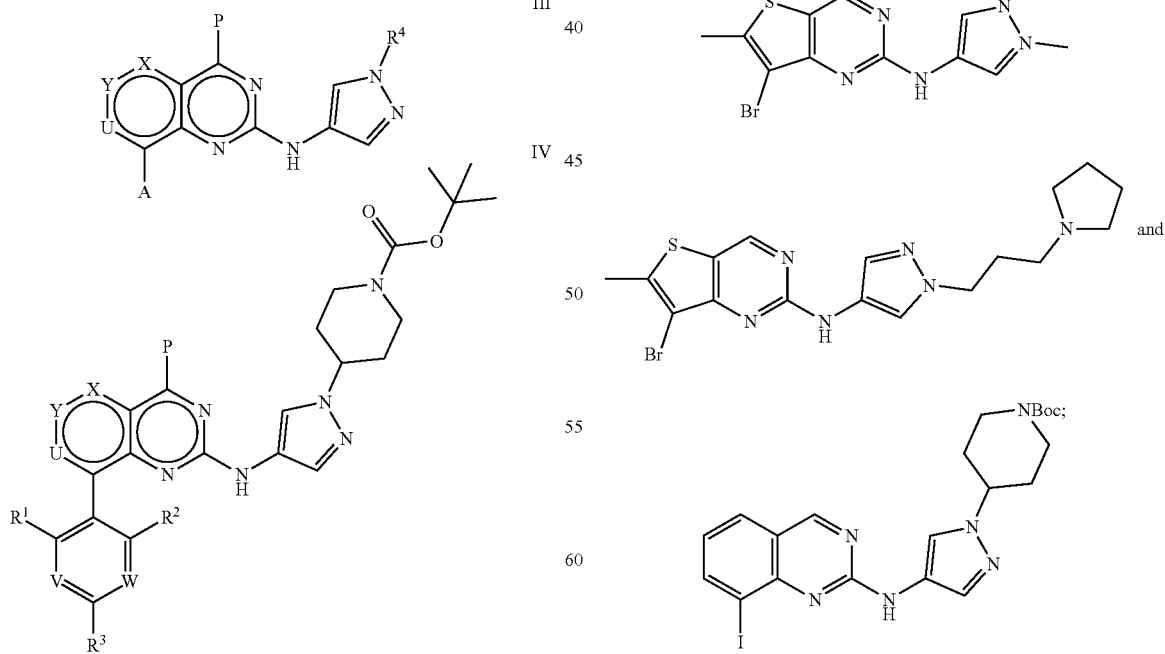
the compound of formula IV is selected from the group consisting of 31-a 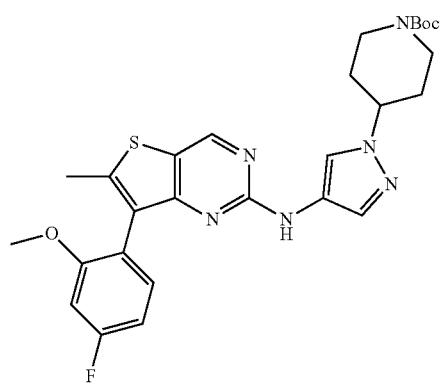
32-a 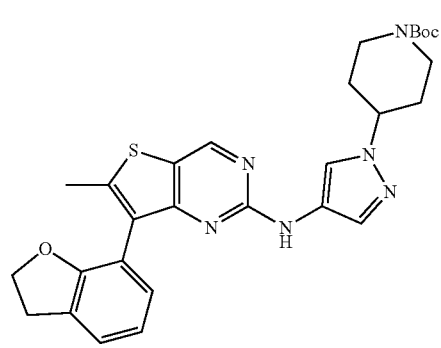
35-a 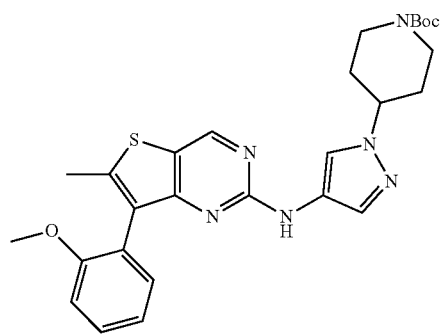
37-a
44-a 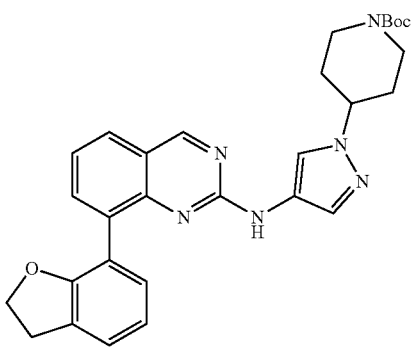
45-a 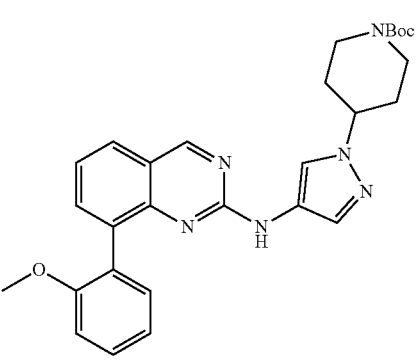
46-a 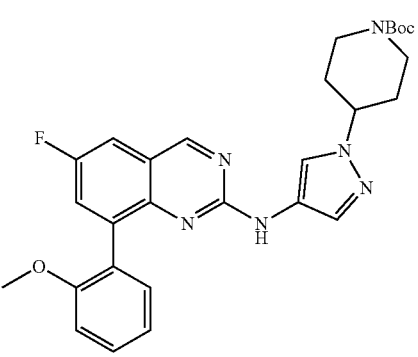
47-a 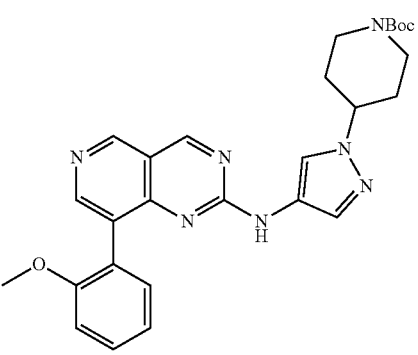

-continued
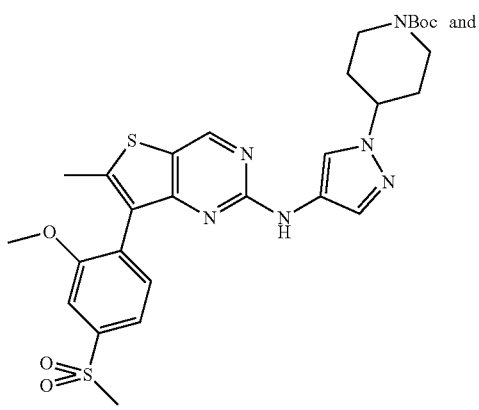
48-a
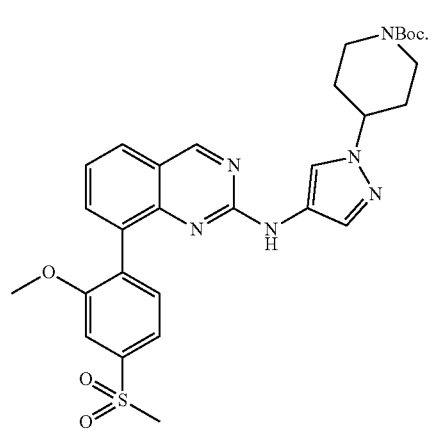
49-a
12. A compound V which is selected from the group consisting of
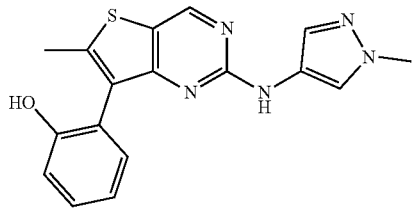
1-a
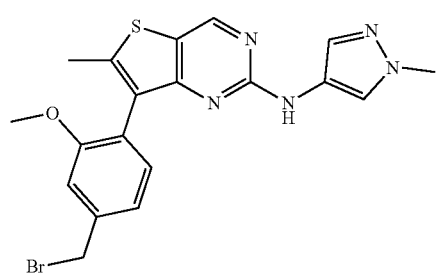
9-a
-continued
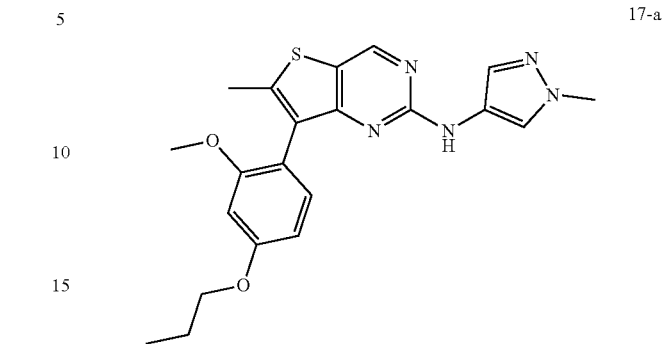
17-a
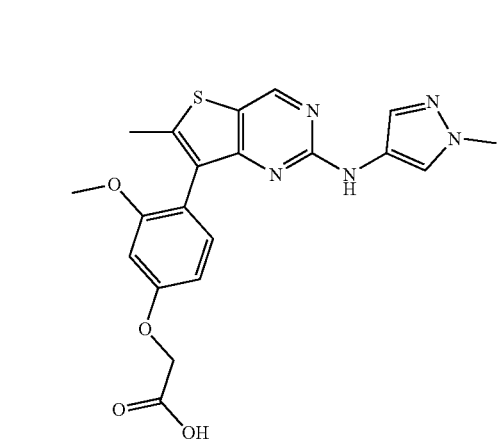
23-a
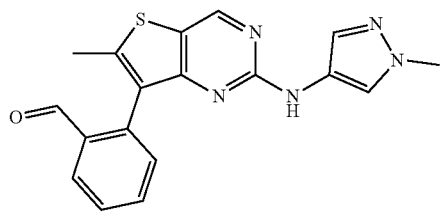
40-a
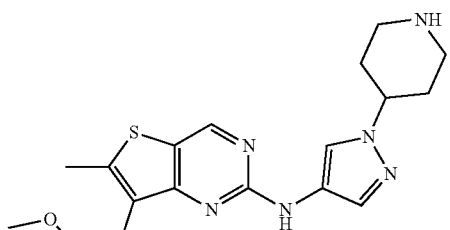
31
and

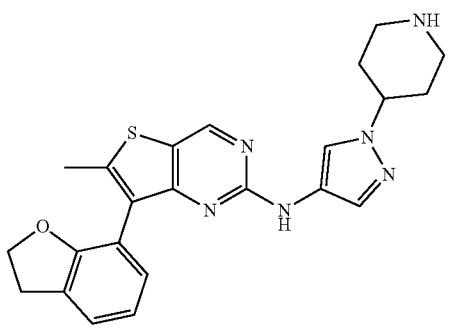

32

13. A method for alleviating or treating the diseases caused by a kinase selected from the group consisting of Janus kinase, FGFR kinase, FLT3 kinase and Src family kinase, wherein the diseases are selected from the group consisting of immune system disease, autoimmune disease, cell proliferative disease, allergic disorder and cardiovascular disease in a subject in need thereof, comprising: administering an effective amount of the fused ring pyrimidine compound, the tautomer, the enantiomer, the diastereoisomer or the pharmaceutically acceptable salt thereof according to claim 1 to the subject.

14. The method according to claim 13, wherein the immune system disease is organ transplant rejection;

and/or, the autoimmune disease is selected from the group consisting of rheumatoid arthritis, psoriasis, Crohn's disease and multiple sclerosis;

and/or, the cell proliferative disease is selected from the group consisting of myelofibrosis, hematological tumor and solid tumor;

and/or, the allergic disorder is bronchial asthma;

and/or, the cardiovascular disease is selected from the group consisting of ischemic cardiomyopathy, heart failure and myocardial infarction.

15. The method according to claim 14, wherein the hematological tumor is leukemia and/or lymphoma;

and/or, the solid tumor is selected from the group consisting of renal cancer, liver cancer, stomach cancer, lung cancer, breast cancer, prostate cancer, pancreatic cancer, thyroid cancer, ovarian cancer, glioblastoma, skin cancer and melanoma.

16. A pharmaceutical composition, comprising the fused ring pyrimidine compound, the tautomer, the enantiomer, the diastereoisomer or the pharmaceutically acceptable salt thereof according to claim 1, and one or more than one pharmaceutically acceptable carrier(s) and/or diluent(s).

17. The pharmaceutical composition according to claim 16, wherein the dose of the fused ring pyrimidine compound, the tautomer, the enantiomer, the diastereoisomer or the pharmaceutically acceptable salt thereof is a therapeutically effective amount;

and/or, the pharmaceutical composition is used in combination with one or more than one clinically used chemotherapeutic agent.

18. The pharmaceutical composition according to claim 17, wherein, in the case where the pharmaceutical composition is used in combination with one or more than one clinically used chemotherapeutic agent, the dosage of which is a liposomal dosage.

* * * * *